(12) United States Patent
Shima et al.

(10) Patent No.: US 8,685,397 B2
(45) Date of Patent: Apr. 1, 2014

(54) COMBINATION THERAPY FOR THE TREATMENT OF OCULAR NEOVASCULAR DISORDERS

(75) Inventors: David Shima, Boston, MA (US); Perry Calias, Melrose, MA (US); Anthony P. Adamis, Boston, MA (US)

(73) Assignee: Ophthotech Corporation, New York, NY (US)

( * ) Notice: Subject to any disclaimer, the term of this patent is extended or adjusted under 35 U.S.C. 154(b) by 242 days.

(21) Appl. No.: 12/641,270

(22) Filed: Dec. 17, 2009

(65) Prior Publication Data

US 2010/0129364 A1    May 27, 2010

Related U.S. Application Data

(62) Division of application No. 10/926,806, filed on Aug. 26, 2004, now Pat. No. 7,759,472.

(60) Provisional application No. 60/556,837, filed on Mar. 26, 2004.

(51) Int. Cl.
| | |
|---|---|
| *A61K 39/395* | (2006.01) |
| *A61K 31/00* | (2006.01) |
| *A61K 31/52* | (2006.01) |
| *A61K 45/06* | (2006.01) |
| *C07K 16/22* | (2006.01) |
| *C07K 14/475* | (2006.01) |

(52) U.S. Cl.
USPC ............. 424/133.1; 424/145.1; 424/158.1; 536/23.1; 536/24.5

(58) Field of Classification Search
None
See application file for complete search history.

(56) References Cited

U.S. PATENT DOCUMENTS

| | | | |
|---|---|---|---|
| 4,914,210 A | 4/1990 | Levenson et al. | |
| 5,194,596 A | 3/1993 | Tischer et al. | |
| 5,270,163 A | 12/1993 | Gold et al. | |
| 5,322,691 A | 6/1994 | Darougar et al. | |
| 5,459,015 A | 10/1995 | Janjic et al. | |
| 5,475,096 A | 12/1995 | Gold et al. | |
| 5,496,938 A | 3/1996 | Gold et al. | |
| 5,668,264 A | 9/1997 | Janjic et al. | |
| 5,670,637 A | 9/1997 | Gold et al. | |
| 5,674,685 A | 10/1997 | Janjic et al. | |
| 5,683,867 A | 11/1997 | Biesecker et al. | |
| 5,696,249 A | 12/1997 | Gold et al. | |
| 5,723,594 A * | 3/1998 | Janjic et al. ................. 536/23.1 |
| 5,756,291 A | 5/1998 | Griffin et al. | |
| 5,811,533 A | 9/1998 | Gold et al. | |
| 5,814,620 A | 9/1998 | Robinson et al. | |
| 5,817,785 A | 10/1998 | Gold et al. | |
| 5,859,228 A | 1/1999 | Janjic et al. | |
| 5,932,462 A | 8/1999 | Harris et al. | |
| 5,932,602 A | 8/1999 | Hirth et al. | |
| 5,958,691 A | 9/1999 | Pieken et al. | |
| 5,990,141 A | 11/1999 | Hirth et al. | |
| 6,005,087 A | 12/1999 | Cook et al. | |
| 6,011,020 A | 1/2000 | Gold et al. | |
| 6,051,698 A | 4/2000 | Janjic et al. | |
| 6,054,297 A | 4/2000 | Carter et al. | |
| 6,113,906 A | 9/2000 | Greenwald et al. | |
| 6,168,778 B1 | 1/2001 | Janjic et al. | |
| 6,207,816 B1 | 3/2001 | Gold et al. | |
| 6,229,002 B1 * | 5/2001 | Janjic et al. ................. 536/23.1 |
| 6,342,219 B1 * | 1/2002 | Thorpe et al. .............. 424/145.1 |
| 6,342,221 B1 | 1/2002 | Thorpe et al. | |
| 6,382,219 B1 | 5/2002 | Jelten | |
| 6,395,888 B1 | 5/2002 | Biesecker et al. | |
| 6,410,322 B1 | 6/2002 | Robinson | |
| 6,416,758 B1 | 7/2002 | Thorpe et al. | |
| 6,426,335 B1 | 7/2002 | Janjic et al. | |
| 6,448,277 B2 | 9/2002 | Altmann et al. | |
| 6,465,188 B1 | 10/2002 | Gold et al. | |
| 6,537,988 B2 | 3/2003 | Lee | |
| 6,559,126 B2 | 5/2003 | Tournaire et al. | |
| 6,566,343 B2 | 5/2003 | Biesecker et al. | |
| 6,582,918 B2 | 6/2003 | Janjic et al. | |
| 6,632,926 B1 * | 10/2003 | Chen et al. ................. 530/387.3 |
| 6,699,843 B2 | 3/2004 | Pietras et al. | |
| 6,719,750 B2 * | 4/2004 | Varner et al. ................. 604/289 |
| 6,808,719 B2 | 10/2004 | Yaacobi | |
| 6,884,879 B1 | 4/2005 | Baca et al. | |
| 7,060,269 B1 | 6/2006 | Baca et al. | |
| 7,070,959 B1 | 7/2006 | Papadopoulos et al. | |
| 7,141,375 B2 | 11/2006 | Pietras et al. | |
| 7,303,747 B2 | 12/2007 | Wiegand et al. | |
| 7,306,799 B2 | 12/2007 | Wiegand et al. | |
| 7,354,581 B2 | 4/2008 | Cedarbaum et al. | |
| 7,365,166 B2 | 4/2008 | Baca et al. | |
| 7,374,757 B2 | 5/2008 | Papadopoulos et al. | |
| 7,374,758 B2 | 5/2008 | Papadopoulos et al. | |
| 7,459,436 B2 | 12/2008 | Lehmann et al. | |
| 7,531,173 B2 | 5/2009 | Wiegand et al. | |
| 7,608,261 B2 | 10/2009 | Furfine et al. | |
| 7,759,472 B2 | 7/2010 | Shima et al. | |
| 7,879,993 B2 | 2/2011 | Janjic et al. | |
| 7,939,654 B2 | 5/2011 | Janjic et al. | |

(Continued)

FOREIGN PATENT DOCUMENTS

| | | |
|---|---|---|
| CA | 2464007 | 4/2004 |
| EP | 1660057 | 5/2012 |

(Continued)

OTHER PUBLICATIONS

Younes et al, Current Pharmaceutical Design 8(16): 1451-1466, 2002.*

(Continued)

*Primary Examiner* — Phuong Huynh
(74) *Attorney, Agent, or Firm* — Cooley LLP

(57) ABSTRACT

The invention features methods for treating a patient diagnosed with, or at risk of developing, a neovascular disorder by administering a PDGF antagonist and a VEGF antagonist to the patient. The invention also features a pharmaceutical composition containing a PDGF antagonist and a VEGF antagonist for the treatment or prevention of a neovascular disorder.

22 Claims, 38 Drawing Sheets

(56) References Cited

U.S. PATENT DOCUMENTS

| | | | |
|---|---|---|---|
| 8,039,443 B2 | 10/2011 | Grate et al. | |
| 8,187,597 B2 | 5/2012 | Shima et al. | |
| 8,206,707 B2 | 6/2012 | Shima et al. | |
| 2003/0036642 A1 | 2/2003 | Janjic et al. | |
| 2003/0171320 A1 | 9/2003 | Guyer | |
| 2004/0022727 A1 | 2/2004 | Stanton et al. | |
| 2004/0167091 A1 | 8/2004 | Guyer | |
| 2004/0180360 A1 | 9/2004 | Wilson et al. | |
| 2004/0249130 A1 | 12/2004 | Stanton et al. | |
| 2004/0253243 A1 | 12/2004 | Epstein et al. | |
| 2004/0253679 A1 | 12/2004 | Epstein et al. | |
| 2005/0042273 A1 | 2/2005 | Janjic et al. | |
| 2005/0058620 A1 | 3/2005 | Nakamoto et al. | |
| 2005/0096257 A1 | 5/2005 | Shima et al. | |
| 2005/0124565 A1 | 6/2005 | Diener et al. | |
| 2005/0159351 A1 | 7/2005 | Grate et al. | |
| 2005/0244462 A1 | 11/2005 | Farooq | |
| 2005/0244471 A1 | 11/2005 | Shiah et al. | |
| 2005/0244500 A1 | 11/2005 | Whitcup et al. | |
| 2005/0288490 A1 | 12/2005 | Nakamoto et al. | |
| 2006/0018871 A1 | 1/2006 | Benedict et al. | |
| 2006/0073113 A1 | 4/2006 | Nakamoto et al. | |
| 2006/0079477 A1 | 4/2006 | Biesecker et al. | |
| 2006/0115450 A1 | 6/2006 | Nakamoto et al. | |
| 2006/0233860 A1 | 10/2006 | Chang et al. | |
| 2007/0021327 A1 | 1/2007 | Pietras et al. | |
| 2007/0027101 A1 | 2/2007 | Guyer et al. | |
| 2007/0184089 A1 | 8/2007 | Howie et al. | |
| 2008/0145406 A1 | 6/2008 | Asgharian et al. | |
| 2008/0152654 A1 | 6/2008 | Reich | |
| 2008/0207883 A1 | 8/2008 | Janjic et al. | |
| 2008/0286334 A1 | 11/2008 | Shiah et al. | |
| 2008/0305115 A1 | 12/2008 | Tice et al. | |
| 2009/0053138 A1 | 2/2009 | Preiss et al. | |
| 2009/0075342 A1 | 3/2009 | Cload et al. | |
| 2010/0111942 A1 | 5/2010 | Shima et al. | |
| 2010/0119522 A1 | 5/2010 | Shima et al. | |
| 2011/0200593 A1 | 8/2011 | Shima et al. | |
| 2012/0100136 A1 | 4/2012 | Patel et al. | |

FOREIGN PATENT DOCUMENTS

| | | | |
|---|---|---|---|
| WO | WO 95/16032 A1 | 6/1995 | |
| WO | WO 96/27006 A2 | 9/1996 | |
| WO | WO 96/30046 A1 | 10/1996 | |
| WO | WO 96/38579 | 12/1996 | |
| WO | WO 98/18480 | 5/1998 | |
| WO | WO 98/45331 A2 | 10/1998 | |
| WO | WO 98/45331 A3 | 12/1998 | |
| WO | WO 99/31119 | 6/1999 | |
| WO | WO 99/41271 | 8/1999 | |
| WO | WO 00/64946 | 11/2000 | |
| WO | WO 01/27264 A1 | 4/2001 | |
| WO | WO 01/87351 A1 | 11/2001 | |
| WO | WO 03/013541 A1 | 2/2003 | |
| WO | WO 03/039404 | 5/2003 | |
| WO | WO 2004/05282 A1 | 1/2004 | |
| WO | WO 2004/50899 | 6/2004 | |
| WO | WO 2004/094614 | 11/2004 | |
| WO | WO 2005/020972 | 3/2005 | |
| WO | WO 2006/050498 | 5/2006 | |
| WO | WO 2010/127029 | 11/2010 | |

OTHER PUBLICATIONS

Kinose et al, Molecular Vision 11: 366-73, 2005.*
Ruckman et al, J Biol Chem 273(32): 20556-20567, 1998.*
Zhu et al, Investigational New Drugs 17: 195-212, 1999.*
Tol et al, New England Journal of Medicine 360(6):563-72, Feb. 5, 2009.*
Abrams et al., "SU11248 inhibits KIT and platelet-derived growth factor receptor beta in preclinical models of human small cell lung cancer," Mol Cancer Ther 2(5):471-8, 2003.
Akiyama et al., "Intraocular injection of an aptamer that binds PDGF-B: a potential treatment for proliferative retinopathies," J Cell Physiol. May;207(2):407-12, 2006.
Arakelyan et al., "A computer algorithm describing the process of vessel formation and maturation, and its use for predicting the effects of anti-angiogenic and anti-maturation therapy on vascular tumor growth," Angiogenesis 5(3):203-14, 2002.
Balasubramanian et al., "Role of platelet-derived growth factor in vascular remodeling during pulmonary hypertension in the ovine fetus," Am J Physiol Lung Cell Mol Physiol May;284(5):L826-33, 2003.
Benjamin et al., "A plasticity window for blood vessel remodelling is defined by pericyte coverage of the preformed endothelial network and is regulated by PDGF-B and VEGF," Development 125(9):1591-8, 1998.
Bergers, et al. 2003. Benefits of targeting both pericytes and endothelial cells in the tumor vasculature with kinase inhibitors. Journal of Clinical Investigation. 111(9): 1287-1295.
Brown, et al., "Vascular permeability factor/vascular endothelial growth factor: a multifunctional angiogenic cytokine", EXS. 79:233-69, 1997.
Campochiaro. 2000. Retinal and choroidal neovascularization. J. Cell Physiol. 184(3): 301-10.
Castellon, et al. 2002. Effects of angiogenic growth factor combinations on retinal endothelial cells. Exp Eye Res. 74(4):523-35.
Cogburn et al., "Growth, metabolic and endocrine responses of broiler cockerels given a daily subcutaneous injection of natural or biosynthetic chicken growth hormone," J Nutr 119(8):1213-22, 1989.
Cullinan-Bove, et al. 1993. Vascular endothelial growth factor/vascular permeability factor expression in the rat uterus: rapid stimulation by estrogen correlates with estrogen-induced increases in uterine capillary permeability and growth. Endocrinol. 133(2):829-37.
Drolet et al., "Pharmacokinetics and safety of an anti-vascular endothelial growth factor aptamer (NX1838) following injection into the vitreous humor of rhesus monkeys," Pharm Res. Dec;17(12):1503-10, 2000.
Ebos et al., "Imatinib mesylate (STI-571) reduces Bcr-Abl-mediated vascular endothelial growth factor secretion in chronic myelogenous leukemia," Mol Cancer Res 1(2):89-95, 2002.
Fan, et al. 1995. Controlling the vasculature: angiogenesis, anti-angiogenesis and vascular targeting of gene therapy. Trends Pharmacol. Sci. 16(2):57-66.
Floege et al., "Novel approach to specific growth factor inhibition in vivo: antagonism of platelet-derived growth factor in glomerulonephritis by aptamers," Am J Pathol. Jan;154(1):169-79, 1999.
Folkman. 1995. Angiogenesis in cancer, vascular, rheumatoid and other disease. Nature Med. 1(1):27-31.
Foss, et al. 1996. Microvessel count predicts survival in uveal melanoma. Cancer Res. 56(13):2900-3.
George, "Platelet-derived growth factor receptors: a therapeutic target in solid tumors," Semin Oncol 28(5 Suppl 17):27-33, 2001.
Gragoundas, et al. Pegaptanib: the first antiangiogenic agent approved for neovascular macular degeneration. Expert Opinion Pharmacotheraph. 2005; 1421-1423.
Green, et al. 1995. Nuclease-resistant nucleic acid ligands to vascular permeability factor/vascular endothelial growth factor. Chemistry and Biology, Current Biology. 10(2): 683-695.
Guyer, et al. Preclinical and phase 1A clinical evaluation of an anti-VEGF pegylated aptamer (EYE001) for the treatment of exudative age-related macular degeneration. Retina 2002;22:143-152.
Ke, et al. 1998. A novel approach to glioma gene therapy: Down-regulation of the vascular endothelial growth factor in glioma cells using ribozymes. International Journal of Oncology.12(6): 1391-1396.
Kinose, et al Inhibition of retinal and choroidal neovascularization by a novel KDR kinase inhibitor. Mol Vis. May 27, 2005;11:366-73.
Leppänen et al., "Intimal hyperplasia recurs after removal of PDGF-AB and -BB inhibition in the rat carotid artery injury model," Arterioscler Thromb Vasc Biol. Nov;20(11):E89-95, 2000.
Li, et al. 1994. Microvessel count and cerebrospinal fluid basic fibroblast growth factor in children with brain tumours. Lancet. 344(8915):82-6.

(56) References Cited

OTHER PUBLICATIONS

McCarty, et al. Promises and pitfalls of anti-angiogenic therapy in clinical trials. Trends Mol Med. Feb. 2003;9(2):53-8.
Ng et al., "Anti-VEGF aptamer (pegaptanib) therapy for ocular vascular diseases," Ann N Y Acad Sci. Oct;1082:151-71, 2006.
Ng et al., "Pegaptanib, a targeted anti-VEGF aptamer for ocular vascular disease," Nat Rev Drug Discov. Feb;5(2):123-32, 2006.
Ostendorf et al., "Specific antagonism of PDGF prevents renal scarring in experimental glomerulonephritis," J Am Soc Nephrol. May;12(5):909-18, 2001.
Ozaki, et al. Blockade of vascular endothelial cell growth factor receptor signaling is sufficient to completely prevent retinal neovascularization. Am J Pathology. 2000; 156(2):697-707.
Pegaptanib: New drug. In macular degeneration: too many risks for too little benefit, Prescrire Int. Aug; 15(84):127-9 (abstract, no authors listed), 2006.
Pierce et al., "Vascular endothelial growth factor/vascular permeability factor expression in a mouse model of retinal neovascularization," Proc Natl Acad Sci U S A 92(3):905-9, 1995.
Pietras et al., "Inhibition of PDGF receptor signaling in tumor stroma enhances antitumor effect of chemotherapy," Cancer Res. Oct 1;62(19):5476-84, 2002.
Pietras, et al. Inhibition of platelet-derived growth factor receptors reduces interstitial hypertension and increases transcapillary transport in tumors. Cancer Res. Apr. 1, 2001;61(7):2929-34.
Ritter et al., "Three-dimensional in vivo imaging of the mouse intraocular vasculature during development and disease," Invest Ophthalmol Vis Sci 46(9):3021-6, 2005.
Ruckman, et al. 2'-Fluoropyrimidine RNA-based aptamers to the 165-amino acid form of vascular endothelial growth factor (VEGF165). Inhibition of receptor binding and VEGF-induced vascular permeability through interactions requiring the exon 7-encoded domain. J Biol Chem. Aug. 7, 1998;273(32):20556-67.
Ruiz-Ederra and Verkman, "Aquaporin-1 independent microvessel proliferation in a neonatal mouse model of oxygen-induced retinopathy," Invest Ophthalmol Vis Sci 48(10):4802-10, 2007.
Saishin et al., "The kinase inhibitor PKC412 suppresses epiretinal membrane formation and retinal detachment in mice with proliferative retinopathies," Invest Ophthalmol Vis Sci. Aug;44(8):3656-62, 2003.
Senger, et al. 1993. Vascular permeability factor (VPF, VEGF) in tumor biology. Cancer Metastasis Rev. 12(3-4):303-24.
Shawver et al., "Smart drugs: tyrosine kinase inhibitors in cancer therapy," Cancer Cell 1(2):117-23, 2002.
Skolnick, et al. From genes to protein structure and function: novel applications of computational approaches in the genomic era. Trends Biotechnol. Jan. 2000;18(1):34-9.
Steffensmeier, et al. Vitreous injections of pegaptanib sodium triggering allergic reactions. Am J Ophthalmol. Mar. 2007;143(3):512-3.
Thomas. 1996. Vascular endothelial growth factor, a potent and selective angiogenic agent. J. Biol. Chem. 271(2):603-6.
Wallace, et al. Oligonucleotide probes for the screening of recombinant DNA libraries. Methods Enzymol. 1987;152:432-439.
Weidner, et al. 1992. Tumor angiogenesis: a new significant and independent prognostic indicator in early-stage breast carcinoma. J Natl. Cancer Inst. 84(24):1875-87.
Weidner, et al. 1993. Tumor angiogenesis correlates with metastasis in invasive prostate carcinoma. Am J. Pathol.143(2):401-9.
Younes, et al. Labelled oligonucleotides as radiopharmaceuticals: pitfalls, problems and perspectives. Curr Pharm Des. 2002;8(16):1451-66.
Zhang, et al. 2002. A monoclonal antibody that blocks VEGF binding to VEGFR2 (KDR/Flk-1) inhibits vascular expression of Flk-1 and tumor growth in an orthotopic human breast cancer model. Angiogenesis. 5(1-2): 35-44.
Zhang, et al. 2003. Vector-based RNAi, a novel tool for isoform-specific knock-down of VEGF and anti-angiogenesis gene therapy of cancer. Biochemical and Biophysical Research Communications. 303(4): 1169-1178.

Shima et al., U.S. Appl. No. 12/465,051 entitled "Combination therapy for the treatment of ocular neovascular disorders," filed May 13, 2009.
Shima et al., U.S. Appl. No. 12/564,863 entitled "Combination therapy for the treatment of ocular neovascular disorders," filed Sep. 22, 2009.
Sorbera, L. A. et al., "Pegaptanib Sodium," Drugs of the Future, 27(9):841 (2002).
Office Action for U.S. Appl. No. 13/284,221, mailed Feb. 11, 2013.
Stryer et al., In: Biochemistry, pp. 86 and 92, Third Edition, W. H. Freeman and Company, New York (1988).
Office Action for U.S. Appl. No. 10/926,806, mailed Oct. 1, 2009.
Office Action for U.S. Appl. No. 10/926,806, mailed May 27, 2009.
Office Action for U.S. Appl. No. 10/926,806, mailed Sep. 30, 2008.
Office Action for U.S. Appl. No. 10/926,806, mailed Jan. 24, 2008.
Office Action for U.S. Appl. No. 10/926,806, mailed May 7, 2007.
International Search Report and Written Opinion for International Application No. PCT/US2004/027612, mailed Sep. 19, 2005.
International Preliminary Report on Patentability for International Application No. PCT/US2004/027612, dated Aug. 27, 2006.
European Search Report for European Application No. EP10013061, dated Nov. 30, 2010.
Office Action for U.S. Appl. No. 12/465,051, mailed Sep. 28, 2011.
Office Action for U.S. Appl. No. 12/465,051, mailed Jan. 19, 2011.
Office Action for U.S. Appl. No. 12/564,863, mailed Jul. 13, 2011.
Office Action for U.S. Appl. No. 12/987,508, mailed Aug. 16, 2011.
Office Action for U.S. Appl. No. 12/987,508, mailed Dec. 13, 2011.
International Search Report and Written Opinion for International Application No. PCT/US2010/032816, mailed Sep. 17, 2010.
International Preliminary Report on Patentability for International Application No. PCT/US2010/032816, dated Nov. 1, 2011.
A Phase 1, Safety, Tolerability and Pharmacokinetic Profile of Intravitreous Injections of E10030 (Anti-PDGF Pegylated Aptamer) in Subjects With Neovascular Age-Related Macular Degeneration, ClinicalTrials.gov [online], Jan. 16, 2012. Retrieved from the Internet: <URL: http://ClinicalTrials.gov/show/NCT00569140>, 5 pages.
A Safety and Efficacy Study of E10030 (Anti-PDGF Pegylated Aptamer) Plus Lucentis for Neovascular Age-Related Macular Degeneration, ClinicalTrials.gov [online], Jan. 16, 2012. Retrieved from the Internet: <URL: http://ClinicalTrials.gov/show/NCT01089517>, 6 pages.
Campochiaro, P. A. et al., "The pathogenesis of choroidal neovascularization in patients with age-related macular degeneration," Molecular Vision, 5:34-38 (1999).
Carmeliet, P., "Angiogenesis in health and disease," Nature Medicine, 9(6):653-660 (2003).
Jain, R. K., "Molecular regulation of vessel maturation," Nature Medicine, 9(6):685-693 (2003).
Jain, R. K. et al., "What brings pericytes to tumor vessels?", The Journal of Clinical Investigation, 112(8):1134-1136 (2003).
Lindahl, P. et al., "Pericyte loss and microaneurysm formation in PDGF-B-deficient mice," Science, 277:242-245 (1997).
Tobe, T. et al., "Targeted disruption of the FGF2 gene does not prevent choroidal neovascularization in a murine model," American Journal of Pathology, 153(5):1641-1646 (1998).
Witte, L. et al., "Monoclonal antibodies targeting the VEGF receptor-2 (Flk1/KDR) as an anti-angiogenic therapeutic strategy," Cancer and Metastasis Reviews, 17:155-161 (1998).
Enge et al., "Endothelium-specific platelet-derived growth factor-B ablation mimics diabetic retinopathy," EMBO J 21(16):4307-16 (2002).
Erber et al., "Combined inhibition of VEGF and PDGF signaling enforces tumor vessel regression by interfering with pericyte-mediated endothelial cell survival mechanisms," FASEB J 18(2):338-40 (2004).
Jo et al., "Inhibition of platelet-derived growth factor B signaling enhances the efficacy of anti-vascular endothelial growth factor therapy in multiple models of ocular neovascularization," Am J Pathol 168(6):2036-2053 (2006).
Mayer and Jenne, "Aptamers in Research and Drug Development," BioDrugs 18(6):315-359 (2004).

(56) References Cited

OTHER PUBLICATIONS

Boyer, D. S., "Combined Inhibition of Platelet Derived (PDGF) and Vascular Endothelial (VEGF) Growth Factors for the Treatment of Neovascular Age-Related Macular Degeneration (NV-AMD)—Results of a Phase 1 Study," [online], Presentation Abstract, May 4, 2009, 2 pages. [Retrieved from the Internet on Mar. 26, 2009.] URL: <http://arvo.abstractsonline.com/Plan/AbstractPrintView.aspx?mID=2281&sKey=f6e4ae6c-...>.
Cao, R. et al., "VEGFR1-mediated pericyte ablation links VEGF and PlGF to cancer-associated retinopathy," PNAS, 107(2):856-861 (2010).
Cousins, S. W. et al., Patterns of CNV Fluorescein and Indocyanine Green Angiographic Regression Responses After Anti-VEGF Monotherapy or Anti-VEGF Plus Anti-PDGF Combotherapy, [online], Presentation Abstract, May 4, 2009, 2 pages. [Retrieved from the Internet on Mar. 26, 2009.] URL: <http://arvo.abstractsonline.com/Plan/AbstractPrintView.aspx?mID=2281&sKey=f6e4ae6c-...>.
Everett, R., "Aptamers in Age Related Macular Degeneration: Above and Beyond Anti-VEGF," AAPS Presentation, Jun. 23, 2009, 2 pages.
Everett, R., "E10030, A Pegylated Aptamer Targeting Pericytes: Therapeutic Application for Age-Related Macular Degeneration (AMD)," DIA Presentation, Sep. 23, 2008, 25 pages.
"Particulate matter in ophthalmic solutions," USP789, U.S. Pharmacopeia, Pharmacopeial Forum, 28(5):1496 (undated).
"Particulate matter in injections," USP788, Revision Bulletin, The United States Pharmacopeial Convention (2011), 3 pages.
Pontes de Carvalho, R. A. et al., "Delivery from episcleral exoplants," Invest Ophthalmol Vis Sci., 47(1):4532-4539 (2006).
Boyer, D. S., A phase 2b study of Fovista, a platelet derived growth factor (PDGF) inhibitor in combination with a vascular endothelial growth factor (VEGF) inhibitor for neovascular age-related macular degeneratoin (AMD), ARVO 2013 Annual Meeting Abstracts, 280 AMD and Drugs, 618-620 Paper Session, Program No. 2175 (May 6, 2013), 1 page.
Kawada, H. et al., "Multifunctional antioxidants protect cells from mitochondrial dysfunction and ABETA neurotoxicity," ARVO 2013 Annual Meeting Abstracts, 280 AMD and Drugs, 618-620 Paper Session, Program No. 2176 (May 6, 2013), 1 page.
Kaiser, P. K. et al., "Integrin peptide therapy: The first wet AMD experience," ARVO 2013 Annual Meeting Abstracts, 280 AMD and Drugs, 618-620 Paper Session, Program No. 2177 (May 6, 2013), 2 pages.
Singh, R. et al., "Topical Pazopanib for the treatment of previously untreated choroidal neovascularization due to age-related macular degeneration," ARVO 2013 Annual Meeting Abstracts, 280 AMD and Drugs, 618-620 Paper Session, Program No. 2178 (May 6, 2013), 1 page.
Li, Q. et al., "IKK2 inhibition using TPCA-1/PLGA microspheres attenuates the laser induced choroidal neovascularization," ARVO 2013 Annual Meeting Abstracts, 280 AMD and Drugs, 618-620 Paper Session, Program No. 2179 (May 6, 2013), 2 pages.
Schraermeyer, U. et al., " Effects of intravitreally injected ranibizumab and aflibercept on retina and choroid of monkey eyes," ARVO 2013 Annual Meeting Abstracts, 280 AMD and Drugs, 618-620 Paper Session, Program No. 2180 (May 6, 2013), 1 page.
Magno, A. L. et al., "Development and implementation of an ELISA to detect 'anti-Ranibizumab' immunity in age-related macular degeneration patients," ARVO 2013 Annual Meeting Abstracts, 280 AMD and Drugs, 618620 Paper Session, Program No. 2181 (May 6, 2013), 2 pages.
Brown et al., Ranibizumab versus Verteporfin for Neovascular Age-Related Macular Degeneration. The New England Journal of Medicine. 2006. 355(14):1432-1444.
Do et al. Neovascular Age-Related Macular Degeneration. FocalPoints, Clinical Modules for Ophthalmologists. vol. XCVIII. No. 12 Dec. 2010 (Module 3 of 3) pp. 1-14.
Riemer et al. Matching of trastuzumab (Herceptin) epitope mimics onto the surface of Her-2/neu—a new method of epitope definition. Mol Immunol. May 2005;42(9):1121-4. Epub Jan. 8, 2005.
Rosenfeld et al. Ranibizumab for Neovascular Age-Related Macular Degeneration. The New England Journal of Medicine. 2006. 355(14):1419-1431.
Sang et al., Study on PDGF receptor beta pathway in glomerular formation in neonate mice. Ann N Y Acad Sci. 2001. 947:303-5.
Tol et al. Chemotherapy, bevacizumab, and cetuximab in metastatic colorectal cancer. N Engl J Med. Feb. 5, 2009;360(6):563-72.
Yu et al. Interaction between bevacizumab and murine VEGF-A: a reassessment. Invest. Ophthalmol. Vis Sci. 2008. 49(2):522-7.
Avastin (Bevacizumab), Labeling Text, Genentech, Inc. (Feb. 26, 2004), 27 pages.
Burke, D. H. et al., "Recombination, RNA evolution, and bifunctional RNA molecules isolated through chimeric SELEX," RNA, 4(9):1165-1175 (1998).
Campochiaro, P. A., "Pathogenic mechanisms in proliferative vitreoretinopathy," Archives of Ophthalmology, 115(2):237-241 (1997).
Chaudhary, V. et al., "The effect of triamcinolone acetonide as an adjunctive treatment to verteporfin therapy in neovascular age-related macular degeneration: A prospective, randomized, placebo controlled pilot clinical trial," Invest. Ophthalmol. Vis. Sci., 46:E-Abstract 2308 (2005).
Dugel, P. U., "Anti-PDGF therapy offers new approach to AMD treatment," Retina Times (2012), 8 pages.
Ergun, E. et al., "Photodynamic therapy with verteporfin and intravitreal triamcinolone acetonide in the treatment of neovascular age-related macular degeneration," Am. J. Ophthalmol., 142:10-16 (2006).
Eylea (Aflibercept) Injection, Highlights of Prescribing Information, Regeneron Pharmaceuticals, Inc. (Nov. 18, 2011), 15 pages.
Gomi, F. et al., "Pharmacological therapy for age-related macular degeneration," Ophthalmology, 46(12):1709-1716 (2004) (Translation).
Lucentis (ranibizumab injection), Highlights of Prescribing Information, Genentech, Inc. (Jun. 30, 2006), 7 pages.
Patel, S., "New innovations in AMD technology may be promising," Retina Today, pp. 24-25 (2008).
Patel, S., "Combination therapy for age-related macular degeneration," Retina, 29:S45-S48 (2009).
Tahiri-Alaoui, A. et al., "High affinity nucleic acid aptamers for streptavidin incorporated into bi-specific capture ligands," Nucleic Acids Research, 30(10):e45 (2002), 9 pages.
Yoshida, S. et al., "Involvement of interleukin-8, vascular endothelial growth factor, and basic fibroblast growth factor in tumor necrosis factor alpha-dependent angiogenesis," Molecular and Cellular Biology, 17(7):4015-4023 (1997).
Brody and Gold, "Aptamers as therapeutic and diagnostic agents," J Biotechnol 74(1):5-13 (2000).
Biesecker et al., "Derivation of RNA aptamer inhibitors of human complement C5," Immunopharmacology 42(1-3):219-30 (1999).
Burcovich et al., "Branched polyethylene glycol (bPEG) conjugated antisense oligonucleotides," Nucleosides and Nucleotides 17:1567-1570 (1998).
Rimmele, "Nucleic acid aptamers as tools and drugs: recent developments," ChemBioChem 4:963-971 (2003).
Benelli et al., "Trapidil inhibits endothelial cell proliferation and angiogenesis in the chick chorioallantoic membrane and in the rat cornea," J Ocul Pharmacol Ther 11(2):157-66, 1995.
Cao et al., "Angiogenesis stimulated by PDGF-CC, a novel member in the PDGF family, involves activation of PDGFR-alphaalpha and -alphabeta receptors," FASEB J 16(12):1575-83, 2002.
Lai et al., "Inhibition of corneal neovascularization by recombinant adenovirus mediated antisense VEGF RNA," Exp Eye Res 75(6):625-34, 2002.
Nakabayashi et al., "HGF/NK4 inhibited VEGF-induced angiogenesis in in vitro cultured endothelial cells and in vivo rabbit model," Diabetologia 46(1):115-23, 2003.
Lu, C. et al., "Targeting pericytes with a PDGF-B aptamer in human ovarian carcinoma models," Cancer Biol. Ther., 9(3):176-182 (2010).
Sennino, B. et al., "Sequential loss of tumor vessel pericytes and endothelial cells after inhibition of platelet-derived growth factor B by selective aptamer AX102," Cancer Research, 67(15):7358-7367 (2007).

(56) References Cited

OTHER PUBLICATIONS

Koyama, N. et al., Migratory and proliferative effect of platelet-derived growth factor in rabbit retinal endothelial cells: evidence of an autocrine pathway of platelet-derived growth factor, *J Cell Physiol*, 1994, vol. 158, No. 1, p. 1 to 6.

Chalam, K. V. et al., Anti platelet derived growth factor antibody inhibits retinal pigment epithelial cell induced collagen contraction, *IOVS*, 1998, vol. 39, No. 4, p. 5864.

Shami, M., et al., The use of antisense DNA against the receptors for platelet derived growth factor, fibroblast growth factor, and phosphoinositol-3-kinase in vitro and to block PVR in a rabbit model using human pigment epithelial cells, *IOVS*, 1998, vol. 39, No. 4, p. S580.

Office Action for U.S. Appl. No. 13/284,221, mailed Jun. 15, 2012.

Ngo, J. T. et al., "Computational complexity, protein structure prediction, and the levinthal paradox," In The Protein Folding Problem and Tertiary Structure Prediction, Merz, Jr. et al. (eds.), Brikhauser Boston, pp. 492-495 (1994).

Petrukhin, K., "New therapeutic targets in atrophic age-related macular degeneration," Expert Opin. Ther. Targets, 11(5):625-630 (2007).

L. Cerchia, et al., "Nucleic acid aptamers in cancer medicine", FEBS Letters 528, 2002, pp. 12-16.

Supplementary European Search Report and Opinion for European Application No. EP10770279.7, mailed Feb. 19, 2013.

Do, D. V. et al.,"An exploratory study of the safety, tolerability and bioactivity of a single intravitreal injection of vascular endothelial growth factor Trap-Eye in patients with diabetic macular oedema," British Journal of Ophthalmology, 93(2):144-149 (2009).

Pechan, P. et al., "Novel anti-VEGF chimeric molecules delivered by AAV vectors for inhibition of retinal neovascularization," Gene Therapy, 16(1):10-16 (2009).

Zhang, M. et al., "Recombinant anti-vascular endothelial growth factor fusion protein efficiently suppresses choridal neovasularization in monkeys," Molecular Vision, 14:37-49 (2008).

\* cited by examiner

Figure 1 (A) Sequence of PDGF-B nucleic acid (GenBank Accession No. X02811) (SEQ ID NO: 1)

```
   1  CCCTGCCTGC CTCCCTGCGC ACCCGCAGCC TCCCCCGCTG CCTCCCTAGG GCTCCCCTCC
  61  GGCCGCCAGC GCCCATTTTT CATTCCCTAG ATAGAGATAC TTTGCGCGCA CACACATACA
 121  TACGCGCGCA AAAGGAAAA AAAAAAAAAA AAGCCCACCC TCCAGCCTCG CTGCAAAGAG
 181  AAAACCGGAG CAGCCGCAGC TCGCAGCTCG CAGCCCGCAG CCCGCAGAGG ACGCCCAGAG
 241  CGGCGAGCGG GCGGGCAGAC GGACCGACGG ACTCGCGCCG CGTCCACCTG TCGGCCGGGC
 301  CCAGCCGAGC GCGCAGCGGG CACGCCGCGC GCGCGGAGCA GCCGTGCCCG CCGCCCGGGC
 361  CCGCCGCCAG GGCGCACACG CTCCCGCCCC CCTACCCGGC CCGGGCGGGA GTTTGCACCT
 421  CTCCCTGCCC GGGTGCTCGA GCTGCCGTTG CAAAGCCAAC TTTGGAAAAA GTTTTTTGGG
 481  GGAGACTTGG GCCTTGAGGT GCCCAGCTCC GCGCTTTCCG ATTTTGGGGG CCTTTCCAGA
 541  AAATGTTGCA AAAAAGCTAA GCCGGCGGGC AGAGGAAAAC GCCTGTAGCC GGCGAGTGAA
 601  GACGAACCAT CGACTGCCGT GTTCCTTTTC CTCTTGGAGG TTGGAGTCCC CTGGGCGCCC
 661  CCACACGGCT AGACGCCTCG GCTGGTTCGC GACGCAGCCC CCGGCCGTG GATGCTGCAC
 721  TCGGGCTCGG GATCCGCCCA GGTAGCGGCC TCGGACCCAG GTCCTGCGCC CAGGTCCTCC
 781  CCTGCCCCCC AGCGACGGAG CCGGGGCCGG GGCGGCGGC GCCGGGGCA TGCGGGTGAG
 841  CCGCGGCTGC AGAGGCCTGA GCGCCTGATC GCCGCGGACC CGAGCCGAGC CCACCCCCCT
 901  CCCCAGCCCC CCACCCTGGC CGCGGGGGCG GCGCGCTCGA TCTACGCGTT CGGGGCCCCG
 961  CGGGGCCGGG CCCGGAGTCG GCATGAATCG CTGCTGGGCG CTCTTCCTGT CTCTCTGCTG
1021  CTACCTGCGT CTGGTCAGCG CCGAGGGGGA CCCCATTCCC GAGGAGCTTT ATGAGATGCT
1081  GAGTGACCAC TCGATCCGCT CCTTTGATGA TCTCCAACGC TGCTGCACG GAGACCCCGG
1141  AGAGGAAGAT GGGGCCGAGT GGACCTGAA CATGACCCGC TCCCACTCTG GAGGCGAGCT
1201  GGAGAGCTTG GCTCGTGGAA GAAGGAGCCT GGGTTCCCTG ACCATTGCTG AGCCGGCCAT
1261  GATCGCCGAG TGCAAGACGC GCACCGAGGT GTTCGAGATC TCCCGGCGCC TCATAGACCG
1321  CACCAACGCC AACTTCCTGG TGTGGCCGCC CTGTGTGGAG GTGCAGCGCT GCTCCGGCTG
1381  CTGCAACAAC CGCAACGTGC AGTGCCGCCC CACCCAGGTG CAGCTGCGAC CTGTCCAGGT
1441  GAGAAAGATC GAGATTGTGC GGAAGAAGCC AATCTTTAAG AAGGCCACGG TGACGCTGGA
1501  AGACCACCTG GCATGCAAGT GTGAGACAGT GGCAGCTGCA CGGCCTGTGA CCCGAAGCCC
1561  GGGGGGTTCC CAGGAGCAGC GAGCCAAAAC GCCCCAAACT CGGGTGACCA TTCGGACGGT
```

```
1621  GCGAGTCCGC CGGCCCCCCA AGGGCAAGCA CCGGAAAATTC AAGCACACGC ATGACAAGAC
1681  GGCACTGAAG GAGACCCTTG GAGCCTAGGG GCATCGGCAG GAGAGTGTGT GGGCAGGGTT
1741  ATTTAATATG GTATTTGCTG TATTGCCCCC ATGGGGCCTT GGAGTAGATA ATATTGTTTC
1801  CCTCGTCCGT CTGTCTCGAT GCCTGATTCG GACGGCCAAT GGTGCCTCCC CCACCCCTCC
1861  ACGTGTCCGT CCACCCTTCC ATCAGCGGGT CTCCTCCCAG CGGCCTCCGG CTCTTGCCCA
1921  GCAGCTCAAG AAGAAAAAGA AGGACTGAAC TCCATCGCCA TCTTCTTCCC TTAACTCCAA
1981  GAACTTGGGA TAAGAGTGTG AGAGAGACTG ATGGGGTCGC TCTTTGGGGG AAACGGGTTC
2041  CTTCCCCTGC ACCTGGCCTG GGCCACACCT GAGCGCTGTG GACTGTCCTG AGGAGCCCTG
2101  AGGACCTCTC AGCATAGCCT GCCTGATCCC TGAACCC
```

Figure 1(A) Cont.

Figure 1 (B) Sequence of PDGF-B propeptide (GenBank Accession No. CAA26579) (SEQ ID NO: 2)

```
  1  MNRCWALFLS LCCYLRLVSA EGDPIPEELY EMLSDHSIRS FDDLQRLLHG DPGEEDGAEL
 61  DLNMTRSHSG GELESLARGR RSLGSLTIAE PAMIAECKTR TEVFEISRRL IDRTNANFLV
121  WPPCVEVQRC SGCCNNRNVQ CRPTQVQLRP VQVRKIEIVR KKPIFKKATV TLEDHLACKC
181  ETVAAARPVT RSPGGSQEQR AKTPQTRVTI RTVRVRRPPK GKHRKFKHTH DKTALKETLG
241  A
```

Figure 1 (C) Sequence of PDGF-A nucleic acid (GenBank Accession No. X06374) (SEQ ID NO: 11)

```
   1  TTCTTGGGGC TGATGTCCGC AAATATGCAG AATTACCGGC CGGGTCGCTC CTGAAGCCAG
  61  CGCGGGGAGC GAGCGCGGCG GCGGCCAGCA CCGGAACGC  ACCGAGGAAG AAGCCCAGCC
 121  CCCGCCCTCC GCCCCTTCCG TCCCCACCCC CTACCCGGCG GCCCAGGAGG CTCCCCGGCT
 181  GCGGCGCGCA CTCCCTGTTT CTCCTCCTCC TGGCTGGCGC TGCCTGCCTC TCCGCACTCA
 241  CTGCTCGCCG GGCGCCGTCC GCCAGCTCCG TGCTCCCCGC GCCACCCTCC TCCGGGCCGC
 301  GCTCCCTAAG GGATGGTACT GAATTTCGCC GCCACAGGAG ACCGGCTGGA GCGCCCGCCC
 361  CGCGCCTCGC CTCTCCTCCG AGCAGCCAGC GCCTCGGGAC GCGATGAGGA CCTTGGCTTG
 421  CCTGCTGCTC CTCGGCTGCG GATACCTCGC CCATGTTCTG GCCGAGGAAG CCGAGATCCC
 481  CCGCGAGGTG ATCGAGAGGC TGGCCCGCAG TCAGATCCAC AGCATCCGGG ACCTCCAGCG
 541  ACTCCTGGAG ATAGACTCCG TAGGGAGTGA GGATTCTTTG GACACCAGCC TGAGAGCTCA
 601  CGGGGTCCAC GCCACTAAGC ATGTGCCCGA GAAGCGGCCC CTGCCCATTC GGAGGAAGAG
 661  AAGCATCGAG GAAGCTGTCC CCGCTGTCTG CAAGACCAGG ACGGTCATTT ACGAGATTCC
 721  TCGGAGTCAG GTCGACCCCA CGTCCGCCAA CTTCCTGATC TGGCCCCCGT GCGTGGAGGT
 781  GAAACGCTGC ACCGGCTGCT GCAACACGAG CAGTGTCAAG TGCCAGCCCT CCCGCGTCCA
 841  CCACCGCAGC GTCAAGGTGG CCAAGGTGGA ATACGTCAGG AAGAAGCCAA AATTAAAAGA
 901  AGTCCAGGTG AGGTTAGAGG AGCATTTGGA GTGCGCCTGC GCGACCACAA GCCTGAATCC
 961  GGATTATCGG GAAGAGGACA CGGATGTGAG GTGAGGATGA GCCGCAGCCC TTTCCTGGGA
1021  CATGGATGTA CATGGCGTGT TACATTCCTG AACCTACTAT GTACGGTGCT TTATTGCCAG
1081  TGTGCGGTCT TTGTTCTCCT CCGTGAAAAA CTGTGTCCGA GAACACTCGG GAGAACAAAG
1141  AGACAGTGCA CATTTGTTTA ATGTGACATC AAAGCAAGTA TTGTAGCACT CGGTGAAGCA
1201  GTAAGAAGCT TCCTTGTCAA AAGAGAGAG  AGAGAGAGAG AGAGAGAAAA CAAAACCACA
```

1261 AATGACAAAA ACAAAACGGA CTCACAAAAA TATCTAAACT CGATGAGATG GAGGGTCGCC

1321 CCGTGGGATG GAAGTGCAGA GGTCTCAGCA GACTGGATTT CTGTCCGGGT GGTCACAGGT

1381 GCTTTTTTGC CGAGGATGCA GAGCCTGCTT TGGAACGAC TCCAGAGGGG TGCTGGTGGG

1441 CTCTGCAGGG CCCGCAGGAA GCAGGAATGT CTTGGAAACC GCCACGCGAA CTTTAGAAAC

1501 CACACCTCCT CGCTGTAGTA TTTAAGCCCA TACAGAAACC TTCCTGAGAG CCTTAAGTGG

1561 TTTTTTTTT TGTTTTTGTT TTGTTTTTTT TTTTTTGTT TTTTTTTTT TTTTTTTTT

1621 TTACACCATA AAGTGATTAT TAAGCTTCCT TTTACTCTTT GGCTAGCTTT TTTTTTTTT

1681 TTTTTTTTT TTTTTTTAA TTATCTCTTG GATGACATTT ACACCGATAA CACACAGGCT

1741 GCTGTAACTG TCAGGACAGT GCGACGGTAT TTTTCCTAGC AAGATGCAAA CTAATGAGAT

1801 GTATTAAAAT AAACATGGTA TACCTACCTA TGCATCATTT CCTAAATGTT TCTGGCTTTG

1861 TGTTTCTCCC TTACCCTGCT TTATTTGTTA ATTTAAGCCA TTTTGAAAGA ACTATGCGTC

1921 AACCAATCGT ACGCCGTCCC TGCGGCACCT GCCCAGAGC CCGTTTGTGG CTGAGTGACA

1981 ACTTGTTCCC CGCAGTGCAC ACCTAGAATG CTGTGTTCCC ACGCGGCACG TGAGATGCAT

2041 TGCCGCTTCT GTCTGTGTTG TTGGTGTGCC CTGGTGCCGT GGTGGCGGTC ACTCCCTCTG

2101 CTGCCAGTGT TTGGACAGAA CCCAAATTCT TTATTTTTGG TAAGATATTG TGCTTTACCT

2161 GTATTAACAG AAATGTGTGT GTGTGGTTTG TTTTTTTGTA AAGGTGAAGT TTGTATGTTT

2221 ACCTAATATT ACCTGTTTTG TATACCTGAG AGCCTGCTAT GTTCTTCTTT TGTTGATCCA

2281 AAATTAAAAA AAAAATACCA CCAAC

Figure 1(C) Cont.

Figure 1 (D) Sequence of PDGF-A polypeptide (GenBank Accession No. CAA29677) (SEQ ID NO: 12)

```
  1   MRTLACLLLL GCGYLAHVLA EEAEIPREVI ERLARSQIHS IRDLQRLLEI DSVGSEDSLD
 61   TSLRAHGVHA TKHVPEKRPL PIRRKRSIEE AVPAVCKTRT VIYEIPRSQV DPTSANFLIW
121   PPCVEVKRCT GCCNTSSVKC QPSRVHHRSV KVAKVEYVRK KPKLKEVQVR LEEHLECACA
181   TTSLNPDYRE EDTDVR
```

Figure 2 (A) Sequence of VEGF nucleic acid (GenBank Accession No: NM 003376) (SEQ ID NO: 3)

```
   1  TCGCGGAGGC TTGGGGCAGC CGGGTAGCTC GGAGGTCGTG GCGCTGGGGG CTAGCACCAG
  61  CGCTCTGTCG GGAGGCGCAG CGGTTAGGTG GACCGGTCAG CGGACTCACC GGCCAGGGCG
 121  CTCGGTGCTG GAATTTGATA TTCATTGATC CGGGTTTTAT CCCTCTTCTT TTTTCTTAAA
 181  CATTTTTTTT TAAAACTGTA TTGTTTCTCG TTTTAATTTA TTTTTGCTTG CCATTCCCCA
 241  CTTGAATCGG CCGACGGCT TGGGGAGATT GCTCTACTTC CCCAAATCAC TGTGGATTTT
 301  GGAAACCAGC AGAAAGAGGA AAGAGGTAGC AAGAGCTCCA GAGAGAAGTC GAGGAAGAGA
 361  GAGACGGGGT CAGAGAGAGC GCGCGGGCGT GCGAGCAGCG AAAGCGACAG GGGCAAAGTG
 421  AGTGACCTGC TTTTGGGGGT GACCGCCGGA GCGCGGCGTG AGCCCTCCCC CTTGGGATCC
 481  CGCAGCTGAC CAGTCGCGCT GACGGACAGA CAGACAGACA CCGCCCCCAG CCCCAGCTAC
 541  CACCTCCTCC CCGGCCGGCG GCGGACAGTG GACGCGGCGG CGAGCCGCGG GCAGGGGCCG
 601  GAGCCCGCGC CCGGAGGCGG GGTGGAGGGG GTCGGGGCTC GCGGCGTCGC ACTGAAACTT
 661  TTCGTCCAAC TTCTGGGCTG TTCTCGCTTC GGAGGAGCCG TGGTCCGCGC GGGGGAAGCC
 721  GAGCCGAGCG GAGCCGCGAG AAGTGCTAGC TCGGGCCGGG AGGAGCCGCA GCCGGAGGAG
 781  GGGGAGGAGG AAGAAGAGAA GGAAGAGGAG AGGGGGCCGC AGTGGCGACT CGGCGCTCGG
 841  AAGCCGGGCT CATGACGGG TGAGGCGGCG GTGTGCGCAG ACAGTGCTCC AGCCGCGCGC
 901  GCTCCCCAGG CCCTGGCCCG GGCCTCGGGC CGGGGAGGAA GAGTAGCTCG CCGAGGCGCC
 961  GAGGAGAGCG GGCCGCCCCA CAGCCCGAGC GGAGAGGGA GCGCGAGCCG CGCCGGCCCC
1021  GGTCGGGCCT CCGAAACCAT GAACTTTCTG CTGTCTTGGG TGCATTGGAG CCTTGCCTTG
1081  CTGCTCTACC TCCACCATGC CAAGTGGTCC CAGGCTGCAC CCATGGCAGA AGGAGGAGGG
1141  CAGAATCATC ACGAAGTGGT GAAGTTCATG GATGTCTATC AGCGCAGCTA CTGCCATCCA
1201  ATCGAGACCC TGGTGGACAT CTTCCAGGAG TACCCTGATG AGATCGAGTA CATCTTCAAG
1261  CCATCCTGTG TGCCCCTGAT GCGATGCGGG GGCTGCTGCA ATGACGAGGG CCTGGAGTGT
1321  GTGCCCACTG AGGAGTCCAA CATCACCATG CAGATTATGC GGATCAAACC TCACCAAGGC
1381  CAGCACATAG GAGAGATGAG CTTCCTACAG CACAACAAAT GTGAATGCAG ACCAAAGAAA
1441  GATAGAGCAA GACAAGAAAA AAAATCAGTT CGAGGAAAGG GAAAGGGGCA AAAACGAAAG
1501  CGCAAGAAAT CCCGGTATAA GTCCTGGAGC GTTCCCTGTG GGCCTTGCTC AGAGCGGAGA
1561  AAGCATTTGT TTGTACAAGA TCCGCAGACG TGTAAATGTT CCTGCAAAAA CACAGACTCG
```

```
1621  CGTTGCAAGG CGAGGCAGCT TGAGTTAAAC GAACGTACTT GCAGATGTGA CAAGCCGAGG
1681  CGGTGAGCCG GGCAGGAGGA AGGAGCCTCC CTCAGGGTTT CGG
```

Figure 2(A) Cont.

Figure 2 (B) Sequence of VEGF polypeptide (GenBank Accession No. NP 003367) (SEQ ID NO: 4)

```
  1  MNFLLSWVHW SLALLLYLHH AKWSQAAPMA EGGGQNHHEV VKFMDVYQRS YCHPIETLVD

61  IFQEYPDEIE YIFKPSCVPL MRCGGCCNDE GLECVPTEES NITMQIMRIK PHQGQHIGEM

121  SFLQHNKCEC RPKKDRARQE KKSVRGKGKG QKRKRKKSRY KSWSVPCGPC SERRKHLFVQ

181  DPQTCKCSCK NTDSRCKARQ LELNERTCRC DKPRR
```

Figure 3 (A) Sequence of PDGFR-B nucleic acid (GenBank Accession No. NM 002609) (SEQ ID NO: 5)

```
   1  GGCCCCTCAG CCCTGCTGCC CAGCACGAGC CTGTGCTCGC CCTGCCCAAC GCAGACAGCC
  61  AGACCCAGGG CGGCCCCTCT GGCGGCTCTG CTCCTCCCGA AGGATGCTTG GGGAGTGAGG
 121  CGAAGCTGGG CGCTCCTCTC CCTACAGCA GCCCCCTTCC TCCATCCCTC TGTTCTCCTG
 181  AGCCTTCAGG AGCCTGCACC AGTCCTGCCT GTCCTTCTAC TCAGCTGTTA CCCACTCTGG
 241  GACCAGCAGT CTTTCTGATA CTGGGAGAG GCAGTAAGG AGGACTTCCT GGAGGGGGTG
 301  ACTGTCCAGA GCCTGGAACT GTGCCCACAC CAGAAGCCAT CAGCAGCAAG ACACCATGC
 361  GGCTTCCGGG TGCGATGCCA GCTCTGGCCC TCAAAGGCGA GCTGCTGTTG CTGTCTCTCC
 421  TGTTACTTCT GGAACCACAG ATCTCTCAGG GCCTGGTCGT CACACCCCCG GGGCCAGAGC
 481  TTGTCCTCAA TGTCTCCAGC ACCTTCGTTC TGACCTGCTC GGGTTCAGCT CCGGTGGTGT
 541  GGGAACGGAT GTCCCAGGAG CCCCCACAGG AAATGGCCAA GGCCCAGGAT GGCACCTTCT
 601  CCAGCGTGCT CACACTGACC AACCTCACTG GGCTAGACAC GGGAGAATAC TTTTGCACCC
 661  ACAATGACTC CCGTGGACTG GAGACCGATG AGCGGAAACG GCTCTACATC TTTGTGCCAG
 721  ATCCCACCGT GGGCTTCCTC CCTAATGATG CCGAGGAACT ATTCATCTTT CTCACGGAAA
 781  TAACTGAGAT CACCATTCCA TGCCGAGTAA CAGACCCACA GCTGGTGGTG ACACTGCACG
 841  AGAAGAAAGG GGACGTTGCA CTGCCTGTCC CCTATGATCA CCAACGTGGC TTTTCTGGTA
 901  TCTTTGAGGA CAGAAGCTAC ATCTGCAAAA CCACCATTGG GGACAGGGAG GTGGATTCTG
 961  ATGCCTACTA TGTCTACAGA CTCCAGGTGT CATCCATCAA CGTCTCTGTG AACGCAGTGC
1021  AGACTGTGGT CCGCCAGGGT GAGAACATCA CCCTCATGTG CATTGTGATC GGGAATGAGG
1081  TGGTCAACTT CGAGTGGACA TACCCCCGCA AAGAAAGTGG GCGGCTGGTG GAGCCGGTGA
1141  CTGACTTCCT CTTGGATATG CCTTACCACA TCCGCTCCAT CCTGCACATC CCCAGTGCCG
1201  AGTTAGAAGA CTCGGGGACC TACACCTGCA ATGTGACGGA GAGTGTGAAT GACCATCAGG
1261  ATGAAAAGGC CATCAACATC ACCGTGGTTG AGAGCGGCTA CGTGCGGCTC CTGGGAGAGG
1321  TGGGCACACT ACAATTTGCT GAGCTGCATC GGAGCCGGAC ACTGCAGGTA GTGTTCGAGG
1381  CCTACCCACC GCCCACTGTC CTGTGGTTCA AGACAACCG CACCCTGGGC GACTCCAGCG
1441  CTGGCGAAAT CGCCCTGTCC ACGCGCAACG TGTCGGAGAC CCGGTATGTG TCAGAGCTGA
1501  CACTGGTTCG CGTGAAGGTG GCAGAGGCTG CCACTACAC CATGCGGGCC TTCCATGAGG
1561  ATGCTGAGGT CCAGCTCTCC TTCCAGCTAC AGATCAATGT CCCTGTCCGA GTGCTGGAGC
```

```
1621  TAAGTGAGAG CCACCCTGAC AGTGGGGAAC AGACAGTCCG CTGTCGTGGC CGGGGCATGC
1681  CCCAGCCGAA CATCATCTGG TCTGCCTGCA GAGACCTCAA AAGGTGTCCA CGTGAGCTGC
1741  CGCCCACGCT GCTGGGGAAC AGTTCCGAAG AGGAGAGCCA GCTGGAGACT AACGTGACGT
1801  ACTGGGAGGA GGAGCAGGAG TTTGAGGTGG TGAGCACACT GCGTCTGCAG CACGTGGATC
1861  GGCCACTGTC GGTGCGCTGC ACGCTGCGCA ACGCTGTGGG CCAGGACACG CAGGAGGTCA
1921  TCGTGGTGCC ACACTCCTTG CCCTTTAAGG TGGTGGTGAT CTCAGCCATC CTGGCCCTGG
1981  TGGTGCTCAC CATCATCTCC CTTATCATCC TCATCATGCT TTGGCAGAAG AAGCCACGTT
2041  ACGAGATCCG ATGGAAGGTG ATTGAGTCTG TGAGCTCTGA CGGCCATGAG TACATCTACG
2101  TGGACCCCAT GCAGCTGCCC TATGACTCCA CGTGGGAGCT GCCGCGGGAC CAGCTTGTGC
2161  TGGGACGCAC CCTCGGCTCT GGGGCCTTTG GCAGGTGGT GGAGGCCACG GCTCATGGCC
2221  TGAGCCATTC TCAGGCCACG ATGAAAGTGG CCGTCAAGAT GCTTAAATCC ACAGCCCGCA
2281  GCAGTGAGAA GCAAGCCCTT ATGTCGGAGC TGAAGATCAT GAGTCACCTT GGGCCCACC
2341  TGAACGTGGT CAACCTGTTG GGGGCCTGCA CCAAAGGAGG ACCCATCTAT ATCATCACTG
2401  AGTACTGCCG CTACGGAGAC CTGGTGGACT ACCTGCACCG CAACAAACAC ACCTTCCTGC
2461  AGCACCACTC CGACAAGCGC CGCCCGCCCA GCGCGGAGCT CTACAGCAAT GCTCTGCCCG
2521  TTGGGCTCCC CCTGCCCAGC CATGTGTCCT TGACCGGGGA GAGCGACGGT GGCTACATGG
2581  ACATGAGCAA GGACGAGTCG GTGGACTATG TGCCCATGCT GGACATGAAA GGAGACGTCA
2641  AATATGCAGA CATCGAGTCC TCCAACTACA TGGCCCCTTA CGATAACTAC GTTCCCTCTG
2701  CCCCTGAGAG GACCTGCCGA GCAACTTTGA TCAACGAGTC TCCAGTGCTA AGCTACATGG
2761  ACCTCGTGGG CTTCAGCTAC CAGGTGGCCA ATGGCATGGA GTTTCTGGCC TCCAAGAACT
2821  GCGTCCACAG AGACCTGGCG GCTAGGAACG TGCTCATCTG TGAAGGCAAG CTGGTCAAGA
2881  TCTGTGACTT TGGCCTGGCT CGAGACATCA TGCGGGACTC GAATTACATC TCCAAAGGCA
2941  GCACCTTTTT GCCTTTAAAG TGGATGGCTC CGGAGAGCAT CTTCAACAGC CTCTACACCA
3001  CCCTGAGCGA CGTGTGGTCC TTCGGGATCC TGCTCTGGGA GATCTTCACC TTGGGTGGCA
3061  CCCCTTACCC AGAGCTGCCC ATGAACGAGC AGTTCTACAA TGCCATCAAA CGGGGTTACC
3121  GCATGGCCCA GCCTGCCCAT GCCTCCGACG AGATCTATGA GATCATGCAG AAGTGCTGGG
3181  AAGAGAAGTT TGAGATTCGG CCCCCCTTCT CCCAGCTGGT GCTGCTTCTC GAGAGACTGT
3241  TGGGCGAAGG TTACAAAAAG AAGTACCAGC AGGTGGATGA GGAGTTTCTG AGGAGTGACC
```

Figure 3(A) Cont.

```
3301  ACCCAGCCAT CCTTCGGTCC CAGGCCCGCT TGCCTGGGTT CCATGGCCTC CGATCTCCCC
3361  TGGACACCAG CTCCGTCCTC TATACTGCCG TGCAGCCCAA TGAGGGTGAC AACGACTATA
3421  TCATCCCCCT GCCTGACCCC AAACCCGAGG TTGCTGACGA GGGCCCACTG GAGGGTTCCC
3481  CCAGCCTAGC CAGCTCCACC CTGAATGAAG TCAACACCTC CTCAACCATC TCCTGTGACA
3541  GCCCCCTGGA GCCCCAGGAC GAACCAGAGC CAGAGCCCCA GCTTGAGCTC CAGGTGGAGC
3601  CGGAGCCAGA GCTGGAACAG TTGCCGGATT CGGGGTGCCC TGCGCCTCGG GCGGAAGCAG
3661  AGGATAGCTT CCTGTAGGGG GCTGGCCCCT ACCCTGCCCT GCCTGAAGCT CCCCCCCTGC
3721  CAGCACCCAG CATCTCCTGG CCTGGCCTGA CCGGGCTTCC TGTCAGCCAG GCTGCCCTTA
3781  TCAGCTGTCC CCTTCTGGAA GCTTTCTGCT CCTGACGTGT TGTGCCCCAA ACCCTGGGGC
3841  TGGCTTAGGA GGCAAGAAAA CTGCAGGGGC CGTGACCAGC CCTCTGCCTC CAGGGAGGCC
3901  AACTGACTCT GAGCCAGGGT TCCCCCACGG AACTCAGTTT TCCCATATGT AAGATGGGAA
3961  AGTTAGGCTT GATGACCCAG AATCTAGGAT TCTCTCCCTG GCTGACAGGT GGGGAGACCG
4021  AATCCCTCCC TGGGAAGATT CTTGGAGTTA CTGAGGTGGT AAATTAACTT TTTTCTGTTC
4081  AGCCAGCTAC CCCTCAAGGA ATCATAGCTC TCTCCTCGCA CTTTTTATCC ACCCAGGAGC
4141  TAGGGAAGAG ACCCTAGCCT CCCTGGCTGC TGGCTGAGCT AGGGCCTAGC CTTGAGCAGT
4201  GTTGCCTCAT CCAGAAGAAA GCCAGTCTCC TCCCTATGAT GCCAGTCCCT GCGTTCCCTG
4261  GCCCGAGCTG GTCTGGGGCC ATTAGGCAGC CTAATTAATG CTGGAGGCTG AGCCAAGTAC
4321  AGGACACCCC CAGCCTGCAG CCCTTGCCCA GGGCACTTGG AGCACACGCA GCCATAGCAA
4381  GTGCCTGTGT CCCTGTCCTT CAGGCCCATC AGTCCTGGGG CTTTTTCTTT ATCACCCTCA
4441  GTCTTAATCC ATCCACCAGA GTCTAGAAGG CCAGACGGGC CCCGCATCTG TGATGAGAAT
4501  GTAAATGTGC CAGTGTCCAC TGCCCACGTG TGTGTGCCAG TATATGGCCC TGGCTCTGCA
4561  TTGGACCTGC TATGAGGCTT TGGAGGAATC CCTCACCCTC TCTGGGCCTC AGTTTCCCCT
4621  TCAAAAAATG AATAAGTCGG ACTTATTAAC TCTGAGTGCC TTGCCAGCAC TAACATTCTA
4681  GAGTATTCCA GGTGGTTGCA CATTTGTCCA GATGAAGCAA GGCCATATAC CCTAAACTTC
4741  CATCCTGGGG GTCAGCTGGG CTCCTGGGAG ATTCCAGATC ACACATCACA CTCTGGGGAC
4801  TCAGGAACCA TGCCCCTTCC CCAGGCCCCC AGCAAGTCTC AAGAACACAG CTGCACAGGC
4861  CTTGACTTAG AGTGACAGCC GGTGTCCTGG AAACCCCAA GCAGCTGCCC CAGGGACATG
4921  GCAAGACCAC GGGACCTCTT TCACTACCCA CGATGACCTC CGGGGTATC CTGGGCAAAA
```

Figure 3(A) Cont.

```
4981  GGGACAAAGA GGGCAAATGA GATCACCTCC TGCAGCCCAC CACTCCAGCA CCTGTGCCGA
5041  GGTCTGCGTC GAAGACAGAA TGGACAGTGA GGACAGTTAT GTCTTGTAAA AGACAAGAAG
5101  CTTCAGATGG TACCCCAAGA AGGATGTGAG AGGTGGCCGC TTGGAGTTTG CCCCTCACCC
5161  ACCAGCTGCC CCATCCCTGA GGCAGCGCTC CATGGGGGTA TGGTTTTGTC ACTGCCCAGA
5221  CCTAGCAGTG ACATCTCATT GTCCCCAGCC CAGTGGGCAT GGAGGTGCC AGGGGAGTCA
5281  GGGTTGTAGC CAAGACGCCC CCGCACGGGG AGGGTTGGGA AGGGGGTGCA GGAAGCTCAA
5341  CCCCTCTGGG CACCAACCCT GCATTGCAGG TTGGCACCTT ACTTCCCTGG GATCCCCAGA
5401  GTTGGTCCAA GGAGGGAGAG TGGGTTCTCA ATACGGTACC AAAGATATAA TCACCTAGGT
5461  TTACAAATAT TTTTAGGACT CACGTTAACT CACATTTATA CAGCAGAAAT GCTATTTTGT
5521  ATGCTGTTAA GTTTTTCTAT CTGTGTACTT TTTTTTAAGG GAAAGATTTT AATATTAAAC
5581  CTGGTGCTTC TCACTCAC
```

Figure 3(A) Cont.

Figure 3 (B) Sequence of PDGFR-B polypeptide (GenBank Accession No. NP_002600) (SEQ ID NO: 6)

```
   1  MRLPGAMPAL ALKGELLLLS LLLLLEPQIS QGLVVTPPGP ELVLNVSSTF VLTCSGSAPV
  61  VWERMSQEPP QEMAKAQDGT FSSVLTLTNL TGLDTGEYFC THNDSRGLET DERKRLYIFV
 121  PDPTVGFLPN DAEELFIFLT EITEITIPCR VTDPQLVVTL HEKKGDVALP VPYDHQRGFS
 181  GIFEDRSYIC KTTIGDREVD SDAYYVYRLQ VSSINVSVNA VQTVVRQGEN ITLMCIVIGN
 241  EVVNFEWTYP RKESGRLVEP VTDFLLDMPY HIRSILHIPS AELEDSGTYT CNVTESVNDH
 301  QDEKAINITV VESGYVRLLG EVGTLQFAEL HRSRTLQVVF EAYPPPTVLW FKDNRTLGDS
 361  SAGEIALSTR NVSETRYVSE LTLVRVKVAE AGHYTMRAFH EDAEVQLSFQ LQINVPVRVL
 421  ELSESHPDSG EQTVRCRGRG MPQPNIIWSA CRDLKRCPRE LPPTLLGNSS EEESQLETNV
 481  TYWEEEQEFE VVSTLRLQHV DRPLSVRCTL RNAVGQDTQE VIVVPHSLPF KVVVISAILA
 541  LVVLTIISLI ILIMLWQKKP RYEIRWKVIE SVSSDGHEYI YVDPMQLPYD STWELPRDQL
 601  VLGRTLGSGA FGQVVEATAH GLSHSQATMK VAVKMLKSTA RSSEKQALMS ELKIMSHLGP
 661  HLNVVNLLGA CTKGGPIYII TEYCRYGDLV DYLHRNKHTF LQHHSDKRRP PSAELYSNAL
 721  PVGLPLPSHV SLTGESDGGY MDMSKDESVD YVPMLDMKGD VKYADIESSN YMAPYDNYVP
 781  SAPERTCRAT LINESPVLSY MDLVGFSYQV ANGMEFLASK NCVHRDLAAR NVLICEGKLV
 841  KICDFGLARD IMRDSNYISK GSTFLPLKWM APESIFNSLY TTLSDVWSFG ILLWEIFTLG
 901  GTPYPELPMN EQFYNAIKRG YRMAQPAHAS DEIYEIMQKC WEEKFEIRPP FSQLVLLLER
 961  LLGEGYKKKY QQVDEEFLRS DHPAILRSQA RLPGFHGLRS PLDTSSVLYT AVQPNEGDND
1021  YIIPLPDPKP EVADEGPLEG SPSLASSTLN EVNTSSTISC DSPLEPQDEP EPEPQLELQV
1081  EPEPELEQLP DSGCPAPRAE AEDSFL
```

Figure 3 (C) Sequence of PDGFR-A nucleic acid (GenBank Accession No. NM 006206) (SEQ ID NO: 13)

```
   1  TTCTCCCCGC CCCCCAGTTG TTGTCGAAGT CTGGGGGTTG GGACTGGACC CCCTGATTGC
  61  GTAAGAGCAA AAAGCGAAGG CGCAATCTGG ACACTGGGAG ATTCGGAGCG CAGGGAGTTT
 121  GAGAGAAACT TTTATTTTGA AGAGACCAAG GTTGAGGGGG GGCTTATTTC CTGACAGCTA
 181  TTTACTTAGA GCAAATGATT AGTTTTAGAA GGATGGACTA TAACATTGAA TCAATTACAA
 241  AACGCGGTTT TTGAGCCCAT TACTGTTGGA GCTACAGGGA GAGAAACAGG AGGAGACTGC
 301  AAGAGATCAT TTGGGAAGGC CGTGGGCACG CTCTTTACTC CATGTGTGGG ACATTCATTG
 361  CGGAATAACA TCGGAGGAGA AGTTTCCCAG AGCTATGGGG ACTTCCCATC CGGCGTTCCT
 421  GGTCTTAGGC TGTCTTCTCA CAGGGCTGAG CCTAATCCTC TGCCAGCTTT CATTACCCTC
 481  TATCCTTCCA AATGAAAATG AAAAGGTTGT GCAGCTGAAT TCATCCTTTT CTCTGAGATG
 541  CTTTGGGGAG AGTGAAGTGA GCTGGCAGTA CCCCATGTCT GAAGAAGAGA GCTCCGATGT
 601  GGAAATCAGA AATGAAGAAA ACAACAGCGG CCTTTTTGTG ACGGTCTTGG AAGTGAGCAG
 661  TGCCTCGGCG GCCCACACAG GGTTGTACAC TTGCTATTAC AACCACACTC AGACAGAAGA
 721  GAATGAGCTT GAAGGCAGGC ACATTTACAT CTATGTGCCA GACCCAGATG TAGCCTTTGT
 781  ACCTCTAGGA ATGACGGATT ATTTAGTCAT CGTGGAGGAT GATGATTCTG CCATTATACC
 841  TTGTCGCACA ACTGATCCCG AGACTCCTGT AACCTTACAC AACAGTGAGG GGGTGGTACC
 901  TGCCTCCTAC GACAGCAGAC AGGGCTTTAA TGGGACCTTC ACTGTAGGGC CTATATCTG
 961  TGAGGCCACC GTCAAAGGAA AGAAGTTCCA GACCATCCCA TTTAATGTTT ATGCTTTAAA
1021  AGCAACATCA GAGCTGGATC TAGAAATGGA AGCTCTTAAA ACCGTGTATA AGTCAGGGGA
1081  AACGATTGTG GTCACCTGTG CTGTTTTTAA CAATGAGGTG GTTGACCTTC AATGGACTTA
1141  CCCTGGAGAA GTGAAAGGCA AAGGCATCAC AATGCTGGAA GAAATCAAAG TCCCATCCAT
1201  CAAATTGGTG TACACTTTGA CGGTCCCCGA GGCCACGGTG AAAGACAGTG GAGATTACGA
1261  ATGTGCTGCC CGCCAGGCTA CCAGGGAGGT CAAAGAAATG AAGAAAGTCA CTATTTCTGT
1321  CCATGAGAAA GGTTTCATTG AAATCAAACC CACCTTCAGC CAGTTGGAAG CTGTCAACCT
1381  GCATGAAGTC AAACATTTTG TTGTAGAGGT GCGGGCCTAC CCACCTCCCA GGATATCCTG
1441  GCTGAAAAAC AATCTGACTC TGATTGAAAA TCTCACTGAG ATCACCACTG ATGTGGAAAA
1501  GATTCAGGAA ATAAGGTATC GAAGCAAATT AAAGCTGATC CGTGCTAAGG AAGAAGACAG
1561  TGGCCATTAT ACTATTGTAG CTCAAAATGA AGATGCTGTG AAGAGCTATA CTTTTGAACT
```

```
1621  GTTAACTCAA GTTCCTTCAT CCATTCTGGA CTTGGTCGAT GATCACCATG GCTCAACTGG
1681  GGGACAGACG GTGAGGTGCA CAGCTGAAGG CACGCCGCTT CCTGATATTG AGTGGATGAT
1741  ATGCAAAGAT ATTAAGAAAT GTAATAATGA AACTTCCTGG ACTATTTGG CCAACAATGT
1801  CTCAAACATC ATCACGGAGA TCCACTCCCG AGACAGGAGT ACCGTGGAGG GCCGTGTGAC
1861  TTTCGCCAAA GTGGAGGAGA CCATCGCCGT GCGATGCCTG GCTAAGAATC TCCTTGGAGC
1921  TGAGAACCGA GAGCTGAAGC TGGTGGCTCC CACCCTGCGT TCTGAACTCA CGGTGGCTGC
1981  TGCAGTCCTG GTGCTGTTGG TGATTGTGAT CATCTCACTT ATTGTCCTGG TTGTCATTTG
2041  GAAACAGAAA CCGAGGTATG AAATTCGCTG GAGGGTCATT GAATCAATCA GCCCGGATGG
2101  ACATGAATAT ATTTATGTGG ACCCGATGCA GCTGCCTTAT GACTCAAGAT GGGAGTTTCC
2161  AAGAGATGGA CTAGTGCTTG GTCGGGTCTT GGGGTCTGGA GCGTTTGGGA AGGTGGTTGA
2221  AGGAACAGCC TATGGATTAA GCCGGTCCCA ACCTGTCATG AAAGTTGCAG TGAAGATGCT
2281  AAAACCCACG GCCAGATCCA GTGAAAAACA AGCTCTCATG TCTGAACTGA AGATAATGAC
2341  TCACCTGGGG CCACATTTGA ACATTGTAAA CTTGCTGGGA GCCTGCACCA AGTCAGGCCC
2401  CATTTACATC ATCACAGAGT ATTGCTTCTA TGGAGATTTG GTCAACTATT TGCATAAGAA
2461  TAGGGATAGC TTCCTGAGCC ACCACCCAGA GAAGCCAAAG AAAGAGCTGG ATATCTTTGG
2521  ATTGAACCCT GCTGATGAAA GCACACGGAG CTATGTTATT TTATCTTTTG AAAACAATGG
2581  TGACTACATG GACATGAAGC AGGCTGATAC TACACAGTAT GTCCCCATGC TAGAAAGGAA
2641  AGAGGTTTCT AAATATTCCG ACATCCAGAG ATCACTCTAT GATCGTCCAG CCTCATATAA
2701  GAAGAAATCT ATGTTAGACT CAGAAGTCAA AAACCTCCTT TCAGATGATA ACTCAGAAGG
2761  CCTTACTTTA TTGGATTTGT TGAGCTTCAC CTATCAAGTT GCCCGAGGAA TGGAGTTTTT
2821  GGCTTCAAAA AATTGTGTCC ACCGTGATCT GGCTGCTCGC AACGTCCTCC TGCACAAGG
2881  AAAAATTGTG AAGATCTGTG ACTTTGGCCT GGCCAGAGAC ATCATGCATG ATTCGAACTA
2941  TGTGTCGAAA GGCAGTACCT TTCTGCCCGT GAAGTGGATG GCTCCTGAGA GCATCTTTGA
3001  CAACCTCTAC ACCACACTGA GTGATGTCTG GTCTTATGGC ATTCTGCTCT GGAGATCTT
3061  TTCCCTTGGT GGCACCCCTT ACCCCGGCAT GATGGTGGAT TCTACTTTCT ACAATAAGAT
3121  CAAGAGTGGG TACCGGATGG CCAAGCCTGA CCACGCTACC AGTGAAGTCT ACGAGATCAT
3181  GGTGAAATGC TGGAACAGTG AGCCGGAGAA GAGACCCTCC TTTTACCACC TGAGTGAGAT
3241  TGTGGAGAAT CTGCTGCCTG GACAATATAA AAAGAGTTAT GAAAAAATTC ACCTGGACTT
```

Figure 3(C) Cont.

```
3301  CCTGAAGAGT GACCATCCTG CTGTGGCACG CATGCGTGTG GACTCAGACA ATGCATACAT
3361  TGGTGTCACC TACAAAAACG AGGAAGACAA GCTGAAGGAC TGGGAGGGTG GTCTGGATGA
3421  GCAGAGACTG AGCGCTGACA GTGGCTACAT CATTCCTCTG CCTGACATTG ACCCTGTCCC
3481  TGAGGAGGAG GACCTGGGCA AGAGGAACAG ACACAGCTCG CAGACCTCTG AAGAGAGTGC
3541  CATTGAGACG GGTTCCAGCA GTTCCACCTT CATCAAGAGA GAGGACGAGA CCATTGAAGA
3601  CATCGACATG ATGGACGACA TCGGCATAGA CTCTTCAGAC CTGGTGGAAG ACAGCTTCCT
3661  GTAACTGGCG GATTCGAGGG GTTCCTTCCA CTTCTGGGGC CACCTCTGGA TCCCGTTCAG
3721  AAAACCACTT TATTGCAATG CGGAGGTTGA GAGGAGGACT TGGTTGATGT TTAAAGAGAA
3781  GTTCCCAGCC AAGGGCCTCG GGAGCGTTC TAAATATGAA TGAATGGGAT ATTTTGAAAT
3841  GAACTTTGTC AGTGTTGCCT CTCGCAATGC CTCAGTAGCA TCTCAGTGGT GTGTGAAGTT
3901  TGGAGATAGA TGGATAAGGG AATAATAGGC CACAGAAGGT GAACTTTGTG CTTCAAGCAC
3961  ATTGGTGAGA GTCCAACAGA CACAATTTAT ACTGCGACAG AACTTCAGCA TTGTAATTAT
4021  GTAAATAACT CTAACCAAGG CTGTGTTTAG ATTGTATTAA CTATCTTCTT TGGACTTCTG
4081  AAGAGACCAC TCAATCCATC CATGTACTTC CCTCTTGAAA CCTGATGTCA GCTGCTGTTG
4141  AACTTTTTAA AGAAGTGCAT GAAAAACCAT TTTTGAACCT TAAAAGGTAC TGGTACTATA
4201  GCATTTGCT ATCTTTTTA GTGTTAAGAG ATAAAGAATA ATAATTAACC AACCTTGTTT
4261  AATAGATTTG GGTCATTTAG AAGCCTGACA ACTCATTTTC ATATTGTAAT CTATGTTTAT
4321  AATACTACTA CTGTTATCAG TAATGCTAAA TGTGTAATAA TGTAACATGA TTTCCCTCCA
4381  GAGAAAGCAC AATTTAAAAC AATCCTTACT AAGTAGGTGA TGAGTTTGAC AGTTTTTGAC
4441  ATTTATATTA ATAACATGT TTCTCTATAA AGTATGGTAA TAGCTTTAGT GAATTAAATT
4501  TAGTTGAGCA TAGAGAACAA AGTAAAAGTA GTGTTGTCCA GGAAGTCAGA ATTTTTAACT
4561  GTACTGAATA GGTTCCCCAA TCCATCGTAT TAAAAAACAA TTAACTGCCC TCTGAAATAA
4621  TGGGATTAGA AACAAACAAA ACTCTTAAGT CCTAAAAGTT CTCAATGTAG AGGCATAAAC
4681  CTGTGCTGAA CATAACTTCT CATGTATATT ACCCAATGGA AAATATAATG ATCAGCAAAA
4741  AGACTGGATT TGCAGAAGTT TTTTTTTTT TTCTTCATGC CTGATGAAAG CTTTGGCAAC
4801  CCCAATATAT GTATTTTTTG AATCTATGAA CCTGAAAAGG GTCAGAAGGA TGCCCAGACA
4861  TCAGCCTCCT TCTTTCACCC CTTACCCCAA AGAGAAAGAG TTTGAAACTC GAGACCATAA
4921  AGATATTCTT TAGTGGAGGC TGGATGTGCA TTAGCCTGGA TCCTCAGTTC TCAAATGTGT
```

Figure 3(C) Cont.

```
4981  GTGGCAGCCA GGATGACTAG ATCCTGGGTT TCCATCCTTG AGATTCTGAA GTATGAAGTC
5041  TGAGGGAAAC CAGAGTCTGT ATTTTTCTAA ACTCCCTGGC TGTTCTGATC GGCCAGTTTT
5101  CGGAAACACT GACTTAGGTT TCAGGAAGTT GCCATGGGAA ACAAATAATT TGAACTTTGG
5161  AACAGGGTTG GAATTCAACC ACGCAGGAAG CCTACTATTT AAATCCTTGG CTTCAGGTTA
5221  GTGACATTTA ATGCCATCTA GCTAGCAATT GCGACCTTAA TTTAACTTTC CAGTCTTAGC
5281  TGAGGCTGAG AAAGCTAAAG TTGGTTTTG ACAGGTTTTC CAAAAGTAAA GATGCTACTT
5341  CCCACTGTAT GGGGAGATT GAACTTTCCC CGTCTCCGT CTTCTGCCTC CCACTCCATA
5401  CCCCGCCAAG GAAAGGCATG TACAAAAATT ATGCAATTCA GTGTTCCAAG TCTCTGTGTA
5461  ACCAGCTCAG TGTTTTGGTG GAAAAAACAT TTAAGTTTT ACTGATAATT TGAGGTTAGA
5521  TGGGAGGATG AATTGTCACA TCTATCCACA CTGTCAAACA GGTTGGTGTG GGTTCATTGG
5581  CATTCTTTGC AATACTGCTT AATTGCTGAT ACCATATGAA TGAAACATGG GCTGTGATTA
5641  CTGCAATCAC TGTGCTATCG GCAGATGATG CTTTGGAAGA TGCAGAAGCA ATAATAAAGT
5701  ACTTGACTAC CTACTGGTGT AATCTCAATG CAAGCCCCAA CTTTCTTATC CAACTTTTTC
5761  ATAGTAAGTG CGAAGACTGA GCCAGATTGG CCAATTAAAA ACGAAAACCT GACTAGGTTC
5821  TGTAGAGCCA ATTAGACTTG AAATACGTTT GTGTTTCTAG AATCACAGCT CAAGCATTCT
5881  GTTTATCGCT CACTCTCCCT TGTACAGCCT TATTTGTTG GTGCTTTGCA TTTTGATATT
5941  GCTGTGAGCC TTGCATGACA TCATGAGGCC GGATGAAACT TCTCAGTCCA GCAGTTTCCA
6001  GTCCTAACAA ATGCTCCCAC CTGAATTTGT ATATGACTGC ATTTGTGGGT GTGTGTGTGT
6061  TTTCAGCAAA TTCCAGATTT GTTTCCTTTT GGCCTCCTGC AAAGTCTCCA GAAGAAAATT
6121  TGCCAATCTT TCCTACTTTC TATTTTTATG ATGACAATCA AGCCGGCCT GAGAAACACT
6181  ATTTGTGACT TTTTAAACGA TTAGTGATGT CCTTAAAATG TGGTCTGCCA ATCTGTACAA
6241  AATGGTCCTA TTTTTGTGAA GAGGGACATA AGATAAAATG ATGTTATACA TCAATATGTA
6301  TATATGTATT TCTATATAGA CTTGGAGAAT ACTGCCAAAA CATTTATGAC AAGCTGTATC
6361  ACTGCCTTCG TTTATATTTT TTAACTGTG ATAATCCCCA CAGGCACATT AACTGTTGCA
6421  CTTTTGAATG TCCAAAATTT ATATTTAGA AATAATAAAA AGAAAGATAC TTACATGTTC
6481  CCAAAACAAT GGTGTGGTGA ATGTGTGAGA AAAACTAACT TGATAGGGTC TACCAATACA
6541  AAATGTATTA CGAATGCCCC TGTTCATGTT TTTGTTTTAA AACGTGTAAA TGAAGATCTT
6601  TATATTTCAA TAAATGATAT ATAATTTAAA GTT
```

Figure 3(C) Cont.

Figure 3 (D) Sequence of human PDGFR-A polypeptide (GenBank Accession No. NP 006197) (SEQ ID NO: 14)

```
   1   MGTSHPAFLV  LGCLLTGLSL  ILCQLSLPSI  LPNENEKVVQ  LNSSFSLRCF  GESEVSWQYP
  61   MSEEESSDVE  IRNEENNSGL  FVTVLEVSSA  SAAHTGLYTC  YYNHTQTEEN  ELEGRHIYIY
 121   VPDPDVAFVP  LGMTDYLVIV  EDDDSAIIPC  RTTDPETPVT  LHNSEGVVPA  SYDSRQGFNG
 181   TFTVGPYICE  ATVKGKKFQT  IPFNVYALKA  TSELDLEMEA  LKTVYKSGET  IVVTCAVFNN
 241   EVVDLQWTYP  GEVKGKGITM  LEEIKVPSIK  LVYTLTVPEA  TVKDSGDYEC  AARQATREVK
 301   EMKKVTISVH  EKGFIEIKPT  FSQLEAVNLH  EVKHFVVEVR  AYPPPRISWL  KNNLTLIENL
 361   TEITTDVEKI  QEIRYRSKLK  LIRAKEEDSG  HYTIVAQNED  AVKSYTFELL  TQVPSSILDL
 421   VDDHHGSTGG  QTVRCTAEGT  PLPDIEWMIC  KDIKKCNNET  SWTILANNVS  NIITEIHSRD
 481   RSTVEGRVTF  AKVEETIAVR  CLAKNLLGAE  NRELKLVAPT  LRSELTVAAA  VLVLLVIVII
 541   SLIVLVVIWK  QKPRYEIRWR  VIESISPDGH  EYIYVDPMQL  PYDSRWEFPR  DGLVLGRVLG
 601   SGAFGKVVEG  TAYGLSRSQP  VMKVAVKMLK  PTARSSEKQA  LMSELKIMTH  LGPHLNIVNL
 661   LGACTKSGPI  YIITEYCFYG  DLVNYLHKNR  DSFLSHHPEK  PKKELDIFGL  NPADESTRSY
 721   VILSFENNGD  YMDMKQADTT  QYVPMLERKE  VSKYSDIQRS  LYDRPASYKK  KSMLDSEVKN
 781   LLSDDNSEGL  TLLDLLSFTY  QVARGMEFLA  SKNCVHRDLA  ARNVLLAQGK  IVKICDFGLA
 841   RDIMHDSNYV  SKGSTFLPVK  WMAPESIFDN  LYTTLSDVWS  YGILLWEIFS  LGGTPYPGMM
 901   VDSTFYNKIK  SGYRMAKPDH  ATSEVYEIMV  KCWNSEPEKR  PSFYHLSEIV  ENLLPGQYKK
 961   SYEKIHLDFL  KSDHPAVARM  RVDSDNAYIG  VTYKNEEDKL  KDWEGGLDEQ  RLSADSGYII
1021   PLPDIDPVPE  EEDLGKRNRH  SSQTSEESAI  ETGSSSSTFI  KREDETIEDI  DMMDDIGIDS
1081   SDLVEDSFL
```

Figure 4 (A) Sequence of VEGFR-1 (Flt-1) nucleic acid (GenBank Accession No. AF063657) (SEQ ID NO: 7)

```
   1  ATGGTCAGCT ACTGGGACAC CGGGGTCCTG CTGTGCGCGC TGCTCAGCTG TCTGCTTCTC
  61  ACAGGATCTA GTTCAGGTTC AAAATTAAAA GATCCTGAAC TGAGTTTAAA AGGCACCCAG
 121  CACATCATGC AAGCAGGCCA GACACTGCAT CTCCAATGCA GGGGGGAAGC AGCCCATAAA
 181  TGGTCTTTGC CTGAAATGGT GAGTAAGGAA AGCGAAAGGC TGAGCATAAC TAAATCTGCC
 241  TGTGGAAGAA ATGGCAAACA ATTCTGCAGT ACTTTAACCT GAACACAGC TCAAGCAAAC
 301  CACACTGGCT TCTACAGCTG CAAATATCTA GCTGTACCTA CTTCAAAGAA GAAGGAAACA
 361  GAATCTGCAA TCTATATATT TATTAGTGAT ACAGGTAGAC CTTTCGTAGA GATGTACAGT
 421  GAAATCCCCG AAATTATACA CATGACTGAA GGAAGGGAGC TCGTCATTCC CTGCCGGGTT
 481  ACGTCACCTA ACATCACTGT TACTTTAAAA AAGTTTCCAC TTGACACTTT GATCCCTGAT
 541  GGAAAACGCA TAATCTGGGA CAGTAGAAAG GGCTTCATCA TATCAAATGC AACGTACAAA
 601  GAAATAGGGC TTCTGACCTG TGAAGCAACA GTCAATGGGC ATTTGTATAA GACAAACTAT
 661  CTCACACATC GACAAACCAA TACAATCATA GATGTCCAAA TAAGCACACC ACGCCCAGTC
 721  AAATTACTTA GAGGCCATAC TCTTGTCCTC AATTGTACTG CTACCACTCC CTTGAACACG
 781  AGAGTTCAAA TGACCTGGAG TTACCCTGAT GAAAAAAATA AGAGAGCTTC CGTAAGGCGA
 841  CGAATTGACC AAAGCAATTC CCATGCCAAC ATATTCTACA GTGTTCTTAC TATTGACAAA
 901  ATGCAGAACA AAGACAAAGG ACTTTATACT TGTCGTGTAA GGAGTGGACC ATCATTCAAA
 961  TCTGTTAACA CCTCAGTGCA TATATATGAT AAAGCATTCA TCACTGTGAA ACATCGAAAA
1021  CAGCAGGTGC TTGAAACCGT AGCTGGCAAG CGGTCTTACC GGCTCTCTAT GAAAGTGAAG
1081  GCATTTCCCT CGCCGGAAGT TGTATGGTTA AAAGATGGGT TACCTGCGAC TGAGAAATCT
1141  GCTCGCTATT TGACTCGTGG CTACTCGTTA ATTATCAAGG ACGTAACTGA AGAGGATGCA
1201  GGGAATTATA CAATCTTGCT GAGCATAAAA CAGTCAAATG TGTTTAAAAA CCTCACTGCC
1261  ACTCTAATTG TCAATGTGAA ACCCCAGATT TACGAAAAGG CCGTGTCATC GTTTCCAGAC
1321  CCGGCTCTCT ACCCACTGGG CAGCAGACAA ATCCTGACTT GTACCGCATA TGGTATCCCT
1381  CAACCTACAA TCAAGTGGTT CTGGCACCCC TGTAACCATA ATCATTCCGA AGCAAGGTGT
1441  GACTTTTGTT CCAATAATGA AGAGTCCTTT ATCCTGGATG CTGACAGCAA CATGGGAAAC
1501  AGAATTGAGA GCATCACTCA GCGCATGGCA ATAATAGAAG GAAAGAATAA GATGGCTAGC
```

```
1561    ACCTTGGTTG TGGCTGACTC TAGAATTTCT GGAATCTACA TTTGCATAGC TTCCAATAAA
1621    GTTGGGACTG TGGGAAGAAA CATAAGCTTT TATATCACAG ATGTGCCAAA TGGGTTTCAT
1681    GTTAACTTGG AAAAAATGCC GACGGAAGGA GAGGACCTGA ACTGTCTTG CACAGTTAAC
1741    AAGTTCTTAT ACAGAGACGT TACTTGGATT TTACTGCGGA CAGTTAATAA CAGAACAATG
1801    CACTACAGTA TTAGCAAGCA AAAATGGCC ATCACTAAGG AGCACTCCAT CACTCTTAAT
1861    CTTACCATCA TGAATGTTTC CCTGCAAGAT TCAGGCACCT ATGCCTGCAG AGCCAGGAAT
1921    GTATACACAG GGAAGAAAT CCTCCAGAAG AAAGAAATTA CAATCAGAGA TCAGGAAGCA
1981    CCATACCTCC TGCGAAACCT CAGTGATCAC ACAGTGGCCA TCAGCAGTTC CACCACTTTA
2041    GACTGTCATG CTAATGGTGT CCCCGAGCCT CAGATCACTT GGTTTAAAAA CAACCACAAA
2101    ATACAACAAG AGCCTGGAAT TATTTTAGGA CCAGGAAGCA GCACGCTGTT TATTGAAAGA
2161    GTCACAGAAG AGGATGAAGG TGTCTATCAC TGCAAAGCCA CCAACCAGAA GGGCTCTGTG
2221    GAAAGTTCAG CATACCTCAC TGTTCAAGGA ACCTCGGACA AGTCTAATCT GGAGCTGATC
2281    ACTCTAACAT GCACCTGTGT GGCTGCGACT CTCTTCTGGC TCCTATTAAC CCTCTTTATC
2341    CGAAAAATGA AAGGTCTTC TTCTGAAATA AAGACTGACT ACCTATCAAT TATAATGGAC
2401    CCAGATGAAG TTCCTTTGGA TGAGCAGTGT GAGCGGCTCC CTTATGATGC CAGCAAGTGG
2461    GAGTTTGCCC GGGAGAGACT TAAACTGGGC AAATCACTTG GAAGAGGGGC TTTTGGAAAA
2521    GTGGTTCAAG CATCAGCATT TGGCATTAAG AAATCACCTA CGTGCCGGAC TGTGGCTGTG
2581    AAAATGCTGA AAGAGGGGGC CACGGCCAGC GAGTACAAAG CTCTGATGAC TGAGCTAAAA
2641    ATCTTGACCC ACATTGGCCA CCATCTGAAC GTGGTTAACC TGCTGGGAGC CTGCACCAAG
2701    CAAGGAGGGC CTCTGATGGT GATTGTTGAA TACTGCAAAT ATGGAAATCT CTCCAACTAC
2761    CTCAAGAGCA AACGTGACTT ATTTTTTCTC AACAAGGATG CAGCACTACA CATGGAGCCT
2821    AAGAAAGAAA AAATGGAGCC AGGCCTGGAA CAAGGCAAGA ACCAAGACT AGATAGCGTC
2881    ACCAGCAGCG AAAGCTTTGC GAGCTCCGGC TTTCAGGAAG ATAAAAGTCT GAGTGATGTT
2941    GAGGAAGAGG AGGATTCTGA CGGTTTCTAC AAGGAGCCCA TCACTATGGA AGATCTGATT
3001    TCTTACAGTT TTCAAGTGGC CAGAGGCATG GAGTTCCTGT CTTCCAGAAA GTGCATTCAT
3061    CGGGACCTGG CAGCGAGAAA CATTCTTTTA TCTGAGAACA ACGTGGTGAA GATTTGTGAT
3121    TTTGGCCTTG CCCGGGATAT TTATAAGAAC CCCGATTATG TGAGAAAAGG AGATACTCGA
3181    CTTCCTCTGA AATGGATGCC TCCTGAATCT ATCTTTGACA AAATCTACAG CACCAAGAGC
```

Figure 4(A) Cont.

```
3241  GACGTGTGGT CTTACGGAGT ATTGCTGTGG GAAATCTTCT CCTTAGGTGG GTCTCCATAC
3301  CCAGGAGTAC AAATGGATGA GGACTTTTGC AGTCGCCTGA GGGAAGGCAT GAGGATGAGA
3361  GCTCCTGAGT ACTCTACTCC TGAAATCTAT CAGATCATGC TGGACTGCTG GCACAGAGAC
3421  CCAAAAGAAA GGCCAAGATT TGCAGAACTT GTGGAAAAAC TAGGTGATTT GCTTCAAGCA
3481  AATGTACAAC AGGATGGTAA AGACTACATC CCAATCAATG CCATACTGAC AGGAAATAGT
3541  GGGTTTACAT ACTCAACTCC TGCCTTCTCT GAGGACTTCT TCAAGGAAAG TATTTCAGCT
3601  CCGAAGTTTA ATTCAGGAAG CTCTGATGAT GTCAGATATG TAAATGCTTT CAAGTTCATG
3661  AGCCTGGAAA GAATCAAAAC CTTTGAAGAA CTTTTACCGA ATGCCACCTC CATGTTTGAT
3721  GACTACCAGG GCGACAGCAG CACTCTGTTG GCCTCTCCA TGCTGAAGCG CTTCACCTGG
3781  ACTGACAGCA AACCCAAGGC CTCGCTCAAG ATTGACTTGA GAGTAACCAG TAAAAGTAAG
3841  GAGTCGGGGC TGTCTGATGT CAGCAGGCCC AGTTTCTGCC ATTCCAGCTG TGGGCACGTC
3901  AGCGAAGGCA AGCGCAGGTT CACCTACGAC CACGCTGAGC TGGAAAGGAA AATCGCGTGC
3961  TGCTCCCCGC CCCCAGACTA CAACTCGGTG GTCCTGTACT CCACCCCACC CATCTAG
```

Figure 4(A) Cont.

Figure 4 (B) Sequence of VEGFR-1 (Flt-1) polypeptide (GenBank Accession No.) (SEQ ID NO: 8)

```
   1  MVSYWDTGVL  LCALLSCLLL  TGSSSGSKLK  DPELSLKGTQ  HIMQAGQTLH  LQCRGEAAHK
  61  WSLPEMVSKE  SERLSITKSA  CGRNGKQFCS  TLTLNTAQAN  HTGFYSCKYL  AVPTSKKKET
 121  ESAIYIFISD  TGRPFVEMYS  EIPEIIHMTE  GRELVIPCRV  TSPNITVTLK  KFPLDTLIPD
 181  GKRIIWDSRK  GFIISNATYK  EIGLLTCEAT  VNGHLYKTNY  LTHRQTNTII  DVQISTPRPV
 241  KLLRGHTLVL  NCTATTPLNT  RVQMTWSYPD  EKNKRASVRR  RIDQSNSHAN  IFYSVLTIDK
 301  MQNKDKGLYT  CRVRSGPSFK  SVNTSVHIYD  KAFITVKHRK  QQVLETVAGK  RSYRLSMKVK
 361  AFPSPEVVWL  KDGLPATEKS  ARYLTRGYSL  IIKDVTEEDA  GNYTILLSIK  QSNVFKNLTA
 421  TLIVNVKPQI  YEKAVSSFPD  PALYPLGSRQ  ILTCTAYGIP  QPTIKWFWHP  CNHNHSEARC
 481  DFCSNNEESF  ILDADSNMGN  RIESITQRMA  IIEGKNKMAS  TLVVADSRIS  GIYICIASNK
 541  VGTVGRNISF  YITDVPNGFH  VNLEKMPTEG  EDLKLSCTVN  KFLYRDVTWI  LLRTVNNRTM
 601  HYSISKQKMA  ITKEHSITLN  LTIMNVSLQD  SGTYACRARN  VYTGEEILQK  KEITIRDQEA
 661  PYLLRNLSDH  TVAISSSTTL  DCHANGVPEP  QITWFKNNHK  IQQEPGIILG  PGSSTLFIER
 721  VTEEDEGVYH  CKATNQKGSV  ESSAYLTVQG  TSDKSNLELI  TLTCTCVAAT  LFWLLLTLFI
 781  RKMKRSSSEI  KTDYLSIIMD  PDEVPLDEQC  ERLPYDASKW  EFARERLKLG  KSLGRGAFGK
 841  VVQASAFGIK  KSPTCRTVAV  KMLKEGATAS  EYKALMTELK  ILTHIGHHLN  VVNLLGACTK
 901  QGGPLMVIVE  YCKYGNLSNY  LKSKRDLFFL  NKDAALHMEP  KKEKMEPGLE  QGKKPRLDSV
 961  TSSESFASSG  FQEDKSLSDV  EEEDSDGFY  KEPITMEDLI  SYSFQVARGM  EFLSSRKCIH
1021  RDLAARNILL  SENNVVKICD  FGLARDIYKN  PDYVRKGDTR  LPLKWMAPES  IFDKIYSTKS
1081  DVWSYGVLLW  EIFSLGGSPY  PGVQMDEDFC  SRLREGMRMR  APEYSTPEIY  QIMLDCWHRD
1141  PKERPRFAEL  VEKLGDLLQA  NVQQDGKDYI  PINAILTGNS  GFTYSTPAFS  EDFFKESISA
1201  PKFNSGSSDD  VRYVNAFKFM  SLERIKTFEE  LLPNATSMFD  DYQGDSSTLL  ASPMLKRFTW
1261  TDSKPKASLK  IDLRVTSKSK  ESGLSDVSRP  SFCHSSCGHV  SEGKRRFTYD  HAELERKIAC
1321  CSPPPDYNSV  VLYSTPPI
```

Figure 4 (C) Sequence of VEGFR-2 (KDR/Flk-1) nucleic acid (GenBank Accession No. AF035121) (SEQ ID NO: 9)

```
   1 ACTGAGTCCC GGGACCCCGG GAGAGCGGTC AGTGTGTGGT CGCTGCGTTT CCTCTGCCTG
  61 CGCCGGGCAT CACTTGCGCG CCGCAGAAAG TCCGTCTGGC AGCCTGGATA TCCTCTCCTA
 121 CCGGCACCCG CAGACGCCCC TGCAGCCGCC GGTCGGCGCC CGGGCTCCCT AGCCCTGTGC
 181 GCTCAACTGT CCTGCGCTGC GGGGTGCCGC GAGTTCCACC TCCGCGCCTC CTTCTCTAGA
 241 CAGGCGCTGG GAGAAAGAAC CGGCTCCCGA GTTCTGGGCA TTTCGCCCGG CTCGAGGTGC
 301 AGGATGCAGA GCAAGGTGCT GCTGGCCGTC GCCCTGTGGC TCTGCGTGGA GACCCGGGCC
 361 GCCTCTGTGG GTTTGCCTAG TGTTTCTCTT GATCTGCCCA GGCTCAGCAT ACAAAAAGAC
 421 ATACTTACAA TTAAGGCTAA TACAACTCTT CAAATTACTT GCAGGGGACA GAGGGACTTG
 481 GACTGGCTTT GGCCCAATAA TCAGAGTGGC AGTGAGCAAA GGGTGGAGGT GACTGAGTGC
 541 AGCGATGGCC TCTTCTGTAA GACACTCACA ATTCCAAAAG TGATCGGAAA TGACACTGGA
 601 GCCTACAAGT GCTTCTACCG GGAAACTGAC TTGGCCTCGG TCATTTATGT CTATGTTCAA
 661 GATTACAGAT CTCCATTTAT TGCTTCTGTT AGTGACCAAC ATGGAGTCGT GTACATTACT
 721 GAGAACAAAA ACAAAACTGT GGTGATTCCA TGTCTCGGGT CCATTTCAAA TCTCAACGTG
 781 TCACTTTGTG CAAGATACCC AGAAAAGAGA TTTGTTCCTG ATGGTAACAG AATTTCCTGG
 841 GACAGCAAGA AGGGCTTTAC TATTCCCAGC TACATGATCA GCTATGCTGG CATGGTCTTC
 901 TGTGAAGCAA AAATTAATGA TGAAAGTTAC CAGTCTATTA TGTACATAGT TGTCGTTGTA
 961 GGGTATAGGA TTTATGATGT GGTTCTGAGT CCGTCTCATG AATTGAACT ATCTGTTGGA
1021 GAAAAGCTTG TCTTAAATTG TACAGCAAGA ACTGAACTAA ATGTGGGGAT TGACTTCAAC
1081 TGGGAATACC CTTCTTCGAA GCATCAGCAT AAGAAACTTG TAAACCGAGA CCTAAAAACC
1141 CAGTCTGGGA GTGAGATGAA GAAATTTTTG AGCACCTTAA CTATAGATGG TGTAACCCGG
1201 AGTGACCAAG GATTGTACAC CTGTGCAGCA TCCAGTGGGC TGATGACCAA GAAGAACAGC
1261 ACATTTGTCA GGGTCCATGA AAAACCTTTT GTTGCTTTTG GAAGTGGCAT GGAATCTCTG
1321 GTGGAAGCCA CGGTGGGGGA GCGTGTCAGA ATCCCTGCGA AGTACCTTGG TTACCCACCC
1381 CCAGAAATAA AATGGTATAA AAATGGAATA CCCCTTGAGT CCAATCACAC AATTAAAGCG
1441 GGGCATGTAC TGACGATTAT GGAAGTGAGT GAAAGAGACA CAGGAAATTA CACTGTCATC
1501 CTTACCAATC CCATTTCAAA GGAGAAGCAG AGCCATGTGG TCTCTCTGGT TGTGTATGTC
```

```
1561  CCACCCCAGA TGGTGAGAA  ATCTCTAATC TCTCCTGTGG ATTCCTACCA GTACGGCACC
1621  ACTCAAACGC TGACATGTAC GGTCTATGCC ATTCCTCCCC CGCATCACAT CCACTGGTAT
1681  TGGCAGTTGG AGGAAGAGTG CGCCAACGAG CCCAGCCAAG CTGTCTCAGT GACAAACCCA
1741  TACCCTTGTG AAGAATGGAG AAGTGTGGAG GACTTCCAGG GAGGAAATAA AATTGAAGTT
1801  AATAAAAATC AATTTGCTCT AATTGAAGGA AAAACAAAA  CTGTAAGTAC CCTTGTTATC
1861  CAAGCGGCAA ATGTGTCAGC TTTGTACAAA TGTGAAGCGG TCAACAAAGT CGGGAGAGGA
1921  GAGAGGGTGA TCTCCTTCCA CGTGACCAGG GGTCCTGAAA TTACTTTGCA ACCTGACATG
1981  CAGCCCACTG AGCAGGAGAG CGTGTCTTTG TGGTGCACTG CAGACAGATC TACGTTTGAG
2041  AACCTCACAT GGTACAAGCT TGGCCCACAG CCTCTGCCAA TCCATGTGGG AGAGTTGCCC
2101  ACACCTGTTT GCAAGAACTT GGATACTCTT TGGAAATTGA ATGCCACCAT GTTCTCTAAT
2161  AGCACAAATG ACATTTTGAT CATGGAGCTT AAGAATGCAT CCTTGCAGGA CCAAGGAGAC
2221  TATGTCTGCC TTGCTCAAGA CAGGAAGACC AAGAAAAGAC ATTGCGTGGT CAGGCAGCTC
2281  ACAGTCCTAG AGCGTGTGGC ACCCACGATC ACAGGAAACC TGGAGAATCA GACGACAAGT
2341  ATTGGGGAAA GCATCGAAGT CTCATGCACG GCATCTGGGA ATCCCCTCC  ACAGATCATG
2401  TGGTTTAAAG ATAATGAGAC CCTTGTAGAA GACTCAGGCA TTGTATTGAA GGATGGGAAC
2461  CGGAACCTCA CTATCCGCAG AGTGAGGAAG GAGGACGAAG GCCTCTACAC CTGCCAGGCA
2521  TGCAGTGTTC TTGGCTGTGC AAAAGTGGAG GCATTTTTCA TAATAGAAGG TGCCCAGGAA
2581  AAGACGAACT TGGAAATCAT TATTCTAGTA GGCACGGCGG TGATTGCCAT GTTCTTCTGG
2641  CTACTTCTTG TCATCATCCT ACGGACCGTT AAGCGGGCCA ATGGAGGGGA ACTGAAGACA
2701  GGCTACTTGT CCATCGTCAT GGATCCAGAT GAACTCCCAT TGGATGAACA TTGTGAACGA
2761  CTGCCTTATG ATGCCAGCAA ATGGGAATTC CCCAGAGACC GGCTGAAGCT AGGTAAGCCT
2821  CTTGGCCGTG GTGCCTTTGG CCAAGTGATT GAAGCAGATG CCTTTGGAAT TGACAAGACA
2881  GCAACTTGCA GGACAGTAGC AGTCAAAATG TTGAAAGAAG GAGCAACACA CAGTGAGCAT
2941  CGAGCTCTCA TGTCTGAACT CAAGATCCTC ATTCATATTG GTCACCATCT CAATGTGGTC
3001  AACCTTCTAG GTGCCTGTAC CAAGCCAGGA GGGCCACTCA TGGTGATTGT GGAATTCTGC
3061  AAATTTGGAA ACCTGTCCAC TTACCTGAGG AGCAAGAGAA ATGAATTTGT CCCCTACAAG
3121  ACCAAAGGGG CACGATTCCG TCAAGGGAAA GACTACGTTG GAGCAATCCC TGTGGATCTG
3181  AAACGGCGCT TGGACAGCAT CACCAGTAGC CAGAGCTCAG CCAGCTCTGG ATTTGTGGAG
```

Figure 4(C) Cont.

```
3241  GAGAAGTCCC TCAGTGATGT AGAAGAAGAG GAAGCTCCTG AAGATCTGTA TAAGGACTTC
3301  CTGACCTTGG AGCATCTCAT CTGTTACAGC TTCCAAGTGG CTAAGGGCAT GGAGTTCTTG
3361  GCATCGCGAA AGTGTATCCA CAGGGACCTG GCGGCACGAA ATATCCTCTT ATCGGAGAAG
3421  AACGTGGTTA AAATCTGTGA CTTTGGCTTG GCCCGGGATA TTTATAAAGA TCCAGATTAT
3481  GTCAGAAAAG GAGATGCTCG CCTCCCTTTG AAATGGATGG CCCCAGAAAC AATTTTTGAC
3541  AGAGTGTACA CAATCCAGAG TGACGTCTGG TCTTTTGGTG TTTTGCTGTG GGAAATATTT
3601  TCCTTAGGTG CTTCTCCATA TCCTGGGGTA AAGATTGATG AAGAATTTTG TAGGCGATTG
3661  AAAGAAGGAA CTAGAATGAG GGCCCCTGAT TATACTACAC CAGAAATGTA CCAGACCATG
3721  CTGGACTGCT GGCACGGGGA GCCCAGTCAG AGACCCACGT TTTCAGAGTT GGTGGAACAT
3781  TTGGGAAATC TCTTGCAAGC TAATGCTCAG CAGGATGGCA AAGACTACAT TGTTCTTCCG
3841  ATATCAGAGA CTTTGAGCAT GGAAGAGGAT TCTGGACTCT CTCTGCCTAC CTCACCTGTT
3901  TCCTGTATGG AGGAGGAGGA AGTATGTGAC CCCAAATTCC ATTATGACAA CACAGCAGGA
3961  ATCAGTCAGT ATCTGCAGAA CAGTAAGCGA AAGAGCCGGC CTGTGAGTGT AAAAACATTT
4021  GAAGATATCC CGTTAGAAGA ACCAGAAGTA AAAGTAATCC CAGATGACAA CCAGACGGAC
4081  AGTGGTATGG TTCTTGCCTC AGAAGAGCTG AAAACTTTGG AAGACAGAAC CAAATTATCT
4141  CCATCTTTTG GTGGAATGGT GCCCAGCAAA AGCAGGGAGT CTGTGGCATC TGAAGGCTCA
4201  AACCAGACAA GCGGCTACCA GTCCGGATAT CACTCCGATG ACACAGACAC CACCGTGTAC
4261  TCCAGTGAGG AAGCAGAACT TTTAAAGCTG ATAGAGATTG GAGTGCAAAC CGGTAGCACA
4321  GCCCAGATTC TCCAGCCTGA CTCGGGGACC ACACTGAGCT CTCCTCCTGT TTAAAAGGAA
4381  GCATCCACAC CCCAACTCCC GGACATCACA TGAGAGGTCT GCTCAGATTT TGAAGTGTTG
4441  TTCTTTCCAC CAGCAGGAAG TAGCCGCATT TGATTTTCAT TTCGACAACA GAAAAAGGAC
4501  CTCGGACTGC AGGGAGCCAG TCTTCTAGGC ATATCCTGGA AGAGGCTTGT GACCCAAGAA
4561  TGTGTCTGTG TCTTCTCCCA GTGTTGACCT GATCCTCTTT TTTCATTCAT TTAAAAAGCA
4621  TTATCATGCC CCTGCTGCGG GTCTCACCAT GGGTTTAGAA CAAAGAGCTT CAAGCAATGG
4681  CCCCATCCTC AAAGAAGTAG CAGTACCTGG GGAGCTGACA CTTCTGTAAA ACTAGAAGAT
4741  AAACCAGGCA ACGTAAGTGT TCGAGGTGTT GAAGATGGGA AGGATTTGCA GGGCTGAGTC
4801  TATCCAAGAG GCTTTGTTTA GGACGTGGGT CCCAAGCCAA GCCTTAAGTG TGGAATTCGG
4861  ATTGATAGAA AGGAAGACTA ACGTTACCTT GCTTTGGAGA GTACTGGAGC CTGCAAATGC
```

Figure 4(C) Cont.

```
4921  ATTGTGTTTG CTCTGCTCCA GGTGGGCATG GGGTCTGTTC TGAAATGTAA AGGGTTCAGA
4981  CGGGGTTTCT GGTTTTAGAA GGTTGCGTGT TCTTCGAGTT GGGCTAAAGT AGAGTTCGTT
5041  GTGCTGTTTC TGACTCCTAA TGAGAGTTCC TTCCAGACCG TTAGCTGTCT CCTTGCCAAG
5101  CCCCAGGAAG AAAATGATGC AGCTCTGGCT CCTTGTCTCC CAGGCTGATC CTTTATTCAG
5161  AATACCACAA AGAAAGGACA TTCAGCTCAA GGCTCCCTGC CGTGTTGAAG AGTTCTGACT
5221  GCACAAACCA GCTTCTGGTT TCTTCTGGAA TGAATACCCT CATATCTGTC CTGATGTGAT
5281  ATGTCTGAGA CTGAATGCGG GAGGTTCAAT GTGAAGCTGT GTGTGGTGTC AAAGTTTCAG
5341  GAAGGATTTT ACCCTTTTGT TCTTCCCCCT GTCCCAACC CACTCTCACC CCGCAACCCA
5401  TCAGTATTTT AGTTATTTGG CCTCTACTCC AGTAAACCTG ATTGGGTTTG TTCACTCTCT
5461  GAATGATTAT TAGCCAGACT TCAAAATTAT TTATAGCCC AAATTATAAC ATCTATTGTA
5521  TTATTTAGAC TTTTAACATA TAGAGCTATT TCTACTGATT TTTGCCCTTG TTCTGTCCTT
5581  TTTTTCAAAA AGAAAAATGT GTTTTTTGTT TGGTACCATA GTGTGAAATG CTGGGAACAA
5641  TGACTATAAG ACATGCTATG GCACATATAT TTATAGTCTG TTTATGTAGA AACAAATGTA
5701  ATATATTAAA GCCTTATATA TAATGAACTT TGTACTATTC ACATTTGTA TCAGTATTAT
5761  GTAGCATAAC AAAGGTCATA ATGCTTTCAG CAATTGATGT CATTTATTA AGAACATTG
5821  AAAAACTTGA
```

Figure 4(C) Cont.

Figure 4 (D) Sequence of VEGFR-2 (KDRJFlk-1) polypeptide (GenBank Accession No. AAB88005) (SEQ ID NO: 10)

```
   1  MQSKVLLAVA  LWLCVETRAA  SVGLPSVSLD  LPRLSIQKDI  LTIKANTTLQ  ITCRGQRDLD
  61  WLWPNNQSGS  EQRVEVTECS  DGLFCKTLTI  PKVIGNDTGA  YKCFYRETDL  ASVIYVYVQD
 121  YRSPFIASVS  DQHGVVYITE  NKNKTVVIPC  LGSISNLNVS  LCARYPEKRF  VPDGNRISWD
 181  SKKGFTIPSY  MISYAGMVFC  EAKINDESYQ  SIMYIVVVVG  YRIYDVVLSP  SHGIELSVGE
 241  KLVLNCTART  ELNVGIDFNW  EYPSSKHQHK  KLVNRDLKTQ  SGSEMKKFLS  TLTIDGVTRS
 301  DQGLYTCAAS  SGLMTKKNST  FVRVHEKPFV  AFGSGMESLV  EATVGERVRI  PAKYLGYPPP
 361  EIKWYKNGIP  LESNHTIKAG  HVLTIMEVSE  RDTGNYTVIL  TNPISKEKQS  HVVSLVVYVP
 421  PQIGEKSLIS  PVDSYQYGTT  QTLTCTVYAI  PPPHHIHWYW  QLEEECANEP  SQAVSVTNPY
 481  PCEEWRSVED  FQGGNKIEVN  KNQFALIEGK  NKTVSTLVIQ  AANVSALYKC  EAVNKVGRGE
 541  RVISFHVTRG  PEITLQPDMQ  PTEQESVSLW  CTADRSTFEN  LTWYKLGPQP  LPIHVGELPT
 601  PVCKNLDTLW  KLNATMFSNS  TNDILIMELK  NASLQDQGDY  VCLAQDRKTK  KRHCVVRQLT
 661  VLERVAPTIT  GNLENQTTSI  GESIEVSCTA  SGNPPPQIMW  FKDNETLVED  SGIVLKDGNR
 721  NLTIRRVRKE  DEGLYTCQAC  SVLGCAKVEA  FFIIEGAQEK  TNLEIIILVG  TAVIAMFFWL
 781  LLVIILRTVK  RANGGELKTG  YLSIVMDPDE  LPLDEHCERL  PYDASKWEFP  RDRLKLGKPL
 841  GRGAFGQVIE  ADAFGIDKTA  TCRTVAVKML  KEGATHSEHR  ALMSELKILI  HIGHHLNVVN
 901  LLGACTKPGG  PLMVIVEFCK  FGNLSTYLRS  KRNEFVPYKT  KGARFRQGKD  YVGAIPVDLK
 961  RRLDSITSSQ  SSASSGFVEE  KSLSDVEEEE  APEDLYKDFL  TLEHLICYSF  QVAKGMEFLA
1021  SRKCIHRDLA  ARNILLSEKN  VVKICDFGLA  RDIYKDPDYV  RKGDARLPLK  WMAPETIFDR
1081  VYTIQSDVWS  FGVLLWEIFS  LGASPYPGVK  IDEEFCRRLK  EGTRMRAPDY  TTPEMYQTML
1141  DCWHGEPSQR  PTFSELVEHL  GNLLQANAQQ  DGKDYIVLPI  SETLSMEEDS  GLSLPTSPVS
1201  CMEEEEVCDP  KFHYDNTAGI  SQYLQNSKRK  SRPVSVKTFE  DIPLEEPEVK  VIPDDNQTDS
1261  GMVLASEELK  TLEDRTKLSP  SFGGMVPSKS  RESVASEGSN  QTSGYQSGYH  SDDTDTTVYS
1321  SEEAELLKLI  EIGVQTGSTA  QILQPDSGTT  LSSPPV
```

Effect of PDGFRβ and VEGF signaling inhibitors on normal vasculature

The vasculature of control eyes was unaffected by administration of Gleevec, APB5, PEG or Macugen suggesting that blocking either PDGFRβ or VEGF signaling or both targets new and not established blood vessels.

Area of Choroidal Neovascularization following treatment with Gleevec and Macugen

Figure 12
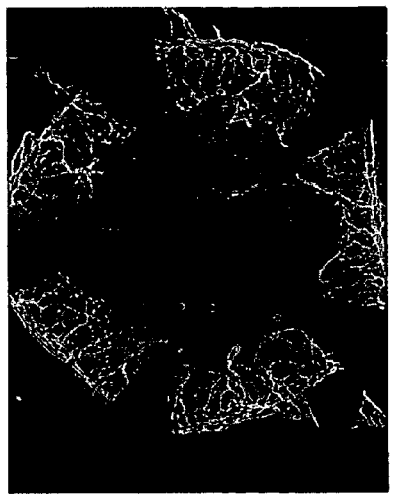
12 A: D20 Control
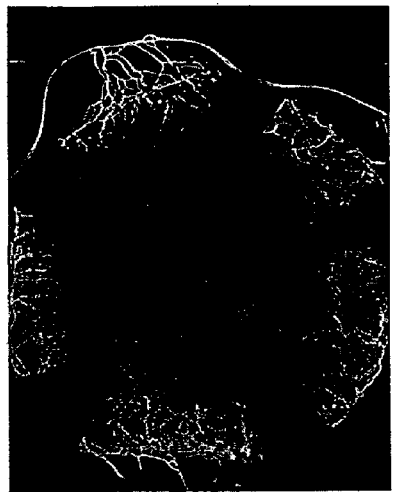
12 B: ARC-127
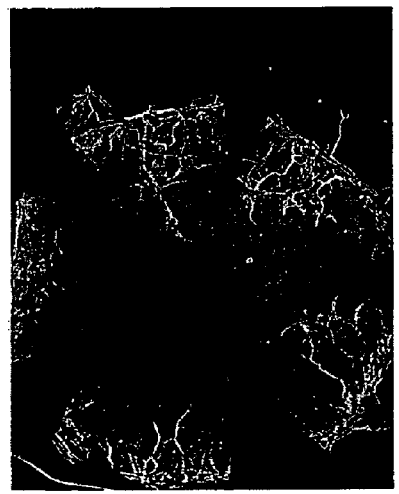
12 C: Macugen
12 D: Macugen + ARC-127

COMBINATION THERAPY FOR THE TREATMENT OF OCULAR NEOVASCULAR DISORDERS

RELATED APPLICATIONS

This application is a division of U.S. application Ser. No. 10/926,806 filed Aug. 26, 2004, now U.S. Pat. No. 7,759,472, which claims the benefit of U.S. Provisional Application Ser. No. 60/556,837, filed Mar. 26, 2004, each of which is hereby incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Mar. 1, 2012, is named OPHT_004_05US_SubSeqList.txt and is 95 Kilobytes in size.

FIELD OF THE INVENTION

This invention relates to the fields of opthalmology and medicine. More specifically, this invention relates to the treatment of neovascular disorders of the eye using a combination of agents that inhibit both platelet-derived growth factor (PDGF) and vascular endothelial growth factor (VEGF).

BACKGROUND OF THE INVENTION

Angiogenesis, also called neovascularization, involves the formation of sprouts from preexistent blood vessels and their invasion into surrounding tissue. A related process, vasculogenesis, involves the differentiation of endothelial cells and angioblasts that are already present throughout a tissue, and their subsequent linking together to form blood vessels.

Angiogenesis occurs extensively during development, and also occurs in the healthy body during wound healing in order to restore blood flow to tissues after injury or insult. Angiogenesis, however, has also been implicated in cancer and tumor formation. Indeed, the quantity of blood vessels in a tumor tissue is a strong negative prognostic indicator in breast cancer (Weidner et al., (1992) *J. Natl. Cancer Inst.* 84:1875-1887), prostate cancer (Weidner et al., (1993) *Am. J. Pathol.* 143:401-409), brain tumors (Li et al., (1994) *Lancet* 344:82-86), and melanoma (Foss et al., (1996) *Cancer Res.* 56:2900-2903). Angiogenesis has also recently been implicated in other disease states in many areas of medicine, including rheumatology, dermatology, cardiology and opthalmology. In particular, undesirable or pathological tissue-specific angiogenesis has been associated with certain specific disease states including rheumatoid arthritis, atherosclerosis, and psoriasis (see e.g., Fan et al., (1995) *Trends Pharmacol. Sci.* 16: 57; and Folkman (1995) *Nature Med.* 1: 27). Furthermore, the alteration of vascular permeability is thought to play a role in both normal and pathological physiological processes (Cullinan-Bove et al., (1993) *Endocrinol.* 133: 829; Senger et al., (1993) *Cancer and Metastasis Reviews* 12: 303). Although the angiogenic process in each of these diseases is likely to share many features with developmental angiogenesis and tumor angiogenesis, each may also have unique aspects conferred by the influence of surrounding cells.

Several ocular disorders involve alterations in angiogenesis. For example, diabetic retinopathy, the third leading cause of adult blindness (accounting for almost 7% of blindness in the USA), is associated with extensive angiogenic events. Nonproliferative retinopathy is accompanied by the selective loss of pericytes within the retina, and their loss results in dilation of associated capillaries dilation and a resulting increase in blood flow. In the dilated capillaries, endothelial cells proliferate and form outpouchings, which become microaneurysms, and the adjacent capillaries become blocked so that the area of retina surrounding these microaneurysms is not perfused. Eventually, shunt vessels appear between adjacent areas of micro aneurysms, and the clinical picture of early diabetic retinopathy with micro aneurysms and areas of nonperfused retina is seen. The microaneurysms leak and capillary vessels may bleed, causing exudates and hemorrhages. Once the initial stages of background diabetic retinopathy are established, the condition progresses over a period of years, developing into proliferative diabetic retinopathy and blindness in about 5% of cases. Proliferative diabetic retinopathy occurs when some areas of the retina continue losing their capillary vessels and become nonperfused, leading to the appearance of new vessels on the disk and elsewhere on the retina. These new blood vessels grow into the vitreous and bleed easily, leading to preretinal hemorrhages. In advanced proliferative diabetic retinopathy, a massive vitreous hemorrhage may fill a major portion of the vitreous cavity. In addition, the new vessels are accompanied by fibrous tissue proliferation that can lead to traction retinal detachment.

Diabetic retinopathy is associated primarily with the duration of diabetes mellitus; therefore, as the population ages and diabetic patients live longer, the prevalence of diabetic retinopathy will increase. Laser therapy is currently used in both nonproliferative and proliferative diabetic retinopathy. Focal laser treatment of the leaking microaneurysms surrounding the macular area reduces visual loss in 50% of patients with clinically significant macular edema. In proliferative diabetic retinopathy, panretinal photocoagulation results in several thousand tiny burns scattered throughout the retina (sparing the macular area); this treatment reduces the rate of blindness by 60 percent. Early treatment of macular edema and proliferative diabetic retinopathy prevents blindness for 5 years in 95% of patients, whereas late treatment prevents blindness in only 50 percent. Therefore, early diagnosis and treatment are essential.

Another ocular disorder involving neovascularization is age-related macular degeneration (AMD), a disease that affects approximately one in ten Americans over the age of 65. AMD is characterized by a series of pathologic changes in the macula, the central region of the retina, which is accompanied by decreased visual acuity, particularly affecting central vision. AMD involves the single layer of cells called the retinal pigment epithelium that lies immediately beneath the sensory retina. These cells nourish and support the portion of the retina in contact with them, i.e., the photoreceptor cells that contain the visual pigments. The retinal pigment epithelium lies on the Bruch membrane, a basement membrane complex which, in AMD, thickens and becomes sclerotic. New blood vessels may break through the Bruch membrane from the underlying choroid, which contains a rich vascular bed. These vessels may in turn leak fluid or bleed beneath the retinal pigment epithelium and also between the retinal pigment epithelium and the sensory retina. Subsequent fibrous scarring disrupts the nourishment of the photoreceptor cells and leads to their death, resulting in a loss of central visual acuity. This type of age-related maculopathy is called the "wet" type because of the leaking vessels and the subretinal edema or blood. The wet type accounts for only 10% of age-related maculopathy cases but results in 90% of cases of legal blindness from macular degeneration in the elderly. The "dry" type of age-related maculopathy involves disintegration of the retinal pigment epithelium along with loss of the overlying photoreceptor cells. The dry type reduces vision but usually only to levels of 20/50 to 20/100.

AMD is accompanied by distortion of central vision with objects appearing larger or smaller or straight lines appearing distorted, bent, or without a central segment. In the wet type of AMD, a small detachment of the sensory retina may be noted in the macular area, but the definitive diagnosis of a subretinal neovascular membrane requires fluorescein angiography. In the dry type, drusen may disturb the pigmentation pattern in the macular area. Drusen are excrescences of the basement membrane of the retinal pigment epithelium that protrude into the cells, causing them to bulge anteriorly; their role as a risk factor in age-related maculopathy is unclear. No treatment currently exists for the dry type of age-related maculopathy. Laser treatment is used in the wet type of age-related maculopathy and initially obliterates the neovascular membrane and prevents further visual loss in about 50% of patients at 18 months. By 60 months, however, only 20% still have a substantial benefit.

Multiple molecular mediators of angiogenesis have been identified including basic and acidic fibroblast growth factors (aFGF, bFGF), transforming growth factors alpha and beta (TGFα, TGFβ), platelet-derived growth factor (PDGF), angiogenin, platelet-derived endothelial cell growth factor (PD-ECGF), interleukin-8 (IL-8), and vascular endothelial growth factor (VEGF). Other stimulators implicated in angiogenesis include angiopoietin-1, Del-1, follistatin, granulocyte colony-stimulating factor (G-CSF), hepatocyte growth factor (HGF), leptin, midkine, placental growth factor, pleiotrophin (PTN), progranulin, proliferin, and tumor necrosis factor-alpha (TNF-alpha). In addition, control of angiogenesis is further mediated by a number of negative regulators of angiogenesis produced by the body including angioarrestin, ngiostatin (plasminogen fragment), antiangiogenic antithrombin III, cartilage-derived inhibitor (CDI), CD59 complement fragment, endostatin (collagen XVIII fragment), fibronectin fragment, gro-beta, heparinases, heparin hexasaccharide fragment, human chorionic gonadotropin (hCG), interferon alpha/beta/gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), retinoids, tetrahydrocortisol-S, thrombospondin-1 (TSP-1), vasculostatin, and vasostatin (calreticulin fragment).

Among these angiogenic regulators, VEGF appears to play a key role as a positive regulator of the abnormal angiogenesis accompanying tumor growth (reviewed in Brown et al., (1996) *Control of Angiogenesis* (Goldberg and Rosen, eds.) Birkhauser, Basel, and Thomas (1996) *J. Biol. Chem.* 271: 603-606). Furthermore, recently the role of the PDGF-B member of the PDGF family of signaling molecules has been under investigation, since it appears to play a role in the formation, expansion and proper function of perivascular cells, sometimes referred to as mural cells, e.g., vascular smooth muscle, mesangial cells, and pericytes.

While much has been learned about angiogenesis, or neovascularization, accompanying development, wound healing and tumor formation, it remains to be determined whether there are differences between these forms of angiogenesis and ocular angiogenesis. Significantly, while angiogenesis accompanying, e.g., collateral blood vessel formation in the heart, may be beneficial and adaptive to the organism, pathological ocular neovascularization accompany, e.g., AMD, has no known benefit and often leads to blindness (for review, see Campochiaro (2000) *J. Cell. Physiol.* 184: 301-10). Therefore, although advances in the understanding of the molecular events accompanying neovascularization have been made, there exists a need to utilize this understanding to develop further methods for treating neovascular diseases disorders, including ocular neovascular diseases and disorders such as the choroidal neovascularization that occurs with AMD and diabetic retinopathy.

SUMMARY OF THE INVENTION

It has been discovered that the combination of anti-VEGF and anti-PDGF agents surprisingly affords synergistic therapeutic benefits for treating an ocular neovascular disease.

Accordingly, the invention features a method for treating a patient diagnosed with or at risk for developing a neovascular disorder. This method includes administering to the patient an anti-VEGF agent and an anti-PDGF agent as a primary or adjunct therapeutic treatment.

In one aspect, the invention provides a method for suppressing a neovascular disorder in a patient in need thereof, by administering to the patient a PDGF antagonist and a VEGF antagonist, simultaneously, or within about 90 days of each other, in amounts sufficient to suppress the neovascular disorder in the patient.

In another aspect, the invention provides a method for treating a patient diagnosed with, or at risk for developing, a neovascular disorder in a patient in need thereof, by administering to the patient a PDGF antagonist and a VEGF antagonist, simultaneously or within 90 days of each other, in amounts sufficient to treat the patient.

In particular embodiments of these aspects, the method of the invention involves administering the PDGF antagonist and the VEGF antagonist within about 10 days of each other. In another embodiment of the method of the invention, the PDGF antagonist and the VEGF antagonist are administered within 5 days of each other. In yet another embodiment of the method of the invention, the PDGF antagonist and the VEGF antagonist are administered within about 24 hours of each other. In a particular embodiment of the method of the invention, the PDGF antagonist and said VEGF antagonist are administered simultaneously.

In another embodiment, the method of the invention involves administration of a PDGF antagonist that is a PDGF-B antagonist. In still another embodiment, the method of the invention involves administration of a VEGF antagonist that is a VEGF-A antagonist.

In certain embodiments, the method of the invention involves administration of a PDGF antagonist that is a nucleic acid molecule, an aptamer, an antisense RNA molecule, a ribozyme, an RNAi molecule, a protein, a peptide, a cyclic peptide, an antibody, a binding fragment of an antibody fragment, a sugar, a polymer, or a small organic compound. In another embodiment, the method of the invention involves administration of a VEGF antagonist that is a nucleic acid molecule, an aptamer, an antisense RNA molecule, a ribozyme, an RNAi molecule, a protein, a peptide, a cyclic peptide, an antibody, a binding fragment of an antibody fragment, a sugar, a polymer, or a small organic compound.

In a particular embodiment, the method of the invention involves administration of a VEGF antagonist that is an aptamer, such as an EYE001 aptamer. In another embodiment, the method of the invention involves administration of a VEGF antagonist that is an antibody or binding fragment thereof.

In a particular embodiment, the method of the invention involves administration of a PDGF antagonist that is an aptamer, an antibody or a binding fragment thereof. In another particular embodiment, the method of the invention involves administration of a PDGF antagonist that is an antisense oligonucleotide.

In yet another embodiment of this aspect of the invention, the PDGF antagonist and/or the VEGF antagonist are pro-drugs.

In one embodiment, the method of the invention provides a means for suppressing or treating an ocular neovascular disorder. In some embodiments, ocular neovascular disorders amenable to treatment or suppression by the method of the invention include ischemic retinopathy, iris neovascularization, intraocular neovascularization, age-related macular degeneration, corneal neovascularization, retinal neovascularization, choroidal neovascularization, diabetic retinal ischemia, or proliferative diabetic retinopathy. In still another embodiment, the method of the invention provides a means for suppressing or treating psoriasis or rheumatoid arthritis in a patient in need thereof or a patient diagnosed with or at risk for developing such a disorder.

The invention also provides a pharmaceutical composition that includes both a PDGF antagonist and a VEGF antagonist, as well a pharmaceutically acceptable carrier. In this aspect, the PDGF and VEGF antagonists are present both in amounts sufficient to suppress the neovascular disorder in the patient.

In one embodiment of this aspect, the pharmaceutical composition includes a PDGF antagonist that is a PDGF-B antagonist. In another embodiment, the pharmaceutical composition includes a VEGF antagonist that is a VEGF-A antagonist.

In certain embodiments, the pharmaceutical composition of the invention includes a PDGF antagonist that is a nucleic acid molecule, an aptamer, an antisense RNA molecule, a ribozyme, an RNAi molecule, a protein, a peptide, a cyclic peptide, an antibody, a binding fragment of an antibody fragment, a sugar, a polymer or a small organic compound. In another embodiment, the pharmaceutical composition of the invention includes a VEGF antagonist that is a nucleic acid molecule, an aptamer, an antisense RNA molecule, a ribozyme, an RNAi molecule, a protein, a peptide, a cyclic peptide, an antibody, a binding fragment of an antibody fragment, a sugar, a polymer, or a small organic compound.

In other particular embodiments, the pharmaceutical composition of the invention includes a VEGF antagonist that is an aptamer, such as an EYE001 aptamer. In one embodiment, the pharmaceutical composition of the invention includes a VEGF antagonist that is an antibody or binding fragment thereof.

In a particular embodiment, the pharmaceutical composition of the invention includes a PDGF antagonist that is an antibody or binding fragment thereof. In another particular embodiment, the pharmaceutical composition of the invention includes a PDGF antagonist that is an antisense oligonucleotide.

The pharmaceutical composition the invention may include a pharmaceutically acceptable carrier which includes a microsphere or a hydrogel formulation.

In yet another embodiment, the PDGF antagonist and/or the VEGF antagonist are pro-drugs.

In another embodiment, the pharmaceutical composition of the invention provides a means for suppressing or treating an ocular neovascular disorder. In some embodiments, ocular neovascular disorders amenable to treatment or suppression by the pharmaceutical composition of the invention include ischemic retinopathy, iris neovascularization, intraocular neovascularization, age-related macular degeneration, corneal neovascularization, retinal neovascularization, choroidal neovascularization, diabetic retinal ischemia, or proliferative diabetic retinopathy. In still other embodiments, the pharmaceutical composition of the invention provides a means for suppressing or treating psoriasis or rheumatoid arthritis in a patient in need thereof, or a patient diagnosed with or at risk for developing such a disorder.

The invention also provides a pharmaceutical pack that includes both a PDGF antagonist and a VEGF antagonist. In one embodiment of this aspect, the pharmaceutical pack includes a PDGF antagonist that is a PDGF-B antagonist. In another embodiment of this aspect, the pharmaceutical pack includes a VEGF antagonist that is a VEGF-A antagonist.

In another embodiment, the PDGF antagonist and VEGF antagonist of the pharmaceutical pack are formulated separately and in individual dosage amounts. In still another embodiment, the PDGF antagonist and VEGF antagonist of the pharmaceutical pack are formulated together.

In some particular embodiments, the pharmaceutical pack of the invention includes a VEGF antagonist that is an aptamer, such as an EYE001 aptamer. In other embodiments, the pharmaceutical pack of the invention includes a VEGF antagonist that is an antibody or binding fragment thereof.

In some embodiments, the pharmaceutical pack of the invention includes a PDGF antagonist that is an antibody or binding fragment thereof. In other particular embodiment, the pharmaceutical pack of the invention includes a PDGF antagonist that is an antisense oligonucleotide. In yet another embodiment of this aspect, the PDGF antagonist and/or the VEGF antagonist are pro-drugs.

BRIEF DESCRIPTION OF THE DRAWINGS

FIG. 1(A) is a schematic representation of the nucleic acid sequence of a human PDGF-B (GenBank Accession No. X02811) (SEQ ID NO: 1).

FIG. 1(B) is a schematic representation of the amino acid sequence of a human PDGF-B (GenBank Accession No. CAA26579) (SEQ ID NO: 2).

FIG. 1(C) is a schematic representation of the nucleic acid sequence of a human PDGF-A (GenBank Accession No. X06374) (SEQ ID NO: 11).

FIG. 1(D) is a schematic representation of the polypeptide sequence of a human PDGF-A (GenBank Accession No. CAA29677) (SEQ ID NO: 12).

FIG. 2(A) is a schematic representation of the nucleic acid sequence of a human VEGF (GenBank Accession No: NM_003376) (SEQ ID NO: 3).

FIG. 2(B) is a schematic representation of the amino acid sequence of a human VEGF polypeptide (GenBank Accession No. NP_003367) (SEQ ID NO: 4).

FIG. 3(A) is a schematic representation of the nucleic acid sequence of a human PDGFR-B (GenBank Accession No. NM_002609) (SEQ ID NO: 5).

FIG. 3(B) is a schematic representation of the polypeptide sequence of a human PDGFR-B (GenBank Accession No. NP_002600) (SEQ ID NO: 6).

FIG. 3(C) is a schematic representation of the nucleic acid sequence of a human PDGFR-A (GenBank Accession No. NM_006206) (SEQ ID NO: 13).

FIG. 3(D) is a schematic representation of the polypeptide sequence of a human PDGFR-A (GenBank Accession No. NP_006197) (SEQ ID NO: 14).

FIG. 4(A) is a schematic representation of the nucleic acid sequence of a human VEGFR-1 (Flt-1) (GenBank Accession No. AF063657) (SEQ ID NO: 7).

FIG. 4(B) is schematic a representation of the polypeptide sequence of a human VEGFR-1 (Flt-1) (GenBank Accession No.) (SEQ ID NO: 8).

FIG. 4(C) is a schematic representation of the nucleic acid sequence of a human VEGFR-2 (KDR/Flk-1) (GenBank Accession No. AF035121) (SEQ ID NO: 9).

FIG. 4(D) is a schematic representation of the polypeptide sequence of a human VEGFR-2 (KDR/Flk-1) (GenBank Accession No. AAB88005) (SEQ ID NO: 10).

FIG. 12(A) is a photographic representation of a fluorescent-microscopic image of corneal neovascularization occurring in control mouse cornea.

FIG. 12(B) is a photographic representation of a fluorescent-microscopic image of corneal neovascularization occurring in a ARC-127-treated mouse cornea.

FIG. 12(C) is a photographic representation of a fluorescent-microscopic image of corneal neovascularization occurring in a Macugen-treated mouse cornea.

FIG. 12(D) is a photographic representation of a fluorescent-microscopic image of corneal neovascularization occurring in a mouse cornea treated with both Macugen and ARC-127.

DETAILED DESCRIPTION OF THE INVENTION

Figure 5:
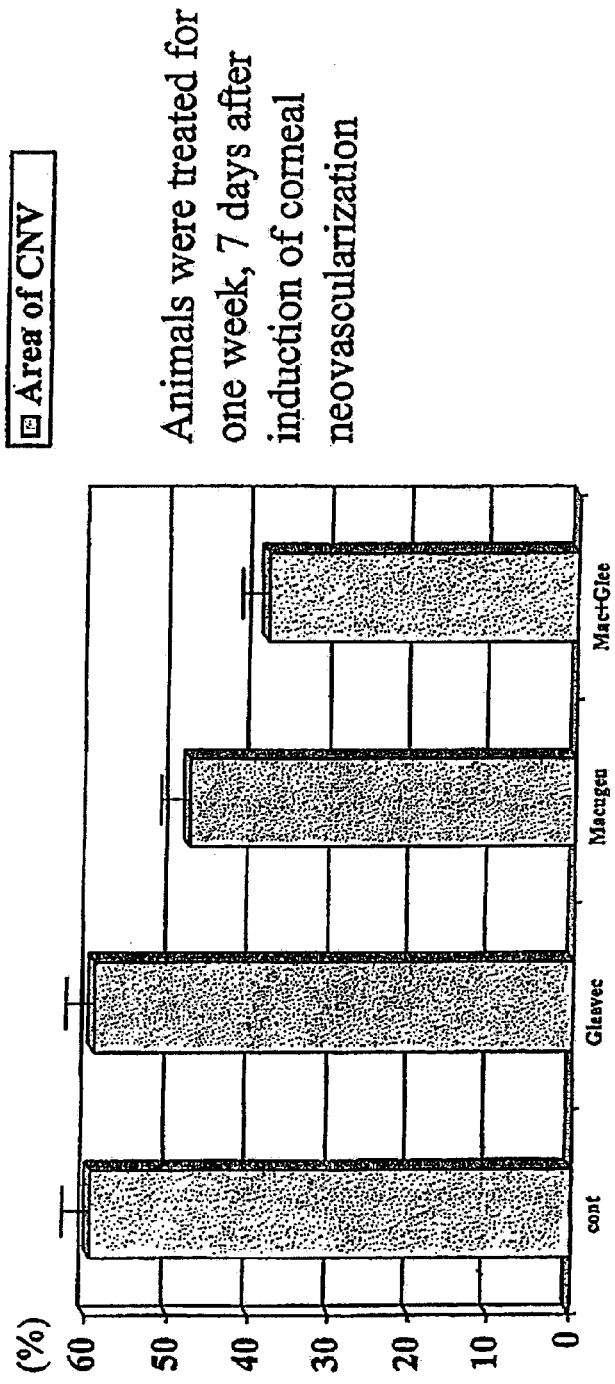
FIG. 5 is a graphical representation of the results of a corneal neovascularization assay comparing a control treatment (cont), Gleevec treatment (an anti-PDGF agent), and Macugen™ treatment (i.e. pegaptanib treatment, an anti-VEGF agent), to the results of a combination treatment with Macugen™ and Gleevec (anti-PDGF/anti-VEGF combination therapy).

All publications, patents, and patent applications mentioned in this specification are herein incorporated by reference.

Definitions

As used herein, the following terms and phrases shall have the meanings set forth below. Unless defined otherwise, all technical and scientific terms used herein have the same meaning as commonly understood to one of ordinary skill in the art to which this invention belongs.

By "antagonist" is meant an agent that inhibits, either partially or fully, the activity or production of a target molecule. In particular, the term "antagonist," as applied selectively herein, means an agent capable of decreasing levels of PDGF, PDGFR, VEGF or VEGFR gene expression, mRNA levels, protein levels or protein activity. Exemplary forms of antagonists include, for example, proteins, polypeptides, peptides (such as cyclic peptides), antibodies or antibody fragments, peptide mimetics, nucleic acid molecules, antisense molecules, ribozymes, aptamers, RNAi molecules, and small organic molecules. Exemplary non-limiting mechanisms of antagonist inhibition of the VEGF/VEGFR and PDGF/PDGFR ligand/receptor targets include repression of ligand synthesis and/or stability (e.g., using, antisense, ribozymes or RNAi compositions targeting the ligand gene/nucleic acid), blocking of binding of the ligand to its cognate receptor (e.g., using anti-ligand aptamers, antibodies or a soluble, decoy cognate receptor), repression of receptor synthesis and/or stability (e.g., using, antisense, ribozymes or RNAi compositions targeting the ligand receptor gene/nucleic acid), blocking of the binding of the receptor to its cognate receptor (e.g., using receptor antibodies) and blocking of the activation of the receptor by its cognate ligand (e.g., using receptor tyrosine kinase inhibitors). In addition, the antagonist may directly or indirectly inhibit the target molecule.

The term "antibody" as used herein is intended to include whole antibodies, e.g., of any isotype (IgG, IgA, IgM, IgE, etc.), and includes fragments thereof which recognize and are also specifically reactive with vertebrate (e.g., mammalian) protein, carbohydrates, etc. Antibodies can be fragmented using conventional techniques and the fragments screened for utility in the same manner as described above for whole antibodies. Thus, the term includes segments of proteolytically cleaved or recombinantly-prepared portions of an antibody molecule that are capable of selectively reacting with a certain protein. Non-limiting examples of such proteolytic and/or recombinant fragments include Fab, $F(ab')_2$, Fab', Fv, and single chain antibodies (scFv) containing a V[L] and/or V[H] domain joined by a peptide linker. The scFv's may be covalently or noncovalently linked to form antibodies having two or more binding sites. The subject invention includes polyclonal, monoclonal, or other purified preparations of antibodies and recombinant antibodies.

The term "aptamer," used herein interchangeably with the term "nucleic acid ligand," means a nucleic acid that, through its ability to adopt a specific three dimensional conformation, binds to and has an antagonizing (i.e., inhibitory) effect on a target. The target of the present invention is PDGF or VEGF (or one of their cognate receptors PDGFR or VEGFR), and hence the term PDGF aptamer or nucleic acid ligand or VEGF aptamer or nucleic acid ligand (or PDGFR aptamer or nucleic acid ligand or VEGFR aptamer or nucleic acid ligand) is used. Inhibition of the target by the aptamer may occur by binding of the target, by catalytically altering the target, by reacting with the target in a way which modifies/alters the target or the functional activity of the target, by covalently attaching to the target as in a suicide inhibitor, by facilitating the reaction between the target and another molecule. Aptamers may be comprised of multiple ribonucleotide units, deoxyribonucleotide units, or a mixture of both types of nucleotide residues. Aptamers may further comprise one or more modified bases, sugars or phosphate backbone units as described in further detail herein.

By "antibody antagonist" is meant an antibody molecule as herein defined which is able to block or significantly reduce one or more activities of a target PDGF or VEGF. For example, an VEGF inhibitory antibody may inhibit or reduce the ability of VEGF to stimulate angiogenesis.

A nucleotide sequence is "complementary" to another nucleotide sequence if each of the bases of the two sequences matches, i.e., are capable of forming Watson Crick base pairs. The term "complementary strand" is used herein interchangeably with the term "complement." The complement of a nucleic acid strand can be the complement of a coding strand or the complement of a non-coding strand.

The phrases "conserved residue" "or conservative amino acid substitution" refer to grouping of amino acids on the basis of certain common properties. A functional way to define common properties between individual amino acids is to analyze the normalized frequencies of amino acid changes between corresponding proteins of homologous organisms. According to such analyses, groups of amino acids may be defined where amino acids within a group exchange preferentially with each other, and therefore resemble each other most in their impact on the overall protein structure (Schulz, G. E. and R. H. Schirmer, *Principles of Protein Structure*, Springer-Verlag). Examples of amino acid groups defined in this manner include:

(i) a charged group, consisting of Glu and Asp, Lys, Arg and His,
(ii) a positively-charged group, consisting of Lys, Arg and His,
(iii) a negatively-charged group, consisting of Glu and Asp,
(iv) an aromatic group, consisting of Phe, Tyr and Trp,
(v) a nitrogen ring group, consisting of His and Trp,
(vi) a large aliphatic nonpolar group, consisting of Val, Leu and Ile,
(vii) a slightly-polar group, consisting of Met and Cys,
(viii) a small-residue group, consisting of Ser, Thr, Asp, Asn, Gly, Ala, Glu, Gln and Pro,
(ix) an aliphatic group consisting of Val, Leu, Ile, Met and Cys, and
(x) a small hydroxyl group consisting of Ser and Thr.

In addition to the groups presented above, each amino acid residue may form its own group, and the group formed by an individual amino acid may be referred to simply by the one and/or three letter abbreviation for that amino acid commonly used in the art.

The term "interact" as used herein is meant to include detectable relationships or association (e.g., biochemical interactions) between molecules, such as interaction between protein-protein, protein-nucleic acid, nucleic acid-nucleic acid, and protein-small molecule or nucleic acid-small molecule in nature.

The term "interacting protein" refers to protein capable of interacting, binding, and/or otherwise associating to a protein of interest, such as for example a PDGF or a VEGF protein, or their corresponding cognate receptors.

The term "isolated" as used herein with respect to nucleic acids, such as DNA or RNA, refers to molecules separated from other DNAs, or RNAs, respectively that are present in the natural source of the macromolecule. Similarly the term "isolated" as used herein with respect to polypeptides refers to protein molecules separated from other proteins that are present in the source of the polypeptide. The term isolated as used herein also refers to a nucleic acid or peptide that is substantially free of cellular material, viral material, or culture medium when produced by recombinant DNA techniques, or chemical precursors or other chemicals when chemically synthesized.

"Isolated nucleic acid" is meant to include nucleic acid fragments, which are not naturally occurring as fragments and would not be found in the natural state. The term "isolated" is also used herein to refer to polypeptides, which are isolated from other cellular proteins and is meant to encompass both purified and recombinant polypeptides.

As used herein, the terms "label" and "detectable label" refer to a molecule capable of detection, including, but not limited to, radioactive isotopes, fluorophores, chemiluminescent moieties, enzymes, enzyme substrates, enzyme cofactors, enzyme inhibitors, dyes, metal ions, ligands (e.g., biotin or haptens) and the like. The term "fluorescer" refers to a substance or a portion thereof, which is capable of exhibiting fluorescence in the detectable range. Particular examples of labels which may be used under the invention include fluorescein, rhodamine, dansyl, umbelliferone, Texas red, luminol, NADPH, alpha-beta-galactosidase and horseradish peroxidase.

The "level of expression of a gene in a cell" refers to the level of mRNA, as well as pre-mRNA nascent transcript(s), transcript processing intermediates, mature mRNA(s) and degradation products, encoded by the gene in the cell, as well as the level of protein translated from that gene.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides, ESTs, chromosomes, cDNAs, mRNAs, and rRNAs are representative examples of molecules that may be referred to as nucleic acids.

The term "oligonucleotide" refers to an oligomer or polymer of nucleotide or nucleoside monomers consisting of naturally occurring bases, sugars and intersugar (backbone) linkages. The term also includes modified or substituted oligomers comprising non-naturally occurring monomers or portions thereof, which function similarly. Incorporation of substituted oligomers is based on factors including enhanced cellular uptake, or increased nuclease resistance and are chosen as is known in the art. The entire oligonucleotide or only portions thereof may contain the substituted oligomers.

The term "percent identical" refers to sequence identity between two amino acid sequences or between two nucleotide sequences. Identity can each be determined by comparing a position in each sequence, which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Various alignment algorithms and/or programs may be used, including Hidden Markov Model (HMM), FASTA and BLAST. HNiM, FASTA and BLAST are available through the National Center for Biotechnology Information, National Library of Medicine, National Institutes of Health, Bethesda, Md. and the European Bioinformatic Institute EBI. In one embodiment, the percent identity of two sequences that can be determined by these GCG programs with a gap weight of 1, e.g., each amino acid gap is weighted as if it were a single amino acid or nucleotide mismatch between the two sequences. Other techniques for alignment are described in *Methods in Enzymology*, vol. 266: *Computer Methods for Macromolecular Sequence Analysis* (1996), ed. Doolittle, Academic Press, Inc., a division of Harcourt Brace & Co., San Diego, Calif., USA. Where desirable, an alignment program that permits gaps in the sequence is utilized to align the sequences. The Smith Waterman is one type of algorithm that permits gaps in sequence alignments (see (1997) *Meth. Mol. Biol*. 70: 173-187). Also, the GAP program using the Needleman and Wunsch alignment method can be utilized to align sequences. More techniques and algorithms including use of the HMM are described in *Sequence Structure and Databanks: A Practical Approach* (2000), ed. Oxford University Press, Incorporated and in *Bioinformatics: Databases and Systems* (1999) ed. Kluwer Academic Publishers. An alternative search strategy uses MPSRCH software, which runs on a MASPAR computer. MPSRCH uses a Smith-Watermnan algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases. Databases with individual sequences are described in *Methods in Enzymology*, ed. Doolittle, supra. Databases include Genbank, EMBL, and DNA Database of Japan (DDBJ).

"Perfectly matched" in reference to a duplex means that the poly- or oligonucleotide strands making up the duplex form a double stranded structure with one other such that every nucleotide in each strand undergoes Watson-Crick basepairing with a nucleotide in the other strand. The term also comprehends the pairing of nucleoside analogs, such as deoxyinosine, nucleosides with 2-aminopurine bases, and the like, that may be employed. A mismatch in a duplex between a target polynucleotide and an oligonucleotide or polynucleotide means that a pair of nucleotides in the duplex fails to undergo Watson-Crick bonding. In reference to a triplex, the term means that the triplex consists of a perfectly matched duplex and a third strand in which every nucleotide undergoes Hoogsteen or reverse Hoogsteen association with a base pair of the perfectly matched duplex.

The term "RNA interference," "RNAi," or "siRNA" all refer to any method by which expression of a gene or gene product is decreased by introducing into a target cell one or more double-stranded RNAs, which are homologous to the gene of interest (particularly to the messenger RNA of the gene of interest, e.g., PDGF or VEGF).

Polymorphic variants also may encompass "single nucleotide polymorphisms" (SNPs) in which the polynucleotide sequence varies by one base (e.g., a one base variation in PDGF or VEGF). The presence of SNPs may be indicative of, for example, a certain population, a disease state, or a propensity for a disease state.

The "profile" of an aberrant, e.g., tumor cell's biological state refers to the levels of various constituents of a cell that change in response to the disease state. Constituents of a cell include levels of RNA, levels of protein abundances, or protein activity levels.

The term "protein" is used interchangeably herein with the terms "peptide" and "polypeptide." The term "recombinant protein" refers to a protein of the present invention which is produced by recombinant DNA techniques, wherein generally DNA encoding the expressed protein or RNA is inserted into a suitable expression vector which is in turn used to transform a host cell to produce the heterologous protein or RNA. Moreover, the phrase "derived from," with respect to a recombinant gene encoding the recombinant protein is meant to include within the meaning of "recombinant protein" those proteins having an amino acid sequence of a native protein, or an amino acid sequence similar thereto which is generated by mutations, including substitutions and deletions, of a naturally occurring protein.

As used herein, the term "transgene" means a nucleic acid sequence (encoding, e.g., one of the target nucleic acids, or an antisense transcript thereto), which has been introduced into a cell. A transgene could be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can also be present in a cell in the form of an episome. A transgene can include one or more transcriptional regulatory sequences and any other nucleic acid, such as introns, that may be necessary for optimal expression of a selected nucleic acid.

By "neovascular disorder" is meant a disorder characterized by altered or unregulated angiogenesis other than one accompanying oncogenic or neoplastic transformation, i.e., cancer. Examples of neovascular disorders include psoriasis, rheumatoid arthritis, and ocular neovascular disorders including diabetic retinopathy and age-related macular degeneration.

As used herein, the terms "neovascularization" and "angiogenesis" are used interchangeably. Neovascularization and angiogenesis refer to the generation of new blood vessels into cells, tissue, or organs. The control of angiogenesis is typically altered in certain disease states and, in many cases, the pathological damage associated with the disease is related to altered, unregulated, or uncontrolled angiogenesis. Persistent, unregulated angiogenesis occurs in a multiplicity of disease states, including those characterized by the abnormal growth by endothelial cells, and supports the pathological damage seen in these conditions including leakage and permeability of blood vessels.

By "ocular neovascular disorder" is meant a disorder characterized by altered or unregulated angiogenesis in the eye of a patient. Exemplary ocular neovascular disorders include optic disc neovascularization, iris neovascularization, retinal neovascularization, choroidal neovascularization, corneal neovascularization, vitreal neovascularization, glaucoma, pannus, pterygium, macular edema, diabetic retinopathy, diabetic macular edema, vascular retinopathy, retinal degeneration, uveitis, inflammatory diseases of the retina, and proliferative vitreoretinopathy.

The term "treating" a neovascular disease in a subject or "treating" a subject having a neovascular disease refers to subjecting the subject to a pharmaceutical treatment, e.g., the administration of a drug, such that at least one symptom of the neovascular disease is decreased. Accordingly, the term "treating" as used herein is intended to encompass curing as well as ameliorating at least one symptom of the neovascular condition or disease. Accordingly, "treating" as used herein, includes administering or prescribing a pharmaceutical composition for the treatment or prevention of an ocular neovascular disorder.

By "patient" is meant any animal. The term "animal" includes mammals, including, but is not limited to, humans and other primates. The term also includes domesticated animals, such as cows, hogs, sheep, horses, dogs, and cats.

By "PDGF" or "platelet-derived growth factor" is meant a mammalian platelet-derived growth factor that affects angiogenesis or an angiogenic process. As used herein, the term "PDGF" includes the various subtypes of PDGF including PDGF-B (see FIGS. 1(A) and (B)), and PDGF-A (see FIGS. 1(C) and (D)). Further, as used herein, the term "PDGF" refers to PDGF-related angiogenic factors such as PDGF-C and PDGF-D that act through a cognate PDGF receptor to stimulate angiogenesis or an angiogenic process. In particular, the term "PDGF" means any member of the class of growth factors that (i) bind to a PDGF receptor such as PDGFR-B (see FIGS. 3(A) and (B)), or PDGFR-A (see FIGS. 3(C) and (D)); (ii) activates a tyrosine kinase activity associated with the VEGF receptor; and (iii) thereby affects angiogenesis or an angiogenic process. As used herein, the term "PDGF" generally refers to those members of the class of growth factors that induce DNA synthesis and mitogenesis through the binding and activation of a platelet-derived growth factor cell surface receptor (i.e., PDGFR) on a responsive cell type. PDGFs effect specific biological effects including, for example: directed cell migration (chemotaxis) and cell activation; phospholipase activation; increased phosphatidylinositol turnover and prostaglandin metabolism; stimulation of both collagen and collagenase synthesis by responsive cells; alteration of cellular metabolic activities, including matrix synthesis, cytokine production, and lipoprotein uptake; induction, indirectly, of a proliferative response in cells lacking PDGF receptors; and potent vasoconstrictor activity. The term "PDGF" is meant to include both a "PDGF" polypeptide and its corresponding "PDGF" encoding gene or nucleic acid.

By "PDGF-A" is meant an A chain polypeptide of PDGF and its corresponding encoding gene or nucleic acid.

By "PDGF-B" is meant a B chain polypeptide of PDGF and its corresponding encoding gene or nucleic acid.

By "VEGF," or "vascular endothelial growth factor," is meant a mammalian vascular endothelial growth factor that affects angiogenesis or an angiogenic process. As used herein, the term "VEGF" includes the various subtypes of VEGF (also known as vascular permeability factor (VPF) and VEGF-A) (see FIGS. 2(A) and (B)) that arise by, e.g., alternative splicing of the VEGF-A/VPF gene including $VEGF_{121}$, $VEGF_{165}$ and $VEGF_{189}$. Further, as used herein, the term "VEGF" refers to VEGF-related angiogenic factors such as PlGF (placenta growth factor), VEGF-B, VEGF-C, VEGF-D and VEGF-E that act through a cognate VEFG receptor to stimulate angiogenesis or an angiogenic process. In particular, the term "VEGF" means any member of the class of growth factors that (i) bind to a VEGF receptor such as VEGFR-1 (Flt-1) (see FIGS. 4(A) and (B)), VEGFR-2 (KDR/Flk-1) (see FIGS. 4(C) and (D)), or VEGFR-3 (FLT-4); (ii) activates a tyrosine kinase activity associated with the VEGF receptor; and (iii) thereby affects angiogenesis or an angiogenic process. The term "VEGF" is meant to include both a "VEGF" polypeptide and its corresponding "VEGF" encoding gene or nucleic acid.

By "PDGF antagonist" is meant an agent that reduces, or inhibits, either partially or fully, the activity or production of a PDGF. A PDGF antagonist may directly or indirectly reduce or inhibit a specific PDGF such as PDGF-B. Furthermore, "PDGF antagonists" consistent with the above definition of "antagonist," may include agents that act on either a PDGF ligand or its cognate receptor so as to reduce or inhibit a PDGF-associated receptor signal. Examples of such "PDGF antagonists" thus include, for example: antisense, ribozymes or RNAi compositions targeting a PDGF nucleic acid; anti-PDGF aptamers, anti-PDGF antibodies or soluble PDGF receptor decoys that prevent binding of a PDGF to its cognate receptor; antisense, ribozymes or RNAi compositions targeting a cognate PDGF receptor (PDGFR) nucleic acid; anti-PDGFR aptamers or anti-PDGFR antibodies that bind to a cognate PDGFR receptor; and PDGFR tyrosine kinase inhibitors.

By "VEGF antagonist" is meant an agent that reduces, or inhibits, either partially or fully, the activity or production of a VEGF. A VEGF antagonist may directly or indirectly reduce or inhibit a specific VEGF such as $VEGF_{165}$. Furthermore, "VEGF antagonists" consistent with the above definition of "antagonist," may include agents that act on either a VEGF ligand or its cognate receptor so as to reduce or inhibit a VEGF-associated receptor signal. Examples of such "VEGF antagonists" thus include, for example: antisense, ribozymes or RNAi compositions targeting a VEGF nucleic acid; anti-VEGF aptamers, anti-VEGF antibodies or soluble VEGF receptor decoys that prevent binding of a VEGF to its cognate receptor; antisense, ribozymes, or RNAi compositions targeting a cognate VEGF receptor (VEGFR) nucleic acid; anti-VEGFR aptamers or anti-VEGFR antibodies that bind to a cognate VEGFR receptor; and VEGFR tyrosine kinase inhibitors.

By "an amount sufficient to suppress a neovascular disorder" is meant the effective amount of an antagonist, in a combination of the invention, required to treat or prevent a neovascular disorder or symptom thereof. The "effective amount" of active antagonists used to practice the present invention for therapeutic treatment of conditions caused by or contributing to the neovascular disorder varies depending upon the manner of administration, anatomical location of the neovascular disorder, the age, body weight, and general health of the patient. Ultimately, a physician or veterinarian will decide the appropriate amount and dosage regimen. Such amount is referred to as an amount sufficient to suppress a neovascular disorder.

Other features and advantages of the invention will be apparent from the following detailed description, and from the claims.

A "variant" of polypeptide X refers to a polypeptide having the amino acid sequence of peptide X in which is altered in one or more amino acid residues. The variant may have "conservative" changes, wherein a substituted amino acid has similar structural or chemical properties (e.g., replacement of leucine, with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR).

The term "variant," when used in the context of a polynucleotide sequence, may encompass a polynucleotide sequence related to that of gene or the coding sequence thereof. This definition may also include, for example, "allelic," "splice," "species," or "polymorphic" variants. A splice variant may have significant identity to a reference molecule, but will generally have a greater or lesser number of polynucleotides due to alternative splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species.

The term "vector" refers to a nucleic acid molecule capable of transporting another nucleic acid to which it has been linked. One type of useful vector is an episome, i.e., a nucleic acid capable of extra-chromosomal replication. Useful vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

Combination Therapy

The invention is based, in part, upon the specific inhibition of both VEGF and PDGF activities using appropriate growth factor antagonists as a potent treatment for patients having a neovascular disorder. The administration of a combination of a PDGF antagonist and a VEGF antagonist affords greater therapeutic benefits for treating an ocular neovascular disorder than either antagonist administered alone. The combined action of anti-VEGF and anti-PDGF agents is unexpected in light of studies evidencing no apparent cooperation between the two factors in stimulating angiogenesis in a retinal endothelial cell system (see Castellon et al., (2001) Exp. Eye Res. 74: 523-35).

PDGF and VEGF are important stimuli for the growth of new blood vessels throughout the body, especially in the eye. Combination therapy directed at inhibiting both PDGF and VEGF biological activities provides a method for treating or preventing the neovascular disorder.

Accordingly, the invention features methods and compositions for suppressing a neovascular disorder using combination therapy. In particular, the present invention utilizes two distinct intercellular communication signaling pathways operative in vascular cells, namely PDGF and VEGF signaling, as therapeutic targets in the treatment of a neovascular disorder, such as an ocular neovascular disorder. This combination method is especially useful for treating any number of ophthamalogical diseases and disorders marked by the development of ocular neovascularization, including, but not limited to, optic disc neovascularization, iris neovascularization, retinal neovascularization, choroidal neovascularization, corneal neovascularization, vitreal neovascularization, glaucoma, pannus, pterygium, macular edema, diabetic macular edema, vascular retinopathy, retinal degeneration, macular degeneration, uveitis, inflammatory diseases of the retina, and proliferative vitreoretinopathy. The combination therapy, consisting of antagonists that inhibit PDGF (such as PDGF-B) and VEGF (such as VEGF-A) signaling results in an increased treatment efficacy compared to either of the two therapies being used independently. While the examples discussed below describe the combination of a single PDGF antagonist and a single VEGF antagonist, it is understood that the combination of multiple antagonistic agents may be desirable.

Anti-PDGF and anti-VEGF combination therapy according to the invention may be performed alone or in conjunction with another therapy and may be provided at home, the doctor's office, a clinic, a hospital's outpatient department, or a hospital. Treatment generally begins at a hospital so that the doctor can observe the therapy's effects closely and make any adjustments that are needed. The duration of the combination therapy depends on the type of neovascular disorder being treated, the age and condition of the patient, the stage and type of the patient's disease, and how the patient responds to the treatment. Additionally, a person having a greater risk of developing a neovascular disorder (e.g., a diabetic patient) may receive treatment to inhibit or delay the onset of symptoms. One significant advantage provided by the present invention is that the combination of a PDGF antagonist and a VEGF antagonist for the treatment of a neovascular disorder allows for the administration of a low dose of each antagonist and less total active antagonist, thus providing similar efficacy with less toxicity and side effects, and reduced costs.

The dosage and frequency of administration of each component of the combination can be controlled independently. For example, one antagonist may be administered three times per day, while the second antagonist may be administered once per day. Combination therapy may be given in on-and-off cycles that include rest periods so that the patient's body has a chance to recover from any as yet unforeseen side-effects. The antagonists may also be formulated together such that one administration delivers both antagonists.

PDGF and VEGF Antagonist Targets

PDGF was originally isolated from platelet lysates and identified as the major growth-promoting activity present in serum but not in plasma. The mitogenic activity of PDGF was first shown to act on connective tissue cells, such as fibroblasts and smooth muscle cells, and in glial cells in culture. Two homologous PDGF isoforms have been identified, PDGF A and B, which are encoded by separate genes (on chromosomes 7 and 22). The most abundant species from platelets is the AB heterodimer, although all three possible dimers (AA, AB and BB) occur naturally. Following translation, PDGF dimers are processed into approximately 30 kDa secreted proteins.

Two cell surface proteins that bind PDGF with high affinity have been identified, alpha. and beta. (Heldin et al., (1981) *Proc. Natl. Acad. Sci.* (USA) 78: 3664; Williams et al., (1981) *Proc. Natl. Acad. Sci.* (USA) 79: 5867). Both species contain five immunoglobulin-like extracellular domains, a single transmembrane domain and an intracellular tyrosine kinase domain separated by a kinase insert domain. In the last several years, the specificities of the three PDGF isoforms for the three receptor dimers (alpha/alpha, alpha/beta, and beta/beta.) have been elucidated. The alpha-receptor homodimer binds all three PDGF isoforms with high affinity, the beta-receptor homodimer binds only PDGF BB with high affinity and PDGF AB with approximately 10-fold lower affinity, and the alpha/beta.-receptor heterodimer binds PDGF BB and PDGF AB with high affinity (Westermark & Heldin (1993) *Acta Oncologica* 32:101). The specificity pattern appears to result from the ability of the A-chain to bind only to the alpha-receptor and of the B-chain to bind to both alpha and beta-receptor subunits with high affinity.

In general, the invention provides for agents that inhibit one or more PDGF activities. These PDGF-inhibitory agents, or PDGF antagonists may act on one or more forms of the PDGF ligand. Platelet derived growth factors includes homo- or heterodimers of A-chain (PDGF-A) and B-chain (PDGF-B) that exert their action via binding to and dimerization of two related receptor tyrosine kinases, [alpha]-receptors (PDGFR-[alpha]) and [beta]-receptors (PDGFR-[beta]. In addition, PDGF-C and PDGF-D, two new protease-activated ligands for the PDGFR complexes, have been identified (see Li et al., (2000) *Nat. Cell. Biol.* 2: 302-9; Bergsten et al., (2001) *Nat. Cell. Biol.* 3: 512-6; and Uutele et al., (2001) *Circulation* 103: 2242-47). Due to the different ligand binding specificities of the PDGFRs it is known that PDGFR-[alpha][alpha] binds PDGF-AA, PDGF-BB, PDGF-AB, and PDGF-CC; PDGFR-[beta][beta] binds PDGF-BB and PDGF-DD; whereas PDGFR-[alpha][beta] binds PDGF-AB, PDGF-BB, PDGF-CC, and PDGF-DD (see Betsholtz et al., (2001) *BioEssays* 23: 494-507).

VEGF is a secreted disulfide-linked homodimer that selectively stimulates endothelial cells to proliferate, migrate, and produce matrix-degrading enzymes (Conn et al., (1990) *Proc. Natl. Acad. Sci.* (USA) 87:1323-1327); Ferrara and Henzel (1989) *Biochem. Biophys. Res. Commun.* 161: 851-858); Pepper et al., (1991) *Biochem. Biophys. Res. Commun.* 181: 902-906; Unemori et al., (1992) *J. Cell. Physiol.* 153:557-562), all of which are processes required for the formation of new vessels. VEGF occurs in four forms (VEGF-121, VEGF-165, VEGF-189, VEGF-206) as a result of alternative splicing of the VEGF gene (Houck et al., (1991) *Mol. Endocrinol.* 5:1806-1814; Tischer et al., (1991) *J. Biol. Chem.* 266:11947-11954). The two smaller forms are diffusible whereas the larger two forms remain predominantly localized to the cell membrane as a consequence of their high affinity for heparin. VEGF-165 also binds to heparin and is the most abundant form. VEGF-121, the only form that does not bind to heparin, appears to have a lower affinity for VEGF receptors (Gitay-Goren et al., (1996) *J. Biol. Chem.* 271:5519-5523) as well as lower mitogenic potency (Keyt et al., (1996) *J. Biol. Chem.* 271:7788-7795). The biological effects of VEGF are mediated by two tyrosine kinase receptors (Flt-1 and Flk-1/KDR) whose expression is highly restricted to cells of endothelial origin (de Vries et al., (1992) *Science* 255:989-991; Millauer et al., (1993) *Cell* 72:835-846; Terman et al., (1991) *Oncogene* 6:519-524). While the expression of both functional receptors is required for high affinity binding, the chemotactic and mitogenic signaling in endothelial cells appears to occur primarily through the KDR receptor (Park et al., (1994) *J. Biol. Chem.* 269:25646-25654; Seetharam et al., (1995) *Oncogene* 10:135-147; Waltenberger et al., (1994) *J. Biol. Chem.* 26988-26995). The importance of VEGF and VEGF receptors for the development of blood vessels has recently been demonstrated in mice lacking a single allele for the VEGF gene (Carmeliet et al., (1996) *Nature* 380:435-439; Ferrara et al., (1996) *Nature* 380:439-442) or both alleles of the Flt-1 (Fong et al., (1995) *Nature* 376:66-70) or Flk-1 genes (Shalaby et al., (1995) *Nature* 376:62-66). In each case, distinct abnormalities in vessel formation were observed resulting in embryonic lethality.

Compensatory angiogenesis induced by tissue hypoxia is now known to be mediated by VEGF (Levy et al., (1996) *J. Biol. Chem.* 2746-2753); Shweiki et al., (1992) *Nature* 359: 843-845). Studies in humans have shown that high concentrations of VEGF are present in the vitreous in angiogenic retinal disorders but not in inactive or non-neovascularization disease states. Human choroidal tissue excised after experimental submacular surgery have also shown high VEGF levels.

In addition to being the only known endothelial cell specific mitogen, VEGF is unique among angiogenic growth factors in its ability to induce a transient increase in blood vessel permeability to macromolecules (hence its original and alternative name, vascular permeability factor, VPF) (see Dvorak et al., (1979) *J. Immunol.* 122:166-174; Senger et al., (1983) *Science* 219:983-985; Senger et al., (1986) *Cancer Res.* 46:5629-5632). Increased vascular permeability and the resulting deposition of plasma proteins in the extravascular space assists the new vessel formation by providing a provisional matrix for the migration of endothelial cells (Dvorak et al., (1995) *Am. J. Pathol.* 146:1029-1039). Hyperpermeability is indeed a characteristic feature of new vessels, including those associated with tumors.

PDGF and VEGF Antagonists

General

The invention provides antagonists (i.e., inhibitors) of PDGF and VEGF for use together in combination therapy for neovascular disorders. Specific PDGF antagonists and VEGF antagonists are known in the art and are described briefly in the sections that follow. Still other PDGF antagonists and VEGF antagonists that are now, or that have become, available to the skilled artisan include the antibodies, aptamers, antisense oligomers, ribozymes, and RNAi compositions that may be identified and produced using practices that are routine in the art in conjunction with the teachings and guidance of the specification, including the further-provided sections appearing below.

PDGF Antagonists

Generally, inhibition of PDGF (for example, PDGF-B) may be accomplished in a variety of ways. For example, a variety of PDGF antagonists that inhibit the activity or production of PDGF are available and can be used in the methods of the present invention. Exemplary PDGF antagonists include nucleic acid ligands or aptamers of PDGF, such as those described below. Alternatively, the PDGF antagonist may be, for example, an anti-PDGF antibody or antibody fragment. Accordingly, the PDGF molecule is rendered inactive by inhibiting its binding to a receptor. In addition, nucleic acid molecules such as antisense RNA, ribozymes, and RNAi molecules that inhibit PDGF expression at the nucleic acid level are useful as antagonists in the invention. Other PDGF antagonists include peptides, proteins, cyclic peptides, or small organic compounds. Furthermore, the signaling activity of PDGF may be inhibited by disrupting its downstream signaling, for example, by using a number of small molecule tyrosine kinase inhibitory antagonists including those described below. The ability of a compound or agent to serve as a PDGF antagonist may be determined according to the methods known in art and, further, as set forth in, e.g., Dai et al., (2001) *Genes & Dev.* 15: 1913-25; Zippel, et al., (1989) *Eur. J. Cell Biol.* 50(2):428-34; and Zwiller, et al., (1991) *Oncogene* 6: 219-21.

The invention further includes PDGF antagonists known in the art as well as those supported below and any and all equivalents that are within the scope of ordinary skill to create. For example, inhibitory antibodies directed against PDGF are known in the art, e.g., those described in U.S. Pat. Nos. 5,976,534, 5,833,986, 5,817,310, 5,882,644, 5,662,904, 5,620,687, 5,468,468, and PCT WO 2003/025019, the contents of which are incorporated by reference in their entirety. In addition, the invention include N-phenyl-2-pyrimidine-amine derivatives that are PDGF antagonists, such as those disclosed in U.S. Pat. No. 5,521,184, as well as WO2003/013541, WO2003/078404, WO2003/099771, WO2003/015282, and WO2004/05282 which are hereby incorporated in their entirety by reference.

Small molecules that block the action of PDGF are known in the art, e.g., those described in U.S. Pat. No. 6,528,526 (PDGFR tyrosine kinase inhibitors), U.S. Pat. No. 6,524,347 (PDGFR tyrosine kinase inhibitors), U.S. Pat. No. 6,482,834 (PDGFR tyrosine kinase inhibitors), U.S. Pat. No. 6,472,391 (PDGFR tyrosine kinase inhibitors), U.S. Pat. Nos. 6,696,434, 6,331,555, 6,251,905, 6,245,760, 6,207,667, 5,990,141, 5,700,822, 5,618,837 and 5,731,326, the contents of which are incorporated by reference in their entirety.

Proteins and polypeptides that block the action of PDGF are known in the art, e.g., those described in U.S. Pat. No. 6,350,731 (PDGF peptide analogs), U.S. Pat. No. 5,952,304, the contents of which are incorporated by reference in their entirety.

Bis mono- and bicyclic aryl and heteroaryl compounds which inhibit EGF and/or PDGF receptor tyrosine kinase are known in the art, e.g., those described in, e.g. U.S. Pat. Nos. 5,476,851, 5,480,883, 5,656,643, 5,795,889, and 6,057,320, the contents of which are incorporated by reference in their entirety.

Antisense oligonucleotides for the inhibition of PDGF are known in the art, e.g., those described in U.S. Pat. Nos. 5,869,462, and 5,821,234, the contents of each of which are incorporated by reference in their entirety.

Aptamers (also known as nucleic acid ligands) for the inhibition of PDGF are known in the art, e.g., those described in, e.g., U.S. Pat. Nos. 6,582,918, 6,229,002, 6,207,816, 5,668,264, 5,674,685, and 5,723,594, the contents of each of which are incorporated by reference in their entirety.

Other compounds for inhibiting PDGF known in the art include those described in U.S. Pat. Nos. 5,238,950, 5,418,135, 5,674,892, 5,693,610, 5,700,822, 5,700,823, 5,728,726, 5,795,910, 5,817,310, 5,872,218, 5,932,580, 5,932,602, 5,958,959, 5,990,141, 6,358,954, 6,537,988 and 6,673,798, the contents of each of which are incorporated by reference in their entirety.

VEGF Antagonists

Inhibition of VEGF (for example, VEGF-A) is accomplished in a variety of ways. For example, a variety of VEGF antagonists that inhibit the activity or production of VEGF, including nucleic acid molecules such as aptamers, antisense RNA, ribozymes, RNAi molecules, and VEGF antibodies, are available and can be used in the methods of the present invention. Exemplary VEGF antagonists include nucleic acid ligands or aptamers of VEGF, such as those described below. A particularly useful antagonist to VEGF-A is EYE001 (previously referred to as NX1838), which is a modified, PEGylated aptamer that binds with high and specific affinity to the major soluble human VEGF isoform (see, U.S. Pat. Nos. 6,011,020; 6,051,698; and 6,147,204). The aptamer binds and inactivates VEGF in a manner similar to that of a high-affinity antibody directed towards VEGF. Another useful VEGF aptamer is EYE001 in its non-pegylated form. Alternatively, the VEGF antagonist may be, for example, an anti-VEGF antibody or antibody fragment. Accordingly, the VEGF molecule is rendered inactive by inhibiting its binding to a receptor. In addition, nucleic acid molecules such as antisense RNA, ribozymes, and RNAi molecules that inhibit VEGF expression or RNA stability at the nucleic acid level are useful antagonists in the methods and compositions of the invention. Other VEGF antagonists include peptides, proteins, cyclic peptides, and small organic compound. For example, soluble truncated forms of VEGF that bind to the VEGF receptor without concomitant signaling activity also serve as antagonists. Furthermore, the signaling activity of VEGF may be inhibited by disrupting its downstream signaling, for example, by using a number of antagonists including small molecule inhibitors of a VEGF receptor tyrosine kinase activity, as described further below.

The ability of a compound or agent to serve as a VEGF antagonist may be determined according to any number of standard methods well known in the art. For example, one of the biological activities of VEGF is to increase vascular permeability through specific binding to receptors on vascular endothelial cells. The interaction results in relaxation of the tight endothelial junctions with subsequent leakage of vascular fluid. Vascular leakage induced by VEGF can be measured in vivo by following the leakage of Evans Blue Dye from the vasculature of the guinea pig as a consequence of an intradermal injection of VEGF (Dvorak et al., in *Vascular Permeability Factor/Vascular Endothelial Growth Factor Microvascular Hyperpermeability and Angiogenesis*; and (1995) *Am. J. Pathol.* 146:1029). Similarly, the assay can be used to measure the ability of an antagonist to block this biological activity of VEGF.

In one useful example of a vascular permeability assay, $VEGF_{165}$ (20-30 nM) is premixed ex vivo with EYE001 (30 nM to 1 µM) or a candidate VEGF antagonist and subsequently administered by intradermal injection into the shaved skin on the dorsum of guinea pigs. Thirty minutes following injection, the Evans Blue dye leakage around the injection sites is quantified according to standard methods by use of a computerized morphometric analysis system. A compound that inhibits VEGF-induced leakage of the indicator dye from the vasculature is taken as being a useful antagonist in the methods and compositions of the invention.

Another assay for determining whether a compound is a VEGF antagonist is the so-called corneal angiogenesis assay. In this assay, methacyrate polymer pellets containing $VEGF_{165}$ (3 pmol) are implanted into the corneal stroma of rats to induce blood vessel growth into the normally avascular cornea. A candidate VEGF antagonist is then administered intravenously to the rats at doses of 1 mg/kg, 3 mg/kg, and 10 mg/kg either once or twice daily for 5 days. At the end of the treatment period, all of the individual corneas are photomicrographed. The extent to which new blood vessels develop in the corneal tissue, and their inhibition by the candidate compound, are then quantified by standardized morphometric analysis of the photomicrographs. A compound that inhibits VEGF-dependent angiogenesis in the cornea when compared to treatment with phosphate buffered saline (PBS) is taken as being a useful antagonist in the methods and compositions of the invention.

Candidate VEGF antagonists are also identified using the mouse model of retinopathy of prematurity. In one useful example, litters of 9, 8, 8, 7, and 7 mice, respectively, are left in room air or made hyperoxic and are treated intraperitoneally with phosphate buffered saline (PBS) or a candidate VEGF antagonist (for example, at 1 mg/kg, 3 mg/kg, or 10 mg/kg/day). The endpoint of the assay, outgrowth of new capillaries through the inner limiting membrane of the retina into the vitreous humor, is then assessed by microscopic identification and counting of the neovascular buds in histologic sections of each eye from all of the treated and control mice. A reduction in retinal neovasculature in the treated mice relative to the untreated control is taken as identifying a useful VEGF antagonist.

In still another exemplary screening assay, candidate VEGF antagonists are identified using an in vivo human tumor xenograft assay. In this screening assay, in vivo efficacy of a candidate VEGF antagonist is tested in human tumor xenografts (A673 rhabdomyosarcoma and Wilms tumor) implanted in nude mice. Mice are then treated with the candidate VEGF antagonist (e.g., 10 mg/kg given intraperitoneally once a day following development of established tumors (200 mg)). Control groups are treated with a control agent. Candidate compounds identified as inhibiting A673 rhabdomyosarcoma tumor growth and Wilms tumor relative to the control are taken as being useful antagonists in the methods and compositions of the invention.

Additional methods of assaying for a VEGF antagonist activity are known in the art and described in further detail below.

The invention further includes VEGF antagonists known in the art as well as those supported below and any and all equivalents that are within the scope of ordinary skill to create. For example, inhibitory antibodies directed against VEGF are known in the art, e.g., those described in U.S. Pat. Nos. 6,524,583, 6,451,764 (VRP antibodies), 6,448,077, 6,416,758, 6,403,088 (to VEGF-C), 6,383,484 (to VEGF-D), 6,342,221 (anti-VEGF antibodies), 6,342,219 6,331,301 (VEGF-B antibodies), and 5,730,977, and PCT publications WO 96/30046, WO 97/44453, and WO 98/45331, the contents of which are incorporated by reference in their entirety. The invention further provides an anti-VEGF antibody heavy chain variable domain comprising the amino acid sequence: EVQLVESGGGLVQPGGSLRLSCAASGYX$_1$FTX$_2$YGMNWVROAPGKGLEWVGWINTYTGEP TYAADFKRRFTFSLDTSKSTAYLQMNSLRAEDTAVYYCAKYPX$_3$YYGX$_4$SHWYFDVWGOG TLVTVSS (SEQ ID NO: 125 of WO 98/45331) (SEQ ID NO: 28), wherein X$_1$ is T or D; X$_2$ is N or H; X$_3$ is Y or H and X$_4$ is S or T. One particularly useful heavy chain variable domain sequence is that of the F (ab)-12 humanized antibody of Example 1 of WO98/45331 and comprises the heavy chain variable domain sequence of SEQ ID NO: 7 of WO 98/45331, i.e., EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPHYYGSSHWYF DVWGQGTL (SEQ ID NO: 26). Such preferred heavy chain variable domain sequences may be combined with the following preferred light chain variable domain sequences or with other light chain variable domain sequences, provided that the antibody so produced binds human VEGF. The invention also provides preferred light chain variable domain sequences which may be combined with the above-identified heavy chain variable domain sequences or with other heavy chain variable domain sequences, provided that the antibody so produced retains the ability to bind to human VEGF. For example, the light chain variable domain may comprise hypervariable regions with the following amino acid sequences: CDRL1 (SASQDISNYLN; SEQ ID NO: 4 of WO 98/45331) (SEQ ID NO: 29), CDRL2 (FTSSLHS; SEQ ID NO: 5 of WO 98/45331) (SEQ ID NO: 30) and CDRL3 (QQYSTVPWT; SEQ ID NO: 6 of WO 98/45331) (SEQ ID NO: 31). Preferably, the three light chain hypervariable regions are provided in a human framework region, e.g., as a contiguous sequence represented by the following formula: FR1-CDRL1-FR2-CDRL2-FR3-CDRL3-FR4. In one embodiment, the invention provides a humanized anti-VEGF antibody light chain variable domain comprising the amino acid sequence: DIQX$_1$TQSPSSLSASVGDRVTITCSASQDISNYLNWYQQKPGKAPKVLIYFTSSLHSGVPSRFS GSGSGTDFTLTISSLQPEDFATYYCQQYSTVPWTFGQGTKVEIKR (SEQ ID NO: 124 of WO 98/45331) (SEQ ID NO: 32), wherein X$_1$ is M or L. One particularly useful light chain variable domain sequence is that of the F (ab)-12 humanized antibody of Example 1 of WO98/45331 and comprises the light chain variable domain sequence of SEQ ID NO: 8 of WO 98/45331, i.e., DIQMTQSPSSLSASVGDRVTITCSASQDISNYLNWYQQKP GKAPKVLIYFTSSLHSGVPSRFSGSGSGTDFTLTISSLQPEDFATYYCQQYSTVPWTFGQ GTKVEIKRTV (SEQ ID NO: 27). The invention also provides a variant of a parent anti-VEGF antibody (which parent antibody is preferably a humanized or human anti-VEGF antibody), wherein the variant binds human VEGF and comprises an amino acid substitution in a hypervariable region of the heavy or light chain variable domain of the parent anti-VEGF antibody. The variant preferably has one or more substitution (s) in one or more hypervariable region (s) of the anti-VEGF antibody. Preferably, the substitution (s) are in the heavy chain variable domain of the parent antibody. For example, the amino acid substitution (s) may be in the CDRH1 and/or CDRH3 of the heavy chain variable domain. Preferably, there are substitutions in both these hypervariable regions. Such "affinity matured" variants are demonstrated in WO98/45331 to bind human VEGF more strongly than the parent anti-VEGF antibody from which they are generated, i.e., they have a Kd value which is significantly less than that of the parent anti-VEGF antibody. Preferably, the variant has an ED50 value for inhibiting VEGF-induced proliferation of endothelial cells in vitro which is at least about 10 fold lower, preferably at least about 20 fold lower, and most preferably at least about 50 fold lower, than that of the parent anti-VEGF antibody. One particularly preferred variant is the Y0317 variant of Example 3 of WO98/45331, which has a CDRH1 comprising the amino acid sequence: GYDFTHYGMN (SEQ ID NO: 126 of WO 98/45331) (SEQ ID NO: 33) and a CDRH3 comprising the amino acid sequence: YPYYYGTSHWYFDV (SEQ ID NO: 127 of WO 98/45331) (SEQ ID NO: 34). These hypervariable regions and CDRH2 are generally provided in a human framework region, e.g., resulting in a heavy chain variable domain comprising the amino acid sequence of SEQ ID NO: 116 of WO 98/45331, i.e., EVQLVESGGGLVQPGGSLRL SCAASGYDFTHYGMNWVRQAPGKGLEWVGWINTYTGEPTYAADFKRRFTFSLDTSKSTAY LQMNSLRAEDTAVYYCAKYPYYYGTSHWYFDVWGQGTL (SEQ ID NO: 24). Such heavy chain variable domain sequences are optionally combined with a light chain variable domain comprising the amino acid sequence of SEQ ID NO: 124 of WO 98/45331 (SEQ ID NO: 32), and preferably the light chain variable domain amino acid sequence of SEQ ID NO: 115 of WO 98/45331, i.e., DIQLTQSPSS LSASVGDRVT ITCSASQDISNYLNWYQQKPGKAPKVLIYFTSSLHSGVPSRFSGSGSGTD FTLTISSLQPEDFATYYCQQYSTVPWTFGQGTKVEIKRTV (SEQ ID NO: 25).

Antibodies to VEGF receptors are also known in the art, such as those described in, for example, U.S. Pat. Nos. 5,840, 301, 5,874,542, 5,955,311, 6,365,157, and PCT publication WO 04/003211, the contents of which are incorporated by reference in their entirety.

Small molecules that block the action of VEGF by, e.g., inhibiting a VEGFR-associated tyrosine kinase activity, are known in the art, e.g., those described in U.S. Pat. Nos. 6,514,971, 6,448,277, 6,414,148, 6,362,336, 6,291,455, 6,284,751, 6,177,401, 6071,921, and 6001,885 (retinoid inhibitors of VEGF expression), the contents of each of which are incorporated by reference in their entirety.

Proteins and polypeptides that block the action of VEGF are known in the art, e.g., those described in U.S. Pat. Nos. 6,576,608, 6,559,126, 6,541,008, 6,515,105, 6,383,486 (VEGF decoy receptor), 6,375,929 (VEGF decoy receptor), 6,361,946 (VEFG peptide analog inhibitors), 6,348,333 (VEGF decoy receptor), 6,559,126 (polypeptides that bind VEGF and block binding to VEGFR), 6,100,071 (VEGF decoy receptor), and 5,952,199, the contents of each of which are incorporated by reference in their entirety.

Short interfering nucleic acids (siNA), short interfering RNA (siRNA), double stranded RNA (dsRNA), microRNA (miRNA) and short hairpin RNA (shRNA) capable of mediating RNA interference (RNAi) against VEGF and/or VEGFR gene expression and/or activity are known in the art, for example, as disclosed in PCT publication WO 03/070910, the contents of which is incorporated by reference in its entirety.

Antisense oligonucleotides for the inhibition of VEGF are known in the art, e.g., those described in, e.g., U.S. Pat. Nos. 5,611,135, 5,814,620, 6,399,586, 6,410,322, and 6,291,667, the contents of each of which are incorporated by reference in their entirety.

Aptamers (also known as nucleic acid ligands) for the inhibition of VEGF are known in the art, e.g., those described in, e.g., U.S. Pat. Nos. 6,762,290, 6,426,335, 6,168,778, 6,051,698, and 5,859,228, the contents of each of which are incorporated by reference in their entirety.

Antibody Antagonists

The invention includes antagonist antibodies directed against PDGF and VEGF as well as their cognate receptors PDGFR and VEGFR. The antibody antagonists of the invention block binding of a ligand with its cognate receptor. Accordingly, a PDGF antagonist antibody of the invention includes antibodies directed against a PDGF as well as a PDGFR target.

The antagonist antibodies of the invention include monoclonal inhibitory antibodies. Monoclonal antibodies, or fragments thereof, encompass all immunoglobulin classes such as IgM, IgG, IgD, IgE, IgA, or their subclasses, such as the IgG subclasses or mixtures thereof. IgG and its subclasses are useful, such as $IgG_1$, $IgG_2$, $IgG_{2a}$, $IgG_{2b}$, $IgG_3$ or $IgG_M$. The IgG subtypes $IgG_{1/kappa}$ and $IgG_{2b/kapp}$ are included as useful embodiments. Fragments which may be mentioned are all truncated or modified antibody fragments with one or two antigen-complementary binding sites which show high binding and neutralizing activity toward mammalian PDGF or VEGF (or their cognate receptors), such as parts of antibodies having a binding site which corresponds to the antibody and is formed by light and heavy chains, such as Fv, Fab or F(ab')$_2$ fragments, or single-stranded fragments. Truncated double-stranded fragments such as Fv, Fab or F(ab')$_2$ are particularly useful. These fragments can be obtained, for example, by enzymatic means by eliminating the Fc part of the antibody with enzymes such as papain or pepsin, by chemical oxidation or by genetic manipulation of the antibody genes. It is also possible and advantageous to use genetically manipulated, non-truncated fragments. The anti-PDGF or VEGF antibodies or fragments thereof can be used alone or in mixtures.

The novel antibodies, antibody fragments, mixtures or derivatives thereof advantageously have a binding affinity for PDGF or VEGF (or their cognate receptors) in a range from $1\times10^{-7}$ M to $1\times10^{-12}$ M, or from $1\times10^{-8}$ M to $1\times10^{-11}$ M, or from $1\times10^{-9}$ M to $5\times10^{-10}$ M.

The antibody genes for the genetic manipulations can be isolated, for example from hybridoma cells, in a manner known to the skilled worker. For this purpose, antibody-producing cells are cultured and, when the optical density of the cells is sufficient, the mRNA is isolated from the cells in a known manner by lysing the cells with guanidinium thiocyanate, acidifying with sodium acetate, extracting with phenol, chloroform/isoamyl alcohol, precipitating with isopropanol and washing with ethanol. cDNA is then synthesized from the mRNA using reverse transcriptase. The synthesized cDNA can be inserted, directly or after genetic manipulation, for example, by site-directed mutagenesis, introduction of insertions, inversions, deletions, or base exchanges, into suitable animal, fungal, bacterial or viral vectors and be expressed in appropriate host organisms. Useful bacterial or yeast vectors are pBR322, pUC18/19, pACYC184, lambda or yeast mu vectors for the cloning of the genes and expression in bacteria such as *E. coli* or in yeasts such as *Saccharomyces cerevisiae*.

The invention furthermore relates to cells that synthesize PDGF or VEGF antibodies. These include animal, fungal, bacterial cells or yeast cells after transformation as mentioned above. They are advantageously hybridoma cells or trioma cells, typically hybridoma cells. These hybridoma cells can be produced, for example, in a known manner from animals immunized with PDGF or VEGF (or their cognate receptors) and isolation of their antibody-producing B cells, selecting these cells for PDGF or VEGF-binding antibodies and subsequently fusing these cells to, for example, human or animal, for example, mouse myeloma cells, human lymphoblastoid cells or heterohybridoma cells (see, e.g., Koehler et al., (1975) *Nature* 256: 496) or by infecting these cells with appropriate viruses to produce immortalized cell lines. Hybridoma cell lines produced by fusion are useful and mouse hybridoma cell lines are particularly useful. The hybridoma cell lines of the invention secrete useful antibodies of the IgG type. The binding of the mAb antibodies of the invention bind with high affinity and reduce or neutralize the biological (e.g., angiogenic) activity of PDGF or VEGF.

The invention further includes derivatives of these anti-PDGF or VEGF antibodies which retain their PDGF or VEGF-inhibiting activity while altering one or more other properties related to their use as a pharmaceutical agent, e.g., serum stability or efficiency of production. Examples of such anti-PDGF or VEGF antibody derivatives include peptides, peptidomimetics derived from the antigen-binding regions of the antibodies, and antibodies, antibody fragments or peptides bound to solid or liquid carriers such as polyethylene glycol, glass, synthetic polymers such as polyacrylamide, polystyrene, polypropylene, polyethylene or natural polymers such as cellulose, Sepharose or agarose, or conjugates with enzymes, toxins or radioactive or nonradioactive markers such as $^{3}$H, $^{123}$I, $^{125}$I, $^{131}$I, $^{32}$P, $^{35}$S, $^{14}$C, $^{51}$Cr, $^{36}$Cl, $^{57}$Co, $^{55}$Fe, $^{59}$Fe, $^{90}$Y, $^{99m}$Tc, $^{75}$Se, or antibodies, fragments, or peptides covalently bonded to fluorescent/chemiluminescent labels such as rhodamine, fluorescein, isothiocyanate, phycoerythrin, phycocyanin, fluorescamine, metal chelates, avidin, streptavidin or biotin.

The novel antibodies, antibody fragments, mixtures, and derivatives thereof can be used directly, after drying, for example freeze drying, after attachment to the abovementioned carriers or after formulation with other pharmaceutical active and ancillary substances for producing pharmaceutical preparations. Examples of active and ancillary substances which may be mentioned are other antibodies, antimicrobial active substances with a microbiocidal or microbiostatic action such as antibiotics in general or sulfonamides, antitumor agents, water, buffers, salines, alcohols, fats, waxes, inert vehicles or other substances customary for parenteral products, such as amino acids, thickeners or sugars. These pharmaceutical preparations are used to control diseases, and are useful to control ocular neovascular disorders and diseases including AMD and diabetic retinopathy.

The novel antibodies, antibody fragments, mixtures or derivatives thereof can be used in therapy or diagnosis directly or after coupling to solid or liquid carriers, enzymes, toxins, radioactive or nonradioactive labels or to fluorescent/chemiluminescent labels as described above.

The human PDGF or VEGF monoclonal antibodies of the present invention may be obtained by any means known in the art. For example, a mammal is immunized with human PDGF or VEGF (or their cognate receptors). Purified human PDGF and VEGF is commercially available (e.g., from Cell Sciences, Norwood, Mass., as well as other commercial vendors). Alternatively, human PDGF or VEGF (or their cognate receptors) may be readily purified from human placental tissue. The mammal used for raising anti-human PDGF or VEGF antibody is not restricted and may be a primate, a rodent (such as mouse, rat or rabbit), bovine, sheep, goat or dog.

Next, antibody-producing cells such as spleen cells are removed from the immunized animal and are fused with myeloma cells. The myeloma cells are well-known in the art (e.g., p3x63-Ag8-653, NS-0, NS-1 or P3U1 cells may be used). The cell fusion operation may be carried out by any conventional method known in the art.

The cells, after being subjected to the cell fusion operation, are then cultured in HAT selection medium so as to select hybridomas. Hybridomas which produce antihuman monoclonal antibodies are then screened. This screening may be carried out by, for example, sandwich enzyme-linked immunosorbent assay (ELISA) or the like in which the produced monoclonal antibodies are bound to the wells to which human PDGF or VEGF (or their cognate receptor) is immobilized. In this case, as the secondary antibody, an antibody specific to the immunoglobulin of the immunized animal, which is labeled with an enzyme such as peroxidase, alkaline phosphatase, glucose oxidase, beta-D-galactosidase, or the like, may be employed. The label may be detected by reacting the labeling enzyme with its substrate and measuring the generated color. As the substrate, 3,3-diaminobenzidine, 2,2-diaminobis-o-dianisidine, 4-chloronaphthol, 4-aminoantipyrine, o-phenylenediamine or the like may be produced.

By the above-described operation, hybridomas which produce anti-human PDGF or VEGF antibodies can be selected. The selected hybridomas are then cloned by the conventional limiting dilution method or soft agar method. If desired, the cloned hybridomas may be cultured on a large scale using a serum-containing or a serum free medium, or may be inoculated into the abdominal cavity of mice and recovered from ascites, thereby a large number of the cloned hybridomas may be obtained.

From among the selected anti-human PDGF or VEGF monoclonal antibodies, those that have an ability to prevent binding and activation of the corresponding ligand/receptor pair (e.g., in a cell-based PDGF or VEGF assay system (see above)) are then chosen for further analysis and manipulation. If the antibody blocks receptor/ligand binding and/or activation, it means that the monoclonal antibody tested has an ability to reduce or neutralize the PDGF or VEGF activity of human PDGF or VEGF. That is, the monoclonal antibody specifically recognizes and/or interferes with the critical binding site of human PDGF or VEGF (or their cognate receptors).

The monoclonal antibodies herein further include hybrid and recombinant antibodies produced by splicing a variable (including hypervariable) domain of an anti-PDGF or VEGF antibody with a constant domain (e.g., "humanized" antibodies), or a light chain with a heavy chain, or a chain from one species with a chain from another species, or fusions with heterologous proteins, regardless of species of origin or immunoglobulin class or subclass designation, as well as antibody fragments, [e.g., Fab, F(ab)$_2$, and Fv], so long as they exhibit the desired biological activity. [See, e.g., U.S. Pat. No. 4,816,567 and Mage & Lamoyi, in *Monoclonal Antibody Production Techniques and Applications*, pp. 79-97 (Marcel Dekker, Inc.), New York (1987)].

Thus, the term "monoclonal" indicates that the character of the antibody obtained is from a substantially homogeneous population of antibodies, and is not to be construed as requiring production of the antibody by any particular method. For example, the monoclonal antibodies to be used in accordance with the present invention may be made by the hybridoma method first described by Kohler & Milstein, *Nature* 256:495 (1975), or may be made by recombinant DNA methods (U.S. Pat. No. 4,816,567). The "monoclonal antibodies" may also be isolated from phage libraries generated using the techniques described in McCafferty et al., *Nature* 348:552-554 (1990), for example.

"Humanized" forms of non-human (e.g., murine) antibodies are specific chimeric immunoglobulins, immunoglobulin chains or fragments thereof (such as Fv, Fab, Fab', F(ab)$_2$ or other antigen-binding subsequences of antibodies) which contain minimal sequence derived from non-human immunoglobulin. For the most part, humanized antibodies are human immunoglobulins (recipient antibody) in which residues from the complementary determining regions (CDRs) of the recipient antibody are replaced by residues from the CDRs of a non-human species (donor antibody) such as mouse, rat or rabbit having the desired specificity, affinity and capacity. In some instances, Fv framework region (FR) residues of the human immunoglobulin are replaced by corresponding non-human FR residues. Furthermore, the humanized antibody may comprise residues that are found neither in the recipient antibody nor in the imported CDR or FR sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR residues are those of a human immunoglobulin consensus sequence.

The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., (1986) *Nature* 321: 522-525; Riechmann et al., (1988) *Nature* 332: 323-327; and Verhoeyen et al., (1988) *Science* 239: 1534-1536), by substituting rodent CDRs or CDR sequences for the corresponding sequences of a human antibody. Accordingly, such "humanized" antibodies are chimeric antibodies, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., (1993) *J. Immunol.,* 151:2296; and Chothia and Lesk (1987) *J. Mol. Biol.,* 196:901). Another method uses a particular framework derived from the consensus sequence of all human antibodies of a particular subgroup of light or heavy chains. The same framework may be used for several different humanized antibodies (Carter et al., (1992) *Proc. Natl. Acad. Sci.* (USA), 89: 4285; and Presta et al., (1993) *J. Immunol.,* 151:2623).

It is further important that antibodies be humanized with retention of high affinity for the antigen and other favorable biological properties. To achieve this goal, according to one useful method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

Human monoclonal antibodies directed against PDGF or VEGF are also included in the invention. Such antibodies can be made by the hybridoma method. Human myeloma and mouse-human heteromyeloma cell lines for the production of human monoclonal antibodies have been described, for example, by Kozbor (1984) *J. Immunol.,* 133, 3001; Brodeur, et al., *Monoclonal Antibody Production Techniques and Applications,* pp. 51-63 (Marcel Dekker, Inc., New York, 1987); and Boerner et al., (1991) *J. Immunol.,* 147:86-95.

It is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such gem-line mutant mice will result in the production of human antibodies upon antigen challenge (see, e.g., Jakobovits et al., (1993) *Proc. Natl. Acad. Sci.* (USA), 90: 2551; Jakobovits et al., (1993) *Nature,* 362:255-258; and Bruggermann et al., (1993) *Year in Immuno.,* 7:33).

Alternatively, phage display technology (McCafferty et al., (1990) *Nature,* 348: 552-553) can be used to produce human antibodies and antibody fragments in vitro, from immunoglobulin variable (V) domain gene repertoires from unimmunized donors (for review see, e.g., Johnson et al., (1993) *Current Opinion in Structural Biology,* 3:564-571). Several sources of V-gene segments can be used for phage display. For example, Clackson et al., ((1991) *Nature,* 352: 624-628) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., ((1991) *J. Mol. Biol.,* 222:581-597, or Griffith et al., (1993) *EMBO J.,* 12:725-734).

In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (see Marks et al., (1992) *Bio. Technol.,* 10:779-783). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the nM range. A strategy for making very large phage antibody repertoires has been described by Waterhouse et al., ((1993) *Nucl. Acids Res.,* 21:2265-2266).

Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable capable of restoring a functional antigen-binding site, i.e., the epitope governs (imprints) the choice of partner. When the process is repeated in order to replace the remaining rodent V domain, a human antibody is obtained (see PCT WO 93/06213, published 1 Apr. 1993) Unlike traditional humanization of rodent antibodies by CDR grafting, this technique provides completely human antibodies, which have no framework or CDR residues of rodent origin.

Aptamer Antagonists

The invention provides aptamer antagonists directed against PDGF and/or VEGF (or their cognate receptors). Aptamers, also known as nucleic acid ligands, are non-naturally occurring nucleic acids that bind to and, generally, antagonize (i.e., inhibit) a pre-selected target.

Aptamers can be made by any known method of producing oligomers or oligonucleotides. Many synthesis methods are known in the art. For example, 2'-O-allyl modified oligomers that contain residual purine ribonucleotides, and bearing a suitable 3'-terminus such as an inverted thymidine residue (Ortigao et al., *Antisense Research and Development*, 2:129-146 (1992)) or two phosphorothioate linkages at the 3'-terminus to prevent eventual degradation by 3'-exonucleases, can be synthesized by solid phase beta-cyanoethyl phosphoramidite chemistry (Sinha et al., *Nucleic Acids Res.*, 12:4539-4557 (1984)) on any commercially available DNA/RNA synthesizer. One method is the 2'-O-tert-butyldimethylsilyl (TBDMS) protection strategy for the ribonucleotides (Usman et al., *J. Am. Chem. Soc.*, 109:7845-7854 (1987)), and all the required 3'-O-phosphoramidites are commercially available. In addition, aminomethylpolystyrene may be used as the support material due to its advantageous properties (McCollum and Andrus (1991) *Tetrahedron Lett.*, 32:4069-4072). Fluorescein can be added to the 5'-end of a substrate RNA during the synthesis by using commercially available fluorescein phosphoramidites. In general, an aptamer oligomer can be synthesized using a standard RNA cycle. Upon completion of the assembly, all base labile protecting groups are removed by an eight hour treatment at 55° C. with concentrated aqueous ammonia/ethanol (3:1 v/v) in a sealed vial. The ethanol suppresses premature removal of the 2'-O-TBDMS groups that would otherwise lead to appreciable strand cleavage at the resulting ribonucleotide positions under the basic conditions of the deprotection (Usman et al., (1987) *J. Am. Chem. Soc.*, 109:7845-7854). After lyophilization, the TBDMS protected oligomer is treated with a mixture of triethylamine trihydrofluoride/triethylamine/N-methylpyrrolidinone for 2 hours at 60° C. to afford fast and efficient removal of the silyl protecting groups under neutral conditions (see Wincott et al., (1995) *Nucleic Acids Res.*, 23:2677-2684). The fully deprotected oligomer can then be precipitated with butanol according to the procedure of Cathala and Brunel ((1990) *Nucleic Acids Res.*, 18:201). Purification can be performed either by denaturing polyacrylamide gel electrophoresis or by a combination of ion-exchange HPLC (Sproat et al., (1995) *Nucleosides and Nucleotides*, 14:255-273) and reversed phase HPLC. For use in cells, synthesized oligomers are converted to their sodium salts by precipitation with sodium perchlorate in acetone. Traces of residual salts may then be removed using small disposable gel filtration columns that are commercially available. As a final step the authenticity of the isolated oligomers may be checked by matrix assisted laser desorption mass spectrometry (Pieles et al., (1993) *Nucleic Acids Res.*, 21:3191-3196) and by nucleoside base composition analysis.

The disclosed aptamers can also be produced through enzymatic methods, when the nucleotide subunits are available for enzymatic manipulation. For example, the RNA molecules can be made through in vitro RNA polymerase T7 reactions. They can also be made by strains of bacteria or cell lines expressing T7, and then subsequently isolated from these cells. As discussed below, the disclosed aptamers can also be expressed in cells directly using vectors and promoters.

The aptamers, like other nucleic acid molecules of the invention, may further contain chemically modified nucleotides. One issue to be addressed in the diagnostic or therapeutic use of nucleic acids is the potential rapid degration of oligonucleotides in their phosphodiester form in body fluids by intracellular and extracellular enzymes such as endonucleases and exonucleases before the desired effect is manifest. Certain chemical modifications of the nucleic acid ligand can be made to increase the in vivo stability of the nucleic acid ligand or to enhance or to mediate the delivery of the nucleic acid ligand (see, e.g., U.S. Pat. No. 5,660,985, entitled "High Affinity Nucleic Acid Ligands Containing Modified Nucleotides") which is specifically incorporated herein by reference.

Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications can also include 3' and 5' modifications such as capping or modification with sugar moieties. In some embodiments of the instant invention, the nucleic acid ligands are RNA molecules that are 2'-fluoro (2'-F) modified on the sugar moiety of pyrimidine residues.

The stability of the aptamer can be greatly increased by the introduction of such modifications and as well as by modifications and substitutions along the phosphate backbone of the RNA. In addition, a variety of modifications can be made on the nucleobases themselves which both inhibit degradation and which can increase desired nucleotide interactions or decrease undesired nucleotide interactions. Accordingly, once the sequence of an aptamer is known, modifications or substitutions can be made by the synthetic procedures described below or by procedures known to those of skill in the art.

Other modifications include the incorporation of modified bases (or modified nucleoside or modified nucleotides) that are variations of standard bases, sugars and/or phosphate backbone chemical structures occurring in ribonucleic (i.e., A, C, G and U) and deoxyribonucleic (i.e., A, C, G and T) acids. Included within this scope are, for example: Gm (2'-methoxyguanylic acid), Am (2'-methoxyadenylic acid), Cf (2'-fluorocytidylic acid), Uf (2'-fluorouridylic acid), Ar (riboadenylic acid). The aptamers may also include cytosine or any cytosine-related base including 5-methylcytosine, 4-acetylcytosine, 3-methylcytosine, 5-hydroxymethyl cytosine, 2-thiocytosine, 5-halocytosine (e.g., 5-fluorocytosine, 5-bromocytosine, 5-chlorocytosine, and 5-iodocytosine),5-propynyl cytosine, 6-azocytosine, 5-trifluoromethylcytosine, N4, N4-ethanocytosine, phenoxazine cytidine, phenothiazine cytidine, carbazole cytidine or pyridoindole cytidine. The aptamer may further include guanine or any guanine-related base including 6-methylguanine, 1-methylguanine, 2,2-dimethylguanine, 2-methylguanine, 7-methylguanine, 2-propylguanine, 6-propylguanine, 8-haloguanine (e.g., 8-fluoroguanine, 8-bromoguanine, 8-chloroguanine, and 8-iodoguanine), 8-aminoguanine, 8-sulfhydrylguanine, 8-thioalkylguanine, 8-hydroxylguanine, 7-methylguanine, 8-azaguanine, 7-deazaguanine or 3-deazaguanine. The aptamer may still further include adenine or any adenine-related base including 6-methyladenine, N6-isopentenyladenine, N6-methyladenine, 1-methyladenine, 2-methyladenine, 2-methylthio-N6-isopentenyladenine, 8-haloadenine (e.g., 8-fluoroadenine, 8-bromoadenine, 8-chloroadenine, and 8-iodoadenine), 8-aminoadenine, 8-sulfhydryladenine, 8-thioalkyladenine, 8-hydroxyladenine, 7-methyladenine, 2-haloadenine (e.g., 2-fluoroadenine, 2-bromoadenine, 2-chloroadenine, and 2-iodoadenine), 2-aminoadenine, 8-azaadenine, 7-deazaadenine or 3-deazaadenine. Also included are uracil or any uracil-related base including 5-halouracil (e.g., 5-fluorouracil, 5-bromouracil, 5-chlorouracil, 5-iodouracil), 5-(carboxyhydroxylmethyl)uracil, 5-carboxymethylaminomethyl-2-thiouracil, 5-carboxymethylaminomethyluracil, dihydrouracil, 1-methylpseudouracil, 5-methoxyaminomethyl-2-thiouracil, 5'-methoxycarbonylmethyluracil, 5-methoxyuracil, 5-methyl-2-thiouracil, 2-thiouracil, 4-thiouracil, 5-methyluracil, uracil-5-oxyacetic acid methylester, uracil-5-oxyacetic acid, pseudouracil, 5-methyl-2-thiouracil, 2-thiouracil, 3-(3-amino-3-N-2-carboxypropyl)uracil, 5-methylaminomethyluracil, 5-propynyl uracil, 6-azouracil, or 4-thiouracil.

Examples of other modified base variants known in the art include, without limitation, those listed at 37 C.F.R. §1.822 (p) (1), e.g., 4-acetylcytidine, 5-(carboxyhydroxylmethyl) uridine, 2'-methoxycytidine, 5-carboxymethylaminomethyl-2-thioridine, 5-carboxymethylaminomethyluridine, dihydrouridine, 2'-O-methylpseudouridine, b-D-galactosylqueosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, b-D-mannosylqueosine, 5-methoxycarbonylmethyluridine, 5-methoxyuridine, 2-methylthio-N-6-isopentenyladenosine, N-((9-b-D-ribofuranosyl-2-methylthiopurine-6-yl)carbamoyl)threonine, N-((9-b-D-ribofuranosylpurine-6-yl)N-methyl-carbamoyl)threonine, urdine-5-oxyacetic acid methylester, uridine-5-oxyacetic acid (v), wybutoxosine, pseudouridine, queosine, 2-thiocytidine, 5-methyl-2-thiouridine, 2-thiouridine, 4-thiouridine, 5-methyluridine, N-((9-b-D-ribofuranosylpurine-6-yl)carbamoyl)threonine, 2'-O-methyl-5-methyluridine, methyluridine, wybutosine, 3-(3-amino-3-carboxypropyl)uridine.

Also included are the modified nucleobases described in U.S. Pat. Nos. 3,687,808, 3,687,808, 4,845,205, 5,130,302, 5,134,066, 5,175,273, 5,367,066, 5,432,272, 5,457,187, 5,459,255, 5,484,908, 5,502,177, 5,525,711, 5,552,540, 5,587,469, 5,594,121, 5,596,091, 5,614,617, 5,645,985, 5,830,653, 5,763,588, 6,005,096, and 5,681,941. Examples of modified nucleoside and nucleotide sugar backbone variants known in the art include, without limitation, those having, e.g., 2' ribosyl substituents such as F, SH, SCH3, OCN, Cl, Br, CN, CF3, OCF3, SOCH3, SO2, CH3, ONO2, NO2, N3, NH2, OCH2CH2OCH3, O(CH2)2ON(CH3)2, OCH2OCH2N(CH3)2, O(C1-10 alkyl), O(C2-10 alkenyl), O(C2-10 alkynyl), S(C1-10 alkyl), S(C2-10 alkenyl), S(C2-10 alkynyl), NH(C1-10 alkyl), NH(C2-10 alkenyl), NH(C2-10 alkynyl), and O-alkyl-O-alkyl. Desirable 2' ribosyl substituents include 2'-methoxy (2'-OCH3), 2'-aminopropoxy (2' OCH2CH2CH2NH2), 2'-allyl (2'-CH2-CH=CH2), 2'-O-allyl (2'-O—CH2-CH=CH2), 2'-amino (2'-NH2), and 2'-fluoro (2'-F). The 2'-substituent may be in the arabino (up) position or ribo (down) position.

The aptamers of the invention may be made up of nucleotides and/or nucleotide analogs such as described above, or a combination of both, or are oligonucleotide analogs. The aptamers of the invention may contain nucleotide analogs at positions which do not effect the function of the oligomer to bind PDGF or VEGF (or their cognate receptors).

There are several techniques that can be adapted for refinement or strengthening of the nucleic acid Ligands binding to a particular target molecule or the selection of additional aptamers. One technique, generally referred to as "in vitro genetics" (see Szostak (1992) TIBS, 19:89), involves isolation of aptamer antagonists by selection from a pool of random sequences. The pool of nucleic acid molecules from which the disclosed aptamers may be isolated may include invariant sequences flanking a variable sequence of approximately twenty to forty nucleotides. This method has been termed Selective Evolution of Ligands by EXponential Enrichment (SELEX). Compositions and methods for generating aptamer antagonists of the invention by SELEX and related methods are known in the art and taught in, for example, U.S. Pat. No. 5,475,096 entitled "Nucleic Acid Ligands," and U.S. Pat. No. 5,270,163, entitled "Methods for Identifying Nucleic Acid Ligands," each of which is specifically incorporated by reference herein in its entirety. The SELEX process in general, and VEGF and PDGF aptamers and formulations in particular, are further described in, e.g., U.S. Pat. Nos. 5,668,264, 5,696,249, 5,670,637, 5,674,685, 5,723,594, 5,756,291, 5,811,533, 5,817,785, 5,958,691, 6,011,020, 6,051,698, 6,147,204, 6,168,778, 6,207,816, 6,229,002, 6,426,335, 6,582,918, the contents of each of which is specifically incorporated by reference herein.

Briefly, the SELEX method involves selection from a mixture of candidate oligonucleotides and step-wise iterations of binding to a selected target, partitioning and amplification, using the same general selection scheme, to achieve virtually any desired criterion of binding affinity and selectivity. Starting from a mixture of nucleic acids, typically comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule.

The basic SELEX method has been modified to achieve a number of specific objectives. For example, U.S. Pat. No. 5,707,796, entitled "Method for Selecting Nucleic Acids on the Basis of Structure," describes the use of the SELEX process in conjunction with gel electrophoresis to select nucleic acid molecules with specific structural characteristics, such as bent DNA. U.S. Pat. No. 5,763,177 entitled "Systematic Evolution of Ligands by Exponential Enrichment: Photoselection of Nucleic Acid Ligands and Solution SELEX" describe a SELEX based method for selecting nucleic acid ligands containing photoreactive groups capable of binding and/or photocrosslinking to and/or photoinactivating a target molecule. U.S. Pat. No. 5,580,737 entitled "High-Affinity Nucleic Acid Ligands That Discriminate Between Theophylline and Caffeine," describes a method for identifying highly specific nucleic acid ligands able to discriminate between closely related molecules, which can be non-peptidic, termed Counter-SELEX. U.S. Pat. No. 5,567,588 entitled "Systematic Evolution of Ligands by EXponential Enrichment: Solution SELEX," describes a SELEX-based method which achieves highly efficient partitioning between oligonucleotides having high and low affinity for a target molecule.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX process-identified nucleic acid ligands containing modified nucleotides are described in U.S. Pat. No. 5,660,985 entitled "High Affinity Nucleic Acid Ligands Containing Modified Nucleotides," that describes oligonucleotides containing nucleotide derivatives chemically modified at the 5- and 2'-positions of pyrimidines. U.S. Pat. No. 5,580,737, supra, describes highly specific nucleic acid ligands containing one or more nucleotides modified with 2'-amino (2'-NH2), 2'-fluoro (2'-F), and/or 2'-O-methyl (2'-OMe). U.S. patent Ser. No. 08/264,029, filed Jun. 22, 1994, entitled "Novel Method of Preparation of Known and Novel 2' Modified Nucleosides by Intramolecular Nucleophilic Displacement," now abandoned, describes oligonucleotides containing various 2'-modified pyrimidines.

The SELEX method encompasses combining selected oligonucleotides with other selected oligonucleotides and non-oligonucleotide functional units as described in U.S. Pat. No. 5,637,459 entitled "Systematic Evolution of Ligands by EXponential Enrichment: Chimeric SELEX," and U.S. Pat. No. 5,683,867 entitled "Systematic Evolution of Ligands by EXponential Enrichment: Blended SELEX," respectively. These patents allow for the combination of the broad array of shapes and other properties, and the efficient amplification and replication properties, of oligonucleotides with the desirable properties of other molecules.

The SELEX method further encompasses combining selected nucleic acid ligands with lipophilic compounds or non-immunogenic, high molecular weight compounds in a diagnostic or therapeutic complex as described in U.S. Pat. No. 6,011,020, entitled "Nucleic Acid Ligand Complexes," which is specifically incorporated by reference herein in their entirety.

The aptamer antagonists can also be refined through the use of computer modeling techniques. Examples of molecular modeling systems are the CHARMm and QUANTA programs, Polygen Corporation (Waltham, Mass.). CHARMm performs the energy minimization and molecular dynamics functions. QUANTA performs the construction, graphic modeling and analysis of molecular structure. QUANTA allows interactive construction, modification, visualization, and analysis of the behavior of molecules with each other. These applications can be adapted to define and display the secondary structure of RNA and DNA molecules.

Aptamers with these various modifications can then be tested for function using any suitable assay for the PDGF or VEGF function of interest, such as a PDGF cell-based proliferation activity assay.

The modifications can be pre- or post-SELEX process modifications. Pre-SELEX process modifications yield nucleic acid ligands with both specificity for their SELEX target and improved in vivo stability. Post-SELEX process modifications made to 2'-OH nucleic acid ligands can result in improved in vivo stability without adversely affecting the binding capacity of the nucleic acid ligand.

Other modifications useful for producing aptamers of the invention are known to one of ordinary skill in the art. Such modifications may be made post-SELEX process (modification of previously identified unmodified ligands) or by incorporation into the SELEX process.

It has been observed that aptamers, or nucleic acid ligands, in general, and VEGF aptamers in particular, are most stable, and therefore efficacious when 5'-capped and 3'-capped in a manner which decreases susceptibility to exonucleases and increases overall stability. Accordingly, the invention is based in one embodiment, upon the capping of aptamers in general, and anti-VEGF aptamers in particular, with a 5'-5' inverted nucleoside cap structure at the 5' end and a 3'-3' inverted nucleoside cap structure at the 3' end. Accordingly, the invention provides anti-VEGF and/or anti-PDGF aptamers, i.e., nucleic acid ligands, that are capped at the 5' end with a 5'-5-inverted nucleoside cap and at the 3' end with a 3'-3' inverted nucleoside cap.

Certain particularly useful aptamers of the invention are anti-VEGF aptamer compositions, including, but not limited to, those having both 5'-5' and 3'-3' inverted nucleotide cap structures at their ends. Such anti-VEGF capped aptamers may be RNA aptamers, DNA aptamers or aptamers having a mixed (i.e., both RNA and DNA) composition. Suitable anti-VEGF aptamer sequences of the invention include the nucleotide sequence GAAGAAUUGG (SEQ ID NO: 15); or the nucleotide sequence UUGGACGC (SEQ ID NO: 16); or the nucleotide sequence GUGAAUGC (SEQ ID NO: 17). Particularly useful are capped anti-VEGF aptamers of the invention have the sequence:

(SEQ ID NO: 18)
X-5'-5'-CGGAAUCAGUGAAUGCUUAUACAUCCG-3'-3'-X where each C, G, A, and U represents, respectively, the naturally-occurring nucleotides cytidine, guanidine, adenine, and uridine, or modified nucleotides corresponding thereto; X-5'-5' is an inverted nucleotide capping the 5' terminus of the aptamer; 3'-3'-X is an inverted nucleotide capping the 3' terminus of the aptamer; and the remaining nucleotides or modified nucleotides are sequentially linked via 5'-3' phosphodiester linkages. In some embodiments, each of the nucleotides of the capped anti-VEGF aptamer, individually carries a 2' ribosyl substitution, such as —OH (which is standard for ribonucleic acids (RNAs)), or —H (which is standard for deoxyribonucleic acids (DNAs)). In other embodiments the 2' ribosyl position is substituted with an $O(C_{1-10}$ alkyl), an $O(C_{1-10}$ alkenyl), a F, an N3, or an NH2 substituent.

In a still more particular non-limiting example, the 5'-5' capped anti-VEGF aptamer may have the structure:

(SEQ ID NO: 19)
$T_d$-5'-5'-$C_fG_mG_mA_rA_rU_fC_fA_mG_mU_fG_mA_mA_mU_fG_mC_fU_fU_fA_mU_fA_m$ $C_fA_mU_fC_fC_fG_m$3'-3'-$T_d$ where "$G_m$" represents 2'-methoxyguanylic acid, "$A_m$" represents 2'-methoxyadenylic acid, "$C_f$" represents 2'-fluorocytidylic acid, "$U_f$" represents 2'-fluorouridylic acid, "$A_r$" represents riboadenylic acid, and "$T_d$" represents deoxyribothymidylic acid.

Antisense, Ribozymes, and DNA Enzyme Antagonists

Antisense oligonucleotides and ribozymes that are targeted to PDGF and VEGF effect PDGF/VEGF inhibition by inhibiting protein translation from these messenger RNAs or by targeting degradation of the corresponding PDGF or VEGF mRNs, respectively. These PDGF- and VEGF-targeted nucleic acids described above provide useful sequences for the design and synthesis of these PDGF and VEGF ribozymes and antisense oligonucleotides. Methods of design and synthesis of antisense oligonucleotides and ribozymes are known in the art. Additional guidance is provided herein.

One issue in designing specific and effective mRNA-targeted oligonucleotides (antisense ODNs) and ribozymes and antisense is that of identifying accessible sites of antisense pairing within the target mRNA (which is itself folded into a partially self-paired secondary structure). A combination of computer-aided algorithms for predicting RNA pairing accessibility and molecular screening allow for the creation of specific and effective ribozymes and/or antisense oligonucleotides directed against most mRNA targets. Indeed several approaches have been described to determine the accessibility of a target RNA molecule to antisense or ribozyme inhibitors. One approach uses an in vitro screening assay applying as many antisense oligodeoxynucleotides as possible (see Monia et al., (1996) *Nature Med.,* 2:668-675; and Milner et al., (1997) *Nature Biotechnol.,* 15:537-541). Another utilizes random libraries of ODNs (Ho et al., (1996) *Nucleic Acids Res.,* 24:1901-1907; Birikh et al., (1997) *RNA* 3:429-437; and Lima et al., (1997) *J. Biol. Chem.,* 272:626-638). The accessible sites can be monitored by RNase H cleavage (see Birikh et al., supra; and Ho et al., (1998) *Nature Biotechnol.,* 16:59-63). RNase H catalyzes the hydrolytic cleavage of the phosphodiester backbone of the RNA strand of a DNA-RNA duplex.

In another approach, involving the use of a pool of semi-random, chimeric chemically synthesized ODNs, is used to identify accessible sites cleaved by RNase H on an in vitro synthesized RNA target. Primer extension analyses are then used to identify these sites in the target molecule (see Lima et al., supra). Other approaches for designing antisense targets in RNA are based upon computer assisted folding models for RNA. Several reports have been published on the use of random ribozyme libraries to screen effective cleavage (see Campbell et al., (1995) *RNA* 1:598-609; Lieber et al., (1995) *Mol. Cell Biol.,* 15: 540-551; and Vaish et al., (1997) *Biochem.,* 36:6459-6501).

Other in vitro approaches, which utilize random or semi-random libraries of ODNs and RNase H may be more useful than computer simulations (Lima et al., supra). However, use of in vitro synthesized RNA does not predict the accessibility of antisense ODNs in vivo because recent observations suggest that annealing interactions of polynucleotides are influenced by RNA-binding proteins (see Tsuchihashi et al., (1993) *Science,* 267:99-102; Portman et al., (1994) *EMBO J.,* 13:213-221; and Bertrand and Rossi (1994) *EMBO J.,* 13:2904-2912). U.S. Pat. No. 6,562,570, the contents of which are incorporated herein by reference, provides compositions and methods for determining accessible sites within an mRNA in the presence of a cell extract, which mimics in vivo conditions.

Briefly, this method involves incubation of native or in vitro-synthesized RNAs with defined antisense ODNs, ribozymes, or DNAzymes, or with a random or semi-random ODN, ribozyme or DNAzyme library, under hybridization conditions in a reaction medium which includes a cell extract containing endogenous RNA-binding proteins, or which mimics a cell extract due to presence of one or more RNA-binding proteins. Any antisense ODN, Ribozyme, or DNAzyme, which is complementary to an accessible site in the target RNA will hybridize to that site. When defined ODNs or an ODN library is used, RNase H is present during hybridization or is added after hybridization to cleave the RNA where hybridization has occurred. RNase H can be present when ribozymes or DNAzymes are used, but is not required, since the ribozymes and DNAzymes cleave RNA where hybridization has occurred. In some instances, a random or semi-random ODN library in cell extracts containing endogenous mRNA, RNA-binding proteins and RNase H is used.

Next, various methods can be used to identify those sites on target RNA to which antisense ODNs, ribozymes or DNAzymes have bound and cleavage has occurred. For example, terminal deoxynucleotidyl transferase-dependent polymerase chain reaction (TDPCR) may be used for this purpose (see Komura and Riggs (1998) *Nucleic Acids Res.,* 26:1807-11). A reverse transcription step is used to convert the RNA template to DNA, followed by TDPCR. In this invention, the 3' termini needed for the TDPCR method is created by reverse transcribing the target RNA of interest with any suitable RNA dependent DNA polymerase (e.g., reverse transcriptase). This is achieved by hybridizing a first ODN primer (P1) to the RNA in a region which is downstream (i.e., in the 5' to 3' direction on the RNA molecule) from the portion of the target RNA molecule which is under study. The polymerase in the presence of dNTPs copies the RNA into DNA from the 3' end of P1 and terminates copying at the site of cleavage created by either an antisense ODN/RNase H, a ribozyme or a DNAzyme. The new DNA molecule (referred to as the first strand DNA) serves as first template for the PCR portion of the TDPCR method, which is used to identify the corresponding accessible target sequence present on the RNA.

For example, the TDPCR procedure may then be used, i.e., the reverse-transcribed DNA with guanosine triphosphate (rGTP) is reacted in the presence of terminal deoxynucleotidyl transferase (TdT) to add an (rG)2-4 tail on the 3' termini of the DNA molecules. Next is ligated a double-stranded ODN linker having a 3'2-4 overhang on one strand that base-pairs with the (rG)2-4 tail. Then two PCR primers are added. The first is a linker primer (LP) that is complementary to the strand of the TDPCR linker which is ligated to the (rG)2-4 tail (sometimes referred to as the lower strand). The other primer (P2) can be the same as P1, but may be nested with respect to P1, i.e., it is complementary to the target RNA in a region which is at least partially upstream (i.e., in the 3' to 5' direction on the RNA molecule) from the region which is bound by P1, but it is downstream of the portion of the target RNA molecule which is under study. That is, the portion of the target RNA molecule, which is under study to determine whether it has accessible binding sites is that portion which is upstream of the region that is complementary to P2. Then PCR is carried out in the known manner in presence of a DNA polymerase and dNTPs to amplify DNA segments defined by primers LP and P2. The amplified product can then be captured by any of various known methods and subsequently sequenced on an automated DNA sequencer, providing precise identification of the cleavage site. Once this identity has been determined, defined sequence antisense DNA or ribozymes can be synthesized for use in vitro or in vivo.

Antisense intervention in the expression of specific genes can be achieved by the use of synthetic antisense oligonucleotide sequences (see, e.g., Lefebvre-d'Hellencourt et al., (1995) *Eur. Cyokine Netw.,* 6:7; Agrawal (1996) *TIBTECH,* 14: 376; and Lev-Lehman et al., (1997) *Antisense Therap.* Cohen and Smicek, eds. (Plenum Press, New York)). Briefly, antisense oligonucleotide sequences may be short sequences of DNA, typically 15-30mer but may be as small as 7mer (see Wagner et al., (1994) *Nature,* 372: 333) designed to complement a target mRNA of interest and form an RNA:AS duplex. This duplex formation can prevent processing, splicing, transport or translation of the relevant mRNA. Moreover, certain AS nucleotide sequences can elicit cellular RNase H activity when hybridized with their target mRNA, resulting in mRNA degradation (see Calabretta et al., (1996) *Semin. Oncol.,* 23:78). In that case, RNase H will cleave the RNA component of the duplex and can potentially release the AS to further hybridize with additional molecules of the target RNA. An additional mode of action results from the interaction of AS with genomic DNA to form a triple helix that may be transcriptionally inactive.

In as a non-limiting example of, addition to, or substituted for, an antisense sequence as discussed herein above, ribozymes may be utilized for suppression of gene function. This is particularly necessary in cases where antisense therapy is limited by stoichiometric considerations. Ribozymes can then be used that will target the same sequence. Ribozymes are RNA molecules that possess RNA catalytic ability that cleave a specific site in a target RNA. The number of RNA molecules that are cleaved by a ribozyme is greater than the number predicted by a 1:1 stoichiometry (see Hampel and Tritz (1989) *Biochem.*, 28: 4929-33; and Uhlenbeck (1987) *Nature*, 328: 596-600). Therefore, the present invention also allows for the use of the ribozyme sequences targeted to an accessible domain of an PDGF or VEGF mRNA species and containing the appropriate catalytic center. The ribozymes are made and delivered as known in the art and discussed further herein. The ribozymes may be used in combination with the antisense sequences.

Ribozymes catalyze the phosphodiester bond cleavage of RNA. Several ribozyme structural families have been identified including Group I introns, RNase P, the hepatitis delta virus ribozyme, hammerhead ribozymes and the hairpin ribozyme originally derived from the negative strand of the tobacco ringspot virus satellite RNA (sTRSV) (see Sullivan (1994) *Investig. Dermatolog.*, (Suppl.) 103: 95S; and U.S. Pat. No. 5,225,347). The latter two families are derived from viroids and virusoids, in which the ribozyme is believed to separate monomers from oligomers created during rolling circle replication (see Symons (1989) *TIBS*, 14: 445-50; Symons (1992) *Ann. Rev. Biochem.*, 61: 641-71). Hammerhead and hairpin ribozyme motifs are most commonly adapted for trans-cleavage of mRNAs for gene therapy. The ribozyme type utilized in the present invention is selected as is known in the art. Hairpin ribozymes are now in clinical trial and are a particularly useful type. In general the ribozyme is from 30-100 nucleotides in length.

Ribozyme molecules designed to catalytically cleave a target mRNA transcript are known in the art (e.g., PDGF (SEQ ID NO: 1) or VEGF (SEQ ID NO:3) and can also be used to prevent translation of mRNA (see, e.g., PCT International Pub. WO90/11364; Sarver et al., (1990) *Science*, 247: 1222-1225 and U.S. Pat. No. 5,093,246). While ribozymes that cleave mRNA at site specific recognition sequences can be used to destroy particular mRNAs, the use of hammerhead ribozymes is particularly useful. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach ((1988) *Nature*, 334: 585).

The ribozymes of the present invention also include RNA endoribonucleases (hereinafter "Cech-type ribozymes") such as the one which occurs naturally in Tetrahymena thermophila (known as the IVS, or L-19 IVS RNA), and which has been extensively described by Thomas Cech and collaborators (see Zaug et al., (1984) *Science*, 224:574-578; Zaug and Cech (1986) *Science*, 231:470-475; Zaug, et al., (1986) *Nature*, 324:429-433; International patent application No. WO88/04300; Been and Cech (1986) *Cell*, 47:207-216). The Cech-type ribozymes have an eight base pair active site, which hybridizes to a target RNA sequence where after cleavage of the target RNA takes place. The invention encompasses those Cech-type ribozymes, which target eight base-pair active site sequences. While the invention is not limited to a particular theory of operative mechanism, the use of hammerhead ribozymes in the invention may have an advantage over the use of PDGF/VEGF-directed antisense, as recent reports indicate that hammerhead ribozymes operate by blocking RNA translation and/or specific cleavage of the mRNA target.

As in the antisense approach, the ribozymes can be composed of modified oligonucleotides (e.g., for improved stability, targeting, etc.) and are delivered to cells expressing the target mRNA. A useful method of delivery involves using a DNA construct "encoding" the ribozyme under the control of a strong constitutive pol III or pol II promoter, so that transfected cells will produce sufficient quantities of the ribozyme to destroy targeted messages and inhibit translation. Because ribozymes, unlike antisense molecules, are catalytic, a lower intracellular concentration is required for efficiency.

As described above, nuclease resistance, where needed, is provided by any method known in the art that does not substantially interfere with biological activity of the antisense oligodeoxynucleotides or ribozymes as needed for the method of use and delivery (Iyer et al., (1990) *J. Org. Chem.*, 55: 4693-99; Eckstein (1985) *Ann. Rev. Biochem.*, 54: 367-402; Spitzer and Eckstein (1988) *Nucleic Acids Res.*, 18: 11691-704; Woolf et al., (1990) *Nucleic Acids Res.*, 18: 1763-69; and Shaw et al., (1991) *Nucleic Acids Res.*, 18: 11691-704). As described above for aptamers, non-limiting representative modifications that can be made to antisense oligonucleotides or ribozymes in order to enhance nuclease resistance include modifying the phosphorous or oxygen heteroatom in the phosphate backbone, short chain alkyl or cycloalkyl intersugar linkages or short chain heteroatomic or heterocyclic intersugar linkages. These include, e.g., preparing 2'-fluoridated, O-methylated, methyl phosphonates, phosphorothioates, phosphorodithioates and morpholino oligomers. For example, the antisense oligonucleotide or ribozyme may have phosphorothioate bonds linking between four to six 3'-terminus nucleotide bases. Alternatively, phosphorothioate bonds may link all the nucleotide bases. Phosphorothioate antisense oligonucleotides do not normally show significant toxicity at concentrations that are effective and exhibit sufficient pharmacodynamic half-lives in animals (see Agarwal et al., (1996) *TIBTECH*, 14: 376) and are nuclease resistant. Alternatively the nuclease resistance for the AS-ODN can be provided by having a 9 nucleotide loop forming sequence at the 3'-terminus having the nucleotide sequence CGCGAAGCG. The use of avidin-biotin conjugation reaction can also be used for improved protection of AS-ODNs against serum nuclease degradation (see Boado and Pardridge (1992) *Bioconj. Chem.*, 3: 519-23). According to this concept the AS-ODN agents are monobiotinylated at their 3'-end. When reacted with avidin, they form tight, nuclease-resistant complexes with 6-fold improved stability over non-conjugated ODNs.

Other studies have shown extension in vivo of antisense oligodeoxynucleotides (Agarwal et al., (1991) *Proc. Natl. Acad. Sci.* (USA) 88: 7595). This process, presumably useful as a scavenging mechanism to remove alien AS-oligonucleotides from the circulation, depends upon the existence of free 3'-termini in the attached oligonucleotides on which the extension occurs. Therefore partial phosphorothioate, loop protection or biotin-avidin at this important position should be sufficient to ensure stability of these AS-oligodeoxynucleotides.

In addition to using modified bases as described above, analogs of nucleotides can be prepared wherein the structure of the nucleotide is fundamentally altered and that are better suited as therapeutic or experimental reagents. An example of a nucleotide analog is a peptide nucleic acid (PNA) wherein the deoxyribose (or ribose) phosphate backbone in DNA (or RNA) is replaced with a polyamide backbone, which is similar to that found in peptides. PNA analogs have been shown to be resistant to degradation by enzymes and to have extended lives in vivo and in vitro. Further, PNAs have been shown to bind stronger to a complementary DNA sequence than a DNA molecule. This observation is attributed to the lack of charge repulsion between the PNA strand and the DNA strand. Other modifications that can be made to oligonucleotides include polymer backbones, morpholino polymer backbones (see, e.g., U.S. Pat. No. 5,034,506, the contents of which are incorporated herein by reference), cyclic backbones, or acyclic backbones, sugar mimetics or any other modification including which can improve the pharmacodynamics properties of the oligonucleotide.

A further aspect of the invention relates to the use of DNA enzymes to decrease expression of the target mRNA as, e.g., PDGF or VEGF. DNA enzymes incorporate some of the mechanistic features of both antisense and ribozyme technologies. DNA enzymes axe designed so that they recognize a particular target nucleic acid sequence, much like an antisense oligonucleotide, however much like a ribozyme they are catalytic and specifically cleave the target nucleic acid.

There are currently two basic types of DNA enzymes, and both of these were identified by Santoro and Joyce (see, for example, U.S. Pat. No. 6,110,462). The 10-23 DNA enzyme comprises a loop structure which connect two arms. The two arms provide specificity by recognizing the particular target nucleic acid sequence while the loop structure provides catalytic function under physiological conditions.

Briefly, to design DNA enzyme that specifically recognizes and cleaves a target nucleic acid, one of skill in the art must first identify the unique target sequence. This can be done using the same approach as outlined for antisense oligonucleotides. In certain instances, the unique or substantially sequence is a G/C rich of approximately 18 to 22 nucleotides. High G/C content helps insure a stronger interaction between the DNA enzyme and the target sequence.

When synthesizing the DNA enzyme, the specific antisense recognition sequence that targets the enzyme to the message is divided so that it comprises the two arms of the DNA enzyme, and the DNA enzyme loop is placed between the two specific arms.

Methods of making and administering DNA enzymes can be found, for example, in U.S. Pat. No. 6,110,462. Similarly, methods of delivery DNA ribozymes in vitro or in vivo include methods of delivery RNA ribozyme, as outlined herein. Additionally, one of skill in the art will recognize that, like antisense oligonucleotides, DNA enzymes can be optionally modified to improve stability and improve resistance to degradation.

RNAi Antagonists

Some embodiments of the invention make use of materials and methods for effecting repression of VEGF and PDGF by means of RNA interference (RNAi). RNAi is a process of sequence-specific post-transcriptional gene repression that can occur in eukaryotic cells. In general, this process involves degradation of an mRNA of a particular sequence induced by double-stranded RNA (dsRNA) that is homologous to that sequence. For example, the expression of a long dsRNA corresponding to the sequence of a particular single-stranded mRNA (ss mRNA) will labilize that message, thereby "interfering" with expression of the corresponding gene. Accordingly, any selected gene may be repressed by introducing a dsRNA which corresponds to all or a substantial part of the mRNA for that gene. It appears that when a long dsRNA is expressed, it is initially processed by a ribonuclease III into shorter dsRNA oligonucleotides of as few as 21 to 22 base pairs in length. Accordingly, RNAi may be effected by introduction or expression of relatively short homologous dsRNAs. Indeed the use of relatively short homologous dsRNAs may have certain advantages as discussed below.

Mammalian cells have at least two pathways that are affected by double-stranded RNA (dsRNA). In the RNAi (sequence-specific) pathway, the initiating dsRNA is first broken into short interfering (si) RNAs, as described above. The siRNAs have sense and antisense strands of about 21 nucleotides that form approximately 19 nucleotide si RNAs with overhangs of two nucleotides at each 3' end. Short interfering RNAs are thought to provide the sequence information that allows a specific messenger RNA to be targeted for degradation. In contrast, the nonspecific pathway is triggered by dsRNA of any sequence, as long as it is at least about 30 base pairs in length. The nonspecific effects occur because dsRNA activates two enzymes: PKR (double-stranded RNA-activated protein kinase), which in its active form phosphorylates the translation initiation factor eIF2 to shut down all protein synthesis, and 2', 5' oligoadenylate synthetase (2',5'-AS), which synthesizes a molecule that activates RNase L, a nonspecific enzyme that targets all mRNAs. The nonspecific pathway may represent a host response to stress or viral infection, and, in general, the effects of the nonspecific pathway are minimized in particularly useful methods of the present invention. Significantly, longer dsRNAs appear to be required to induce the nonspecific pathway and, accordingly, dsRNAs shorter than about 30 bases pairs are particular useful to effect gene repression by RNAi (see, e.g., Hunter et al., (1975) *J. Biol. Chem.*, 250: 409-17; Manche et al., (1992) *Mol. Cell Biol.*, 12: 5239-48; Minks et al., (1979) *J. Biol. Chem.*, 254: 10180-3; and Elbashir et al., (2001) *Nature*, 411: 494-8).

Certain double stranded oligonucleotides used to effect RNAi are less than 30 base pairs in length and may comprise about 25, 24, 23, 22, 21, 20, 19, 18 or 17 base pairs of ribonucleic acid. Optionally, the dsRNA oligonucleotides of the invention may include 3' overhang ends. Non-limiting exemplary 2-nucleotide 3' overhangs may be composed of ribonucleotide residues of any type and may even be composed of 2'-deoxythymidine resides, which lowers the cost of RNA synthesis and may enhance nuclease resistance of siRNAs in the cell culture medium and within transfected cells (see Elbashi et al., (2001) *Nature*, 411: 494-8).

Longer dsRNAs of 50, 75, 100 or even 500 base pairs or more may also be utilized in certain embodiments of the invention. Exemplary concentrations of dsRNAs for effecting RNAi are about 0.05 nM, 0.1 nM, 0.5 nM, 1.0 nM, 1.5 nM, 25 nM or 100 nM, although other concentrations may be utilized depending upon the nature of the cells treated, the gene target and other factors readily discernable the skilled artisan. Exemplary dsRNAs may be synthesized chemically or produced in vitro or in vivo using appropriate expression vectors. Exemplary synthetic RNAs include 21 nucleotide RNAs chemically synthesized using methods known in the art (e.g., Expedite RNA phosphoramidites and thymidine phosphoramidite (Proligo, Germany)). Synthetic oligonucleotides may be deprotected and gel-purified using methods known in the art (see e.g., Elbashir et al., (2001) *Genes Dev.*, 15: 188-200). Longer RNAs may be transcribed from promoters, such as T7 RNA polymerase promoters, known in the art. A single RNA target, placed in both possible orientations downstream of an in vitro promoter, will transcribe both strands of the target to create a dsRNA oligonucleotide of the desired target sequence.

The specific sequence utilized in design of the oligonucleotides may be any contiguous sequence of nucleotides contained within the expressed gene message of the target (e.g., of PDGF (e.g., SEQ ID NO:2) or VEGF (e.g., SEQ ID NO: 4). Programs and algorithms, known in the art, may be used to select appropriate target sequences. In addition, optimal sequences may be selected, as described additionally above, utilizing programs designed to predict the secondary structure of a specified single stranded nucleic acid sequence and allow selection of those sequences likely to occur in exposed single stranded regions of a folded mRNA. Methods and compositions for designing appropriate oligonucleotides may be found in, for example, U.S. Pat. No. 6,251,588, the contents of which are incorporated herein by reference. mRNA is generally thought of as a linear molecule that contains the information for directing protein synthesis within the sequence of ribonucleotides. However, studies have revealed a number of secondary and tertiary structures exist in most mRNAs. Secondary structure elements in RNA are formed largely by Watson-Crick type interactions between different regions of the same RNA molecule. Important secondary structural elements include intramolecular double stranded regions, hairpin loops, bulges in duplex RNA and internal loops. Tertiary structural elements are formed when secondary structural elements come in contact with each other or with single stranded regions to produce a more complex three-dimensional structure. A number of researchers have measured the binding energies of a large number of RNA duplex structures and have derived a set of rules which can be used to predict the secondary structure of RNA (see e.g., Jaeger et al., (1989) *Proc. Natl. Acad. Sci.* (USA) 86:7706 (1989); and Turner et al., (1988) *Ann. Rev. Biophys. Biophys. Chem.,* 17:167). The rules are useful in identification of RNA structural elements and, in particular, for identifying single stranded RNA regions, which may represent particularly useful segments of the mRNA to target for silencing RNAi, ribozyme or antisense technologies. Accordingly, particular segments of the mRNA target can be identified for design of the RNAi mediating dsRNA oligonucleotides as well as for design of appropriate ribozyme and hammerhead ribozyme compositions of the invention.

The dsRNA oligonucleotides may be introduced into the cell by transfection with an heterologous target gene using carrier compositions such as liposomes, which are known in the art, e.g., Lipofectamine 2000 (Life Technologies, Rockville Md.) as described by the manufacturer for adherent cell lines. Transfection of dsRNA oligonucleotides for targeting endogenous genes may be carried out using Oligofectamine (Life Technologies). Transfection efficiency may be checked using fluorescence microscopy for mammalian cell lines after co-transfection of hGFP encoding pAD3 (Kehlenback et al., (1998) *J. Cell Biol.,* 141: 863-74). The effectiveness of the RNAi may be assessed by any of a number of assays following introduction of the dsRNAs. These include, but are not limited to, Western blot analysis using antibodies which recognize the targeted gene product following sufficient time for turnover of the endogenous pool after new protein synthesis is repressed, and Northern blot analysis to determine the level of existing target mRNA.

Still further compositions, methods and applications of RNAi technology for use in the invention are provided in U.S. Pat. Nos. 6,278,039, 5,723,750 and 5,244,805, which are incorporated herein by reference.

Receptor Tyrosine Kinase Inhibitor Antagonists

Also included in the invention are tyrosine kinase antagonists known in the art and variants and alternatives thereto that may be obtained using routine skill in the art and the teachings of the art incorporated herein by reference. The extracellular signal of PDGF (and VEGF) is communicated to other parts of the cell via a tyrosine kinase mediated phosphorylation event effected by the PDGF receptor (and VEGF receptor) and which affects substrate proteins downstream of the cell membrane bound signaling complex. Accordingly, antagonists acting at the receptor kinase stage of PDGF (and/or VEGF) signaling are also effective in the method of the invention.

A number of types of tyrosine kinase inhibitors that are selective for tyrosine kinase receptor enzymes such as PDGFR or VEGFR, are known (see, e.g., Spada and Myers ((1995) *Exp. Opin. Ther. Patents,* 5: 805) and Bridges ((1995) *Exp. Opin. Ther. Patents,* 5: 1245). Additionally Law and Lydon have summarized the anticancer potential of tyrosine kinase inhibitors ((1996) *Emerging Drugs: The Prospect For Improved Medicines,* 241-260). For example, U.S. Pat. No. 6,528,526 describes substituted quinoxaline compounds that exhibit selectively inhibit platelet-derived growth factor-receptor (PDGFR) tyrosine kinase activity. The known inhibitors of PDGFR tyrosine kinase activity includes quinoline-based inhibitors reported by Maguire et al., ((1994) *J. Med. Chem.,* 37: 2129), and by Dolle, et al., ((1994) *J. Med. Chem.,* 37: 2627). A class of phenylamino-pyrimidine-based inhibitors was recently reported by Traxler, et al., in EP 564409 and by Zimmerman et al., ((1996) *Biorg. Med. Chem. Lett.,* 6: 1221-1226) and by Buchdunger, et al., ((1995) *Proc. Nat. Acad. Sci.* (USA), 92: 2558). Quinazoline derivatives that are useful in inhibiting PDGF receptor tyrosine kinase activity include bismono- and bicyclic aryl compounds and heteroaryl compounds (see, e.g., WO 92/20642), quinoxaline derivatives (see (1994) *Cancer Res.,* 54: 6106-6114), pyrimidine derivatives (Japanese Published Patent Application No. 87834/94) and dimethoxyquinoline derivatives (see *Abstracts of the 116th Annual Meeting of the Pharmaceutical Society of Japan* (Kanazawa), (1996), 2, p. 275, 29(C2) 15-2).

Examples of VEGFR tyrosine kinase inhibitors include cinnoline derivatives, e.g., those described in U.S. Pat. No. 6,514,971, the contents of which are incorporated herein in their entirety. Other such cinnoline derivatives are also known. For example, (1995) *J. Med Chem.,* 38: 3482-7 discloses 4-(3-bromoanilino)cinnoline; (1968) *J. Chem. Soc. C,* (9):1152-5 discloses 6-chloro-4-phenoxycinnoline; (1984) *J. Karnatak Univ.,* Sci., 29: 82-6 discloses certain 4-anilinocinnolines; and (1973) *Indian J. Chem.,* 11: 211-13 discloses certain 4-phenylthiocinnolines. Furthermore, (1973) *J. Karnatak Univ.,* 18: 25-30 discloses certain 4-phenoxycinnolines, (1984) *J. Karnatak Univ. Sci.,* 29: 82-6 discloses two compounds: 4-(4-methoxyanilino)-6,7-dimethoxycinnoline and 4-(3-chloroanilino)-6,7-dimethoxycinnoline. Furthermore, certain cinnolines with a phenyl ring linked via a group selected from —O—, —S—, —NH— and —CH2- at the 4-position are described in U.S. Pat. No. 5,017,579, U.S. Pat. No. 4,957,925, U.S. Pat. No. 4,994,474, and EP 0302793 A2.

Still other related compounds for inhibition of VEGFR and/or PDGFR are available by screening novel compounds for their effect on the receptor tyrosine kinase activity of interest using a convention assay. Effective inhibition by a candidate PDGFR or VEGFR small molecule organic inhibitor can be monitored using a cell-based assay system as well as other assay systems known in the art.

For example, one test for activity against VEGF-receptor tyrosine kinase is as follows. The test is conducted using Flt-1

VEGF-receptor tyrosine kinase. The detailed procedure is as follows: 30 µl kinase solution (10 ng of the kinase domain of Flt-1 (see Shibuya, et al., (1990) *Oncogene*, 5: 519-24) in 20 mM Tris.HCl pH 7.5, 3 mM manganese dichloride ($MnCl_2$), 3 mM magnesium chloride ($MgCl_2$), 10 uM sodium vanadate, 0.25 mg/ml polyethylenglycol (PEG) 20000, 1 mM dithiothreitol and 3 ug/.mu.1 poly(Glu,Tyr) 4:1 (Sigma, Buchs, Switzerland), 8 uM [$^{33}$P]-ATP (0.2 uCi), 1% dimethyl sulfoxide, and 0 to 100 µM of the compound to be tested are incubated together for 10 minutes at room temperature. The reaction is then terminated by the addition of 10 µl 0.25 M ethylenediaminetetraacetate (EDTA) pH 7. Using a multichannel dispenser (LAB SYSTEMS, USA), an aliquot of 20 µl is applied to a PVDF (=polyvinyl difluoride) Immobilon P membrane (Millipore, USA), through a microtiter filter manifold and connected to a vacuum. Following complete elimination of the liquid, the membrane is washed 4 times successively in a bath containing 0.5% phosphoric acid ($H_3 PO_4$) and once with ethanol, incubated for 10 minutes each time while shaking, then mounted in a Hewlett Packard TopCount Manifold and the radioactivity measured after the addition of 10 µl Microscint® (beta-scintillation counter liquid). $IC_{50}$-values are determined by linear regression analysis of the percentages for the inhibition of each compound in three concentrations (as a rule 0.01 µmol, 0.1 µmol, and 1 µmol). The $IC_{50}$-values of active tyrosine inhibitor compounds may be in the range of 0.01 µM to 100 µM.

Furthermore, inhibition of a VEGF-induced VEGFR tyrosine kinase/autophosphorylation activity can be confirmed with a further experiment on cells. Briefly, transfected CHO cells, which permanently express human VEGF receptor (VEGFR/KDR), are seeded in complete culture medium (with 10% fetal call serum (FCS) in 6-well cell-culture plates and incubated at 37° C. under 5% $CO_2$ until they show about 80% confluency. The compounds to be tested are then diluted in culture medium (without FCS, with 0.1% bovine serum albumin) and added to the cells. (Controls comprise medium without test compounds). After a two hour incubation at 37° C., recombinant VEGF is added; the final VEGF concentration is 20 ng/ml). After a further five minutes incubation at 37° C., the cells are washed twice with ice-cold PBS and immediately lysed in 100 µl lysis buffer per well. The lysates are then centrifuged to remove the cell nuclei, and the protein concentrations of the supernatants are determined using a commercial protein assay (BIORAD). The lysates can then either be immediately used or, if necessary, stored at ±200° C.

A sandwich ELISA is then carried out to measure the KDR-receptor phosphorylation: a monoclonal antibody to KDR is immobilized on black ELISA plates (OptiPlate™, HTRF-96 from Packard). The plates are then washed and the remaining free protein-binding sites are saturated with 1% BSA in PBS. The cell lysates (20 µg protein per well) are then incubated in these plates overnight at 4° C. together with an antiphosphotyrosine antibody coupled with alkaline phosphatase (e.g., PY20:AP from Transduction Laboratories, Lexington, Ky.). The plates are washed again and the binding of the antiphosphotyrosine antibody to the captured phosphorylated receptor is then demonstrated using a luminescent AP substrate (CDP-Star, ready to use, with Emerald II; Applied-Biosystems TROPIX Bedford, Mass.). The luminescence is measured in a Packard Top Count Microplate Scintillation Counter. The difference between the signal of the positive control (stimulated with VEGF or PDGF) and that of the negative control (not stimulated with VEGF or PDGF) corresponds to VEGF-induced KDR-receptor phosphorylation (=100%). The activity of the tested substances is calculated as % inhibition of VEGF-induced KDR-receptor phosphorylation, wherein the concentration of substance that induces half the maximum inhibition is defined as the $ED_{50}$ (effective dose for 50% inhibition). Active tyrosine inhibitor compound have $ED_{50}$ values in the range of 0.001 µM to 6 µM, typically 0.005 µM to 0.5 µM.

Pharmaceutical Formulations and Therapeutic Administration

The anti-VEGF and anti-PDGF agents are useful in the treatment of a neovascular disorder, including psoriasis, rheumatoid arthritis, and ocular neovascular disorders. Of particular interest are therapies using a PDGF-B antagonist compound in combination with a VEGF-A antagonist to suppress an ocular neovascular disorder such as macular degeneration or diabetic retinopathy. Accordingly, once a patient has been diagnosed to be at risk at developing or having a neovascular disorder, the patient is treated by administration of a PDGF antagonist in combination with a VEGF antagonist in order to block respectively the negative effects of PDGF and VEGF, thereby suppressing the development of a neovascular disorder and alleviating deleterious effects associated with neovascularization. The practice of the methods according to the present invention does not result in corneal edema. As is discussed above, a wide variety of PDGF and VEGF antagonists may be used in the present invention.

Anti-PDGF and anti-VEGF combination therapy according to the invention may be performed alone or in conjunction with another therapy and may be provided at home, the doctor's office, a clinic, a hospital's outpatient department, or a hospital. Treatment generally begins at a hospital so that the doctor can observe the therapy's effects closely and make any adjustments that are needed. The duration of the combination therapy depends on the type of neovascular disorder being treated, the age and condition of the patient, the stage and type of the patient's disease, and how the patient responds to the treatment. Additionally, a person having a greater risk of developing a neovascular disorder (e.g., a diabetic patient) may receive treatment to inhibit or delay the onset of symptoms. One significant advantage provided by the present invention is that the combination of a PDGF antagonist and a VEGF antagonist for the treatment of a neovascular disorder allows for the administration of a low dose of each antagonist and less total active antagonist, thus providing similar efficacy with less toxicity and side effects, and reduced costs.

Administration of each antagonist of the combination therapy may be by any suitable means that results in a concentration of the antagonist that, combined with the other antagonist, is effective for the treatment of a neovascular disorder. Each antagonist, for example, may be admixed with a suitable carrier substance, and is generally present in an amount of 1-95% by weight of the total weight of the composition. The composition may be provided in a dosage form that is suitable for ophthalmic, oral, parenteral (e.g., intravenous, intramuscular, subcutaneous), rectal, transdermal, nasal, or inhalant administration. Accordingly, the composition may be in form of, e.g., tablets, capsules, pills, powders, granulates, suspensions, emulsions, solutions, gels including hydrogels, pastes, ointments, creams, plasters, delivery devices, suppositories, enemas, injectables, implants, sprays, or aerosols. The pharmaceutical compositions containing a single antagonist or two or more antagonists may be formulated according to conventional pharmaceutical practice (see, e.g., Remington: *The Science and Practice of Pharmacy*, (20th ed.) ed. A. R. Gennaro, 2000, Lippincott Williams & Wilkins, Philadelphia, Pa. and *Encyclopedia of Pharmaceutical Technology, eds.*, J. Swarbrick and J. C. Boylan, 1988-2002, Marcel Dekker, New York).

Combinations of PDGF and VEGF antagonists are, in one useful aspect, administered parenterally (e.g., by intramuscular, intraperitoneal, intravenous, intraocular, intravitreal, retro-bulbar, subconjunctival, subtenon or subcutaneous injection or implant) or systemically. Formulations for parenteral or systemic administration include sterile aqueous or non-aqueous solutions, suspensions, or emulsions. A variety of aqueous carriers can be used, e.g., water, buffered water, saline, and the like. Examples of other suitable vehicles include polypropylene glycol, polyethylene glycol, vegetable oils, gelatin, hydrogels, hydrogenated naphalenes, and injectable organic esters, such as ethyl oleate. Such formulations may also contain auxiliary substances, such as preserving, wetting, buffering, emulsifying, and/or dispersing agents. Biocompatible, biodegradable lactide polymer, lactide/glycolide copolymer, or polyoxyethylene-polyoxypropylene copolymers may be used to control the release of the active ingredients.

Alternatively, combinations of PDGF and VEGF antagonists can be administered by oral ingestion. Compositions intended for oral use can be prepared in solid or liquid forms, according to any method known to the art for the manufacture of pharmaceutical compositions.

Solid dosage forms for oral administration include capsules, tablets, pills, powders, and granules. Generally, these pharmaceutical preparations contain active ingredients (such as a PDGF small organic molecule antagonist and a VEGF small organic molecule antagonist) admixed with non-toxic pharmaceutically acceptable excipients. These may include, for example, inert diluents, such as calcium carbonate, sodium carbonate, lactose, sucrose, glucose, mannitol, cellulose, starch, calcium phosphate, sodium phosphate, kaolin and the like. Binding agents, buffering agents, and/or lubricating agents (e.g., magnesium stearate) may also be used. Tablets and pills can additionally be prepared with enteric coatings. The compositions may optionally contain sweetening, flavoring, coloring, perfuming, and preserving agents in order to provide a more palatable preparation.

For example, the PDGF and VEGF antagonists may be administer intraocullary by intravitreal injection into the eye as well as subconjunctival and subtenon injections. Other routes of administration include transcleral, retro bulbar, intraperoteneal, intramuscular, and intravenous. Alternatively, a combination of antagonists may be delivered using a drug delivery device or an intraocular implant (see below).

Liquid dosage forms for oral administration include pharmaceutically acceptable emulsions, solutions, suspensions, syrups, and soft gelatin capsules. These forms contain inert diluents commonly used in the art, such as water or an oil medium, and can also include adjuvants, such as wetting agents, emulsifying agents, and suspending agents.

In some instances, the combination of PDGF and VEGF antagonists can also be administered topically, for example, by patch or by direct application to a region, such as the epidermis or the eye, susceptible to or affected by a neovascular disorder, or by iontophoresis.

Formulations for ophthalmic use include tablets containing the active ingredient(s) in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc).

The PDGF and VEGF antagonists may be mixed together in a tablet or other vehicle, or may be partitioned. In one example, the first antagonist is contained on the inside of the tablet, and the second antagonist is on the outside, such that a substantial portion of the second antagonist is released prior to the release of the first antagonist. If desired, antagonists in a tablet form may be delivered using a drug delivery device (see below).

Generally, each of the antagonists should be administered in an amount sufficient to suppress or reduce or eliminate a deleterious effect or a symptom of a neovascular disorder. The amount of an active antagonist ingredient that is combined with the carrier materials to produce a single dosage will vary depending upon the subject being treated and the particular mode of administration.

The dosage of each antagonist of the claimed combinations depends on several factors including the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect dosage used. Furthermore, one skilled in the art will appreciate that the exact individual dosages may be adjusted somewhat depending on a variety of factors, including the specific combination of PDGF and VEGF antagonists being administered, the time of administration, the route of administration, the nature of the formulation, the rate of excretion, the particular neovascular disorder being treated, the severity of the disorder, and the anatomical location of the neovascular disorder (for example, the eye versus the body cavity). Wide variations in the needed dosage are to be expected in view of the differing efficiencies of the various routes of administration. For instance, oral administration generally would be expected to require higher dosage levels than administration by intravenous or intravitreal injection. Variations in these dosage levels can be adjusted using standard empirical routines for optimization, which are well-known in the art. The precise therapeutically effective dosage levels and patterns are typically determined by the attending physician such as an ophthalmologist in consideration of the above-identified factors.

Generally, when orally administered to a human, the dosage of the PDGF antagonist or VEGF antagonist is normally about 0.001 mg to about 200 mg per day, desirably about 1 mg to 100 mg per day, and more desirably about 5 mg to about 50 mg per day. Dosages up to about 200 mg per day may be necessary. For administration of the PDGF antagonist or VEGF antagonist by injection, the dosage is normally about 0.1 mg to about 250 mg per day, desirably about 1 mg to about 20 mg per day, or about 3 mg to about 5 mg per day. Injections may be given up to about four times daily. Generally, when parenterally or systemically administered to a human, the dosage of the VEGF antagonist for use in combination with the PDGF antagonist is normally about 0.1 mg to about 1500 mg per day, or about 0.5 mg to 10 about mg per day, or about 0.5 mg to about 5 mg per day. Dosages up to about 3000 mg per day may be necessary.

When opthalmologically administered to a human, the dosage of the VEGF antagonist for use in combination with the PDGF antagonist is normally about 0.15 mg to about 3.0 mg per day, or at about 0.3 mg to about 3.0 mg per day, or at about 0.1 mg to 1.0 mg per day.

For example, for ophthalmic uses, PDGF-B and VEGF-A aptamer drug substances are formulated in phosphate buffered saline at pH 5-7. Sodium hydroxide or hydrochloric acid may be added for pH adjustment. In one working formulation, a PDGF-B aptamer and a VEGF-A aptamer, such as EYE001, are individually formulated at three different concentrations: 3 mg/100 µl, 2 mg/100 µl and 1 mg/100 µl packaged in a sterile 1 ml, USP Type I graduated glass syringe fitted with a sterile 27-gauge needle. The combination drug product is preservative-free and intended for single use by intravitreous injection only. The active ingredient is PDGF-B and VEGF-A drug substances, at 30 mg/ml, 20 mg/ml and 10 mg/ml concentrations. The excipients are Sodium Chloride, USP; Sodium Phosphate Monobasic, Monohydrate, USP; Sodium Phosphate Dibasic, Heptahydrate, USP; Sodium Hydroxide, USP; Hydrochloric acid, USP; and Water for injection, USP. In this form the PDGF-B and VEGF-A aptamer drug products are in a ready-to-use sterile solution provided in a single-use glass syringe. The syringe is removed from refrigerated storage at least 30 minutes (but not longer than 4 hours) prior to use to allow the solution to reach room temperature. Administration of the syringe contents involves attaching the threaded plastic plunger rod to the rubber stopper inside the barrel of the syringe. The rubber end cap is then removed to allow administration of the product. PDGF-B and VEGF-A aptamers are administered as a 100 µl intravitreal injections on three occasions at 28 day intervals. Patients receive 3 mg/injection per visit. The dose is reduced to 2 mg or 1 mg, and further to 0.1 mg if necessary.

The specific amounts of drugs administered depend on the specific combination of components. In a desired dose combination, the ratio of PDGF antagonist to VEGF antagonist is about 50:1 by weight, about 20:1 by weight, about 10:1 by weight, or about 4:1, about 2:1, or about 1:1 by weight.

A useful combination therapy includes a PDGF-B aptamer antagonist and a VEGF-A aptamer antagonist. The antagonists are used in combination in a weight ratio range from about 0.1 to about 5.0 to about 5.0 to 0.1 of the PDGF-B aptamer antagonist to VEGF-A aptamer antagonist. A useful range of these two antagonists (PDGF-B to VEGF-A antagonist) is from about 0.5 to about 2.0, or from about 2.0 to 0.5, while another useful ratio is from about 1.0 to about 1.0, depending ultimately on the selection of the PDGF-B aptamer antagonist and the VEGF-A aptamer antagonist.

Administration of each drug in the combination therapy can, independently, be one to four times daily for one day to one year, and may even be for the life of the patient. Chronic, long-term administration will be indicated in many cases. The dosage may be administered as a single dose or divided into multiple doses. In general, the desired dosage should be administered at set intervals for a prolonged period, usually at least over several weeks, although longer periods of administration of several months or more may be needed.

In addition to treating pre-existing neovascular disorders, the combination therapy that includes a PDGF antagonist and VEGF antagonist can be administered prophylactically in order to prevent or slow the onset of these disorders. In prophylactic applications, the PDGF and VEGF antagonists are administered to a patient susceptible to or otherwise at risk of a particular neovascular disorder. Again, the precise timing of the administration and amounts that are administered depend on various factors such as the patient's state of health, weight, etc.

In one working example, the combination of the PDGF antagonist and the VEGF antagonist is administered to a mammal in need of treatment therewith, typically in the form of an injectable pharmaceutical composition. In the combination aspect, for example, a PDGF-B aptamer and a VEGF-A aptamer may be administered either separately or in the pharmaceutical composition comprising both. It is generally preferred that such administration be by injection or by using a drug delivery device. Parenteral, systemic, or transdermal administration is also acceptable.

As discussed above, when the PDGF antagonist and VEGF antagonist are administered together, such administration can be sequential in time or simultaneous with the sequential method being one mode of administration. When the PDGF and VEGF antagonists are administered sequentially, the administration of each can be by the same or different methods. For sequential administration, however, it is useful that the method employ administration of the PDGF antagonist over about five seconds (up to about three injections) followed by sustained administration every six weeks for up to about nine injections per year of a VEGF antagonist. The PDGF antagonist may be administered at the time of each VEGF antagonist injection or may be given less often, as determined by the physician. Sequential administration also includes a combination where the individual antagonists may be administered at different times or by different routes or both but which act in combination to provide a beneficial effect, for example, to suppress a neovascular disorder. It is also noted that administration by injection is particularly useful.

Pharmaceutical compositions according to the invention may be formulated to release the active PDGF and VEGF antagonists substantially immediately upon administration or at any predetermined time period after administration, using controlled release formulations. For example, a pharmaceutical composition that includes at least one of each of a PDGF antagonist and a VEGF antagonist may be provided in sustained release compositions. The use of immediate or sustained release compositions depends on the nature of the condition being treated. If the condition consists of an acute or over-acute disorder, treatment with an immediate release form will be typically utilized over a prolonged release composition. For certain preventative or long-term treatments, a sustained released composition may also be appropriate.

Administration of each of the antagonists in controlled release formulations is useful where the antagonist, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window in the gastro-intestinal tract; or (iii) a short biological half-life, so that frequent dosing during a day is required in order to sustain the plasma level at a therapeutic level.

Many strategies can be pursued to obtain controlled release in which the rate of release outweighs the rate of degradation or metabolism of the therapeutic antagonist. For example, controlled release can be obtained by the appropriate selection of formulation parameters and ingredients, including, e.g., appropriate controlled release compositions and coatings. Examples include single or multiple unit tablet or capsule compositions, oil solutions, suspensions, emulsions, microcapsules, microspheres, nanoparticles, patches, and liposomes. Methods for preparing such sustained or controlled release formulations are well known in the art.

Pharmaceutical compositions that include a PDGF antagonist and/or a VEGF antagonist or both may also be delivered using a drug delivery device such as an implant. Such implants may be biodegradable and/or biocompatible implants, or may be non-biodegradable implants. The implants may be permeable or impermeable to the active agent. Ophthalmic drug delivery devices may be inserted into a chamber of the eye, such as the anterior or posterior chambers or may be implanted in or on the sclera, choroidal space, or an avascularized region exterior to the vitreous. In one embodiment, the implant may be positioned over an avascular region, such as on the sclera, so as to allow for transcleral diffusion of the drug to the desired site of treatment, e.g., the intraocular space and macula of the eye. Furthermore, the site of transcleral diffusion may be proximity to a site of neovascularization such as a site proximal to the macula.

As noted above, the invention relates to combining separate pharmaceutical compositions in a pharmaceutical pack. The combination of the invention is therefore provided as components of a pharmaceutical pack. At least two antagonists can be formulated together or separately and in individual dosage amounts. The antagonists of the invention are also useful when formulated as salts.

The pharmaceutical pack, in general, includes (1) an amount of a PDGF antagonist, and a pharmaceutically acceptable carrier, vehicle, or diluent in a first unit dosage form; (2) an amount of a VEGF antagonist, and a pharmaceutically acceptable carrier, vehicle, or diluent in a second unit dosage form; and (3) a container. The container is used to separate components and may include, for example, a divided bottle or a divided foil packet. The separate antagonist compositions may also, if desired, be contained within a single, undivided container. The pharmaceutical pack may also include directions for the administration of the separate PDGF and VEGF antagonists. The pharmaceutical pack is particularly advantageous when the separate components are administered in different dosage forms, are administered at different dosage levels, or when titration of the individual components of the combination is desired by the prescribing physician. In one embodiment, the pharmaceutical pack is designed to dispense doses of the PDGF and VEGF antagonists one at a time in the order of their intended use. In another example, a pharmaceutical pack is designed to contain rows of a PDGF antagonist and a VEGF antagonist placed side by side in the pack, with instructions on the pack to convey to the user that one pair of antagonists is to be administered. An exemplary pharmaceutical pack is the so-called blister pack that is well known in the pharmaceutical packaging industry.

Effectiveness

Suppression of a neovascular disorder is evaluated by any accepted method of measuring whether angiogenesis is slowed or diminished. This includes direct observation and indirect evaluation such as by evaluating subjective symptoms or objective physiological indicators. Treatment efficacy, for example, may be evaluated based on the prevention or reversal of neovascularization, microangiopathy, vascular leakage or vascular edema or any combination thereof. Treatment efficacy for evaluating suppression of an ocular neovascular disorder may also be defined in terms of stabilizing or improving visual acuity.

In determining the effectiveness of a particular combination therapy in treating or preventing an ocular neovascular disorder, patients may also be clinically evaluated by an ophthalmologist several days after injection and at least one-month later just prior to the next injection. ETDRS visual acuities, kodachrome photography, and fluorescein angiography are also performed monthly for the first 4 months as required by the ophthalmologist.

For example, in order to assess the effectiveness of combination PDGF antagonist and VEGF antagonist therapy to treat ocular neovascularization, studies are conducted involving the administration of either single or multiple intravitreal injections of a PDGF-B aptamer in combination with a VEGF-A aptamer (for example, a PEGylated form of EYE001) in patients suffering from subfoveal choroidal neovascularization secondary to age-related macular degeneration according to standard methods well known in the opthalmologic arts. In one working study, patients with subfoveal choroidal neovascularization (CNV) secondary to age-related macular degeneration (AMD) receive a single intravitreal injection of a PDGF-B aptamer and a VEGF-A aptamer. Effectiveness of the combination is monitored, for example, by ophthalmic evaluation. Patients showing stable or improved vision three months after treatment, for example, demonstrating a 3-line or greater improvement in vision on the ETDRS chart, are taken as receiving an effective dosage combination of the PDGF-B aptamer and VEGF-A aptamer that suppresses an ocular neovascular disorder.

In a working study example, patients with subfoveal CNV secondary to age-related macular degeneration and with a visual acuity worse than 20/200 on the ETDRS chart receive a single intravitreous injection of the PDGF-B aptamer and VEGF-A aptamer. The starting dose is 0.25 mg of each antagonist injected once intravitreously. Dosages of 0.5 mg, 1, 2 mg and 3 mg of each antagonist are also tested. Complete ophthalmic examination with fundus photography and fluorescein angiography is also performed. The combination drug product is a ready-to-use sterile solution composed of the PDGF-B aptamer and VEGF-A aptamer dissolved in 10 mM sodium phosphate and 0.9% sodium chloride buffer injection in a sterile and pyrogen free 1 cc glass body syringe barrel, with a coated stopper attached to a plastic plunger, and a rubber end cap on the pre-attached 27 gauge needle. The PDGF-B and VEGF-A aptamers are supplied at drug concentrations of 1 mg/ml, 2.5 mg/ml, 5 mg/ml, 10 mg/ml, 20 mg/ml, or 30 mg/ml for each aptamer (expressed as oligonucleotide content) to provide a 100 μl delivery volume. At approximately 3 months after injection of the PDGF-B and VEGF-A aptamers, acuity studies are performed to evaluate effectiveness of the treatment. Patients showing stable or improved vision after treatment, for example, those showing as a 3-line, or greater, increase in vision on the ETDRS chart, are taken as receiving an effective dosage combination of PDGF-B and VEGF-A aptamers that suppresses an ocular neovascular disorder.

EXAMPLES

The following examples illustrate certain modes of making and practicing the present invention, but are not meant to limit the scope of the invention since alternative methods may be used to obtain similar results.

Example 1

Corneal Neovascularization (Corneal NV)

Corneal Neovascularization is a widely used animal model that allows clear visualization of abnormal vascular growth in the eye. The vessels that grow into the normally avascular cornea, can become well established, making this an attractive model to study vessel regression. To induce experimental corneal NV, male C57BL/6 mice (18-20 g; Charles River, Wilmington, Mass.) were anesthetized with intramuscular ketamine hydrochloride (25 mg/kg) and xylazine (10 mg/kg). NaOH (2 ul of 0.2 mM) was applied topically. The corneal and limbal epithelia were removed by applying a rotary motion parallel to the limbus using #21 blade (Feather, Osaka, Japan). After 7 days, mice were treated with intraperitoneal injections of 25 mg/kg of pegaptanib sodium (Macugen™ (Eyetech Pharmaceuticals, New York, N.Y.), an anti-VEGF aptamer agent also known as EYE001) twice a day or by oral administration of 50 mg/kg of Gleevec®/STI57 ((also known as CGP57148B) a 2-phenylaminopyrimidine-related, tyrosine kinase-inhibiting anti-PDGF agent from Novartis Pharma AG, Basel, Switzerland) by gavage twice a day or both for 7 days. At day 14 following corneal NV induction, mice received 20 ug/g of fluorescein-isothiocyanate coupled concanavalin A lectin (Vector Laboratories, Burlingame, Calif.) intravenously whilst deeply anesthetized with xylazine hydrochloride and ketamine hydrochloride. Thirty minutes later, mice eyes were enucleated, and the corneas flat-mounted. Corneal NV was visualized using fluorescence microscopy and quantified using Openlab software. The percent of cornea covered by vessels was calculated as a percentage of total corneal area.

The effects of pegaptanib sodium and Gleevec on neovascularization of the cornea following NaOH application and injury to the epithilia of the limbus and cornea were investigated. Animals treated with pegaptanib sodium (Macugen) showed a 19.6% (p=0.0014) decrease in vessel growth as compared to both untreated and Gleevec treated eyes (FIG. 5). Animals treated with pegaptanib sodium and Gleevec (Mac+Glee) exhibited significantly less neovascular growth on the cornea (35.6% p<0.0001) as compared to controls and animals treated with Gleevec alone (FIG. 5). Combination treatment was also more effective than pegaptanib sodium (Macugen) alone at reducing vessel growth (16% p<0.0145).

Figure 6:
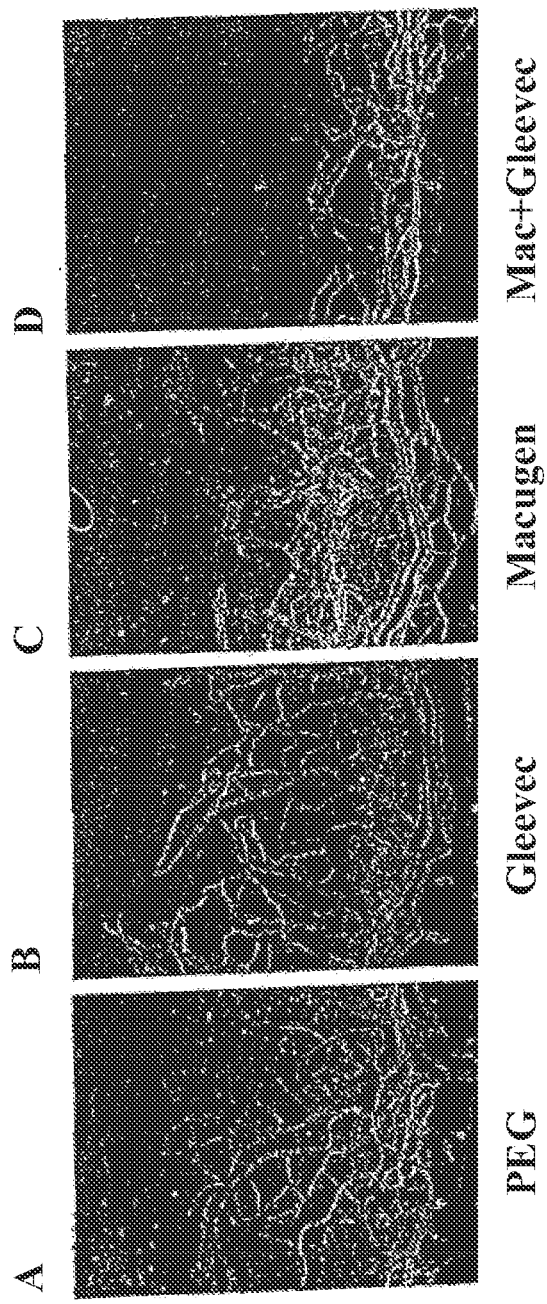
FIG. 6(A) is a photographic representation of a fluorescent-microscopic image of corneal neovascularization occurring in control (PEG-treated) mouse cornea.
FIG. 6(B) is a photographic representation of a fluorescent-microscopic image of corneal neovascularization occurring in a Gleevec-treated mouse cornea.
FIG. 6(C) is a photographic representation of a fluorescent-microscopic image of corneal neovascularization occurring in a Macugen™-treated mouse cornea.
FIG. 6(D) is a photographic representation of a fluorescent-microscopic image of corneal neovascularization occurring in a mouse cornea treated with both Macugen™ and Gleevec.
Figure 7:
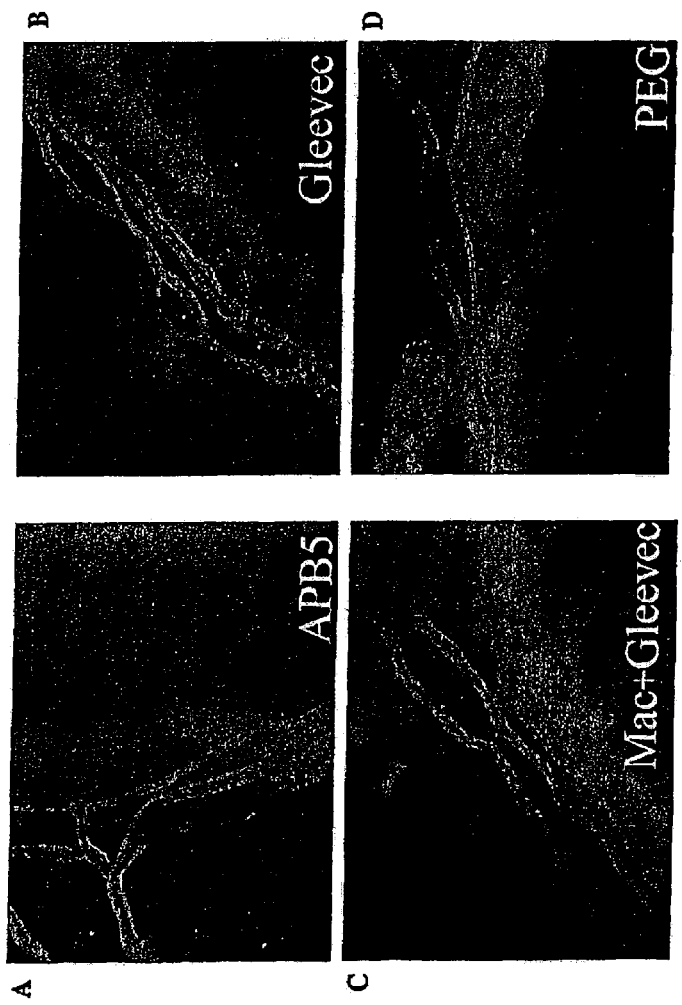
FIG. 7(A) is a photographic representation of a fluorescent-microscopic image showing that normal corneal vasculature is unaffected by administration of APB5 (PDGFR antibody, an anti-PDGF agent).
FIG. 7(B) is a photographic representation of a fluorescent-microscopic image showing that normal corneal vasculature is unaffected by administration of Gleevec.
FIG. 7(C) is a photographic representation of a fluorescent-microscopic image showing that normal corneal vasculature is unaffected by administration of Macugen™ (Mac) and Gleevec together.
FIG. 7(D) is a photographic representation of a fluorescent-microscopic image showing that normal corneal vasculature is unaffected by administration of PEG.

The results of representative corneal neovascularization experiments are also shown in FIGS. 6 and 7. FIG. 6(D) is a photographic representation of a fluorescent-microscopic image showing effective inhibition of new blood vessel formation in combination (Mac+Gleevec)-treated corneas, as compared to individual treatments with Macugen (FIG. 6(C)) or Gleevec (FIG. 6(B)). FIG. 6(A) is a photographic representation of a fluorescent-microscopic image showing the extent of neovascularization in a control (PEG-treated) cornea. FIG. 7 is a photographic representation of a fluorescent-microscopic image showing that the individual (FIG. 7(A) (APB5-treated) and FIG. 7(B) (Gleevec-treated)) and combined treatments (FIG. 7(C)) inhibited only new vessel growth, and did not affect established blood vessels. FIG. 7(D) is a photographic representation of a fluorescent-microscopic image showing the extent of neovascularization in a control (PEG-treated) cornea.

Example 2

Choroidal Neovascularization (CNV)

Experimental CNV is often used as a model for Age-related Macular degeneration (AMD). In this model, vessels of the choroid grow through breaks in Bruch's membrane and into the retina, similar to what is observed in AMD patients. To induce experimental CNV, male C57BL/6 mice (18-20 g; Charles River, Wilmington, Mass.) were anesthetized with intramuscular ketamine hydrochloride (25 mg/kg) and xylazine (10 mg/kg) and the pupils were dilated with 1% tropicamide. Four burns were generated using diode laser photocoagulation (75-μm spot size, 0.1-second duration, 90 mW, Oculight SL laser, IRIDEX, Mountain View, Calif.) and a hand-held cover slide as a contact lens. Burns localized to the 3, 6, 9 and 12 o'clock positions of the posterior pole of the retina. Production of a bubble at the time of laser, which indicates rupture of Bruch's membrane, is an important factor in obtaining choroidal neovascularization, so only mice in which a bubble was produced for all four burns were included in the study. After 7 days, mice were treated with intraperitoneal injections of 25 mg/kg of pegaptanib sodium twice a day or 50 mg/kg of Gleevec®/ST157 (Novartis Pharma AG, Basel, Switzerland) by gavage twice a day or both for 7 days. In experiments using APB5 (an anti-mouse PDGFRb (CD140b) antibody (anti-PDGF agent) from eBioscience, San Diego, Calif.), 5 mg/kg of antibody was administered using intra-peritoneal injections of twice a day. The area of choroidal NV lesions was measured in flat-mounted choroid stained with PECAM. Flat-mounts were examined by fluorescence microscopy and quantified using Openlab software.

Figure 8:
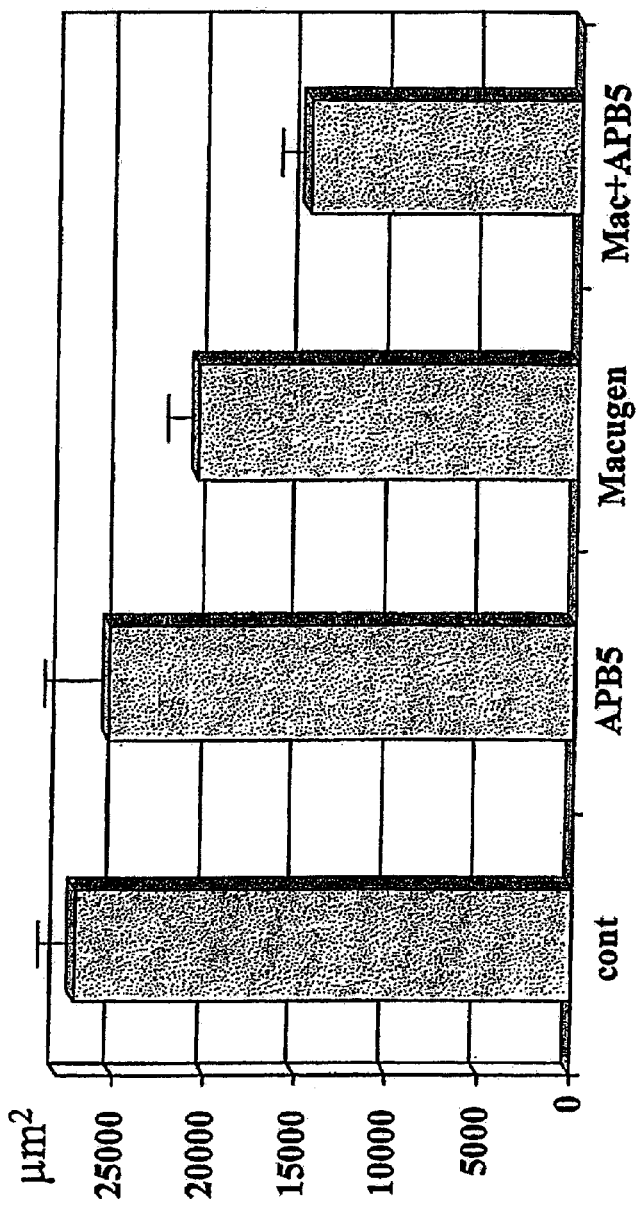
FIG. 8 is a graphical representation of the results of a laser-induced choroidal neovascularization assay comparing a control treatment (cont), Gleevec treatment (an anti-PDGF agent), and Macugen™ treatment (i.e. pegaptanib treatment, an anti-VEGF agent), to the results of a combination treatment with Macugen™ and Gleevec (anti-PDGF/anti-VEGF combination therapy).

Eyes treated with pegaptanib sodium (Macugen™) showed a 24% (p=0.007) decrease in CNV area compared to untreated controls (FIG. 8). In contrast, APB5-treated eyes were not significantly different to controls (6.5% decrease in CNV area compared to control). Eyes treated with both pegaptanib sodium and APB5 showed significantly less (46% p=0.001) CNV area as compared to control eyes or to eyes treated with either pegaptanib sodium (22% p=0.011) or APB5 (39.5% p<0.0001) alone (FIG. 8).

Figure 9:
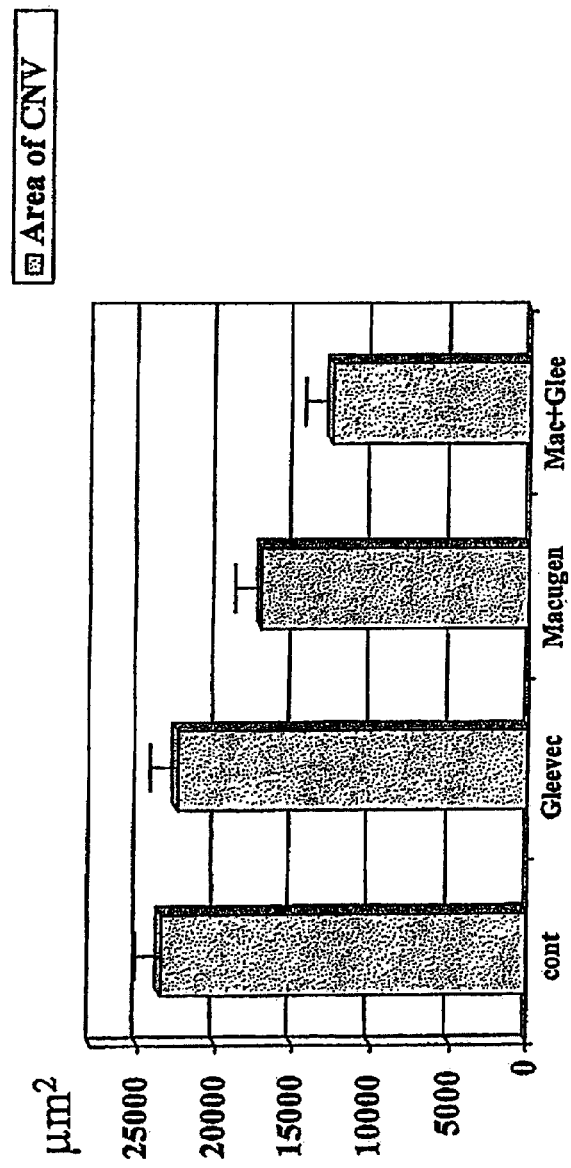
FIG. 9 is a graphical representation of the results of a laser-induced choroidal neovascularization assay comparing a control-treated (cont), APB5-treated (an anti-PGFR antibody, which acts as an anti-PDGF agent), and Macugen treatment (i.e. pegaptanib treatment, an anti-VEGF aptamer), to the results of a combination treatment with Macugen and APB5 (Mac+APB5).

A similar trend was observed when using the PDGFRβ inhibitor. Gleevec® treated eyes showed no significant difference to control eyes (4.2%) (FIG. 9). The area of CNV in pegaptanib sodium (Macugen™) treated eyes, however, was significantly different to that of controls (27% less p=0.0034). Importantly, animals treated with both pegaptanib sodium and Gleevec (Macugen+Gleevec) exhibited the least amount of CNV (46% p<0.0001) compared to control eyes and a 19% decrease in the CNV area as compared to pegaptanib sodium alone treated eyes (p=0.0407) (FIG. 9).

Example 3

Neonatal Mouse Model

The effect of administering pegaptanib sodium (Macugen™), and ARC-127 (Archemix Corp., Cambridge, Mass.), a PEGylated, anti-PDGF aptamer having the sequence CAG-GCUACGN CGTAGAGCAU CANTGATCCU GT (SEQ ID NO: 23, which corresponds to SEQ ID NO: 146 from U.S. Pat. No. 6,582,918, incorporated herein by reference in its entirety) having 2'-fluoro-2'-deoxyuridine at positions 6, 20 and 30, 2'-fluoro-2'-deoxycytidine at positions 8, 21, 28, and 29, 2'-O-Methyl-2'-deoxyguanosine at positions 9, 15, 17, and 31, 2'-O-Methyl-2'-deoxyadenosine at position 22, "N" in positions 10 and 23 from a hexaethylene-glycol phosphoramidite, and an inverted orientation T (i.e., 3'-3'-linked) at position 32, or both on the developing vessels of the retina was investigated. Neonatal C57BL/6 mice were injected daily (in the intra-peritoneal cavity) with 100 μg of ARC-127 or 100 μg of Macugen or both, starting on postnatal day 0 (P0). Mice eyes were enucleated at P4. The retinal vasculature was visualized in flatmounted retinas by immunostaining with PECAM and NG-2 or by perfusion with ConA-FITC and analyzed by fluorescence microscopy.

Injection of ARC-127 completely blocked mural cell recruitment to the developing vessels of the retina. In addition, less vessel growth was observed at P4 as compared to the control non-treated retina. In contrast, Macugen did not interfere with normal blood vessel development. However, mice treated with both Macugen and ARC-127 exhibited similar but significantly more severe defects than mice treated with ARC-127 alone.

Figure 10:
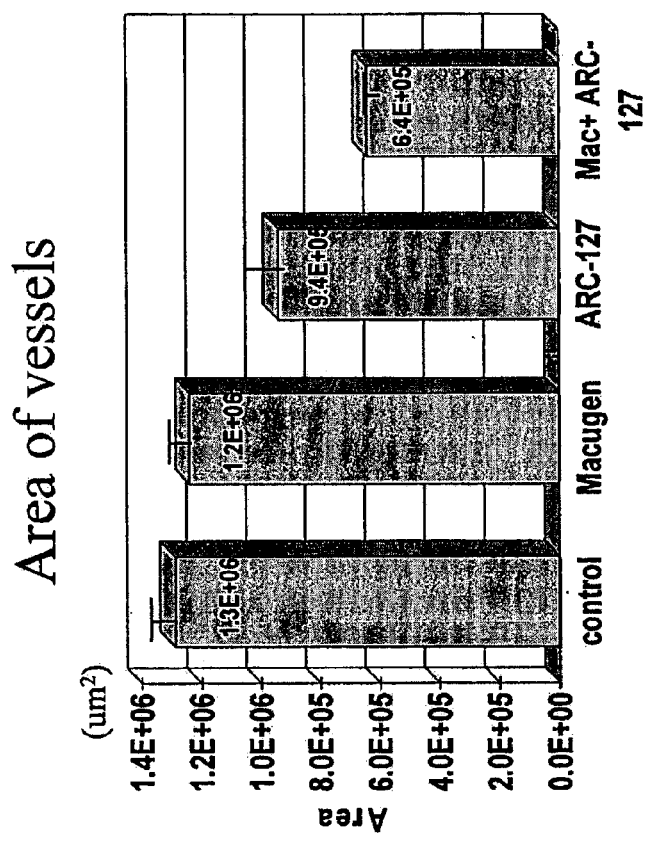
FIG. 10 is a graphical representation of the results of a retinal developmental model comparing a control treatment (cont), ARC-127 treatment (an anti-PDGF agent), and Macugen treatment (i.e. pegaptanib treatment, an anti-VEGF agent), to the results of a combination treatment with Macugen and ARC-127 (anti-PDGF/anti-VEGF combination therapy).

These results, depicted in FIG. 10, show that Macugen has no effect on the blood vessels of the developing retina. PDGFR-B antagonist ARC-127 affects vessels outgrowth and morphology. However, Macugen in combination with ARC-127 affects blood vessels more severely than either of them alone.

Example 4

Combination Therapy with Anti-PDGF Aptamer and Anti-VEGF Antibody

In this example, effectiveness of a combination therapy using anti-PDGF aptamers and an anti-VEGF antibody is demonstrated using the corneal neovascularization model described above. To induce experimental corneal NV, male C57BL/6 mice (18-20 g; Charles River, Wilmington, Mass.) are anesthetized with intramuscular ketamine hydrochloride (25 mg/kg) and xylazine (10 mg/kg). NaOH (2ul of 0.2 mM) are applied topically. The corneal and limbal epithelia are removed by applying a rotary motion parallel to the limbus using #21 blade (Feather, Osaka, Japan). After 7 days, mice are treated with intra-peritoneal injections of 25 mg/kg of an anti-PDGF aptamer having the structure 40 Kd PEG-5'-CAG-GCTACGCGTAG-AGCATCATGATCCTG(iT)-3' (in which iT represents that the final nucleotide is in the inverted orientation (3'-3' linked)) in combination with 100 µg of the anti-VEGF antibody 2C3 described in U.S. Pat. No. 6,342,221 (incorporated herein by reference). At day 14 following corneal NV induction, mice receive 20 µg/g of fluorescein-isothiocyanate coupled concanavalin A lectin (Vector Laboratories, Burlingame, Calif.) intravenously whilst deeply anesthetized with xylazine hydrochloride and ketamine hydrochloride. Thirty minutes later, mice eyes are enucleated, and the corneas flat-mounted. Corneal NV is visualized using fluorescence microscopy and quantified using Openlab software. The percent of cornea covered by vessels is calculated as a percentage of total corneal area. The results demonstrate the efficacy of the combination therapy over individual treatments with the anti-PDGF aptamer or anti-VEGF antibody alone.

In separate experiments, the effects of two related anti-PDGF aptamers are tested in combination with 100 µg of the anti-VEGF antibody 2C3 described in U.S. Pat. No. 6,342,221. PEGylated and un-PEGylated versions of the following two anti-PDGF aptamers are tested: (i) CAGGCUACGN CGTAGAGCAU CANTGATCCU GT (SEQ ID NO: 23, which corresponds to SEQ ID NO: 146 from U.S. Pat. No. 6,582,918, incorporated herein by reference in its entirety) having 2'-fluoro-2'-deoxyuridine at positions 6, 20 and 30, 2'-fluoro-2'-deoxycytidine at positions 8, 21, 28, and 29, 2'-O-Methyl-2'-deoxyguanosine at positions 9, 15, 17, and 31, 2'-O-Methyl-2'-deoxyadenosine at position 22, "N" in positions 10 and 23 from a hexaethylene-glycol phosphoramidite, and an inverted orientation T (i.e., 3'-3'-linked) at position 32; and (ii) CAGGCUACGN CGTAGAGCAU CANTGATCCU GT (see SEQ ID NO: 87 from U.S. Pat. No. 5,723,594, incorporated herein by reference in its entirety) having O-methyl-2 deoxycytidine at C at position 8, 2-O-methyl-2 deoxyguanosine at Gs at positions 9, 17 and 31, 2-O-methyl-2-deoxyadenine at A at position 22, 2-O-methyl-2-deoxyuridine at position 30, 2-fluoro-2 deoxyuridine at U at positions 6 and 20, 2-fluoro-2-deoxycytidine at C at positions 21, 28 and 29, a pentaethylene glycol phosphoramidite spacer at N at positions 10 and 23, and an inverted orientation T (i.e., 3'-3'-linked) at position 32. Appropriate controls are provided to detect the improved anti-neovascular effect of the combination therapy over individual anti-PDGF aptamer or anti-VEGF antibody treatments. The results demonstrate the efficacy of the combination therapy over individual treatments with the anti-PDGF aptamer or anti-VEGF antibody alone.

Example 5

Combination of Anti-PDGF Aptamer and Anti-VEGF Aptamer Block Choroidal Neovascularization (CNV)

In this example, effectiveness of a combination therapy using anti-PDGF aptamers and anti-VEGF aptamers in blocking chorodial neovascularization is demonstrated using the choroidal neovascularization model described above. Experimental CNV is often used as a model for Age-related Macular degeneration (AMD). In this model, vessels of the choroid grow through breaks in Bruch's membrane and into the retina, similar to what is observed in AMD patients. To induce experimental CNV, male C57BL/6 mice (18-20 g; Charles River, Wilmington, Mass.) are anesthetized with intramuscular ketamine hydrochloride (25 mg/kg) and xylazine (10 mg/kg) and the pupils are dilated with 1% tropicamide. Four burns are generated using diode laser photocoagulation (75-µm spot size, 0.1-second duration, 90 mW, Oculight SL laser, IRIDEX, Mountain View, Calif.) and a hand-held cover slide as a contact lens. Burns localized to the 3, 6, 9 and 12 o'clock positions of the posterior pole of the retina. Production of a bubble at the time of laser, which indicates rupture of Bruch's membrane, is an important factor in obtaining choroidal neovascularization, so only mice in which a bubble was produced for all four burns are included in the study. After 7 days, mice are treated with intraperitoneal injections of 25 mg/kg of pegaptanib sodium twice a day. In experiments using anti-PDGF aptamer, 25 mg/kg of an anti-PDGF aptamer having the structure 40 Kd PEG-5'-CAGGC-TACGCGTAGAGCATCATGA-TCCTG(iT)-3' (in which iT represents that the final nucleotide is in the inverted orientation (3'-3' linked)) is co-administered with pegaptanib sodium. The area of choroidal NV lesions is measured in flat-mounted choroid stained with PECAM. Flat-mounts are examined by fluorescence microscopy and quantified using Openlab software. The results demonstrate that eyes treated with the combination therapy showed significantly less CNV area as compared to control eyes or to eyes treated with either pegaptanib sodium or the anti-PDGF aptamer alone.

In separate experiments, the effects of two related anti-PDGF aptamers are tested in combination with the anti-VEGF treatment by intraperitoneal injections of 25 mg/kg of pegaptanib sodium twice a day. PEGylated and un-PEGylated versions of the following two anti-PDGF aptamers are tested: (i) CAGGCUACGN CGTAGAGCAU CANTGATCCU GT (SEQ ID NO: 23, which corresponds to SEQ ID NO: 146 from U.S. Pat. No. 6,582,918, incorporated herein by reference in its entirety) having 2'-fluoro-2'-deoxyuridine at positions 6, 20 and 30, 2'-fluoro-2'-deoxycytidine at positions 8, 21, 28, and 29, 2'-O-Methyl-2'-deoxyguanosine at positions 9, 15, 17, and 31, 2'-O-Methyl-2'-deoxyadenosine at position 22, "N" in positions 10 and 23 from a hexaethylene-glycol phosphoramidite, and an inverted orientation T (i.e., 3'-3'-linked) at position 32; and (ii) CAGGC-UACGN CGTAGAGCAU CANTGATCCU GT (see SEQ ID NO: 87 from U.S. Pat. No. 5,723,594, incorporated herein by reference in its entirety) having O-methyl-2-deoxycytidine at C at position 8, 2-O-methyl-2-deoxyguanosine at Gs at positions 9, 17 and 31, 2-O-methyl-2-deoxyadenine at A at position 22, 2-O-methyl-2-deoxyuridine at position 30, 2-fluoro-2-deoxyuridine at U at positions 6 and 20, 2-fluoro-2-deoxycytidine at C at positions 21, 28 and 29, a pentaethylene glycol phosphoramidite spacer at N at positions 10 and 23, and an inverted orientation T (i.e., 3'-3'-linked) at position 32. Appropriate controls are provided to detect the improved anti-neovascular effect of the combination therapy over individual anti-PDGF aptamer or anti-VEGF aptamer treatments. The results demonstrate the efficacy of the combination therapy in blocking choroidal neovascularization over individual treatments with either of the anti-PDGF aptamers or the anti-VEGF aptamer alone.

Example 6

Corneal Neovasclarization (Corneal NV)—Regression

The corneal NV model of Example 1 was used to investigate the combination of an anti-VEGF aptamer and anti-PDGF aptamer. After 10 days, mice were treated with intra-peritoneal injections of 25 mg/kg of pegaptanib sodium (Macugen™, Eyetech Pharmaceuticals, New York, N.Y.), an anti-VEGF aptamer agent) twice a day and/or of 50 mg/kg of ARC-127 (Archemix Corp., Cambridge, Mass., an anti-PDGF aptamer having the structure 40 Kd PEG-5'-CAGGC-TACGCGTAGAGCATCATGA-TCCTG(iT)-3' (in which iT represents that the final nucleotide is in the inverted orientation (3'-3' linked)) once a day for 10 days. At day 20 following corneal NV induction, eyes were enucleated, and the corneas flat-mounted. Corneal NV was visualized using CD31 staining (BD Biosciences Pharmingen, San Diego, Calif.) and quantified using Metamorph software. The percent of cornea covered by vessels was calculated as a percentage of total corneal area.

Figure 11:
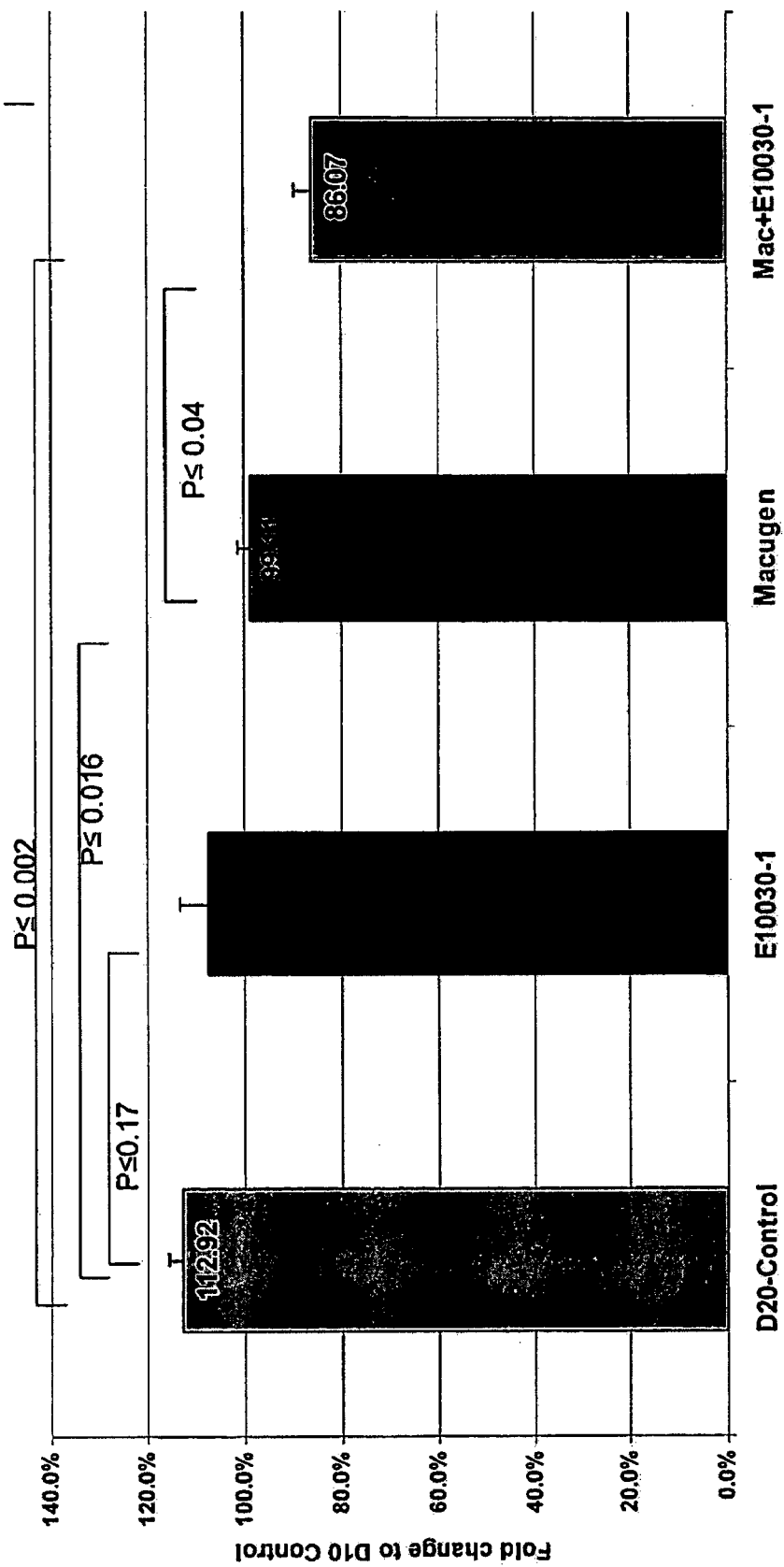
FIG. 11 is a graphical representation of the results of a corneal neovascularization assay comparing a control treatment (cont), ARC-127 treatment (an anti-PDGF agent), and Macugen treatment (i.e. pegaptanib treatment, an anti-VEGF agent), to the results of a combination treatment with Macugen and ARC-127 (anti-PDGF/anti-VEGF combination therapy).

The effects of pegaptanib sodium and/or ARC-127 on the regression of neovascularization of the cornea following NaOH application and injury to the epithilia of the limbus and cornea are depicted in FIGS. 11 and 12. Animals treated with ARC-127 did not show a significant decrease in vessel growth as compared to the day 20 control. The day 20 controls showed a 12.92% increase in corneal neovascularization when compared with the day 10 controls. Animals treated with pegaptanib sodium (Macugen) alone showed a 13.81% ($p \le 0.016$) decrease in vessel growth as compared to day 20 controls. Animals treated with pegaptanib sodium and ARC-127 exhibited significantly less neovascular growth on the cornea (26.85%, $p \le 0.002$) as compared to control.

Example 7

Corneal Neovasclarization (Corneal NV)—Regression

The corneal NV model of Example 1 was used to investigate the combination of an anti-VEGF aptamer and an antibody against the PDGFB receptor. After 14 days, mice were treated with intra-peritoneal injections of 25 mg/kg of pegaptanib sodium (Macugen, an anti-VEGF aptamer agent) twice a day and/or by oral administration of 50 mg/kg of APB5 (a polyclonal antibody against the PDGFB receptor) by gavage twice a day for 14 days. At day 28 following corneal NV induction, mice received 20 ug/g of fluorescein-isothiocyanate coupled concanavalin A lectin (Vector Laboratories, Burlingame, Calif.) intravenously whilst deeply anesthetized with xylazine hydrochloride and ketamine hydrochloride. Thirty minutes later, mice eyes were enucleated, and the corneas flat-mounted. Corneal NV was visualized using fluorescence microscopy and quantified using Openlab software. The percent of cornea covered by vessels was calculated as a percentage of total corneal area.

Figure 13:
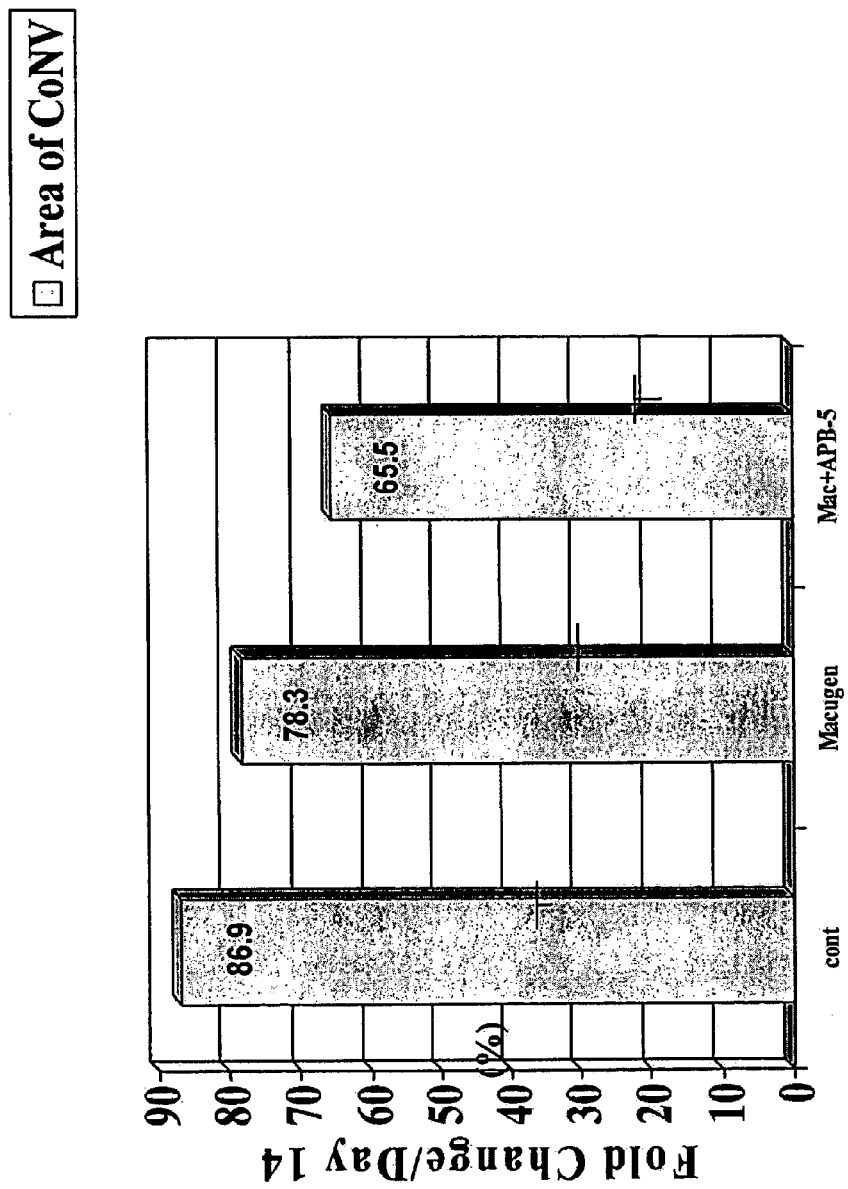
FIG. 13 is a graphical representation of the results of a corneal neovascularization assay comparing a control treatment (cont), APB-5 treatment (an anti-PDGF agent), and Macugen treatment (i.e. pegaptanib treatment, an anti-VEGF agent), to the results of a combination treatment with Macugen and APB-5 (anti-PDGF/anti-VEGF combination therapy).

The effects of pegaptanib sodium and/or APB5 on the regression of neovascularization of the cornea following NaOH application and injury to the epithilia of the limbus and cornea are depicted in FIG. 13. Animals treated with pegaptanib sodium (Macugen) showed an 8.3% decrease in vessel growth as compared to control. Animals treated with pegaptanib sodium and APB5 exhibited significantly less neovascular growth on the cornea (21.4%) as compared to control.

Example 8

Corneal Neovasclarization (Corneal NV)—Regression (Order of Addition of Therapeutic Agent)

Figure 14:
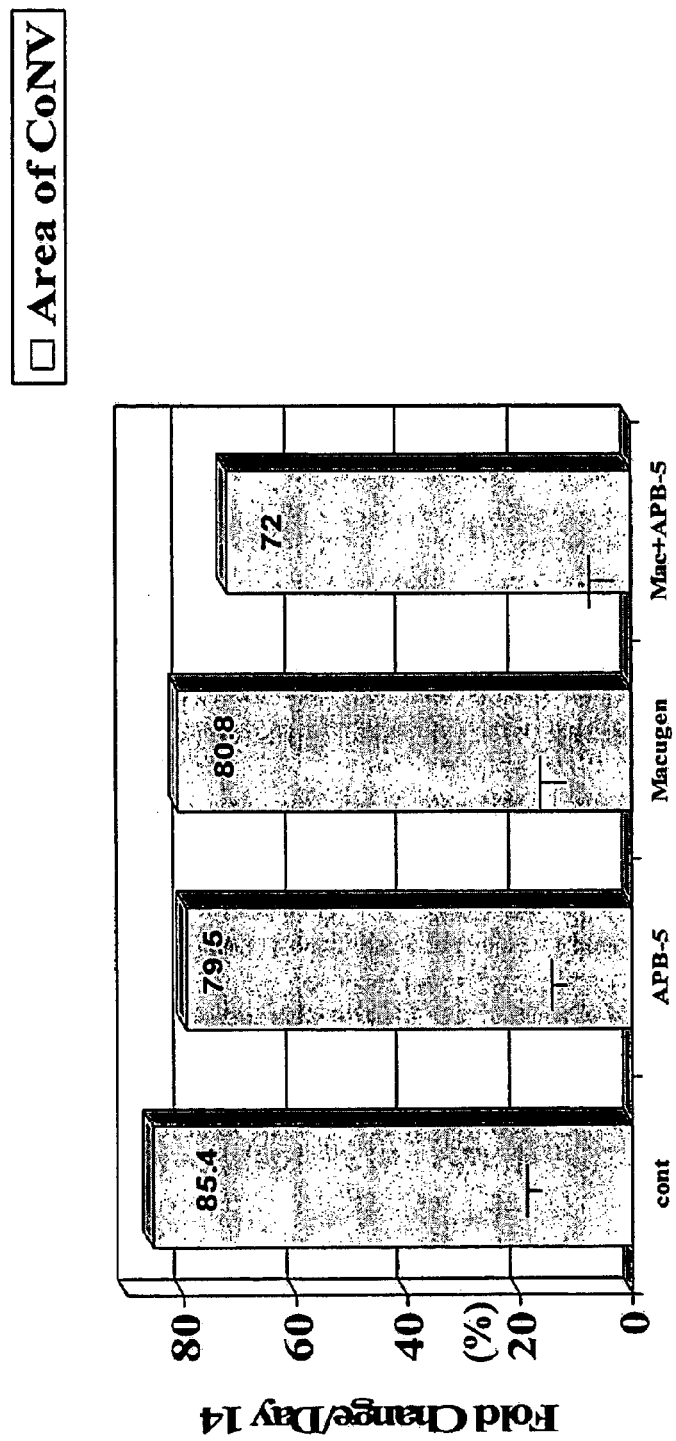
FIG. 14 is a graphical representation of the results of a corneal neovascularization assay comparing a control treatment (cont), APB-5 treatment (an anti-PDGF agent), and Macugen treatment (i.e. pegaptanib treatment, an anti-VEGF agent), to the results of a combination treatment with Macugen and APB-5 (anti-PDGF/anti-VEGF combination therapy).

The corneal NV model of Example 1 was used to investigate the effect of order of addition of the combination therapy using an anti-VEGF aptamer and an antibody against the PDGFB receptor. After 14 days, mice were treated with intra-peritoneal injections of 25 mg/kg of pegaptanib sodium (Macugen, an anti-VEGF aptamer agent) twice a day and/or by oral administration of 50 mg/kg of APB5 (eBioscience, San Diego, Calif.), a polyclonal antibody against the PDGFB receptor, by gavage twice a day for 7 days at different timepoints. At day 28 following corneal NV induction, mice received 20 ug/g of fluorescein-isothiocyanate coupled concanavalin A lectin (Vector Laboratories, Burlingame, Calif.) intravenously whilst deeply anesthetized with xylazine hydrochloride and ketamine hydrochloride. Thirty minutes later, mice eyes were enucleated, and the corneas flat-mounted. Corneal NV was visualized using fluorescence microscopy and quantified using Openlab software. The percent of cornea covered by vessels was calculated as a percentage of total corneal area and the results are depicted in FIG. 14.

The effects of pegaptanib sodium alone from day 21-28 or APB5 alone from day 14-21 followed by no treatment showed little effect compared with control on the regression of neovascularization of the cornea following NaOH application and injury to the epithelia of the limbus and cornea. Animals treated with APB5 from day 14-21 and pegaptanib sodium from day 21-28 exhibited less neovascular growth on the cornea (13.4%) as compared to control.

EQUIVALENTS

Various modifications and variations of the described method and system of the invention will be apparent to those skilled in the art without departing from the scope and spirit of the invention. Although the invention has been described in connection with specific desired embodiments, it should be understood that the invention as claimed should not be unduly limited to such specific embodiments. Those skilled in the art will recognize or be able to ascertain using no more than routine experimentation, many equivalents to the specific embodiments of the invention described herein. Such equivalents are intended to be encompassed in the scope of the present invention.

What is claimed is:

1. A pharmaceutical composition comprising:
   (i) a PDGF-B antagonist, wherein the PDGF-B antagonist is a pegylated aptamer whose sequence is that of SEQ ID NO: 23;
   (ii) a VEGF antagonist, wherein the VEGF antagonist is a humanized anti-VEGF antibody or a binding fragment thereof that binds to human VEGF-A; and
   (iii) a pharmaceutically acceptable carrier, wherein the PDGF-B antagonist and the VEGF antagonist are present in an effective amount effective to improve vision in a human having wet type age-related macular degeneration.

2. The composition of claim 1, wherein the VEGF antagonist is an anti-VEGF antibody having a heavy chain variable domain comprising the amino acid sequence of SEQ ID NO: 26 and a light chain variable domain comprising the amino acid sequence of SEQ ID NO: 27, or an anti-VEGF antibody binding fragment having a light chain variable domain comprising the amino acid sequence of SEQ ID NO: 25 and a heavy chain variable domain comprising the amino acid sequence of SEQ ID NO: 24.

3. The composition of claim 1, wherein the VEGF antagonist is an anti-VEGF antibody binding fragment having a heavy chain variable domain comprising the amino acid sequence of SEQ ID NO: 24 and a light chain variable domain comprising the amino acid sequence of SEQ ID NO: 25.

4. The composition of claim 1, wherein the VEGF antagonist is an anti-VEGF antibody having a heavy chain variable domain comprising the amino acid sequence of SEQ ID NO: 26 and a light chain variable domain comprising the amino acid sequence of SEQ ID NO: 27.

5. A drug delivery device comprising:
   (i) a PDGF-B antagonist, wherein the PDGF-B antagonist is a pegylated aptamer whose sequence is that of SEQ ID NO: 23; and
   (ii) a VEGF antagonist, wherein the VEGF antagonist is a humanized anti-VEGF antibody or a binding fragment thereof that binds to human VEGF-A,
   wherein the PDGF-B antagonist and the VEGF antagonist are present in an amount effective to improve vision in a human having wet type age-related macular degeneration.

6. A pharmaceutical pack comprising:
   (a) a PDGF-B antagonist, wherein the PDGF-B antagonist is a pegylated aptamer whose sequence is that of SEQ ID NO: 23; and
   (b) a VEGF antagonist, wherein the VEGF antagonist is a humanized anti-VEGF antibody or a binding fragment thereof that binds to human VEGF-A,
   wherein the PDGF-B antagonist and the VEGF antagonist are present in an amount effective to improve vision in a human having wet type age-related macular degeneration.

7. The pharmaceutical pack of claim 6, wherein the VEGF antagonist is an anti-VEGF antibody having a heavy chain variable domain comprising the amino acid sequence of SEQ ID NO: 26 and a light chain variable domain comprising the amino acid sequence of SEQ ID NO: 27, or an anti-VEGF antibody binding fragment having a light chain variable domain comprising the amino acid sequence of SEQ ID NO: 25 and a heavy chain variable domain comprising the amino acid sequence of SEQ ID NO: 24.

8. The pharmaceutical pack of claim 6, wherein the VEGF antagonist is an anti-VEGF antibody binding fragment having a heavy chain variable domain comprising the amino acid sequence of SEQ ID NO: 24 and a light chain variable domain comprising the amino acid sequence of SEQ ID NO: 25.

9. The pharmaceutical pack of claim 6, wherein the VEGF antagonist is an anti-VEGF antibody having a heavy chain variable domain comprising the amino acid sequence of SEQ ID NO: 26 and a light chain variable domain comprising the amino acid sequence of SEQ ID NO: 27.

10. The pharmaceutical pack of claim 6, further comprising a pharmaceutically acceptable carrier or diluent.

11. A pharmaceutical pack comprising:
    (a) a composition comprising a PDGF-B antagonist, wherein the PDGF-B antagonist is a pegylated aptamer whose sequence is that of SEQ ID NO: 23, and a pharmaceutically acceptable carrier; and
    (b) a composition comprising a VEGF antagonist, wherein the VEGF antagonist is a humanized anti-VEGF antibody or a binding fragment thereof that binds to human VEGF-A, and a pharmaceutically acceptable carrier,
    wherein the amount of PDGF-B antagonist and VEGF antagonist are present in an amount effective to improve vision in a human having wet type age-related macular degeneration.

12. The pharmaceutical pack of claim 11, wherein the VEGF antagonist is an anti-VEGF antibody having a heavy chain variable domain comprising the amino acid sequence of SEQ ID NO: 26 and a light chain variable domain comprising the amino acid sequence of SEQ ID NO: 27, or an anti-VEGF antibody binding fragment having a light chain variable domain comprising the amino acid sequence of SEQ ID NO: 25 and a heavy chain variable domain comprising the amino acid sequence of SEQ ID NO: 24.

13. The pharmaceutical pack of claim 11, wherein the VEGF antagonist is an anti-VEGF antibody binding fragment having a heavy chain variable domain comprising the amino acid sequence of SEQ ID NO: 24 and a light chain variable domain comprising the sequence of SEQ ID NO: 25.

14. The pharmaceutical pack of claim 11, wherein the VEGF antagonist is an anti-VEGF antibody having a heavy chain variable domain comprising the amino acid sequence of SEQ ID NO: 26 and a light chain variable domain comprising the amino acid sequence of SEQ ID NO: 27.

15. The drug delivery device of claim 5, wherein the VEGF antagonist is an anti-VEGF antibody having a heavy chain variable domain comprising the amino acid sequence of SEQ ID NO: 26 and a light chain variable domain comprising the amino acid sequence of SEQ ID NO: 27, or an anti-VEGF antibody binding fragment having a light chain variable domain comprising the amino acid sequence of SEQ ID NO: 25 and a heavy chain variable domain comprising the amino acid sequence of SEQ ID NO: 24.

16. The drug delivery device of claim 5, wherein the VEGF antagonist is an anti-VEGF antibody binding fragment having a heavy chain variable domain comprising the amino acid sequence of SEQ ID NO: 24 and a light chain variable domain comprising the amino acid sequence of SEQ ID NO: 25.

17. The drug delivery device of claim 5, wherein the VEGF antagonist is an anti-VEGF antibody having a heavy chain variable domain comprising the amino acid sequence of SEQ ID NO: 26 and a light chain variable domain comprising the amino acid sequence of SEQ ID NO: 27.

18. The drug delivery device of claim 5, further comprising a pharmaceutically acceptable carrier.

19. The drug delivery device of claim 5, in the form of an intraocular implant.

20. The composition of claim 1, wherein the PDGF-B antagonist is present at a concentration of 1 mg/mL, 2.5 mg/mL, 5 mg/mL, 10 mg/mL, 20 mg/mL, or 30 mg/mL.

21. The drug delivery device of claim 5, wherein the PDGF-B antagonist is present at a concentration of 1 mg/mL, 2.5 mg/mL, 5 mg/mL, 10 mg/mL, 20 mg/mL, or 30 mg/mL.

22. The pharmaceutical pack of claim 6 or 11, wherein the PDGF-B antagonist is present at a concentration of 1 mg/mL, 2.5 mg/mL, 5 mg/mL, 10 mg/mL, 20 mg/mL, or 30 mg/mL.

\* \* \* \* \*

UNITED STATES PATENT AND TRADEMARK OFFICE
CERTIFICATE OF CORRECTION

| | |
|---|---|
| PATENT NO. | : 8,685,397 B2 |
| APPLICATION NO. | : 12/641270 |
| DATED | : April 1, 2014 |
| INVENTOR(S) | : David Shima et al. |

Page 1 of 1

It is certified that error appears in the above-identified patent and that said Letters Patent is hereby corrected as shown below:

In the Claims:

Column 121, Claim 1, line 11, "an effective amount effective" should read --an amount effective--.

Signed and Sealed this
Third Day of June, 2014

Michelle K. Lee
*Deputy Director of the United States Patent and Trademark Office*

SEQUENCE LISTING

<160> NUMBER OF SEQ ID NOS: 34

<210> SEQ ID NO 1
<211> LENGTH: 2137

<212> TYPE: DNA
<213> ORGANISM: Homo sapiens

<400> SEQUENCE: 1

| | | | | | |
|---|---|---|---|---|---|
| ccctgcctgc | ctccctgcgc | acccgcagcc | tcccccgctg | cctccctagg | gctcccctcc | 60 |
| ggccgccagc | gcccattttt | cattccctag | atagagatac | tttgcgcgca | cacacataca | 120 |
| tacgcgcgca | aaaggaaaa | aaaaaaaaaa | aagcccaccc | tccagcctcg | ctgcaaagag | 180 |
| aaaaccggag | cagccgcagc | tcgcagctcg | cagcccgcag | cccgcagagg | acgcccagag | 240 |
| cggcgagcgg | gcgggcagac | ggaccgacgg | actcgcgccg | cgtccacctg | tcggccgggc | 300 |
| ccagccgagc | gcgcagcggg | cacgccgcgc | gcgcggagca | gccgtgcccg | ccgccgggc | 360 |
| ccgccgccag | ggcgcacacg | ctcccgcccc | cctacccggc | ccgggcggga | gtttgcacct | 420 |
| ctccctgccc | gggtgctcga | gctgccgttg | caaagccaac | tttggaaaaa | gttttttggg | 480 |
| ggagacttgg | gccttgaggt | gcccagctcc | gcgctttccg | attttggggg | cctttccaga | 540 |
| aaatgttgca | aaaagctaa | gccggcgggc | agaggaaaac | gcctgtagcc | ggcgagtgaa | 600 |
| gacgaaccat | cgactgccgt | gttccttttc | ctcttggagg | ttggagtccc | ctgggcgccc | 660 |
| ccacacggct | agacgcctcg | gctggttcgc | gacgcagccc | cccggccgtg | gatgctgcac | 720 |
| tcgggctcgg | gatccgccca | ggtagcggcc | tcggacccag | gtcctgcgcc | caggtcctcc | 780 |
| cctgcccccc | agcgacggag | ccggggccgg | gggcggcggc | gccgggggca | tgcgggtgag | 840 |
| ccgcggctgc | agaggcctga | gcgcctgatc | gccgcggacc | cgagccgagc | ccacccccct | 900 |
| ccccagcccc | ccaccctggc | cgcggggggcg | gcgcgctcga | tctacgcgtt | cggggccccg | 960 |
| cggggccggg | cccggagtcg | gcatgaatcg | ctgctgggcg | ctcttcctgt | ctctctgctg | 1020 |
| ctacctgcgt | ctggtcagcg | ccgagggggga | ccccattccc | gaggagcttt | atgagatgct | 1080 |
| gagtgaccac | tcgatccgct | cctttgatga | tctccaacgc | ctgctgcacg | gagacccgg | 1140 |
| agaggaagat | ggggccgagt | tggacctgaa | catgacccgc | tcccactctg | gaggcgagct | 1200 |
| ggagagcttg | gctcgtggaa | gaaggagcct | gggttccctg | accattgctg | agccggccat | 1260 |
| gatcgccgag | tgcaagacgc | gcaccgaggt | gttcgagatc | tcccgcgcc | tcatagaccg | 1320 |
| caccaacgcc | aacttcctgg | tgtggccgcc | ctgtgtggag | gtgcagcgct | gctccggctg | 1380 |
| ctgcaacaac | cgcaacgtgc | agtgccgcc | cacccaggtg | cagctgcgac | ctgtccaggt | 1440 |
| gagaaagatc | gagattgtgc | ggaagaagcc | aatctttaag | aaggccacgg | tgacgctgga | 1500 |
| agaccacctg | gcatgcaagt | gtgagacagt | ggcagctgca | cggcctgtga | cccgaagccc | 1560 |
| gggggggttcc | caggagcagc | gagccaaaac | gccccaaaact | cgggtgacca | ttcggacggt | 1620 |
| gcgagtccgc | cggccccca | agggcaagca | ccggaaattc | aagcacacgc | atgacaagac | 1680 |
| ggcactgaag | gagacccttg | gagcctaggg | gcatcggcag | gagagtgtgt | gggcagggtt | 1740 |
| atttaatatg | gtatttgctg | tattgccccc | atggggcctt | ggagtagata | atattgtttc | 1800 |
| cctcgtccgt | ctgtctcgat | gcctgattcg | gacggccaat | ggtgcctccc | ccaccctcc | 1860 |
| acgtgtccgt | ccaccttcc | atcagcgggt | ctcctcccag | cggcctccgg | ctcttgccca | 1920 |
| gcagctcaag | aagaaaaaga | aggactgaac | tccatcgcca | tcttcttccc | ttaactccaa | 1980 |
| gaacttggga | taagagtgtg | agagagactg | atgggtcgc | tctttggggg | aaacgggttc | 2040 |
| cttccctgc | acctggcctg | ggccacacct | gagcgctgtg | gactgtcctg | aggagccctg | 2100 |
| aggacctctc | agcatagcct | gcctgatccc | tgaaccc | | | 2137 |

<210> SEQ ID NO 2
<211> LENGTH: 241

```
<212> TYPE: PRT
<213> ORGANISM: Homo sapiens

<400> SEQUENCE: 2

Met Asn Arg Cys Trp Ala Leu Phe Leu Ser Leu Cys Cys Tyr Leu Arg
1               5                   10                  15

Leu Val Ser Ala Glu Gly Asp Pro Ile Pro Glu Glu Leu Tyr Glu Met
            20                  25                  30

Leu Ser Asp His Ser Ile Arg Ser Phe Asp Asp Leu Gln Arg Leu Leu
        35                  40                  45

His Gly Asp Pro Gly Glu Glu Asp Gly Ala Glu Leu Asp Leu Asn Met
    50                  55                  60

Thr Arg Ser His Ser Gly Gly Glu Leu Glu Ser Leu Ala Arg Gly Arg
65                  70                  75                  80

Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
            100                 105                 110

Arg Thr Asn Ala Asn Phe Leu Val Trp Pro Pro Cys Val Glu Val Gln
        115                 120                 125

Arg Cys Ser Gly Cys Cys Asn Asn Arg Asn Val Gln Cys Arg Pro Thr
    130                 135                 140

Gln Val Gln Leu Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Val Ala Ala Ala Arg Pro Val Thr Arg Ser
            180                 185                 190

Pro Gly Gly Ser Gln Glu Gln Arg Ala Lys Thr Pro Gln Thr Arg Val
        195                 200                 205

Thr Ile Arg Thr Val Arg Val Arg Arg Pro Pro Lys Gly Lys His Arg
    210                 215                 220

Lys Phe Lys His Thr His Asp Lys Thr Ala Leu Lys Glu Thr Leu Gly
225                 230                 235                 240

Ala

<210> SEQ ID NO 3
<211> LENGTH: 1723
<212> TYPE: DNA
<213> ORGANISM: Homo sapiens

<400> SEQUENCE: 3
tcgcggaggc ttggggcagc cgggtagctc ggaggtcgtg gcgctggggg ctagcaccag      60
cgctctgtcg ggaggcgcag cggttaggtg gaccggtcag cggactcacc ggccagggcg     120
ctcggtgctg gaatttgata ttcattgatc cgggttttat ccctcttctt ttttcttaaa     180 cattttttt taaaactgta ttgtttctcg ttttaattta ttttgcttg ccattcccca       240 cttgaatcgg gccgacggct tgggagatt gctctacttc cccaaatcac tgtggatttt      300
ggaaaccagc agaaagagga aagaggtagc aagagctcca gagagaagtc gaggaagaga     360 gagacgggt cagagagagc gcgcgggcgt gcgagcagcg aaagcgacag ggcaaagtg       420 agtgacctgc ttttgggggt gaccgccgga gcgcggcgtg agccctcccc cttgggatcc     480
cgcagctgac cagtcgcgct gacgacagaca cagacagaca ccgcccccag ccccagctac    540
cacctcctcc ccggccggcg gcggacagtg gacgcggcgg cgagccgcgg gcaggggccg     600
```

-continued

```
gagcccgcgc ccggaggcgg ggtggagggg gtcggggctc gcggcgtcgc actgaaactt    660
ttcgtccaac ttctgggctg ttctcgcttc ggaggagccg tggtccgcgc ggggggaagcc   720 gagccgagcg gagccgcgag aagtgctagc tcggccgggg aggagccgca gccggaggag    780
ggggaggagg aagaagagaa ggaagaggag agggggccgc agtggcgact cggcgctcgg    840
aagccgggct catggacggg tgaggcggcg gtgtgcgcag acagtgctcc agccgcgcgc    900 gctcccagg ccctggcccg ggcctcgggc cggggaggaa gagtagctcg ccgaggcgcc     960
gaggagagcg ggccgcccca gcccgagc cggagaggga gcgcgagccg cgccggcccc     1020
ggtcgggcct ccgaaaccat gaactttctg ctgtcttggg tgcattggag ccttgccttg   1080
ctgctctacc tccaccatgc caagtggtcc caggctgcac ccatggcaga aggaggaggg  1140
cagaatcatc acgaagtggt gaagttcatg gatgtctatc agcgcagcta ctgccatcca   1200
atcgagaccc tggtggacat cttccaggag taccctgatg agatcgagta catcttcaag   1260
ccatcctgtg tgcccctgat gcgatgcggg ggctgctgca atgacgaggg cctggagtgt   1320
gtgcccactg aggagtccaa catcaccatg cagattatgc ggatcaaacc tcaccaaggc   1380
cagcacatag agagatgag cttcctacag cacaacaaat gtgaatgcag accaaagaaa   1440
gatagagcaa gacaagaaaa aaaatcagtt cgaggaaagg gaaaggggca aaaacgaaag   1500
cgcaagaaat cccggtataa gtcctggagc gttccctgtg ggccttgctc agagcggaga   1560
aagcatttgt ttgtacaaga tccgcagacg tgtaaatgtt cctgcaaaaa cacagactcg   1620
cgttgcaagg cgaggcagct tgagttaaac gaacgtactt gcagatgtga caagccgagg   1680
cggtgagccg ggcaggagga aggagcctcc ctcagggttt cgg                      1723
```

<210> SEQ ID NO 4
<211> LENGTH: 215
<212> TYPE: PRT
<213> ORGANISM: Homo sapiens

<400> SEQUENCE: 4

```
Met Asn Phe Leu Leu Ser Trp Val His Trp Ser Leu Ala Leu Leu
1               5                   10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Pro Cys Gly Pro Cys Ser Glu Arg Arg Lys His
                165                 170                 175

Leu Phe Val Gln Asp Pro Gln Thr Cys Lys Cys Ser Cys Lys Asn Thr
```

```
                        180                 185                 190
Asp Ser Arg Cys Lys Ala Arg Gln Leu Glu Leu Asn Glu Arg Thr Cys
        195                 200                 205
Arg Cys Asp Lys Pro Arg Arg
        210             215

<210> SEQ ID NO 5
<211> LENGTH: 5598
<212> TYPE: DNA
<213> ORGANISM: Homo sapiens

<400> SEQUENCE: 5
ggcccctcag ccctgctgcc cagcacgagc ctgtgctcgc cctgcccaac gcagacagcc      60
agacccaggg cggcccctct ggcggctctg ctcctcccga aggatgcttg gggagtgagg     120
cgaagctggg cgctcctctc ccctacagca gccccttcc tccatccctc tgttctcctg     180
agccttcagg agcctgcacc agtcctgcct gtccttctac tcagctgtta cccactctgg     240
gaccagcagt ctttctgata ctgggagag gcagtaagg aggacttcct ggaggggtg       300 actgtccaga gcctggaact gtgcccacac cagaagccat cagcagcaag acaccatgc     360 ggcttccggg tgcgatgcca gctctggccc tcaaaggcga gctgctgttg ctgtctctcc     420
tgttacttct ggaaccacag atctctcagg gcctggtcgt cacaccccg gggcagagc      480 ttgtcctcaa tgtctccagc accttcgttc tgacctgctc gggttcagct ccggtggtgt     540
gggaacggat gtcccaggag ccccacagg aaatggccaa ggcccaggat ggcaccttct     600
ccagcgtgct cacactgacc aacctcactg gctagacac gggagaatac ttttgcaccc     660
acaatgactc ccgtggactg gagaccgatg agcggaaacg gctctacatc tttgtgccag     720
atcccaccgt gggcttcctc cctaatgatg ccgaggaact attcatcttt ctcacggaaa     780
taactgagat caccattcca tgccgagtaa cagacccaca gctggtggtg acactgcacg     840
agaagaaagg ggacgttgca ctgcctgtcc cctatgatca ccaacgtggc ttttctggta     900
tctttgagga cagaagctac atctgcaaaa ccaccattgg ggacagggag gtggattctg    960
atgcctacta tgtctacaga ctccaggtgt catccatcaa cgtctctgtg aacgcagtgc   1020
agactgtggt ccgccagggt gagaacatca ccctcatgtg cattgtgatc gggaatgagg   1080
tggtcaactt cgagtggaca tacccccgca aagaaagtgg gcggctggtg gagccggtga   1140
ctgacttcct cttggatatg ccttaccaca tccgctccat cctgcacatc cccagtgccg   1200
agttagaaga ctcggggacc tacacctgca atgtgacgga gagtgtgaat gaccatcagg   1260
atgaaaaggc catcaacatc accgtggttg agagcggcta cgtgcggctc tgggagagg    1320 tgggcacact acaatttgct gagctgcatc ggagccggac actgcaggta gtgttcgagg   1380
cctacccacc gcccactgtc ctgtggttca agacaaccg caccctgggc gactccagcg   1440
ctggcgaaat cgccctgtcc acgcgcaacg tgtcggagac ccggtatgtg tcagagctga   1500
cactggttcg cgtgaaggtg gcagaggctg gccactacac catgcgggcc ttccatgagg   1560
atgctgaggt ccagctctcc ttccagctac agatcaatgt ccctgtccga gtgctggagc   1620
taagtgagag ccaccctgac agtggggaac agacagtccg ctgtcgtggc cggggcatgc   1680
cccagccgaa catcatctgg tctgcctgca gagacctcaa aggtgtccca cgtgagctgc   1740
cgcccacgct gctggggaac agttccgaag aggagagcca gctggagact aacgtgacgt   1800
actggggagg ggagcaggag tttgaggtgg tgagcacact gcgtctgcag cacgtggatc   1860
ggccactgtc ggtgcgctgc acgctgcgca acgctgtggg ccaggacacg caggaggtca   1920
```

```
tcgtggtgcc acactccttg cccttttaagg tggtggtgat ctcagccatc ctggccctgg    1980
tggtgctcac catcatctcc cttatcatcc tcatcatgct ttggcagaag aagccacgtt    2040
acgagatccg atggaaggtg attgagtctg tgagctctga cggccatgag tacatctacg    2100
tggaccccat gcagctgccc tatgactcca cgtgggagct gccgcgggac cagcttgtgc    2160
tgggacgcac cctcggctct ggggcctttg ggcaggtggt ggaggccacg gctcatggcc    2220
tgagccattc tcaggccacg atgaaagtgg ccgtcaagat gcttaaatcc acagcccgca    2280
gcagtgagaa gcaagccctt atgtcggagc tgaagatcat gagtcacctt gggccccacc    2340
tgaacgtggt caacctgttg ggggcctgca ccaaaggagg acccatctat atcatcactg    2400
agtactgccg ctacggagac ctggtggact acctgcaccg caacaaacac accttcctgc    2460
agcaccactc cgacaagcgc cgcccgccca gcgcggagct ctacagcaat gctctgcccg    2520
ttgggctccc cctgcccagc catgtgtcct tgaccgggga gagcgacggt ggctacatgg    2580
acatgagcaa ggacgagtcg gtggactatg tgcccatgct ggacatgaaa ggagacgtca    2640
aatatgcaga catcgagtcc tccaactaca tggcccctta cgataactac gttccctctg    2700
cccctgagag gacctgccga gcaactttga tcaacgagtc tccagtgcta agctacatgg    2760
acctcgtggg cttcagctac caggtggcca atggcatgga gtttctggcc tccaagaact    2820
gcgtccacag agacctggcg gctaggaacg tgctcatctg tgaaggcaag ctggtcaaga    2880
tctgtgactt tggcctggct cgagacatca tgcgggactc gaattacatc tccaaaggca    2940
gcaccttttt gccttttaaag tggatggctc cggagagcat cttcaacagc ctctacacca    3000
ccctgagcga cgtgtggtcc ttcgggatcc tgctctggga gatcttcacc ttgggtggca    3060
cccccttaccc agagctgccc atgaacgagc agttctacaa tgccatcaaa cggggttacc    3120
gcatggccca gcctgcccat gcctccgacg agatctatga gatcatgcag aagtgctggg    3180
aagagaagtt tgagattcgg ccccccttct cccagctggt gctgcttctc gagagactgt    3240
tgggcgaagg ttacaaaaag aagtaccagc aggtggatga ggagtttctg aggagtgacc    3300
acccagccat ccttcggtcc caggcccgct tgcctgggtt ccatggcctc cgatctcccc    3360
tggacaccag ctccgtcctc tatactgccg tgcagcccaa tgagggtgac aacgactata    3420
tcatcccccct gcctgacccc aaacccgagg ttgctgacga gggcccactg gagggttccc    3480
ccagcctagc cagctccacc ctgaatgaag tcaacaccct ctcaaccatc tcctgtgaca    3540
gccccctgga gccccaggac gaaccagagc cagagcccca gcttgagctc caggtggagc    3600
cggagccaga gctggaacag ttgccggatt cggggtgccc tgcgcctcgg gcggaagcag    3660
aggatagctt cctgtagggg gctggcccct accctgccct gcctgaagct ccccccctgc    3720
cagcacccag catctcctgg cctggcctga ccgggcttcc tgtcagccag gctgcccttta    3780
tcagctgtcc ccttctggaa gctttctgct cctgacgtgt tgtgccccaa ccctggggc    3840
tggcttagga ggcaagaaaa ctgcaggggc cgtgaccagc cctctgcctc cagggaggcc    3900
aactgactct gagccagggt tcccccaggg aactcagttt tcccatatgt aagatgggaa    3960
agttaggctt gatgacccag aatctaggat tctctccctg gctgacaggt ggggagaccg    4020
aatccctccc tgggaagatt cttggagtta ctgaggtggt aaattaactt tttttctgttc    4080
agccagctac ccctcaagga atcatagctc tctcctcgca ctttttatcc acccaggagc    4140
tagggaagag accctagcct ccctggctgc tggctgagct agggcctagc cttgagcagt    4200
gttgcctcat ccagaagaaa gccagtctcc tccctatgat gccagtccct gcgttccctg    4260
gcccgagctg gtctggggcc attaggcagc ctaattaatg ctggaggctg agccaagtac    4320
```

```
aggacacccc cagcctgcag cccttgccca gggcacttgg agcacacgca gccatagcaa      4380
gtgcctgtgt ccctgtcctt caggcccatc agtcctgggg cttttttcttt atcaccctca    4440 gtcttaatcc atccaccaga gtctagaagg ccagacgggc cccgcatctg tgatgagaat      4500
gtaaatgtgc cagtgtggag tggccacgtg tgtgtgccag tatatggccc tggctctgca      4560
ttggacctgc tatgaggctt tggaggaatc cctcacccte tctgggcctc agtttcccct      4620
tcaaaaaatg aataagtcgg acttattaac tctgagtgcc ttgccagcac taacattcta      4680
gagtattcca ggtggttgca catttgtcca gatgaagcaa ggccatatac cctaaacttc      4740
catcctgggg gtcagctggg ctcctgggag attccagatc acacatcaca ctctggggac      4800
tcaggaacca tgccccttcc ccaggccccc agcaagtctc aagaacacag ctgcacaggc      4860
cttgacttag agtgacagcc ggtgtcctgg aaagccccaa gcagctgccc cagggacatg      4920
ggaagaccac gggacctctt tcactaccca cgatgacctc cgggggtatc ctgggcaaaa      4980
gggacaaaga gggcaaatga gatcacctcc tgcagcccac cactccagca cctgtgccga      5040
ggtctgcgtc gaagacagaa tggacagtga ggacagttat gtcttgtaaa agacaagaag      5100
cttcagatgg taccccaaga aggatgtgag aggtggccgc ttggagtttg ccccctcaccc     5160 accagctgcc ccatccctga ggcagcgctc catgggggta tggttttgtc actgcccaga      5220
cctagcagtg acatctcatt gtccccagcc cagtgggcat tggaggtgcc aggggagtca      5280
gggttgtagc caagacgccc ccgcacgggg agggttggga aggggggtgca ggaagctcaa     5340 cccctctggg caccaaccct gcattgcagg ttggcaccct acttccctgg gatccccaga     5400
gttggtccaa ggagggagag tgggttctca atacggtacc aaagatataa tcacctaggt     5460
ttacaaatat ttttaggact cacgttaact cacatttata cagcagaaat gctattttgt      5520
atgctgttaa gtttttctat ctgtgtactt tttttttaagg gaaagatttt aatattaaac    5580
ctggtgcttc tcactcac                                                    5598
```

<210> SEQ ID NO 6
<211> LENGTH: 1106
<212> TYPE: PRT
<213> ORGANISM: Homo sapiens

<400> SEQUENCE: 6

Met Arg Leu Pro Gly Ala Met Pro Ala Leu Ala Leu Lys Gly Glu Leu
1               5                   10                  15

Leu Leu Leu Ser Leu Leu Leu Leu Glu Pro Gln Ile Ser Gln Gly
            20                  25                  30

Leu Val Val Thr Pro Pro Gly Pro Glu Leu Val Leu Asn Val Ser Ser
        35                  40                  45

Thr Phe Val Leu Thr Cys Ser Gly Ser Ala Pro Val Val Trp Glu Arg
    50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
            100                 105                 110

Arg Lys Arg Leu Tyr Ile Phe Val Pro Asp Pro Thr Val Gly Phe Leu
        115                 120                 125

Pro Asn Asp Ala Glu Glu Leu Phe Ile Phe Leu Thr Glu Ile Thr Glu
    130                 135                 140

Ile Thr Ile Pro Cys Arg Val Thr Asp Pro Gln Leu Val Val Thr Leu

```
                     145                 150                 155                 160
            His Glu Lys Lys Gly Asp Val Ala Leu Pro Val Pro Tyr Asp His Gln
                                165                 170                 175

Arg Gly Phe Ser Gly Ile Phe Glu Asp Arg Ser Tyr Ile Cys Lys Thr
                                180                 185                 190

Thr Ile Gly Asp Arg Glu Val Asp Ser Asp Ala Tyr Val Tyr Arg
                            195                 200                 205

Leu Gln Val Ser Ser Ile Asn Val Ser Val Asn Ala Val Gln Thr Val
                        210                 215                 220

Val Arg Gln Gly Glu Asn Ile Thr Leu Met Cys Ile Val Ile Gly Asn
            225                 230                 235                 240

Glu Val Val Asn Phe Glu Trp Thr Tyr Pro Arg Lys Glu Ser Gly Arg
                            245                 250                 255

Leu Val Glu Pro Val Thr Asp Phe Leu Leu Asp Met Pro Tyr His Ile
                            260                 265                 270

Arg Ser Ile Leu His Ile Pro Ser Ala Glu Leu Glu Asp Ser Gly Thr
                        275                 280                 285

Tyr Thr Cys Asn Val Thr Glu Ser Val Asn Asp His Gln Asp Glu Lys
                    290                 295                 300

Ala Ile Asn Ile Thr Val Val Glu Ser Gly Tyr Val Arg Leu Leu Gly
            305                 310                 315                 320

Glu Val Gly Thr Leu Gln Phe Ala Glu Leu His Arg Ser Arg Thr Leu
                            325                 330                 335

Gln Val Val Phe Glu Ala Tyr Pro Pro Pro Thr Val Leu Trp Phe Lys
                            340                 345                 350

Asp Asn Arg Thr Leu Gly Asp Ser Ser Ala Gly Glu Ile Ala Leu Ser
                        355                 360                 365

Thr Arg Asn Val Ser Glu Thr Arg Tyr Val Ser Glu Leu Thr Leu Val
                    370                 375                 380

Arg Val Lys Val Ala Glu Ala Gly His Tyr Thr Met Arg Ala Phe His
            385                 390                 395                 400

Glu Asp Ala Glu Val Gln Leu Ser Phe Gln Leu Gln Ile Asn Val Pro
                            405                 410                 415

Val Arg Val Leu Glu Leu Ser Glu Ser His Pro Asp Ser Gly Glu Gln
                        420                 425                 430

Thr Val Arg Cys Arg Gly Arg Gly Met Pro Gln Pro Asn Ile Ile Trp
                    435                 440                 445

Ser Ala Cys Arg Asp Leu Lys Arg Cys Pro Arg Glu Leu Pro Pro Thr
            450                 455                 460

Leu Leu Gly Asn Ser Ser Glu Glu Glu Ser Gln Leu Glu Thr Asn Val
            465                 470                 475                 480

Thr Tyr Trp Glu Glu Glu Gln Glu Phe Glu Val Val Ser Thr Leu Arg
                            485                 490                 495

Leu Gln His Val Asp Arg Pro Leu Ser Val Arg Cys Thr Leu Arg Asn
                        500                 505                 510

Ala Val Gly Gln Asp Thr Gln Glu Val Ile Val Val Pro His Ser Leu
                    515                 520                 525

Pro Phe Lys Val Val Val Ile Ser Ala Ile Leu Ala Leu Val Val Leu
                    530                 535                 540

Thr Ile Ile Ser Leu Ile Ile Leu Ile Met Leu Trp Gln Lys Lys Pro
            545                 550                 555                 560

Arg Tyr Glu Ile Arg Trp Lys Val Ile Glu Ser Val Ser Ser Asp Gly
                            565                 570                 575
```

-continued

```
His Glu Tyr Ile Tyr Val Asp Pro Met Gln Leu Pro Tyr Asp Ser Thr
                580                 585                 590

Trp Glu Leu Pro Arg Asp Gln Leu Val Leu Gly Arg Thr Leu Gly Ser
        595                 600                 605

Gly Ala Phe Gly Gln Val Val Glu Ala Thr Ala His Gly Leu Ser His
    610                 615                 620

Ser Gln Ala Thr Met Lys Val Ala Val Lys Met Leu Lys Ser Thr Ala
625                 630                 635                 640

Arg Ser Ser Glu Lys Gln Ala Leu Met Ser Glu Leu Lys Ile Met Ser
                645                 650                 655

His Leu Gly Pro His Leu Asn Val Val Asn Leu Leu Gly Ala Cys Thr
            660                 665                 670

Lys Gly Gly Pro Ile Tyr Ile Ile Thr Glu Tyr Cys Arg Tyr Gly Asp
        675                 680                 685

Leu Val Asp Tyr Leu His Arg Asn Lys His Thr Phe Leu Gln His His
    690                 695                 700

Ser Asp Lys Arg Arg Pro Ser Ala Glu Leu Tyr Ser Asn Ala Leu
705                 710                 715                 720

Pro Val Gly Leu Pro Leu Pro Ser His Val Ser Leu Thr Gly Glu Ser
                725                 730                 735

Asp Gly Gly Tyr Met Asp Met Ser Lys Asp Glu Ser Val Asp Tyr Val
            740                 745                 750

Pro Met Leu Asp Met Lys Gly Asp Val Lys Tyr Ala Asp Ile Glu Ser
        755                 760                 765

Ser Asn Tyr Met Ala Pro Tyr Asp Asn Tyr Val Pro Ser Ala Pro Glu
    770                 775                 780

Arg Thr Cys Arg Ala Thr Leu Ile Asn Glu Ser Pro Val Leu Ser Tyr
785                 790                 795                 800

Met Asp Leu Val Gly Phe Ser Tyr Gln Val Ala Asn Gly Met Glu Phe
                805                 810                 815

Leu Ala Ser Lys Asn Cys Val His Arg Asp Leu Ala Ala Arg Asn Val
            820                 825                 830

Leu Ile Cys Glu Gly Lys Leu Val Lys Ile Cys Asp Phe Gly Leu Ala
        835                 840                 845

Arg Asp Ile Met Arg Asp Ser Asn Tyr Ile Ser Lys Gly Ser Thr Phe
850                 855                 860

Leu Pro Leu Lys Trp Met Ala Pro Glu Ser Ile Phe Asn Ser Leu Tyr
865                 870                 875                 880

Thr Thr Leu Ser Asp Val Trp Ser Phe Gly Ile Leu Leu Trp Glu Ile
                885                 890                 895

Phe Thr Leu Gly Gly Thr Pro Tyr Pro Glu Leu Pro Met Asn Glu Gln
            900                 905                 910

Phe Tyr Asn Ala Ile Lys Arg Gly Tyr Arg Met Ala Gln Pro Ala His
        915                 920                 925

Ala Ser Asp Glu Ile Tyr Glu Ile Met Gln Lys Cys Trp Glu Glu Lys
    930                 935                 940

Phe Glu Ile Arg Pro Pro Phe Ser Gln Leu Val Leu Leu Leu Glu Arg
945                 950                 955                 960

Leu Leu Gly Glu Gly Tyr Lys Lys Lys Tyr Gln Gln Val Asp Glu Glu
                965                 970                 975

Phe Leu Arg Ser Asp His Pro Ala Ile Leu Arg Ser Gln Ala Arg Leu
            980                 985                 990

Pro Gly Phe His Gly Leu Arg Ser Pro Leu Asp Thr Ser Ser Val Leu
        995                 1000                1005
```

| Tyr | Thr | Ala | Val | Gln | Pro | Asn | Glu | Gly | Asp | Asn | Asp | Tyr | Ile | Ile |
|-----|-----|-----|-----|-----|-----|-----|-----|-----|-----|-----|-----|-----|-----|-----|
|     | 1010|     |     |     | 1015|     |     |     |     | 1020|     |     |     |     |

Pro Leu Pro Asp Pro Lys Pro Glu Val Ala Asp Glu Gly Pro Leu
    1025            1030            1035

Glu Gly Ser Pro Ser Leu Ala Ser Ser Thr Leu Asn Glu Val Asn
    1040            1045            1050

Thr Ser Ser Thr Ile Ser Cys Asp Ser Pro Leu Glu Pro Gln Asp
    1055            1060            1065

Glu Pro Glu Pro Glu Pro Gln Leu Glu Leu Gln Val Glu Pro Glu
    1070            1075            1080

Pro Glu Leu Glu Gln Leu Pro Asp Ser Gly Cys Pro Ala Pro Arg
    1085            1090            1095

Ala Glu Ala Glu Asp Ser Phe Leu
    1100            1105

<210> SEQ ID NO 7
<211> LENGTH: 4017
<212> TYPE: DNA
<213> ORGANISM: Homo sapiens

<400> SEQUENCE: 7

```
atggtcagct actgggacac cggggtcctg ctgtgcgcgc tgctcagctg tctgcttctc    60
acaggatcta gttcaggttc aaaattaaaa gatcctgaac tgagtttaaa aggcacccag   120
cacatcatgc aagcaggcca gacactgcat ctccaatgca ggggggaagc agcccataaa   180
tggtctttgc ctgaaatggt gagtaaggaa agcgaaaggc tgagcataac taaatctgcc   240
tgtggaagaa atggcaaaca attctgcagt actttaacct tgaacacagc tcaagcaaac   300
cacactggct tctacagctg caaatatcta gctgtaccta cttcaaagaa gaaggaaaca   360
gaatctgcaa tctatatatt tattagtgat acaggtagac cttttgtaga gatgtacagt   420
gaaatccccg aaattataca catgactgaa ggaagggagc tcgtcattcc ctgccggttt   480
acgtcaccta acatcactgt tactttaaaa aagtttccac ttgacacttt gatccctgat   540
ggaaaacgca taatctggga cagtagaaag ggcttcatca tatcaaatgc aacgtacaaa   600
gaaatagggc ttctgacctg tgaagcaaca gtcaatgggc atttgtataa gacaaactat   660
ctcacacatc gacaaaccaa tacaatcata gatgtccaaa taagcacacc acgcccagtc   720
aaattactta aggccatact tcttgtcctc aattgtactg ctaccactcc cttgaacacg   780
agagttcaaa tgacctggag ttaccctgat gaaaaaata gagagcttc cgtaaggcga   840
cgaattgacc aaagcaattc ccatgccaac atattctaca gtgttcttac tattgacaaa   900
atgcagaaca agacaaagg actttatact tgtcgtgtaa ggagtggacc atcattcaaa   960
tctgttaaca cctcagtgca tatatatgat aaagcattca tcactgtgaa acatcgaaaa  1020
cagcaggtgc ttgaaaccgt agctggcaag cggtcttacc ggctctctat gaaagtgaag  1080
gcatttccct cgccggaagt tgtatggtta aaagatgggt tacctgcgac tgagaaatct  1140
gctcgctatt tgactcgtgg ctactcgtta attatcaagg acgtaactga agaggatgca  1200
gggaattata caatcttgct gagcataaaa cagtcaaatg tgtttaaaaa cctcactgcc  1260
actctaattg tcaatgtgaa acccagatt tacgaaaagg ccgtgtcatc gtttccagac  1320
ccggctctct acccactggg cagcagacaa atcctgactt gtaccgcata tggtatccct  1380
caacctacaa tcaagtggtt ctggcacccc gtaaccata tcattccga agcaaggtgt  1440
gactttgtt ccaataatga gagtccttt atcctggatg ctgacagcaa catgggaaac  1500
```

-continued

| | | | | |
|---|---|---|---|---|
| agaattgaga | gcatcactca | gcgcatggca | ataatagaag | gaaagaataa | gatggctagc | 1560 |
| accttggttg | tggctgactc | tagaatttct | ggaatctaca | tttgcatagc | ttccaataaa | 1620 |
| gttgggactg | tgggaagaaa | cataagcttt | tatatcacag | atgtgccaaa | tgggtttcat | 1680 |
| gttaacttgg | aaaaaatgcc | gacggaagga | gaggacctga | aactgtcttg | cacagttaac | 1740 |
| aagttcttat | acagagacgt | tacttggatt | ttactgcgga | cagttaataa | cagaacaatg | 1800 |
| cactacagta | ttagcaagca | aaaaatggcc | atcactaagg | agcactccat | cactcttaat | 1860 |
| cttaccatca | tgaatgtttc | cctgcaagat | tcaggcacct | atgcctgcag | agccaggaat | 1920 |
| gtatacacag | gggaagaaat | cctccagaag | aaagaaatta | caatcagaga | tcaggaagca | 1980 |
| ccatacctcc | tgcgaaacct | cagtgatcac | acagtggcca | tcagcagttc | caccacttta | 2040 |
| gactgtcatg | ctaatggtgt | ccccgagcct | cagatcactt | ggtttaaaaa | caaccacaaa | 2100 |
| atacaacaag | agcctggaat | tattttagga | ccaggaagca | gcacgctgtt | tattgaaaga | 2160 |
| gtcacagaag | aggatgaagg | tgtctatcac | tgcaaagcca | ccaaccagaa | gggctctgtg | 2220 |
| gaaagttcag | catacctcac | tgttcaagga | acctcggaca | agtctaatct | ggagctgatc | 2280 |
| actctaacat | gcacctgtgt | ggctgcgact | ctcttctggc | tcctattaac | cctctttatc | 2340 |
| cgaaaaatga | aaggtcttc | ttctgaaata | aagactgact | acctatcaat | tataatggac | 2400 |
| ccagatgaag | ttccttttgga | tgagcagtgt | gagcggctcc | cttatgatgc | cagcaagtgg | 2460 |
| gagtttgccc | gggagagact | taaactgggc | aaatcacttg | gaagagggc | ttttggaaaa | 2520 |
| gtggttcaag | catcagcatt | tggcattaag | aaatcaccta | cgtgccggac | tgtggctgtg | 2580 |
| aaaatgctga | agagggggc | cacggccagc | gagtacaaag | ctctgatgac | tgagctaaaa | 2640 |
| atcttgaccc | acattggcca | ccatctgaac | gtggttaacc | tgctgggagc | ctgcaccaag | 2700 |
| caaggagggc | ctctgatggt | gattgttgaa | tactgcaaat | atggaaatct | ctccaactac | 2760 |
| ctcaagagca | acgtgactt | attttttctc | aacaaggatg | cagcactaca | catggagcct | 2820 |
| aagaaagaaa | aaatggagcc | aggcctggaa | caaggcaaga | aaccaagact | agatagcgtc | 2880 |
| accagcagcg | aaagctttgc | gagctccggc | tttcaggaag | ataaaagtct | gagtgatgtt | 2940 |
| gaggaagagg | aggattctga | cggtttctac | aaggagccca | tcactatgga | agatctgatt | 3000 |
| tcttacagtt | ttcaagtggc | cagaggcatg | gagttcctgt | cttccagaaa | gtgcattcat | 3060 |
| cgggacctgg | cagcgagaaa | cattcttta | tctgagaaca | acgtggtgaa | gatttgtgat | 3120 |
| tttggccttg | cccgggatat | ttataagaac | cccgattatg | tgagaaaagg | agatactcga | 3180 |
| cttcctctga | aatggatggc | tcctgaatct | atctttgaca | aaatctacag | caccaagagc | 3240 |
| gacgtgtggt | cttacggagt | attgctgtgg | gaaatcttct | ccttaggtgg | gtctccatac | 3300 |
| ccaggagtac | aaatggatga | ggacttttgc | agtcgcctga | gggaaggcat | gaggatgaga | 3360 |
| gctcctgagt | actctactcc | tgaaatctat | cagatcatgc | tggactgctg | gcacagagac | 3420 |
| ccaaaagaaa | ggccaagatt | tgcagaactt | gtggaaaaac | taggtgattt | gcttcaagca | 3480 |
| aatgtacaac | aggatggtaa | agactacatc | ccaatcaatg | ccatactgac | aggaaatagt | 3540 |
| gggtttacat | actcaactcc | tgccttctct | gaggacttct | tcaaggaaag | tatttcagct | 3600 |
| ccgaagttta | attcaggaag | ctctgatgat | gtcagatatg | taaatgcttt | caagttcatg | 3660 |
| agcctggaaa | gaatcaaaac | ctttgaagaa | cttttaccga | atgccacctc | catgtttgat | 3720 |
| gactaccagg | gcgacagcag | cactctgttg | gcctctccca | tgctgaagcg | cttcacctgg | 3780 |
| actgacagca | acccaaggc | ctcgctcaag | attgacttga | gagtaaccag | taaaagtaag | 3840 |
| gagtcggggc | tgtctgatgt | cagcaggccc | agtttctgcc | attccagctg | tgggcacgtc | 3900 | agcgaaggca agcgcaggtt cacctacgac cacgctgagc tggaaaggaa aatcgcgtgc  3960 tgctccccgc ccccagacta caactcggtg gtcctgtact ccaccccacc catctag     4017

<210> SEQ ID NO 8
<211> LENGTH: 1338
<212> TYPE: PRT
<213> ORGANISM: Homo sapiens

<400> SEQUENCE: 8

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

```
Trp Leu Lys Asp Gly Leu Pro Ala Thr Glu Lys Ser Ala Arg Tyr Leu
    370                 375                 380
Thr Arg Gly Tyr Ser Leu Ile Ile Lys Asp Val Thr Glu Glu Asp Ala
385                 390                 395                 400
Gly Asn Tyr Thr Ile Leu Leu Ser Ile Lys Gln Ser Asn Val Phe Lys
                405                 410                 415
Asn Leu Thr Ala Thr Leu Ile Val Asn Val Lys Pro Gln Ile Tyr Glu
            420                 425                 430
Lys Ala Val Ser Ser Phe Pro Asp Pro Ala Leu Tyr Pro Leu Gly Ser
        435                 440                 445
Arg Gln Ile Leu Thr Cys Thr Ala Tyr Gly Ile Pro Gln Pro Thr Ile
    450                 455                 460
Lys Trp Phe Trp His Pro Cys Asn His Asn His Ser Glu Ala Arg Cys
465                 470                 475                 480
Asp Phe Cys Ser Asn Asn Glu Glu Ser Phe Ile Leu Asp Ala Asp Ser
                485                 490                 495
Asn Met Gly Asn Arg Ile Glu Ser Ile Thr Gln Arg Met Ala Ile Ile
            500                 505                 510
Glu Gly Lys Asn Lys Met Ala Ser Thr Leu Val Val Ala Asp Ser Arg
        515                 520                 525
Ile Ser Gly Ile Tyr Ile Cys Ile Ala Ser Asn Lys Val Gly Thr Val
    530                 535                 540
Gly Arg Asn Ile Ser Phe Tyr Ile Thr Asp Val Pro Asn Gly Phe His
545                 550                 555                 560
Val Asn Leu Glu Lys Met Pro Thr Glu Gly Glu Asp Leu Lys Leu Ser
                565                 570                 575
Cys Thr Val Asn Lys Phe Leu Tyr Arg Asp Val Thr Trp Ile Leu Leu
            580                 585                 590
Arg Thr Val Asn Asn Arg Thr Met His Tyr Ser Ile Ser Lys Gln Lys
        595                 600                 605
Met Ala Ile Thr Lys Glu His Ser Ile Thr Leu Asn Leu Thr Ile Met
    610                 615                 620
Asn Val Ser Leu Gln Asp Ser Gly Thr Tyr Ala Cys Arg Ala Arg Asn
625                 630                 635                 640
Val Tyr Thr Gly Glu Glu Ile Leu Gln Lys Lys Glu Ile Thr Ile Arg
                645                 650                 655
Asp Gln Glu Ala Pro Tyr Leu Leu Arg Asn Leu Ser Asp His Thr Val
            660                 665                 670
Ala Ile Ser Ser Ser Thr Thr Leu Asp Cys His Ala Asn Gly Val Pro
        675                 680                 685
Glu Pro Gln Ile Thr Trp Phe Lys Asn Asn His Lys Ile Gln Gln Glu
    690                 695                 700
Pro Gly Ile Ile Leu Gly Pro Gly Ser Ser Thr Leu Phe Ile Glu Arg
705                 710                 715                 720
Val Thr Glu Glu Asp Glu Gly Val Tyr His Cys Lys Ala Thr Asn Gln
                725                 730                 735
Lys Gly Ser Val Glu Ser Ser Ala Tyr Leu Thr Val Gln Gly Thr Ser
            740                 745                 750
Asp Lys Ser Asn Leu Glu Leu Ile Thr Leu Thr Cys Thr Cys Val Ala
        755                 760                 765
Ala Thr Leu Phe Trp Leu Leu Leu Thr Leu Phe Ile Arg Lys Met Lys
    770                 775                 780
Arg Ser Ser Ser Glu Ile Lys Thr Asp Tyr Leu Ser Ile Ile Met Asp
```

-continued

```
            785                 790                 795                 800
Pro Asp Glu Val Pro Leu Asp Glu Gln Cys Glu Arg Leu Pro Tyr Asp
                    805                 810                 815

Ala Ser Lys Trp Glu Phe Ala Arg Glu Arg Leu Lys Leu Gly Lys Ser
                    820                 825                 830

Leu Gly Arg Gly Ala Phe Gly Lys Val Val Gln Ala Ser Ala Phe Gly
                    835                 840                 845

Ile Lys Lys Ser Pro Thr Cys Arg Thr Val Ala Val Lys Met Leu Lys
                    850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
                    885                 890                 895

Ala Cys Thr Lys Gln Gly Gly Pro Leu Met Val Ile Val Glu Tyr Cys
                    900                 905                 910

Lys Tyr Gly Asn Leu Ser Asn Tyr Leu Lys Ser Lys Arg Asp Leu Phe
                    915                 920                 925

Phe Leu Asn Lys Asp Ala Ala Leu His Met Glu Pro Lys Lys Glu Lys
                    930                 935                 940

Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
                    965                 970                 975

Leu Ser Asp Val Glu Glu Glu Asp Ser Asp Gly Phe Tyr Lys Glu
                    980                 985                 990

Pro Ile Thr Met Glu Asp Leu Ile Ser Tyr Ser Phe Gln Val Ala Arg
                    995                 1000                1005

Gly Met Glu Phe Leu Ser Ser Arg Lys Cys Ile His Arg Asp Leu
    1010                1015                1020

Ala Ala Arg Asn Ile Leu Leu Ser Glu Asn Asn Val Val Lys Ile
    1025                1030                1035

Cys Asp Phe Gly Leu Ala Arg Asp Ile Tyr Lys Asn Pro Asp Tyr
    1040                1045                1050

Val Arg Lys Gly Asp Thr Arg Leu Pro Leu Lys Trp Met Ala Pro
    1055                1060                1065

Glu Ser Ile Phe Asp Lys Ile Tyr Ser Thr Lys Ser Asp Val Trp
    1070                1075                1080

Ser Tyr Gly Val Leu Leu Trp Glu Ile Phe Ser Leu Gly Gly Ser
    1085                1090                1095

Pro Tyr Pro Gly Val Gln Met Asp Glu Asp Phe Cys Ser Arg Leu
    1100                1105                1110

Arg Glu Gly Met Arg Met Arg Ala Pro Glu Tyr Ser Thr Pro Glu
    1115                1120                1125

Ile Tyr Gln Ile Met Leu Asp Cys Trp His Arg Asp Pro Lys Glu
    1130                1135                1140

Arg Pro Arg Phe Ala Glu Leu Val Glu Lys Leu Gly Asp Leu Leu
    1145                1150                1155

Gln Ala Asn Val Gln Gln Asp Gly Lys Asp Tyr Ile Pro Ile Asn
    1160                1165                1170

Ala Ile Leu Thr Gly Asn Ser Gly Phe Thr Tyr Ser Thr Pro Ala
    1175                1180                1185

Phe Ser Glu Asp Phe Phe Lys Glu Ser Ile Ser Ala Pro Lys Phe
    1190                1195                1200
```

-continued

| Asn | Ser | Gly | Ser | Ser | Asp | Asp | Val | Arg | Tyr | Val | Asn | Ala | Phe | Lys |
| --- | --- | --- | --- | --- | --- | --- | --- | --- | --- | --- | --- | --- | --- | --- |
|     | 1205 |     |     |     | 1210 |     |     |     |     | 1215 |     |     |     |     |

| Phe | Met | Ser | Leu | Glu | Arg | Ile | Lys | Thr | Phe | Glu | Glu | Leu | Leu | Pro |
| --- | --- | --- | --- | --- | --- | --- | --- | --- | --- | --- | --- | --- | --- | --- |
|     | 1220 |     |     |     | 1225 |     |     |     |     | 1230 |     |     |     |     |

| Asn | Ala | Thr | Ser | Met | Phe | Asp | Asp | Tyr | Gln | Gly | Asp | Ser | Ser | Thr |
| --- | --- | --- | --- | --- | --- | --- | --- | --- | --- | --- | --- | --- | --- | --- |
|     | 1235 |     |     |     | 1240 |     |     |     |     | 1245 |     |     |     |     |

| Leu | Leu | Ala | Ser | Pro | Met | Leu | Lys | Arg | Phe | Thr | Trp | Thr | Asp | Ser |
| --- | --- | --- | --- | --- | --- | --- | --- | --- | --- | --- | --- | --- | --- | --- |
|     | 1250 |     |     |     | 1255 |     |     |     |     | 1260 |     |     |     |     |

| Lys | Pro | Lys | Ala | Ser | Leu | Lys | Ile | Asp | Leu | Arg | Val | Thr | Ser | Lys |
| --- | --- | --- | --- | --- | --- | --- | --- | --- | --- | --- | --- | --- | --- | --- |
|     | 1265 |     |     |     | 1270 |     |     |     |     | 1275 |     |     |     |     |

| Ser | Lys | Glu | Ser | Gly | Leu | Ser | Asp | Val | Ser | Arg | Pro | Ser | Phe | Cys |
| --- | --- | --- | --- | --- | --- | --- | --- | --- | --- | --- | --- | --- | --- | --- |
|     | 1280 |     |     |     | 1285 |     |     |     |     | 1290 |     |     |     |     |

| His | Ser | Ser | Cys | Gly | His | Val | Ser | Glu | Gly | Lys | Arg | Arg | Phe | Thr |
| --- | --- | --- | --- | --- | --- | --- | --- | --- | --- | --- | --- | --- | --- | --- |
|     | 1295 |     |     |     | 1300 |     |     |     |     | 1305 |     |     |     |     |

| Tyr | Asp | His | Ala | Glu | Leu | Glu | Arg | Lys | Ile | Ala | Cys | Cys | Ser | Pro |
| --- | --- | --- | --- | --- | --- | --- | --- | --- | --- | --- | --- | --- | --- | --- |
|     | 1310 |     |     |     | 1315 |     |     |     |     | 1320 |     |     |     |     |

| Pro | Pro | Asp | Tyr | Asn | Ser | Val | Val | Leu | Tyr | Ser | Thr | Pro | Pro | Ile |
| --- | --- | --- | --- | --- | --- | --- | --- | --- | --- | --- | --- | --- | --- | --- |
|     | 1325 |     |     |     | 1330 |     |     |     |     | 1335 |     |     |     |     |

<210> SEQ ID NO 9
<211> LENGTH: 5830
<212> TYPE: DNA
<213> ORGANISM: Homo sapiens

<400> SEQUENCE: 9

```
actgagtccc gggaccccgg gagagcggtc agtgtgtggt cgctgcgttt cctctgcctg      60
cgccgggcat cacttgcgcg ccgcagaaag tccgtctggc agcctggata tcctctccta     120
ccggcacccg cagacgcccc tgcagccgcc ggtcggcgcc cgggctccct agccctgtgc     180
gctcaactgt cctgcgctgc ggggtgccgc gagttccacc tccgcgcctc cttctctaga     240
caggcgctgg gagaaagaac cggctcccga gttctgggca tttcgcccgg ctcgaggtgc     300
aggatgcaga gcaaggtgct gctggccgtc gccctgtggc tctgcgtgga gacccgggcc     360
gcctctgtgg gtttgcctag tgtttctctt gatctgccca ggctcagcat acaaaaagac     420
atacttacaa ttaaggctaa tacaactctt caaattactt gcaggggaca gagggacttg     480
gactggcttt ggcccaataa tcagagtggc agtgagcaaa gggtggaggt gactgagtgc     540
agcgatggcc tcttctgtaa gacactcaca attccaaaag tgatcggaaa tgacactgga     600
gcctacaagt gcttctaccg ggaaactgac ttggcctcgg tcatttatgt ctatgttcaa     660
gattacagat ctccatttat tgcttctgtt agtgaccaac atggagtcgt gtacattact     720
gagaacaaaa acaaaactgt ggtgattcca tgtctcgggt ccatttcaaa tctcaacgtg     780
tcactttgtg caagataccc agaaaagaga tttgttcctg atggtaacag aatttcctgg     840
gacagcaaga agggcttcac tattcccagc tacatgatca gctatgctgg catggtcttc     900
tgtgaagcaa aaattaatga tgaaagttac cagtctatta tgtacatagt tgtcgttgta     960
gggtatagga tttatgatgt ggttctgagt ccgtctcatg gaattgaact atctgttgga    1020
gaaaagcttg tcttaaattg tacagcaaga actgaactaa atgtggggat tgacttcaac    1080
tgggaatacc cttcttcgaa gcatcagcat aagaaacttg taaaccgaga cctaaaaacc    1140
cagtctggga gtgagatgaa gaaatttttg agcaccttaa ctatagatgg tgtaacccgg    1200
agtgaccaag gattgtacac ctgtgcagca tccagtgggc tgatgaccaa gaagaacagc    1260
acatttgtca gggtccatga aaaacctttt gttgcttttg gaagtggcat ggaatctctg    1320
gtggaagcca cggtggggga gcgtgtcaga atccctgcga agtaccttgg ttacccaccc    1380
```

```
ccagaaataa aatggtataa aaatggaata cccct tgagt ccaatcacac aattaaagcg    1440
gggcatgtac tgacgattat ggaagtgagt gaaagagaca caggaaatta cactgtcatc    1500
cttaccaatc ccatttcaaa ggagaagcag agccatgtgg tctctctggt tgtgtatgtc    1560
ccaccccaga ttggtgagaa atctctaatc tctcctgtgg attcctacca gtacggcacc    1620
actcaaacgc tgacatgtac ggtctatgcc attcctcccc cgcatcacat ccactggtat    1680
tggcagttgg aggaagagtg cgccaacgag cccagccaag ctgtctcagt gacaaaccca    1740 taccct tgtg aagaatggag aagtgtggag acttccagg gaggaaataa aattgaagtt    1800
aataaaaatc aatttgctct aattgaagga aaaacaaaa ctgtaagtac ccttgttatc    1860
caagcggcaa atgtgtcagc tttgtacaaa tgtgaagcgg tcaacaaagt cgggagagga    1920
gagagggtga tctccttcca cgtgaccagg ggtcctgaaa ttactttgca acctgacatg    1980
cagcccactg agcaggagag cgtgtctttg tggtgcactg cagacagatc tacgtttgag    2040
aacctcacat ggtacaagct tggcccacag cctctgccaa tccatgtggg agagttgccc    2100
acacctgttt gcaagaactt ggatactctt tggaaattga atgccaccat gttctctaat    2160
agcacaaatg acattttgat catggagctt aagaatgcat ccttgcagga ccaaggagac    2220
tatgtctgcc ttgctcaaga caggaagacc aagaaaagac attgcgtggt caggcagctc    2280
acagtcctag agcgtgtggc acccacgatc acaggaaacc tggagaatca gacgacaagt    2340
attgggaaaa gcatcgaagt ctcatgcacg gcatctggga atcccccctcc acagatcatg    2400 tggtttaaag ataatgagac ccttgtagaa gactcaggca ttgtattgaa ggatgggaac    2460
cggaacctca ctatccgcag agtgaggaag gaggacgaag gcctctacac ctgccaggca    2520
tgcagtgttc ttggctgtgc aaaagtggag gcattttttca taatagaagg tgcccaggaa    2580
aagacgaact tggaaatcat tattctagta ggcacggcgg tgattgccat gttcttctgg    2640
ctacttcttg tcatcatcct acggaccgtt aagcgggcca atggaggga actgaagaca    2700 ggctacttgt ccatcgtcat ggatccagat gaactcccat tggatgaaca ttgtgaacga    2760 ctgcct tatg atgccagcaa atgggaattc cccagagacc ggctgaagct aggtaagcct    2820
cttggccgtg gtgcctttgg ccaagtgatt gaagcagatg cctttggaat tgacaagaca    2880
gcaacttgca ggacagtagc agtcaaaatg ttgaaagaag gagcaacaca cagtgagcat    2940
cgagctctca tgtctgaact caagatcctc attcatattg gtcaccatct caatgtggtc    3000
aaccttctag gtgcctgtac caagccagga gggccactca tggtgattgt ggaattctgc    3060
aaatttggaa acctgtccac ttacctgagg agcaagagaa atgaatttgt ccccta caag    3120 accaaagggg cacgattccg tcaagggaaa gactacgttg gagcaatccc tgtggatctg    3180
aaacggcgct tggacagcat caccagtagc cagagctcag ccagctctgg atttgtggag    3240
gagaagtccc tcagtgatgt agaagaagag gaagctcctg aagatctgta taaggacttc    3300
ctgaccttgg agcatctcat ctgttacagc ttccaagtgg ctaagggcat ggagttcttg    3360
gcatcgcgaa agtgtatcca cagggacctg cgcacgaa atatcctctt atcgagaag    3420 aacgtggtta aaatctgtga ctttggcttg gcccgggata tttataaaga tccagattat    3480
gtcagaaaag gagatgctcg cctccctttg aaatggatgg ccccagaaac aattttt gac    3540 agagtgtaca caatccagag tgacgtctgg tcttttggtg ttttgctgtg ggaaatattt    3600 tcct taggtg cttctccata tcctggggta aagattgatg aagaattttg taggcgattg    3660
aaagaaggaa ctagaatgag ggcccctgat tatactacac cagaaatgta ccagaccatg    3720
ctggactgct ggcacgggga gcccagtcag agacccacgt tttcagagtt ggtggaacat    3780
```

```
ttgggaaatc tcttgcaagc taatgctcag caggatggca agactacat tgttcttccg    3840 atatcagaga ctttgagcat ggaagaggat tctggactct ctctgcctac ctcacctgtt    3900
tcctgtatgg aggaggagga agtatgtgac cccaaattcc attatgacaa cacagcagga    3960
atcagtcagt atctgcagaa cagtaagcga aagagccggc ctgtgagtgt aaaaacattt    4020
gaagatatcc cgttagaaga accagaagta aaagtaatcc cagatgacaa ccagacggac    4080
agtggtatgg ttcttgcctc agaagagctg aaaactttgg aagacagaac caaattatct    4140
ccatcttttg gtggaatggt gcccagcaaa agcaggagt ctgtggcatc tgaaggctca    4200
aaccagacaa gcggctacca gtccggatat cactccgatg acacagacac caccgtgtac    4260
tccagtgagg aagcagaact tttaaagctg atagagattg gagtgcaaac cggtagcaca    4320
gcccagattc tccagcctga ctcggggacc acactgagct ctcctcctgt ttaaaaggaa    4380
gcatccacac cccaactccc ggacatcaca tgagaggtct gctcagattt tgaagtgttg    4440
ttctttccac cagcaggaag tagccgcatt tgattttcat ttcgacaaca gaaaaaggac    4500
ctcggactgc agggagccag tcttctaggc atatcctgga agaggcttgt gacccaagaa    4560
tgtgtctgtg tcttctccca gtgttgacct gatcctcttt tttcattcat ttaaaaagca    4620
ttatcatgcc cctgctgcgg gtctcaccat gggtttagaa caaagagctt caagcaatgg    4680
ccccatcctc aaagaagtag cagtacctgg ggagctgaca cttctgtaaa actagaagat    4740
aaaccaggca acgtaagtgt tcgaggtgtt gaagatggga aggatttgca gggctgagtc    4800
tatccaagag gctttgttta ggacgtgggt cccaagccaa gccttaagtg tggaattcgg    4860
attgatagaa aggaagacta acgttacctt gctttggaga gtactggagc ctgcaaatgc    4920
attgtgtttg ctctggtgga ggtgggcatg gggtctgttc tgaaatgtaa agggttcaga    4980
cggggtttct ggttttagaa ggttgcgtgt tcttcgagtt gggctaaagt agagttcgtt    5040
gtgctgtttc tgactcctaa tgagagttcc ttccagaccg ttagctgtct ccttgccaag    5100 cccccaggaag aaaatgatgc agctctggct ccttgtctcc caggctgatc ctttattcag    5160
aataccacaa agaaaggaca ttcagctcaa ggctccctgc cgtgttgaag agttctgact    5220
gcacaaacca gcttctggtt tcttctggaa tgaataccct catatctgtc ctgatgtgat    5280
atgtctgaga ctgaatgcgg gaggttcaat gtgaagctgt gtgtggtgtc aaagtttcag    5340
gaaggatttt acccttttgt tcttcccct gtccccaacc cactctcacc ccgcaaccca    5400
tcagtatttt agttatttgg cctctactcc agtaaacctg attgggtttg ttcactctct    5460
gaatgattat tagccagact tcaaaattat tttatagccc aaattataac atctattgta    5520
ttatttagac ttttaacata tagagctatt tctactgatt tttgcccttg ttctgtcctt    5580
tttttcaaaa aagaaaatgt gttttttgtt tggtaccata gtgtgaaatg ctgggaacaa    5640
tgactataag acatgctatg gcacatatat ttatagtctg tttatgtaga aacaaatgta    5700
atatattaaa gccttatata taatgaactt tgtactattc acattttgta tcagtattat    5760
gtagcataac aaaggtcata atgctttcag caattgatgt catttttatta aagaacattg    5820 aaaaacttga                                                            5830

<210> SEQ ID NO 10
<211> LENGTH: 1356
<212> TYPE: PRT
<213> ORGANISM: Homo sapiens

<400> SEQUENCE: 10

Met Gln Ser Lys Val Leu Leu Ala Val Ala Leu Trp Leu Cys Val Glu
```

-continued

```
1               5                   10                  15
Thr Arg Ala Ala Ser Val Gly Leu Pro Ser Val Ser Leu Asp Leu Pro
                20                  25                  30

Arg Leu Ser Ile Gln Lys Asp Ile Leu Thr Ile Lys Ala Asn Thr Thr
                35                  40                  45

Leu Gln Ile Thr Cys Arg Gly Gln Arg Asp Leu Asp Trp Leu Trp Pro
 50                 55                  60

Asn Asn Gln Ser Gly Ser Glu Gln Arg Val Glu Val Thr Glu Cys Ser
 65                 70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
                100                 105                 110

Val Ile Tyr Val Tyr Val Gln Asp Tyr Arg Ser Pro Phe Ile Ala Ser
                115                 120                 125

Val Ser Asp Gln His Gly Val Val Tyr Ile Thr Glu Asn Lys Asn Lys
                130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
                180                 185                 190

Ser Tyr Ala Gly Met Val Phe Cys Glu Ala Lys Ile Asn Asp Glu Ser
                195                 200                 205

Tyr Gln Ser Ile Met Tyr Ile Val Val Val Gly Tyr Arg Ile Tyr
                210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
                260                 265                 270

Val Asn Arg Asp Leu Lys Thr Gln Ser Gly Ser Glu Met Lys Lys Phe
                275                 280                 285

Leu Ser Thr Leu Thr Ile Asp Gly Val Thr Arg Ser Asp Gln Gly Leu
                290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
                340                 345                 350

Lys Tyr Leu Gly Tyr Pro Pro Glu Ile Lys Trp Tyr Lys Asn Gly
                355                 360                 365

Ile Pro Leu Glu Ser Asn His Thr Ile Lys Ala Gly His Val Leu Thr
                370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
                420                 425                 430
```

-continued

```
Asp Ser Tyr Gln Tyr Gly Thr Thr Gln Thr Leu Thr Cys Thr Val Tyr
        435                 440                 445

Ala Ile Pro Pro His His Ile His Trp Tyr Trp Gln Leu Glu Glu
450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Asp Phe Gln Gly Gly Asn Lys
            485                 490                 495

Ile Glu Val Asn Lys Asn Gln Phe Ala Leu Ile Glu Gly Lys Asn Lys
                500                 505                 510

Thr Val Ser Thr Leu Val Ile Gln Ala Ala Asn Val Ser Ala Leu Tyr
            515                 520                 525

Lys Cys Glu Ala Val Asn Lys Val Gly Arg Gly Glu Arg Val Ile Ser
530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
            580                 585                 590

Ile His Val Gly Glu Leu Pro Thr Pro Val Cys Lys Asn Leu Asp Thr
        595                 600                 605

Leu Trp Lys Leu Asn Ala Thr Met Phe Ser Asn Ser Thr Asn Asp Ile
610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Arg His Cys Val Val
            645                 650                 655

Arg Gln Leu Thr Val Leu Glu Arg Val Ala Pro Thr Ile Thr Gly Asn
                660                 665                 670

Leu Glu Asn Gln Thr Thr Ser Ile Gly Glu Ser Ile Glu Val Ser Cys
            675                 680                 685

Thr Ala Ser Gly Asn Pro Pro Pro Gln Ile Met Trp Phe Lys Asp Asn
690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
            740                 745                 750

Ile Ile Glu Gly Ala Gln Glu Lys Thr Asn Leu Glu Ile Ile Ile Leu
        755                 760                 765

Val Gly Thr Ala Val Ile Ala Met Phe Phe Trp Leu Leu Leu Val Ile
770                 775                 780

Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
                805                 810                 815

Cys Glu Arg Leu Pro Tyr Asp Ala Ser Lys Trp Glu Phe Pro Arg Asp
            820                 825                 830

Arg Leu Lys Leu Gly Lys Pro Leu Gly Arg Gly Ala Phe Gly Gln Val
        835                 840                 845

Ile Glu Ala Asp Ala Phe Gly Ile Asp Lys Thr Ala Thr Cys Arg Thr
850                 855                 860
```

-continued

Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
                    885                 890                 895

Asn Val Val Asn Leu Leu Gly Ala Cys Thr Lys Pro Gly Gly Pro Leu
                900                 905                 910

Met Val Ile Val Glu Phe Cys Lys Phe Gly Asn Leu Ser Thr Tyr Leu
                915                 920                 925

Arg Ser Lys Arg Asn Glu Phe Val Pro Tyr Lys Thr Lys Gly Ala Arg
            930                 935                 940

Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ser Ala Ser Ser Gly
                    965                 970                 975

Phe Val Glu Glu Lys Ser Leu Ser Asp Val Glu Glu Glu Glu Ala Pro
                980                 985                 990

Glu Asp Leu Tyr Lys Asp Phe Leu Thr Leu Glu His Leu Ile Cys Tyr
            995                 1000                1005

Ser Phe Gln Val Ala Lys Gly Met Glu Phe Leu Ala Ser Arg Lys
    1010                1015                1020

Cys Ile His Arg Asp Leu Ala Ala Arg Asn Ile Leu Leu Ser Glu
    1025                1030                1035

Lys Asn Val Val Lys Ile Cys Asp Phe Gly Leu Ala Arg Asp Ile
    1040                1045                1050

Tyr Lys Asp Pro Asp Tyr Val Arg Lys Gly Asp Ala Arg Leu Pro
    1055                1060                1065

Leu Lys Trp Met Ala Pro Glu Thr Ile Phe Asp Arg Val Tyr Thr
    1070                1075                1080

Ile Gln Ser Asp Val Trp Ser Phe Gly Val Leu Leu Trp Glu Ile
    1085                1090                1095

Phe Ser Leu Gly Ala Ser Pro Tyr Pro Gly Val Lys Ile Asp Glu
    1100                1105                1110

Glu Phe Cys Arg Arg Leu Lys Glu Gly Thr Arg Met Arg Ala Pro
    1115                1120                1125

Asp Tyr Thr Thr Pro Glu Met Tyr Gln Thr Met Leu Asp Cys Trp
    1130                1135                1140

His Gly Glu Pro Ser Gln Arg Pro Thr Phe Ser Glu Leu Val Glu
    1145                1150                1155

His Leu Gly Asn Leu Leu Gln Ala Asn Ala Gln Gln Asp Gly Lys
    1160                1165                1170

Asp Tyr Ile Val Leu Pro Ile Ser Glu Thr Leu Ser Met Glu Glu
    1175                1180                1185

Asp Ser Gly Leu Ser Leu Pro Thr Ser Pro Val Ser Cys Met Glu
    1190                1195                1200

Glu Glu Glu Val Cys Asp Pro Lys Phe His Tyr Asp Asn Thr Ala
    1205                1210                1215

Gly Ile Ser Gln Tyr Leu Gln Asn Ser Lys Arg Lys Ser Arg Pro
    1220                1225                1230

Val Ser Val Lys Thr Phe Glu Asp Ile Pro Leu Glu Glu Pro Glu
    1235                1240                1245

Val Lys Val Ile Pro Asp Asp Asn Gln Thr Asp Ser Gly Met Val
    1250                1255                1260

Leu Ala Ser Glu Glu Leu Lys Thr Leu Glu Asp Arg Thr Lys Leu

```
                1265                1270                1275
Ser Pro Ser Phe Gly Gly Met Val Pro Ser Lys Ser Arg Glu Ser
    1280                1285                1290

Val Ala Ser Glu Gly Ser Asn Gln Thr Ser Gly Tyr Gln Ser Gly
    1295                1300                1305

Tyr His Ser Asp Asp Thr Asp Thr Thr Val Tyr Ser Ser Glu Glu
    1310                1315                1320

Ala Glu Leu Leu Lys Leu Ile Glu Ile Gly Val Gln Thr Gly Ser
    1325                1330                1335

Thr Ala Gln Ile Leu Gln Pro Asp Ser Gly Thr Thr Leu Ser Ser
    1340                1345                1350

Pro Pro Val
    1355

<210> SEQ ID NO 11
<211> LENGTH: 2305
<212> TYPE: DNA
<213> ORGANISM: Homo sapiens

<400> SEQUENCE: 11
ttcttggggc tgatgtccgc aaatatgcag aattaccggc cgggtcgctc ctgaagccag      60
cgcggggagc gagcgcggcg gcggccagca ccgggaacgc accgaggaag aagcccagcc     120
cccgccctcc gccccttccg tccccacccc ctacccggcg gcccaggagg ctccccggct     180
gcggcgcgca ctccctgttt ctcctcctcc tggctggcgc tgcctgcctc tccgcactca     240
ctgctcgccg ggcgccgtcc gccagctccg tgctccccgc gccaccctcc tccgggccgc     300
gctccctaag ggatggtact gaatttcgcc gccacaggag accggctgga gcgcccgccc     360
cgcgcctcgc ctctcctccg agcagccagc gcctcgggac gcgatgagga ccttggcttg     420
cctgctgctc ctcggctgcg gataccctcgc ccatgttctg gccgaggaag ccagatcccc     480
ccgcgaggtg atcgagaggc tggcccgcag tcagatccac agcatccggg acctccagcg     540
actcctggag atagactccg tagggagtga ggattctttg gacaccagcc tgagagctca     600
cggggtccac gccactaagc atgtgcccga gaagcggccc ctgcccattc ggaggaagag     660
aagcatcgag gaagctgtcc ccgctgtctg caagaccagg acggtcattt acgagattcc     720
tcggagtcag gtcgacccca cgtccgccaa cttcctgatc tggccccccgt gcgtggaggt     780 gaaacgctgc accggctgct gcaacacgag cagtgtcaag tgccagcccc ccgcgtcca      840 ccaccgcagc gtcaaggtgg ccaaggtgga atacgtcagg aagaagccaa aattaaaga      900 agtccaggtg aggttagagg agcatttgga gtgcgcctgc gcgaccacaa gcctgaatcc     960
ggattatcgg gaagaggaca cggatgtgag gtgaggatga gccgcagccc tttcctggga    1020
catggatgta catggcgtgt acattcctg aacctactat gtacggtgct ttattgccag     1080
tgtgcggtct tgttctcctc cgtgaaaaa ctgtgtccga gaacactcgg agaacaaag      1140 agacagtgca catttgttta atgtgacatc aaagcaagta ttgtagcact cggtgaagca    1200
gtaagaagct tccttgtcaa aaagagagag agagagagag agagaaaaa caaaaccaca     1260 aatgacaaaa acaaaacgga ctcacaaaaa tatctaaact cgatgagatg gagggtcgcc    1320
ccgtgggatg gaagtgcaga ggtctcagca gactggattt ctgtccgggt ggtcacaggt    1380
gcttttttgc cgaggatgca gagcctgctt tgggaacgac tccagagggg tgctggtggg    1440
ctctgcaggg cccgcaggaa gcaggaatgt cttggaaacc gccacgcgaa ctttagaaac    1500
cacacctcct cgctgtagta tttaagccca tacagaaacc ttcctgagag ccttaagtgg    1560
```

```
ttttttttt     tgttttgtt     tgttttttt     ttttttgtt     tttttttttt    tttttttttt    1620
ttacaccata    aagtgattat    taagcttcct    tttactcttt    ggctagcttt    tttttttttt    1680
tttttttttt    tttttttaa     ttatctcttg    gatgacattt    acaccgataa    cacacaggct    1740
gctgtaactg    tcaggacagt    gcgacggtat    ttttcctagc    aagatgcaaa    ctaatgagat    1800
gtattaaaat    aaacatggta    tacctaccta    tgcatcattt    cctaaatgtt    tctggctttg    1860
tgtttctccc    ttaccctgct    ttatttgtta    atttaagcca    ttttgaaaga    actatgcgtc    1920
aaccaatcgt    acgccgtccc    tgcggcacct    gccccagagc    ccgtttgtgg    ctgagtgaca    1980
acttgttccc    cgcagtgcac    acctagaatg    ctgtgttccc    acgcggcacg    tgagatgcat    2040
tgccgcttct    gtctgtgttg    ttggtgtgcc    ctggtgccgt    ggtggcggtc    actccctctg    2100
ctgccagtgt    ttggacagaa    cccaaattct    ttattttgg     taagatattg    tgctttacct    2160
gtattaacag    aaatgtgtgt    gtgtggtttg    ttttttttgta   aaggtgaagt    ttgtatgttt    2220
acctaatatt    acctgttttg    tatacctgag    agcctgctat    gttcttcttt    tgttgatcca    2280
aaattaaaaa    aaaaatacca    ccaac                                                   2305
```

<210> SEQ ID NO 12
<211> LENGTH: 196
<212> TYPE: PRT
<213> ORGANISM: Homo sapiens

<400> SEQUENCE: 12

Met Arg Thr Leu Ala Cys Leu Leu Leu Gly Cys Gly Tyr Leu Ala
1               5                   10                  15

His Val Leu Ala Glu Glu Ala Glu Ile Pro Arg Glu Val Ile Glu Arg
            20                  25                  30

Leu Ala Arg Ser Gln Ile His Ser Ile Arg Asp Leu Gln Arg Leu Leu
        35                  40                  45

Glu Ile Asp Ser Val Gly Ser Glu Asp Ser Leu Asp Thr Ser Leu Arg
    50                  55                  60

Ala His Gly Val His Ala Thr Lys His Val Pro Glu Lys Arg Pro Leu
65                  70                  75                  80

Pro Ile Arg Arg Lys Arg Ser Ile Glu Glu Ala Val Pro Ala Val Cys
                85                  90                  95

Lys Thr Arg Thr Val Ile Tyr Glu Ile Pro Arg Ser Gln Val Asp Pro
            100                 105                 110

Thr Ser Ala Asn Phe Leu Ile Trp Pro Pro Cys Val Glu Val Lys Arg
        115                 120                 125

Cys Thr Gly Cys Cys Asn Thr Ser Ser Val Lys Cys Gln Pro Ser Arg
    130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
            180                 185                 190

Thr Asp Val Arg
        195

<210> SEQ ID NO 13
<211> LENGTH: 6633
<212> TYPE: DNA
<213> ORGANISM: Homo sapiens

<400> SEQUENCE: 13

```
ttctccccgc cccccagttg ttgtcgaagt ctgggggttg ggactggacc ccctgattgc      60
gtaagagcaa aaagcgaagg cgcaatctgg acactgggag attcggagcg cagggagttt     120
gagagaaact tttattttga agagaccaag gttgaggggg ggcttatttc ctgacagcta     180
tttacttaga gcaaatgatt agttttagaa ggatggacta taacattgaa tcaattacaa     240
aacgcggttt ttgagcccat tactgttgga gctacaggga gagaaacagg aggagactgc     300
aagagatcat ttgggaaggc cgtgggcacg ctctttactc catgtgtggg acattcattg     360
cggaataaca tcggaggaga agtttcccag agctatgggg acttcccatc cggcgttcct     420
ggtcttaggc tgtcttctca cagggctgag cctaatcctc tgccagcttt cattaccctc     480
tatccttcca aatgaaaatg aaaaggttgt gcagctgaat tcatccttt ctctgagatg      540
ctttggggag agtgaagtga gctggcagta ccccatgtct gaagaagaga gctccgatgt     600
ggaaatcaga aatgaagaaa acaacagcgg cctttttgtg acggtcttgg aagtgagcag     660
tgcctcggcg gcccacacag ggttgtacac ttgctattac aaccacactc agacagaaga     720
gaatgagctt gaaggcaggc acatttacat ctatgtgcca gacccagatg tagcctttgt     780
acctctagga atgacggatt atttagtcat cgtggaggat gatgattctg ccattatacc     840
ttgtcgcaca actgatcccg agactcctgt aaccttacac aacagtgagg gggtggtacc     900
tgcctcctac gacagcagac agggctttaa tgggaccttc actgtagggc cctatatctg     960
tgaggccacc gtcaaaggaa agaagttcca gaccatccca tttaatgttt atgctttaaa    1020
agcaacatca gagctggatc tagaaatgga agctcttaaa accgtgtata agtcagggga    1080
aacgattgtg gtcacctgtg ctgtttttaa caatgaggtg gttgaccttc aatggactta    1140
ccctggagaa gtgaaaggca aaggcatcac aatgctggaa gaaatcaaag tcccatccat    1200
caaattggtg tacactttga cggtccccga ggccacggtg aaagacagtg agattacga     1260
atgtgctgcc cgccaggcta ccagggaggt caaagaaatg aagaaagtca ctatttctgt    1320
ccatgagaaa ggtttcattg aaatcaaacc caccttcagc cagttggaag ctgtcaacct    1380
gcatgaagtc aaacattttg ttgtagaggt gcgggcctac ccacctccca ggatatcctg    1440
gctgaaaaac aatctgactc tgattgaaaa tctcactgag atcaccactg atgtggaaaa    1500
gattcaggaa ataaggtatc gaagcaaatt aaagctgatc cgtgctaagg aagaagacag    1560
tggccattat actattgtag ctcaaaatga agatgctgtg aagagctata cttttgaact    1620
gttaactcaa gttccttcat ccattctgga cttggtcgat gatcaccatg gctcaactgg    1680
gggacagacg gtgaggtgca cagctgaagg cacgccgctt cctgatattg agtggatgat    1740
atgcaaagat attaagaaat gtaataatga aacttcctgg actatttggg ccaacaatgt    1800
ctcaaacatc atcacggaga tccactcccg agacaggagt accgtggagg gccgtgtgac    1860
tttcgccaaa gtggaggaga ccatcgccgt gcgatgcctg gctaagaatc tccttggagc    1920
tgagaaccga gagctgaagc tggtggctcc caccctgcgt tctgaactca cggtggctgc    1980
tgcagtcctg gtgctgttgg tgattgtgat catctcactt attgtcctgg ttgtcatttg    2040
gaaacagaaa ccgaggtatg aaattcgctg gagggtcatt gaatcaatca gcccggatgg    2100
acatgaatat atttatgtgg acccgatgca gctgccttat gactcaagat gggagttccc    2160
aagagatgga ctagtgcttg gtcgggtctt ggggtctgga gcgtttggga aggtggttga    2220
aggaacagcc tatggattaa gccggtccca acctgtcatg aaagttgcag tgaagatgct    2280
aaaacccacg gccagatcca gtgaaaaaca agctctcatg tctgaactga agataatgac    2340
tcacctgggg ccacatttga acattgtaaa cttgctggga gcctgcacca gtcaggccc     2400
```

```
catttacatc atcacagagt attgcttcta tggagatttg gtcaactatt tgcataagaa    2460
tagggatagc ttcctgagcc accacccaga gaagccaaag aaagagctgg atatctttgg    2520
attgaaccct gctgatgaaa gcacacggag ctatgttatt ttatcttttg aaaacaatgg    2580
tgactacatg gacatgaagc aggctgatac tacacagtat gtccccatgc tagaaaggaa    2640
agaggtttct aaatattccg acatccagag atcactctat gatcgtccag cctcatataa    2700
gaagaaatct atgttagact cagaagtcaa aaacctcctt tcagatgata actcagaagg    2760
ccttacttta ttggatttgt tgagcttcac ctatcaagtt gcccgaggaa tggagttttt    2820
ggcttcaaaa aattgtgtcc accgtgatct ggctgctcgc aacgtcctcc tggcacaagg    2880
aaaaattgtg aagatctgtg actttggcct ggccagagac atcatgcatg attcgaacta    2940
tgtgtcgaaa ggcagtacct ttctgcccgt gaagtggatg gctcctgaga gcatctttga    3000
caacctctac accacactga gtgatgtctg gtcttatggc attctgctct gggagatctt    3060
ttcccttggt ggcacccctt accccggcat gatggtggat tctactttct acaataagat    3120
caagagtggg taccggatgg ccaagcctga ccacgctacc agtgaagtct acgagatcat    3180
ggtgaaatgc tggaacagtg agccggagaa gagaccctcc ttttaccacc tgagtgagat    3240
tgtggagaat ctgctgcctg acaatataa aaagagttat gaaaaaattc acctggactt    3300
cctgaagagt gaccatcctg ctgtggcacg catgcgtgtg gactcagaca atgcatacat    3360
tggtgtcacc tacaaaaacg aggaagacaa gctgaaggac tgggagggtg gtctggatga    3420
gcagagactg agcgctgaca gtggctacat cattcctctg cctgacattg accctgtccc    3480
tgaggaggag gacctgggca gaggaacag acacagctcg cagacctctg aagagagtgc    3540
cattgagacg ggttccagca gttccacctt catcaagaga gaggacgaga ccattgaaga    3600
catcgacatg atggacgaca tcggcataga ctcttcagac ctggtggaag acagcttcct    3660
gtaactggcg gattcgaggg gttccttcca cttctggggc cacctctgga tcccgttcag    3720
aaaaccactt tattgcaatg cggaggttga gaggaggact tggttgatgt ttaaagagaa    3780
gttcccagcc aagggcctcg gggagcgttc taaatatgaa tgaatgggat attttgaaat    3840
gaactttgtc agtgttgcct ctcgcaatgc ctcagtagca tctcagtggt gtgtgaagtt    3900
tggagataga tggataaggg aataataggc cacagaaggt gaactttgtg cttcaaggac    3960
attggtgaga gtccaacaga cacaatttat actgcgacag aacttcagca ttgtaattat    4020
gtaaataact ctaaccaagg ctgtgtttag attgtattaa ctatcttctt tggacttctg    4080
aagagaccac tcaatccatc catgtacttc cctcttgaaa cctgatgtca gctgctgttg    4140
aacttttta agaagtgcat gaaaaaccat ttttgaacct taaaaggtac tggtactata    4200
gcattttgct atctttttta gtgttaagag ataaagaata ataattaacc aaccttgttt    4260
aatagatttg ggtcatttag aagcctgaca actcattttc atattgtaat ctatgtttat    4320
aatactacta ctgttatcag taatgctaaa tgtgtaataa tgtaacatga tttccctcca    4380
gagaaagcac aatttaaaac aatccttact aagtaggtga tgagtttgac agttttttgac   4440
atttatatta aataacatgt ttctctataa agtatgctaa tagctttagt gaattaaatt    4500
tagttgagca tagagaacaa agtaaaagta gtgttgtcca ggaagtcaga attttttaact   4560
gtactgaata ggttcccaa tccatcgtat taaaaacaa ttaactgccc tctgaaataa     4620
tgggattaga aacaaacaaa actcttaagt cctaaaagtt ctcaatgtag aggcataaac    4680
ctgtgctgaa cataacttct catgtatatt acccaatgga aaatataatg atcagcaaaa    4740
agactggatt tgcagaagtt tttttttttt ttcttcatgc ctgatgaaag ctttggcaac    4800
```

```
cccaatatat gtattttttg aatctatgaa cctgaaaagg gtcagaagga tgcccagaca    4860
tcagcctcct tctttcaccc cttaccccaa agagaaagag tttgaaactc gagaccataa    4920
agatattctt tagtggaggc tggatgtgca ttagcctgga tcctcagttc tcaaatgtgt    4980
gtggcagcca ggatgactag atcctgggtt tccatccttg agattctgaa gtatgaagtc    5040
tgagggaaac cagagtctgt atttttctaa actccctggc tgttctgatc ggccagtttt    5100
cggaaacact gacttaggtt tcaggaagtt gccatgggaa acaaataatt tgaactttgg    5160
aacagggttg gaattcaacc acgcaggaag cctactattt aaatccttgg cttcaggtta    5220
gtgacattta atgccatcta gctagcaatt gcgacccttaa tttaactttc cagtcttagc    5280
tgaggctgag aaagctaaag tttggttttg acaggttttc caaaagtaaa gatgctactt    5340
cccactgtat gggggagatt gaactttccc cgtctcccgt cttctgcctc ccactccata    5400
ccccgccaag gaaaggcatg tacaaaaatt atgcaattca gtgttccaag tctctgtgta    5460
accagctcag tgttttggtg gaaaaaacat tttaagtttt actgataatt tgaggttaga    5520
tgggaggatg aattgtcaca tctatccaca ctgtcaaaca ggttggtgtg ggttcattgg    5580
cattctttgc aatactgctt aattgctgat accatatgaa tgaaacatgg gctgtgatta    5640
ctgcaatcac tgtgctatcg gcagatgatg ctttggaaga tgcagaagca ataataaagt    5700
acttgactac ctactggtgt aatctcaatg caagccccaa ctttcttatc caactttttc    5760
atagtaagtg cgaagactga gccagattgg ccaattaaaa acgaaaacct gactaggttc    5820
tgtagagcca attagacttg aaatacgttt gtgtttctag aatcacagct caagcattct    5880
gtttatcgct cactctccct tgtacagcct tattttgttg gtgctttgca ttttgatatt    5940
gctgtgagcc ttgcatgaca tcatgaggcc ggatgaaact tctcagtcca gcagtttcca    6000
gtcctaacaa atgctcccac ctgaatttgt atatgactgc atttgtgggt gtgtgtgtgt    6060
tttcagcaaa ttccagattt gtttcctttt ggcctcctgc aaagtctcca gaagaaaatt    6120
tgccaatctt tcctactttc tattttatg atgacaatca aagccggcct gagaaacact    6180
atttgtgact tttaaacga ttagtgatgt ccttaaaatg tggtctgcca atctgtacaa    6240
aatggtccta tttttgtgaa gagggacata agataaaatg atgttataca tcaatatgta    6300
tatatgtatt tctatataga cttggagaat actgccaaaa catttatgac aagctgtatc    6360
actgccttcg tttatatttt tttaactgtg ataatcccca caggcacatt aactgttgca    6420
cttttgaatg tccaaaattt atattttaga aataataaaa agaaagatac ttacatgttc    6480
ccaaaacaat ggtgtggtga atgtgtgaga aaaactaact tgatagggtc taccaataca    6540
aaatgtatta cgaatgcccc tgttcatgtt tttgttttaa aacgtgtaaa tgaagatctt    6600
tatatttcaa taaatgatat ataatttaaa gtt                                 6633
```

<210> SEQ ID NO 14
<211> LENGTH: 1089
<212> TYPE: PRT
<213> ORGANISM: Homo sapiens
<400> SEQUENCE: 14

```
Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
                20                  25                  30

Asn Glu Asn Glu Lys Val Val Gln Leu Asn Ser Ser Phe Ser Leu Arg
            35                  40                  45
```

```
Cys Phe Gly Glu Ser Glu Val Ser Trp Gln Tyr Pro Met Ser Glu Glu
     50                  55                  60

Glu Ser Ser Asp Val Glu Ile Arg Asn Glu Asn Asn Ser Gly Leu
 65                  70                  75                  80

Phe Val Thr Val Leu Glu Val Ser Ser Ala Ser Ala Ala His Thr Gly
                     85                  90                  95

Leu Tyr Thr Cys Tyr Tyr Asn His Thr Gln Thr Glu Glu Asn Glu Leu
                100                 105                 110

Glu Gly Arg His Ile Tyr Ile Tyr Val Pro Asp Pro Asp Val Ala Phe
            115                 120                 125

Val Pro Leu Gly Met Thr Asp Tyr Leu Val Ile Val Glu Asp Asp Asp
130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
            195                 200                 205

Lys Ala Thr Ser Glu Leu Asp Leu Glu Met Glu Ala Leu Lys Thr Val
210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
            275                 280                 285

Glu Cys Ala Ala Arg Gln Ala Thr Arg Glu Val Lys Glu Met Lys Lys
            290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335

Val Glu Val Arg Ala Tyr Pro Pro Pro Arg Ile Ser Trp Leu Lys Asn
            340                 345                 350

Asn Leu Thr Leu Ile Glu Asn Leu Thr Glu Ile Thr Thr Asp Val Glu
            355                 360                 365

Lys Ile Gln Glu Ile Arg Tyr Arg Ser Lys Leu Lys Leu Ile Arg Ala
370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
                405                 410                 415

Ile Leu Asp Leu Val Asp Asp His His Gly Ser Thr Gly Gly Gln Thr
            420                 425                 430

Val Arg Cys Thr Ala Glu Gly Thr Pro Leu Pro Asp Ile Glu Trp Met
            435                 440                 445

Ile Cys Lys Asp Ile Lys Lys Cys Asn Asn Glu Thr Ser Trp Thr Ile
            450                 455                 460

Leu Ala Asn Asn Val Ser Asn Ile Ile Thr Glu Ile His Ser Arg Asp
465                 470                 475                 480
```

```
Arg Ser Thr Val Glu Gly Arg Val Thr Phe Ala Lys Val Glu Glu Thr
                485                 490                 495
Ile Ala Val Arg Cys Leu Ala Lys Asn Leu Leu Gly Ala Glu Asn Arg
                500                 505                 510
Glu Leu Lys Leu Val Ala Pro Thr Leu Arg Ser Glu Leu Thr Val Ala
                515                 520                 525
Ala Ala Val Leu Val Leu Leu Val Ile Val Ile Ser Leu Ile Val
530                 535                 540
Leu Val Val Ile Trp Lys Gln Lys Pro Arg Tyr Glu Ile Arg Trp Arg
545                 550                 555                 560
Val Ile Glu Ser Ile Ser Pro Asp Gly His Glu Tyr Ile Tyr Val Asp
                565                 570                 575
Pro Met Gln Leu Pro Tyr Asp Ser Arg Trp Glu Phe Pro Arg Asp Gly
                580                 585                 590
Leu Val Leu Gly Arg Val Leu Gly Ser Gly Ala Phe Gly Lys Val Val
                595                 600                 605
Glu Gly Thr Ala Tyr Gly Leu Ser Arg Ser Gln Pro Val Met Lys Val
                610                 615                 620
Ala Val Lys Met Leu Lys Pro Thr Ala Arg Ser Ser Glu Lys Gln Ala
625                 630                 635                 640
Leu Met Ser Glu Leu Lys Ile Met Thr His Leu Gly Pro His Leu Asn
                645                 650                 655
Ile Val Asn Leu Leu Gly Ala Cys Thr Lys Ser Gly Pro Ile Tyr Ile
                660                 665                 670
Ile Thr Glu Tyr Cys Phe Tyr Gly Asp Leu Val Asn Tyr Leu His Lys
                675                 680                 685
Asn Arg Asp Ser Phe Leu Ser His His Pro Glu Lys Pro Lys Lys Glu
                690                 695                 700
Leu Asp Ile Phe Gly Leu Asn Pro Ala Asp Glu Ser Thr Arg Ser Tyr
705                 710                 715                 720
Val Ile Leu Ser Phe Glu Asn Asn Gly Asp Tyr Met Asp Met Lys Gln
                725                 730                 735
Ala Asp Thr Thr Gln Tyr Val Pro Met Leu Glu Arg Lys Glu Val Ser
                740                 745                 750
Lys Tyr Ser Asp Ile Gln Arg Ser Leu Tyr Asp Arg Pro Ala Ser Tyr
                755                 760                 765
Lys Lys Lys Ser Met Leu Asp Ser Glu Val Lys Asn Leu Leu Ser Asp
770                 775                 780
Asp Asn Ser Glu Gly Leu Thr Leu Leu Asp Leu Leu Ser Phe Thr Tyr
785                 790                 795                 800
Gln Val Ala Arg Gly Met Glu Phe Leu Ala Ser Lys Asn Cys Val His
                805                 810                 815
Arg Asp Leu Ala Ala Arg Asn Val Leu Leu Ala Gln Gly Lys Ile Val
                820                 825                 830
Lys Ile Cys Asp Phe Gly Leu Ala Arg Asp Ile Met His Asp Ser Asn
                835                 840                 845
Tyr Val Ser Lys Gly Ser Thr Phe Leu Pro Val Lys Trp Met Ala Pro
                850                 855                 860
Glu Ser Ile Phe Asp Asn Leu Tyr Thr Thr Leu Ser Asp Val Trp Ser
865                 870                 875                 880
Tyr Gly Ile Leu Leu Trp Glu Ile Phe Ser Leu Gly Gly Thr Pro Tyr
                885                 890                 895
Pro Gly Met Met Val Asp Ser Thr Phe Tyr Asn Lys Ile Lys Ser Gly
```

```
                         900                 905                 910
Tyr Arg Met Ala Lys Pro Asp His Ala Thr Ser Glu Val Tyr Glu Ile
            915                 920                 925
Met Val Lys Cys Trp Asn Ser Glu Pro Glu Lys Arg Pro Ser Phe Tyr
    930                 935                 940
His Leu Ser Glu Ile Val Glu Asn Leu Leu Pro Gly Gln Tyr Lys Lys
945                 950                 955                 960
Ser Tyr Glu Lys Ile His Leu Asp Phe Leu Lys Ser Asp His Pro Ala
                965                 970                 975
Val Ala Arg Met Arg Val Asp Ser Asp Asn Ala Tyr Ile Gly Val Thr
            980                 985                 990
Tyr Lys Asn Glu Glu Asp Lys Leu  Lys Asp Trp Glu Gly  Gly Leu Asp
                995                  1000                1005
Glu Gln  Arg Leu Ser Ala Asp  Ser Gly Tyr Ile Ile  Pro Leu Pro
    1010                 1015                1020
Asp Ile  Asp Pro Val Pro Glu  Glu Glu Asp Leu Gly  Lys Arg Asn
    1025                 1030                1035
Arg His  Ser Ser Gln Thr Ser  Glu Glu Ser Ala Ile  Glu Thr Gly
    1040                 1045                1050
Ser Ser  Ser Ser Thr Phe Ile  Lys Arg Glu Asp Glu  Thr Ile Glu
    1055                 1060                1065
Asp Ile  Asp Met Met Asp Asp  Ile Gly Ile Asp Ser  Ser Asp Leu
    1070                 1075                1080
Val Glu  Asp Ser Phe Leu
    1085

<210> SEQ ID NO 15
<211> LENGTH: 10
<212> TYPE: RNA
<213> ORGANISM: Artificial Sequence
<220> FEATURE:
<223> OTHER INFORMATION: Synthetic anti-VEGF aptamer

<400> SEQUENCE: 15
gaagaauugg                                                          10

<210> SEQ ID NO 16
<211> LENGTH: 8
<212> TYPE: RNA
<213> ORGANISM: Artificial Sequence
<220> FEATURE:
<223> OTHER INFORMATION: Synthetic anti-VEGF aptamer

<400> SEQUENCE: 16 uuggacgc                                                            8

<210> SEQ ID NO 17
<211> LENGTH: 8
<212> TYPE: RNA
<213> ORGANISM: Artificial Sequence
<220> FEATURE:
<223> OTHER INFORMATION: Synthetic anti-VEGF aptamer

<400> SEQUENCE: 17 gugaaugc                                                            8

<210> SEQ ID NO 18
<211> LENGTH: 27
<212> TYPE: RNA
<213> ORGANISM: Artificial Sequence
<220> FEATURE:
```

```
<223> OTHER INFORMATION: Synthetic anti-VEGF aptamer

<400> SEQUENCE: 18
cggaaucagu gaaugcuuau acauccg                                          27

<210> SEQ ID NO 19
<211> LENGTH: 27
<212> TYPE: RNA
<213> ORGANISM: Artificial Sequence
<220> FEATURE:
<223> OTHER INFORMATION: Synthetic anti-VEGF aptamer

<400> SEQUENCE: 19
cggaaucagu gaaugcuuau acauccg                                          27

<210> SEQ ID NO 20
<211> LENGTH: 32
<212> TYPE: DNA
<213> ORGANISM: Artificial Sequence
<220> FEATURE:
<223> OTHER INFORMATION: Synthetic anti-PDGF aptamer
<220> FEATURE:
<221> NAME/KEY: modified_base
<222> LOCATION: (10)..(10)
<223> OTHER INFORMATION: n=hexaethylene-glycol phosphoramidite
<220> FEATURE:
<221> NAME/KEY: misc_feature
<222> LOCATION: (10)..(10)
<223> OTHER INFORMATION: n is a, c, g, t or u
<220> FEATURE:
<221> NAME/KEY: modified_base
<222> LOCATION: (23)..(23)
<223> OTHER INFORMATION: n=hexaethylene-glycol phosphoramidite
<220> FEATURE:
<221> NAME/KEY: misc_feature
<222> LOCATION: (23)..(23)
<223> OTHER INFORMATION: n is a, c, g, t or u

<400> SEQUENCE: 20
caggcuacgn cgtagagcau cantgatccu gt                                    32

<210> SEQ ID NO 21
<211> LENGTH: 30
<212> TYPE: DNA
<213> ORGANISM: Artificial Sequence
<220> FEATURE:
<223> OTHER INFORMATION: Synthetic anti-PDGF aptamer

<400> SEQUENCE: 21
caggctacgc gtagagcatc atgatcctgt                                       30

<210> SEQ ID NO 22
<211> LENGTH: 32
<212> TYPE: DNA
<213> ORGANISM: Artificial Sequence
<220> FEATURE:
<223> OTHER INFORMATION: Synthetic anti-PDGF aptamer
<220> FEATURE:
<221> NAME/KEY: misc_feature
<222> LOCATION: (10)..(10)
<223> OTHER INFORMATION: n is a, c, g, t or u
<220> FEATURE:
<221> NAME/KEY: misc_feature
<222> LOCATION: (23)..(23)
<223> OTHER INFORMATION: n is a, c, g, t or u

<400> SEQUENCE: 22
caggcuacgn cgtagagcau cantgatccu gt                                    32

<210> SEQ ID NO 23
```

```
<211> LENGTH: 32
<212> TYPE: DNA
<213> ORGANISM: Artificial Sequence
<220> FEATURE:
<223> OTHER INFORMATION: Synthetic anti-PDGF aptamer
<220> FEATURE:
<221> NAME/KEY: misc_feature
<222> LOCATION: (1)..(32)
<223> OTHER INFORMATION: U at positions 6, 20 and 30 is 2'-fluoro-2'-
      deoxyuridine
<220> FEATURE:
<221> NAME/KEY: misc_feature
<222> LOCATION: (1)..(32)
<223> OTHER INFORMATION: C at positions 8, 21, 28 and 29 is 2'-fluoro-
      2'-deoxycytidine
<220> FEATURE:
<221> NAME/KEY: misc_feature
<222> LOCATION: (1)..(32)
<223> OTHER INFORMATION: G at positions 9, 15, 17 and 31 is 2'-O-Methyl-
      2'-deoxyguanosine
<220> FEATURE:
<221> NAME/KEY: misc_feature
<222> LOCATION: (1)..(32)
<223> OTHER INFORMATION: A at position 22 is 2'-O-Methyl-2'-
      deoxyadenosine
<220> FEATURE:
<221> NAME/KEY: misc_feature
<222> LOCATION: (1)..(32)
<223> OTHER INFORMATION: N at positions 10 and 23 is from a hexaethylene
      glycol phosphoramidite
<220> FEATURE:
<221> NAME/KEY: misc_feature
<222> LOCATION: (32)..(32)
<223> OTHER INFORMATION: Nucleotide 32 is an inverted orientation T (3'-
      3'-linked)

<400> SEQUENCE: 23
caggcuacgn cgtagagcau cantgatccu gt                                     32

<210> SEQ ID NO 24
<211> LENGTH: 118
<212> TYPE: PRT
<213> ORGANISM: Artificial Sequence
<220> FEATURE:
<223> OTHER INFORMATION: Synthetic anti-VEGF antibody

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Gly Thr Ser His Trp Tyr Phe Asp Val
            100                 105                 110

Trp Gly Gln Gly Thr Leu
        115

<210> SEQ ID NO 25
<211> LENGTH: 110
<212> TYPE: PRT
<213> ORGANISM: Artificial Sequence
<220> FEATURE:
```

-continued

<223> OTHER INFORMATION: Synthetic anti-VEGF antibody

<400> SEQUENCE: 25

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val
            100                 105                 110

<210> SEQ ID NO 26
<211> LENGTH: 118
<212> TYPE: PRT
<213> ORGANISM: Artificial Sequence
<220> FEATURE:
<223> OTHER INFORMATION: Synthetic anti-VEGF antibody

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu
            115

<210> SEQ ID NO 27
<211> LENGTH: 110
<212> TYPE: PRT
<213> ORGANISM: Artificial Sequence
<220> FEATURE:
<223> OTHER INFORMATION: Synthetic anti-VEGF antibody

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg Thr Val
            100                 105                 110
```

<210> SEQ ID NO 28
<211> LENGTH: 123
<212> TYPE: PRT
<213> ORGANISM: Artificial Sequence
<220> FEATURE:
<223> OTHER INFORMATION: Synthetic anti-VEGF antibody
<220> FEATURE:
<221> NAME/KEY: misc_feature
<222> LOCATION: (28)..(28)
<223> OTHER INFORMATION: Xaa is T or D
<220> FEATURE:
<221> NAME/KEY: misc_feature
<222> LOCATION: (31)..(31)
<223> OTHER INFORMATION: Xaa is N or H
<220> FEATURE:
<221> NAME/KEY: misc_feature
<222> LOCATION: (101)..(101)
<223> OTHER INFORMATION: Xaa is Y or H
<220> FEATURE:
<221> NAME/KEY: misc_feature
<222> LOCATION: (105)..(105)
<223> OTHER INFORMATION: Xaa is S or T

<400> SEQUENCE: 28

```
Glu Val Gln Leu Val Glu Ser Gly Gly Gly Leu Val Gln Pro Gly Gly
 1                5                  10                  15

Ser Leu Arg Leu Ser Cys Ala Ala Ser Gly Tyr Xaa Phe Thr Xaa Tyr
             20                  25                  30

Gly Met Asn Trp Val Arg Gln Ala Pro Gly Lys Gly Leu Glu Trp Val
             35                  40                  45

Gly Trp Ile Asn Thr Tyr Thr Gly Glu Pro Thr Tyr Ala Ala Asp Phe
         50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro Xaa Tyr Tyr Gly Xaa Ser His Trp Tyr Phe Asp Val
            100                 105                 110

Trp Gly Gln Gly Thr Leu Val Thr Val Ser Ser
        115                 120
```

<210> SEQ ID NO 29
<211> LENGTH: 11
<212> TYPE: PRT
<213> ORGANISM: Artificial Sequence
<220> FEATURE:
<223> OTHER INFORMATION: Synthetic anti-VEGF antibody

<400> SEQUENCE: 29

```
Ser Ala Ser Gln Asp Ile Ser Asn Tyr Leu Asn
 1                5                  10
```

<210> SEQ ID NO 30
<211> LENGTH: 7
<212> TYPE: PRT
<213> ORGANISM: Artificial Sequence
<220> FEATURE:
<223> OTHER INFORMATION: Synthetic anti-VEGF antibody

```
-continued

<400> SEQUENCE: 30

Phe Thr Ser Ser Leu His Ser
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic anti-VEGF antibody

<400> SEQUENCE: 31

Gln Gln Tyr Ser Thr Val Pro Trp Thr
1               5

<210> SEQ ID NO 32
<211> LENGTH: 108
<212> TYPE: PRT
<213> ORGANISM: Artificial Sequence
<220> FEATURE:
<223> OTHER INFORMATION: Synthetic anti-VEGF antibody
<220> FEATURE:
<221> NAME/KEY: misc_feature
<222> LOCATION: (4)..(4)
<223> OTHER INFORMATION: Xaa is M or L

<400> SEQUENCE: 32

Asp Ile Gln Xaa Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg
            100                 105

<210> SEQ ID NO 33
<211> LENGTH: 10
<212> TYPE: PRT
<213> ORGANISM: Artificial Sequence
<220> FEATURE:
<223> OTHER INFORMATION: Synthetic anti-VEGF antibody

<400> SEQUENCE: 33

Gly Tyr Asp Phe Thr His Tyr Gly Met Asn
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Synthetic anti-VEGF antibody

<400> SEQUENCE: 34

Tyr Pro Tyr Tyr Tyr Gly Thr Ser His Trp Tyr Phe Asp Val
1               5                   10
```